(12) United States Patent
Lee et al.

(10) Patent No.: US 11,133,477 B2
(45) Date of Patent: Sep. 28, 2021

(54) HETEROCYCLIC COMPOUND AND ORGANIC LIGHT EMITTING ELEMENT USING SAME

(71) Applicant: LT MATERIALS CO., LTD., Yongin (KR)

(72) Inventors: Yun-Ji Lee, Osan-si (KR); Jun-Tae Mo, Osan-si (KR); Yong-Geun Jung, Seoul (KR); Won-Jang Jeong, Hwaseong-si (KR); Jin-Seok Choi, Suwon-si (KR); Dae-Hyuk Choi, Yongin-si (KR); Joo-Dong Lee, Seongnam-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 370 days.

(21) Appl. No.: 16/315,066

(22) PCT Filed: Jul. 11, 2017

(86) PCT No.: PCT/KR2017/007395
§ 371 (c)(1),
(2) Date: Jan. 3, 2019

(87) PCT Pub. No.: WO2018/012845
PCT Pub. Date: Jan. 18, 2018

(65) Prior Publication Data
US 2019/0312211 A1    Oct. 10, 2019

(30) Foreign Application Priority Data

Jul. 11, 2016    (KR) .................. 10-2016-0087507

(51) Int. Cl.
*H01L 51/00* (2006.01)
*C07D 221/18* (2006.01)
(Continued)

(52) U.S. Cl.
CPC ........ *H01L 51/0072* (2013.01); *C07D 221/18* (2013.01); *C07D 401/10* (2013.01);
(Continued)

(58) Field of Classification Search
None
See application file for complete search history.

(56) References Cited

U.S. PATENT DOCUMENTS 10,087,145 B2    10/2018    Kim et al.
2014/0131664 A1    5/2014    Yen et al.
(Continued)

FOREIGN PATENT DOCUMENTS

| KR | 10-2012-0007312 A | 1/2012 |
| KR | 10-2015-0076029 A | 7/2015 |
| KR | 10-2015-0126563 A | 11/2015 |

OTHER PUBLICATIONS

International Search Report, issued in PCT/KR2017/007395, PCT/ISA/210, dated Oct. 19, 2017.
(Continued)

*Primary Examiner* — Jay Yang
(74) *Attorney, Agent, or Firm* — Birch, Stewart, Kolasch & Birch, LLP

(57) ABSTRACT

The present application relates to a hetero-cyclic compound represented by Chemical Formula 1, and an organic light emitting device comprising the same.

11 Claims, 3 Drawing Sheets

(51) Int. Cl.
    *C09K 11/06*     (2006.01)
    *C07D 401/10*     (2006.01)
    *C07D 471/04*     (2006.01)
    *C07D 401/14*     (2006.01)
    *C07D 405/10*     (2006.01)
    *C07F 9/576*     (2006.01)
    *C07D 403/10*     (2006.01)
    *H01L 51/50*     (2006.01)
    *C07D 403/14*     (2006.01)
    *H01L 51/52*     (2006.01)

(52) U.S. Cl.
    CPC ......... *C07D 401/14* (2013.01); *C07D 403/10* (2013.01); *C07D 403/14* (2013.01); *C07D 405/10* (2013.01); *C07D 471/04* (2013.01); *C07F 9/5765* (2013.01); *C09K 11/06* (2013.01); *H01L 51/00* (2013.01); *H01L 51/0052* (2013.01); *H01L 51/0054* (2013.01); *H01L 51/0056* (2013.01); *H01L 51/0058* (2013.01); *H01L 51/0067* (2013.01); *H01L 51/50* (2013.01); *C09K 2211/1018* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5278* (2013.01)

(56) References Cited

U.S. PATENT DOCUMENTS

| | | |
|---|---|---|
| 2014/0151645 A1 | 6/2014 | Yen et al. |
| 2014/0284556 A1 | 9/2014 | Cheng et al. |
| 2015/0318490 A1* | 11/2015 | Kim .................... C09B 5/00 257/40 |
| 2015/0340628 A1 | 11/2015 | Hamada et al. |

OTHER PUBLICATIONS

Kuwabara et al. "Thermally Stable Multilayered Organic Electroluminescent Devices Using Novel Starburst Molecules, 4,4',4"-Tri(N-carbazolyl)triphenylamine (TCTA) and 4,4',4"-Tris(3-methysphenylphenyl-amino)triphenylamine (m-MTDATA), as Hole-Transport Materials", Advanced Materials, 1994, 6, No. 9, p. 677-679.

* cited by examiner

[FIG. 1]
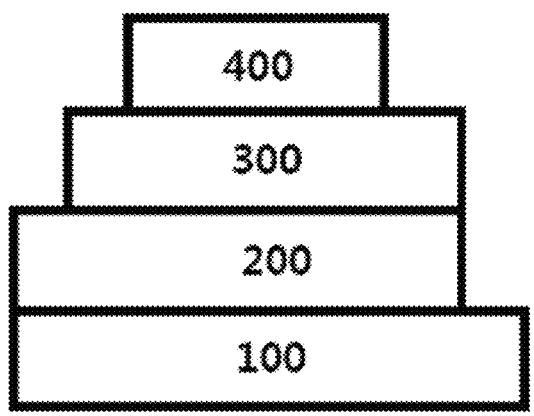
[FIG. 2]
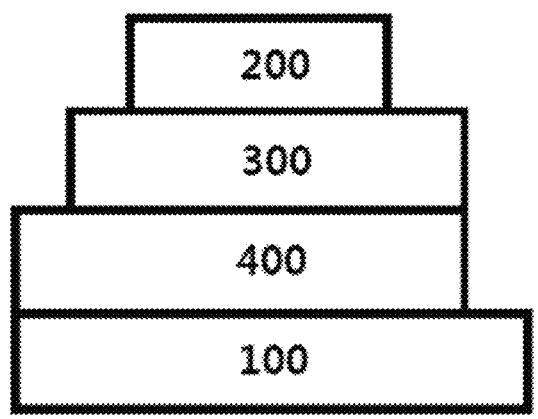

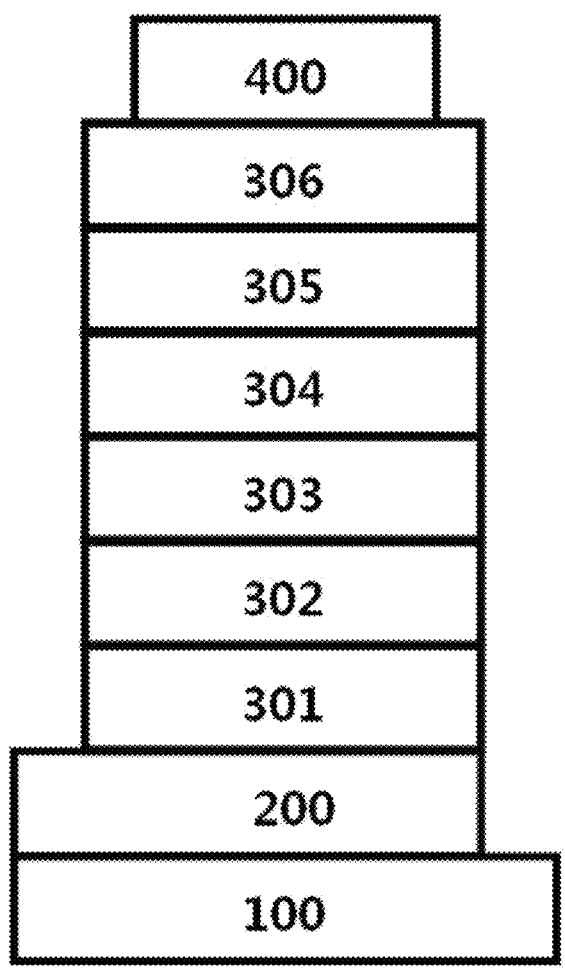
[FIG. 3]

[FIG. 4]

| CATHODE |
|---|
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT EMITTING ELEMENT USING SAME

TECHNICAL FIELD

This application claims priority to and the benefits of Korean Patent Application No. 10-2016-0087507, filed with the Korean Intellectual Property Office on Jul. 11, 2016, the entire contents of which are incorporated herein by reference.

The present application relates to a hetero-cyclic compound and an organic light emitting device using the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves may be used alone, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifespan or efficiency of an organic light emitting device.

PRIOR ART DOCUMENTS

Patent Documents

U.S. Pat. No. 4,356,429

DISCLOSURE

Technical Problem

The present application is directed to providing a novel hetero-cyclic compound and an organic light emitting device using the same.

Technical Solution

One embodiment of the present application provides a hetero-cyclic compound represented by the following Chemical Formula 1:

[Chemical Formula 1]

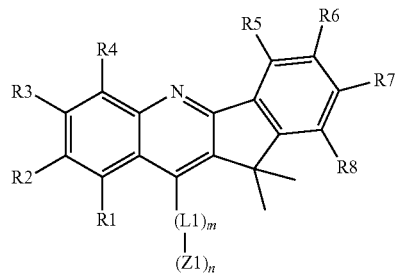

in Chemical Formula 1,

L1 is a direct bond; a substituted or unsubstituted $C_6$ to $C_{60}$ arylene group; or a substituted or unsubstituted $C_2$ to $C_{60}$ heteroarylene group, Z1 is selected from the group consisting of hydrogen; deuterium; a halogen group; —CN; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —SiRR'R''; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, m is an integer of 0 to 4, n is an integer of 1 to 4, R1 to R8 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_0$ alkenyl group; a substituted or unsubstituted $C_2$ to $C_6$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R''; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, or two or more groups adjacent to each other bond to each other to form a substituted or unsubstituted aliphatic or aromatic hydrocarbon ring, R, R' and R'' are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

Another embodiment of the present application provides an organic light emitting device comprising an anode, a cathode and one or more organic material layers provided between the anode and the cathode, wherein one or more layers of the organic material layers comprise the hetero-cyclic compound represented by Chemical Formula 1.

Advantageous Effects

A hetero-cyclic compound according to one embodiment of the present application can be used as an organic material layer material of an organic light emitting device. The hetero-cyclic compound can be used as a material of a hole injection layer, a hole transfer layer, a light emitting layer, an electron transfer layer, an electron injection layer, a charge generation layer or the like in an organic light emitting device. Particularly, the hetero-cyclic compound represented by Chemical Formula 1 can be used as a material of an electron transfer layer or a charge generation layer in an organic light emitting device. In addition, using the hetero-cyclic compound represented by Chemical Formula 1 in an organic light emitting device lowers a driving voltage of the device, enhances light efficiency, and can enhance a lifespan property of the device with thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode Mode for Disclosure Hereinafter, the present application will be described in detail.

A hetero-cyclic compound according to one embodiment of the present application is represented by Chemical Formula 1. More specifically, the hetero-cyclic compound represented by Chemical Formula 1 is capable of being used as an organic material layer material of an organic light emitting device with such a core structure and structural characteristics of substituents.

In one embodiment of the present application, when m of Chemical Formula 1 is 2 or greater, two or more L1s may be the same as or different from each other. In addition, when n of Chemical Formula 1 is 2 or greater, two or more Z1s may be the same as or different from each other.

In one embodiment of the present application, m of Chemical Formula 1 may be an integer of 1 to 4.

In one embodiment of the present application, R1 and R2 of Chemical Formula 1 may bond to each other to form a substituted or unsubstituted aliphatic or aromatic hydrocarbon ring. In addition, in one embodiment of the present application, R3 and R4 of Chemical Formula 1 may bond to each other to form a substituted or unsubstituted aliphatic or aromatic hydrocarbon ring.

According to one embodiment of the present application, Chemical Formula 1 may be represented by any one of the following Chemical Formulae 2 to 7.

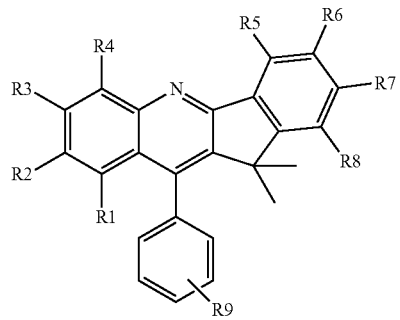

[Chemical Formula 2]

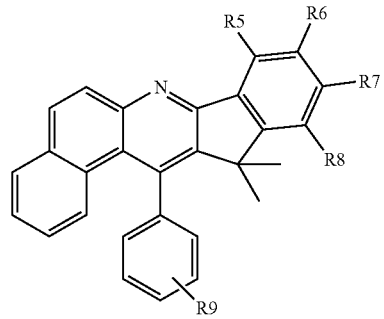

[Chemical Formula 3]

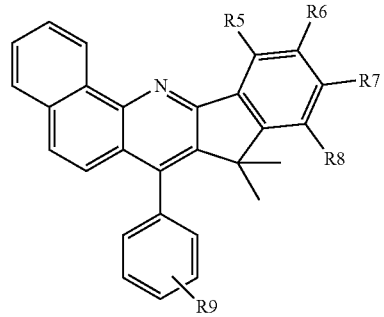

[Chemical Formula 4]

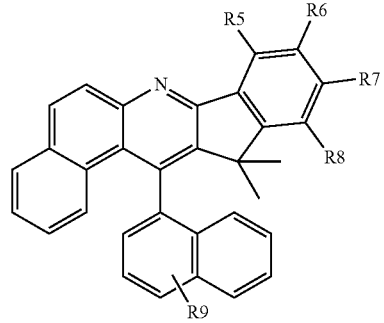

[Chemical Formula 5]

-continued

[Chemical Formula 6]

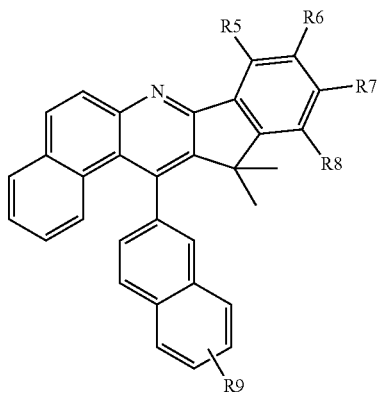

[Chemical Formula 7]

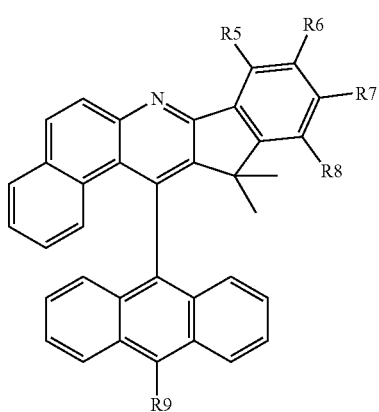

In Chemical Formulae 2 to 7,

R9 is represented by -(L2)p-(Z2)q,

L2 has the same definition as L1 of Chemical Formula 1 and Z2 has the same definition as Z1 of Chemical Formula 1, p is an integer of 0 to 3, q is an integer of 1 to 4, and R1 to R8 have the same definitions as in Chemical Formula 1.

In one embodiment of the present application, R5 to R8 of Chemical Formula 1 may be each independently hydrogen or deuterium.

In one embodiment of the present application, L1 and L2 of Chemical Formulae 1 to 7 are each independently a direct bond; a substituted or unsubstituted $C_6$ to $C_{60}$ arylene group; or a substituted or unsubstituted $C_2$ to $C_{60}$ heteroarylene group.

In another embodiment, L1 and L2 of Chemical Formulae 1 to 7 are each independently a direct bond; a substituted or unsubstituted $C_6$ to $C_{40}$ arylene group; or a substituted or unsubstituted $C_2$ to $C_{40}$ heteroarylene group.

In another embodiment, L1 and L2 of Chemical Formulae 1 to 7 are each independently a direct bond; a $C_6$ to $C_{40}$ arylene group; or a $C_2$ to $C_{40}$ heteroarylene group.

In another embodiment, L1 and L2 of Chemical Formulae 1 to 7 may be each independently a direct bond; a phenylene group; a naphthylene group; a pyrenylene group; a biphenylylene group; a triphenylenylene group; an anthracenylene group; a divalent pyridine group; a divalent pyrimidine group; a divalent triazine group; a divalent quinoline group; or a divalent pyrazine group.

In one embodiment of the present application, Z1 and Z2 of Chemical Formulae 1 to 7 are each independently selected from the group consisting of hydrogen; deuterium; a substituted or unsubstituted $C_6$ to $C_{60}$ aryl group; a substituted or unsubstituted $C_2$ to $C_{60}$ heteroaryl group; and —P(=O)RR', and R and R' are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_6$ aryl group; or a substituted or unsubstituted $C_2$ to $C_6$ heteroaryl group.

In another embodiment, Z1 and Z2 of Chemical Formulae 1 to 7 are each independently selected from the group consisting of hydrogen; deuterium; a substituted or unsubstituted $C_6$ to $C_{40}$ aryl group; a substituted or unsubstituted $C_2$ to $C_{40}$ heteroaryl group; and —P(=O)RR', and R and R' are the same as or different from each other, and each independently hydrogen; deuterium; or a substituted or unsubstituted $C_6$ to $C_{40}$ aryl group.

In another embodiment, Z1 and Z2 of Chemical Formulae 1 to 7 are each independently selected from the group consisting of hydrogen; a $C_6$ to $C_{40}$ aryl group unsubstituted or substituted with one or more substituents selected from the group consisting of a $C_6$ to $C_{40}$ aryl group, a $C_2$ to $C_{40}$ heteroaryl group and P(=O)RR'; a $C_2$ to $C_{40}$ heteroaryl group unsubstituted or substituted with one or more substituents selected from the group consisting of a $C_6$ to $C_{40}$ aryl group, a $C_2$ to $C_{40}$ heteroaryl group and P(=O)RR'; and —P(=O)RR', and R and R' are the same as or different from each other and each independently a $C_6$ to $C_{40}$ aryl group.

In another embodiment, Z1 and Z2 of Chemical Formulae 1 to 7 are each independently selected from the group consisting of hydrogen; a phenyl group unsubstituted or substituted with one or more substituents selected from the group consisting of a pyridine group, a quinoline group and P(=O)RR'; a naphthyl group unsubstituted or substituted with P(=O)RR'; an anthracene group unsubstituted or substituted with a phenyl group; a pyrene group unsubstituted or substituted with one or more substituents selected from the group consisting of a pyridine group and a pyrimidine group; a fluoranthenyl group; a triphenylene group unsubstituted or substituted with a pyrazine group; a biphenylene group; a fluorene group unsubstituted or substituted with one or more substituents selected from the group consisting of a phenyl group and a xanthene group; a phenanthrene group and a spirobifluorene group, and R and R' are the same as or different from each other and each independently a phenyl group.

In another embodiment, Z1 and Z2 of Chemical Formulae 1 to 7 are each independently selected from the group consisting of hydrogen; a pyridine group unsubstituted or substituted with one or more substituents selected from the group consisting of a phenyl group, a biphenyl group and a pyridine group; a quinoline group unsubstituted or substituted with one or more substituents selected from the group consisting of a pyridine group, a pyrimidine group and —P(=O)RR'; a phenanthroline group unsubstituted or substituted with one or more substituents selected from the group consisting of a phenyl group and a pyridine group; a pyrimidine group unsubstituted or substituted with one or more substituents selected from the group consisting of a phenyl group, a biphenyl group and a pyridine group; a quinazoline group; a benzimidazole group unsubstituted or substituted with a phenyl group; a triazine group unsubstituted or substituted with one or more substituents selected from the group consisting of a phenyl group and a biphenyl group; an indole group unsubstituted or substituted with a phenyl group; a carbazole group; a pyrido[2,3-b]indole group unsubstituted or substituted with a pyridine group; a phenanthro[9,10-b]imidazole group unsubstituted or substituted with a phenyl group; and a pyrazine group unsubstituted or substituted with an imidazo[1,2-a]pyridine group and a phenyl group, and R and R' are the same as or different from each other and each independently a phenyl group.

In another embodiment, Z1 and Z2 of Chemical Formulae 1 to 7 may be each independently P(=O)RR', and R and R' are the same as or different from each other and each independently a phenyl group.

In one embodiment of the present application, R1 and R2 of Chemical Formula 1 bond to each other to form an aromatic hydrocarbon ring, or R3 and R4 bond to each other to form an aromatic hydrocarbon ring, and, among R1 to R4, groups that do not form the aromatic hydrocarbon ring may be hydrogen or deuterium.

In another embodiment, R1 and R2 of Chemical Formula 1 bond to each other to form a benzene ring, or R3 and R4 bond to each other to form a benzene ring, and, among R1 to R4, groups that do not form the benzene ring may be hydrogen.

In one embodiment of the present application, R, R' and R" of Chemical Formulae 1 to 7 are the same as or different from each other, and may be each independently hydrogen; a substituted or unsubstituted $C_1$ to $C_{60}$ alkyl group; or a substituted or unsubstituted $C_6$ to $C_{60}$ aryl group.

In the present specification, the term "substituted or unsubstituted" means being substituted with one or more substituents selected from the group consisting of deuterium; a halogen group; —CN; a $C_1$ to $C_0$ alkyl group; a $C_2$ to $C_{60}$ alkenyl group; a $C_2$ to $C_{60}$ alkynyl group; a $C_3$ to $C_{60}$ cycloalkyl group; a $C_2$ to $C_{60}$ heterocycloalkyl group; a $C_6$ to $C_{60}$ aryl group; a $C_2$ to $C_{60}$ heteroaryl group; —SiRR'R"; —P(=O)RR'; a $C_1$ to $C_{20}$ alkylamine group; a $C_6$ to $C_6$ arylamine group; and a $C_2$ to $C_{60}$ heteroarylamine group, or being unsubstituted, or being substituted with a substituent bonding two or more of the above-mentioned substituents, or being substituted, or being substituted with a substituent linking two or more substituents selected from among the above-mentioned substituents, or being unsubstituted. For example, "a substituent linking two or more substituents" may comprise a biphenyl group. In other words, a biphenyl group may be an aryl group, or may be interpreted as a substituent linking two phenyl groups. The additional substituents may be further substituted. R, R' and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

According to one embodiment of the present application, the "substituted or unsubstituted" means being substituted with one or more substituents selected from the group consisting of deuterium, a halogen group, —CN, SiRR'R", P(=O)RR', a $C_1$ to $C_{20}$ linear or branched alkyl group, a $C_6$ to $C_{60}$ aryl group, and a $C_2$ to $C_{60}$ heteroaryl group, or being unsubstituted, and R, R' and R" are the same as or different from each other, and each independently hydrogen; deuterium; —CN; a $C_1$ to $C_{60}$ alkyl group unsubstituted or substituted with deuterium, a halogen group, —CN, a $C_1$ to $C_{20}$ alkyl group, a $C_6$ to $C_{60}$ aryl group and a $C_2$ to $C_{60}$ heteroaryl group; a $C_3$ to $C_{60}$ cycloalkyl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group; a $C_6$ to $C_{60}$ aryl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group; or a $C_2$ to $C_{60}$ heteroaryl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, however, may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, however, may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, however, may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the spiro group is a group comprising a spiro structure, and may have 15 to 60 carbon atoms. For example, the spiro group may comprise a structure in which a 2,3-dihydro-1H-indene group or a cyclohexane group spiro bonds to a fluorenyl group. Specifically, the following spiro group may comprise any one of the groups having the following structural formulae.

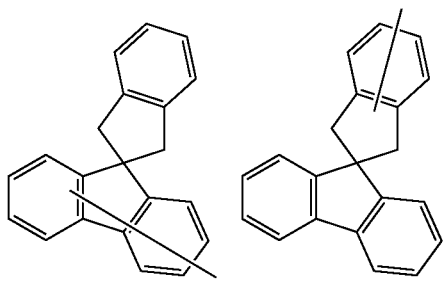

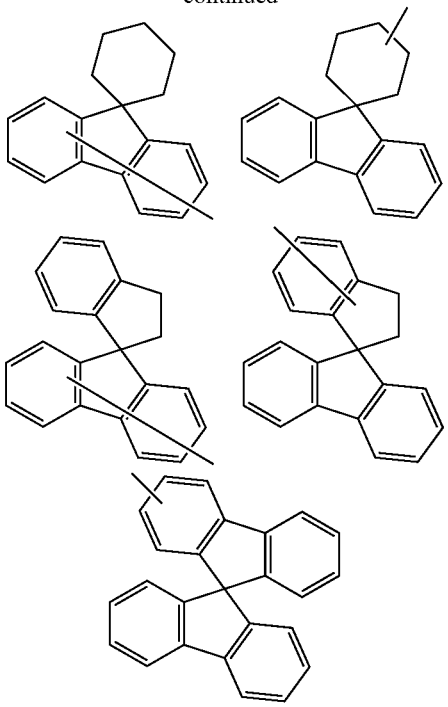

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, however, may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a xanthene group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a] carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a phenanthro[9,10-d]imidazole group, a benzo[c][1,2,5]thiadiazolyl group, a 5,10-dihydrobenzo[b,e][1,4]azasilinyl, a pyrazolo[1,5-c]quinazolinyl group, a pyrido[2,3-b]indole group, a pyrido[1,2-b]indazolyl group, a pyrido[1,2-a]imidazo[1,2-e]indolinyl group, an imidazo[1,2-a]pyridine group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH₂; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

According to one embodiment of the present application, Chemical Formula 1 may be represented by any one of the following compounds, but is not limited thereto.

1

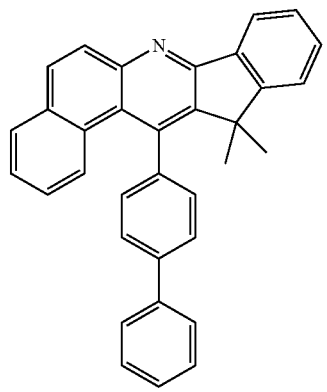

2

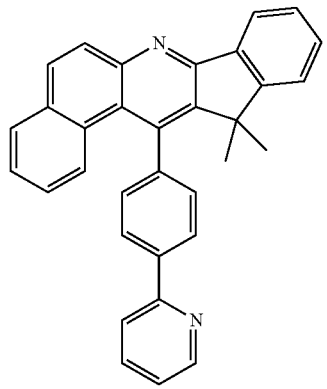 [SMILES: CC1(C)c2ccccc2-c2nc3ccc4ccccc4c3c(-c3ccc(-c4ccccc4)cc3)c21]

3

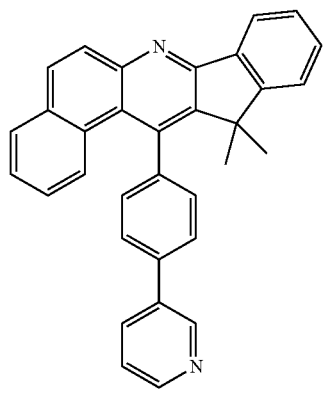

4

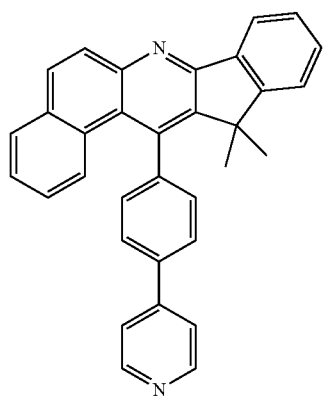

5

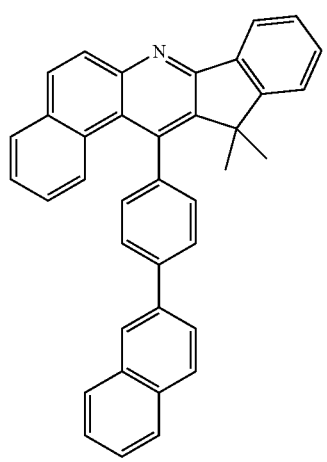 [SMILES: CC1(C)c2ccccc2-c2nc3ccc4ccccc4c3c(-c3ccc(-c4cnc5ccccc5c4)cc3)c21]

-continued
6
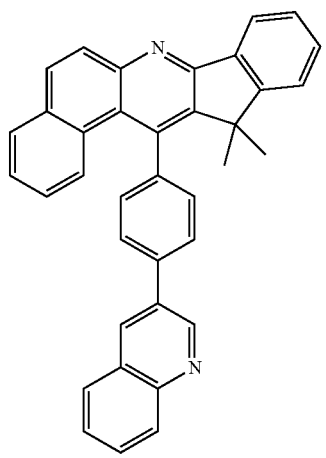
5
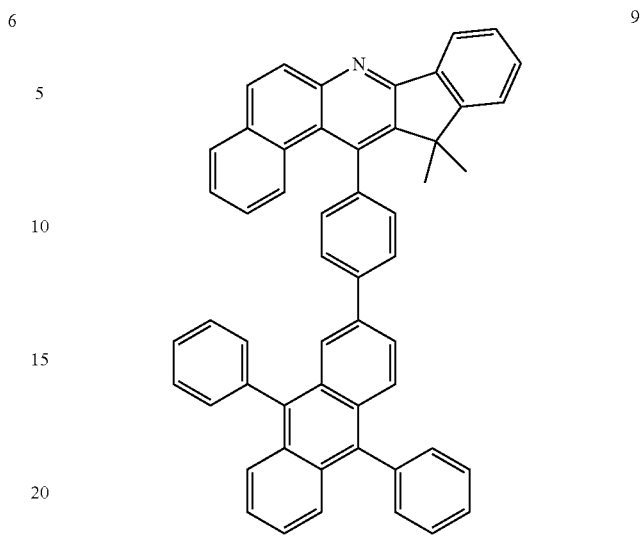
7
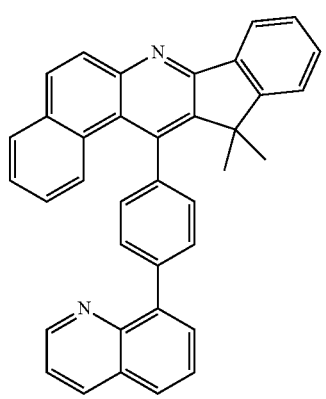
10
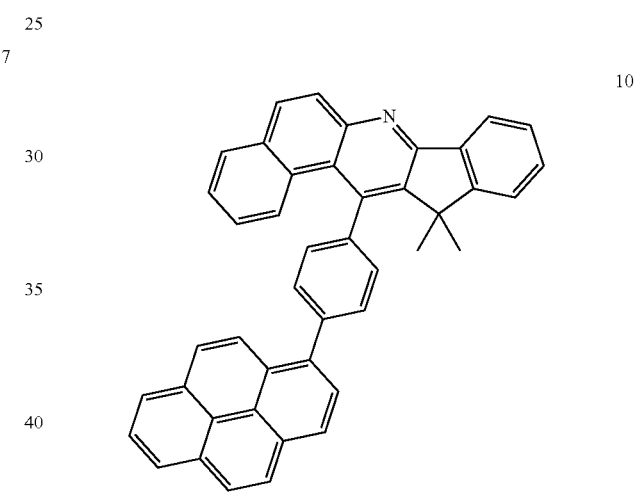
8
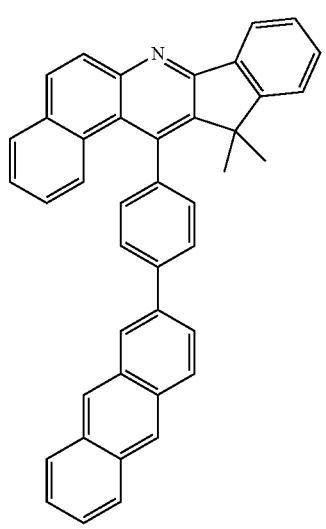
11
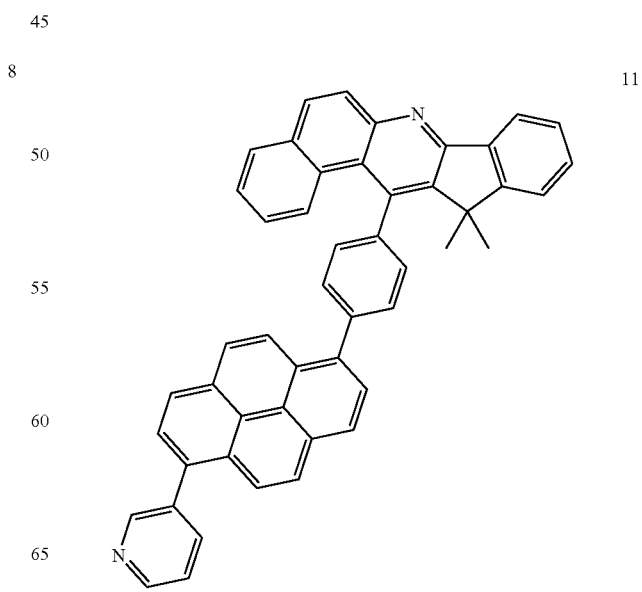

12
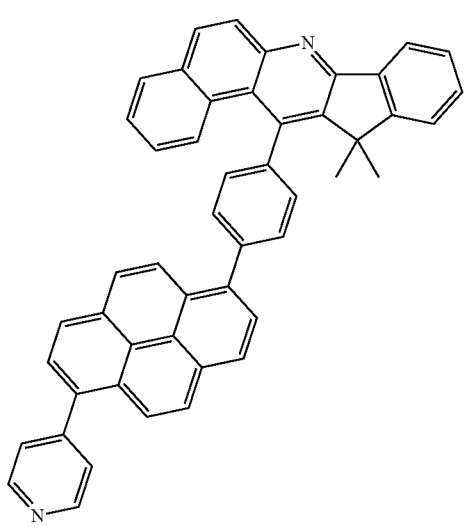
13
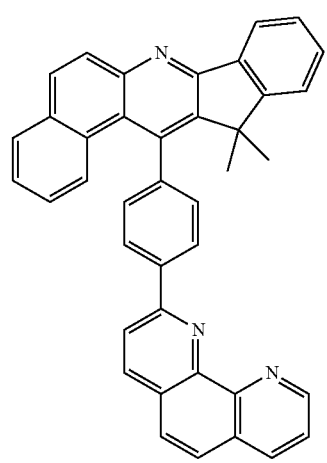 [SMILES: CC1(C)c2ccccc2-c2nc3ccc4ccccc4c3c(-c3ccc(-c4ccc5ccc6cccnc6c5n4)cc3)c21]
14
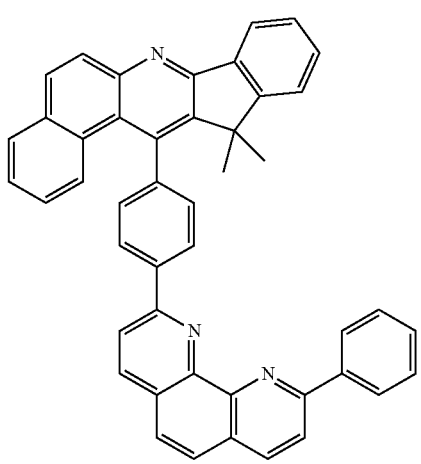 [SMILES: CC1(C)c2ccccc2-c2nc3ccc4ccccc4c3c(-c3ccc(-c4ccc5ccc6ccc(-c7ccccc7)nc6c5n4)cc3)c21]
15
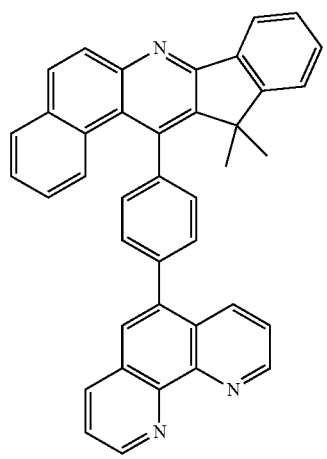 [SMILES: CC1(C)c2ccccc2-c2nc3ccc4ccccc4c3c(-c3ccc(-c4cc5cccnc5c5ncccc45)cc3)c21]
16
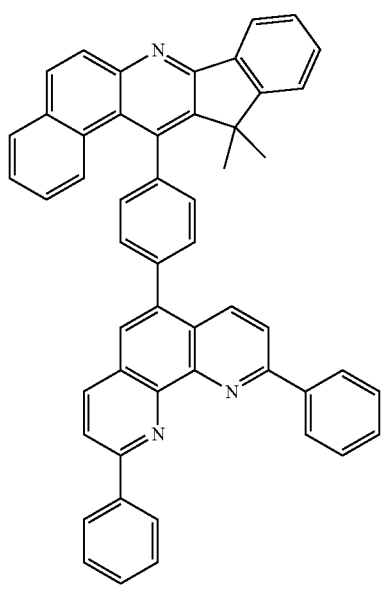
17
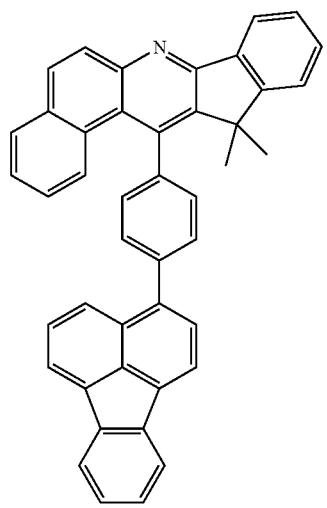

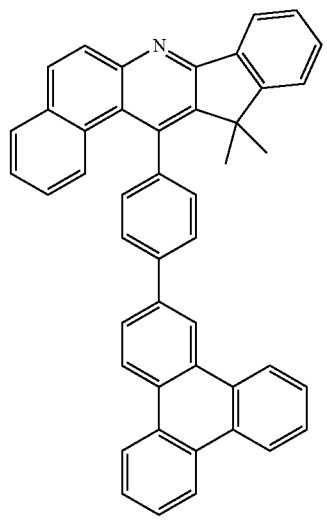
18
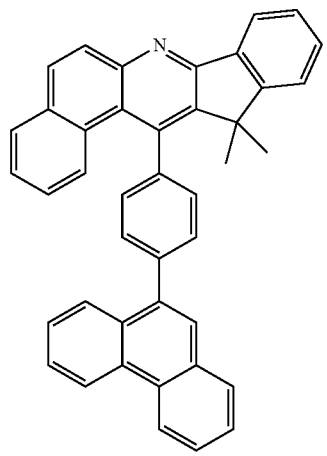
21
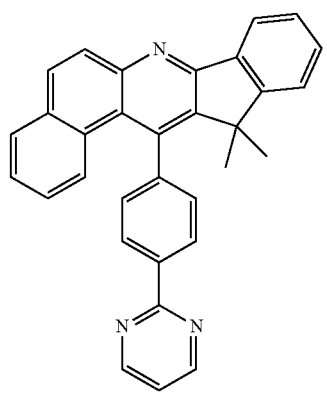
19
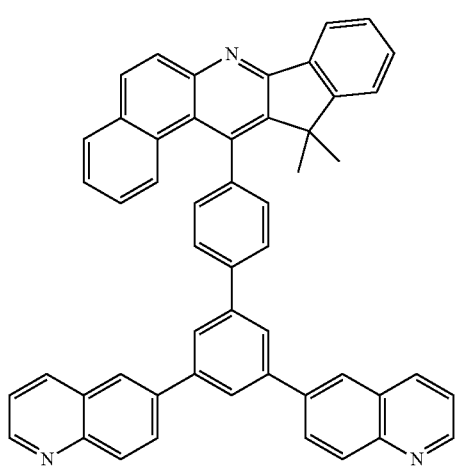
22
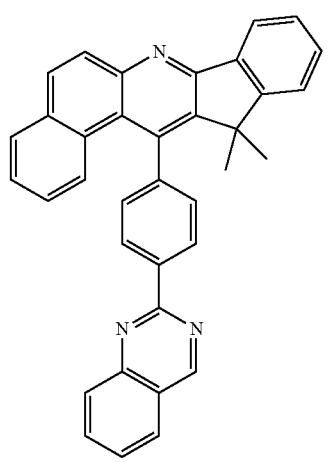
20
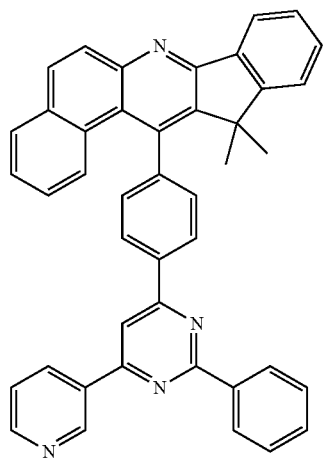
23

24
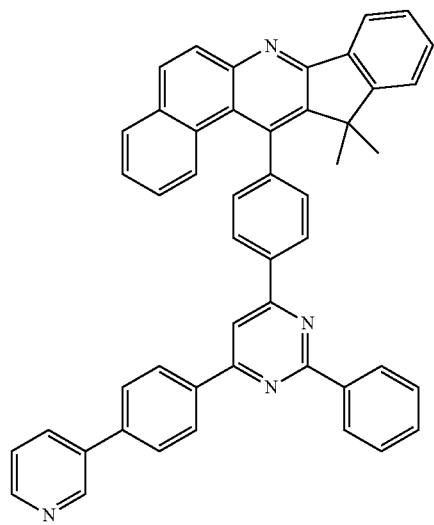
25
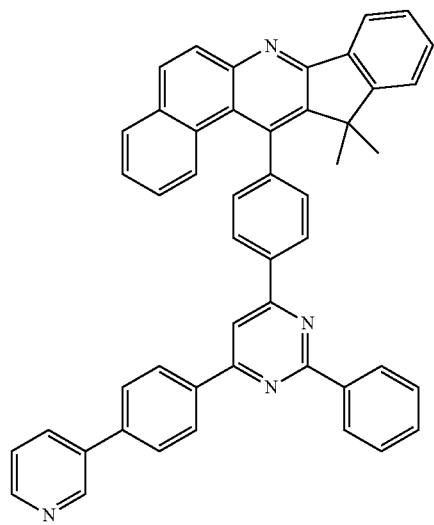
26
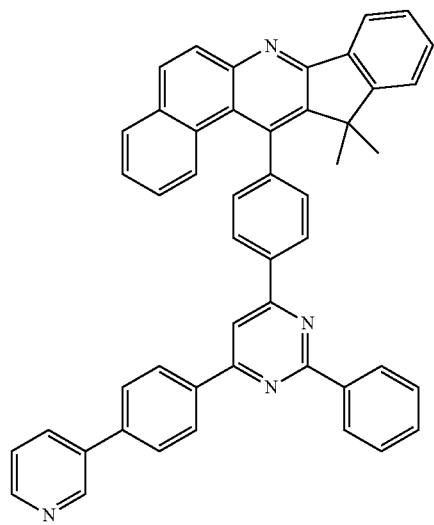
27
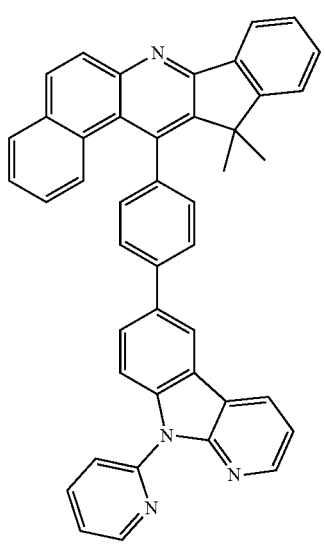
28
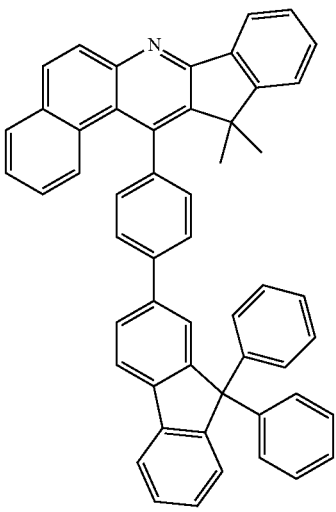
29
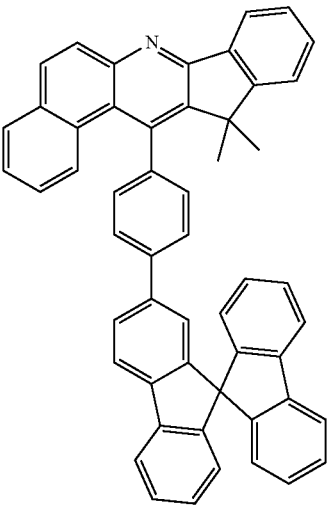

21
-continued
30
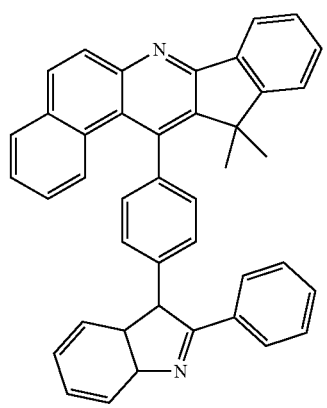
31
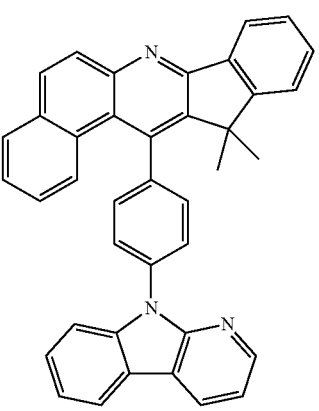
32
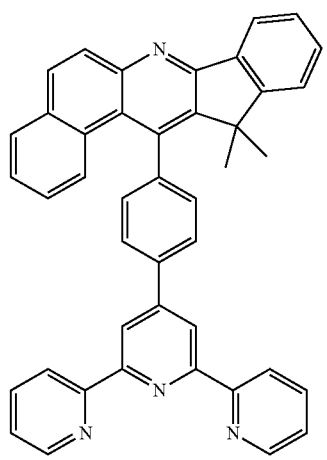
22
-continued
33
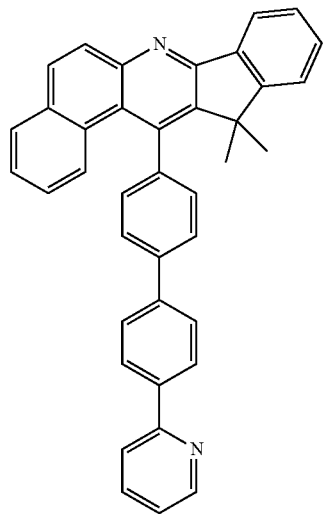
34
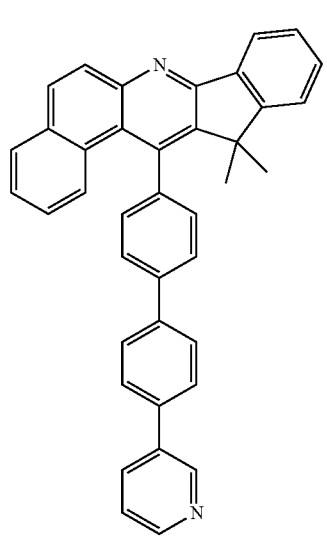
35
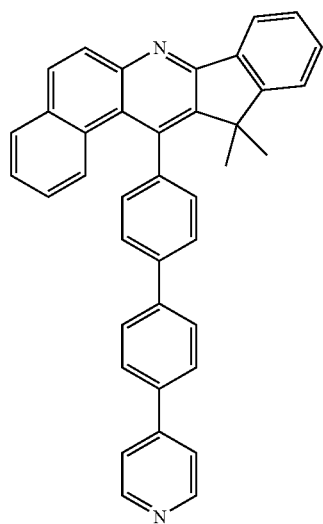

36
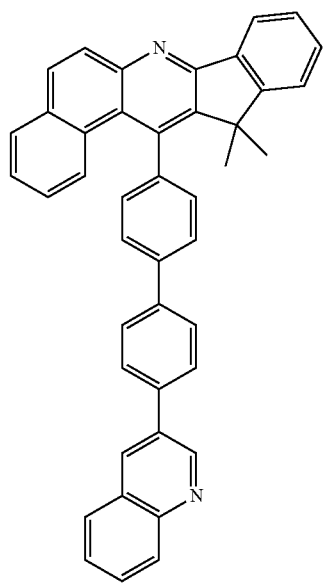
37
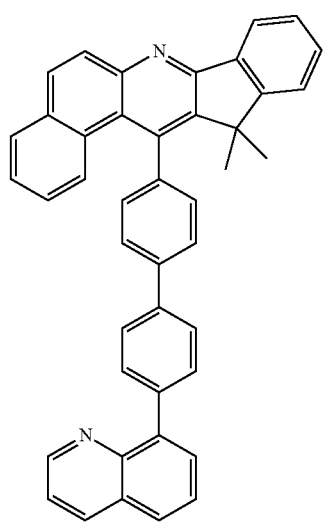
38
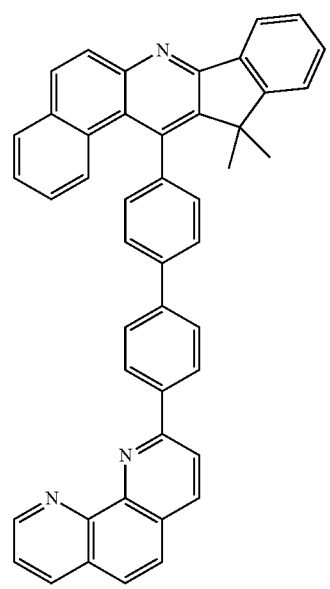
39
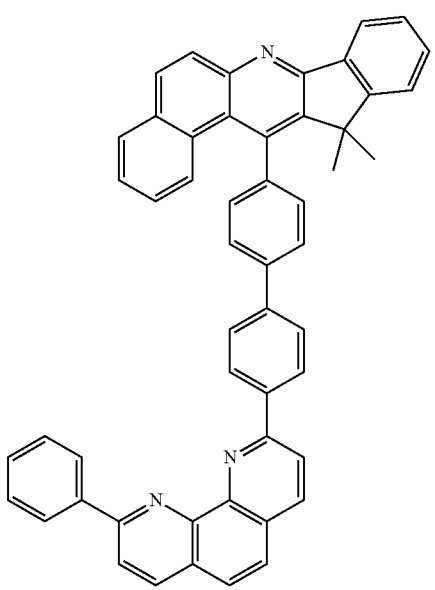

25
-continued
40
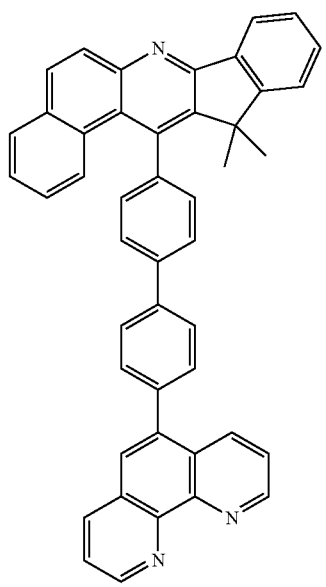
41
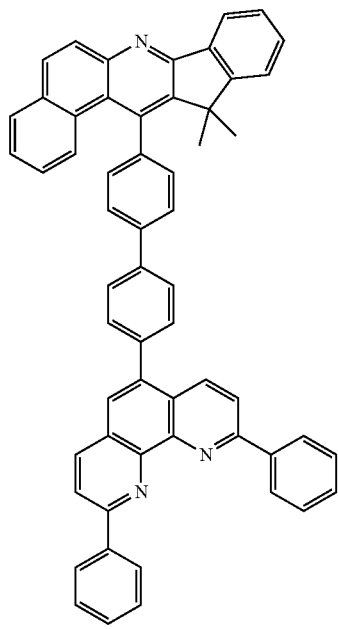
26
-continued
42
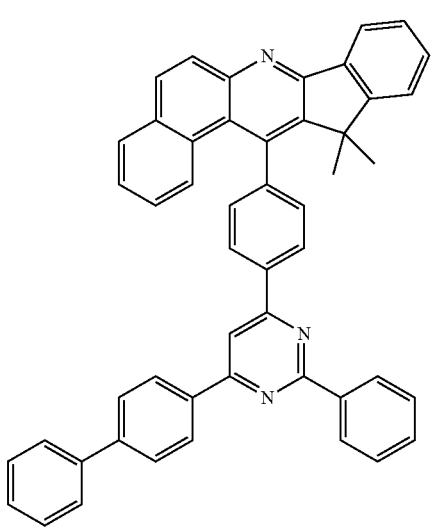
43
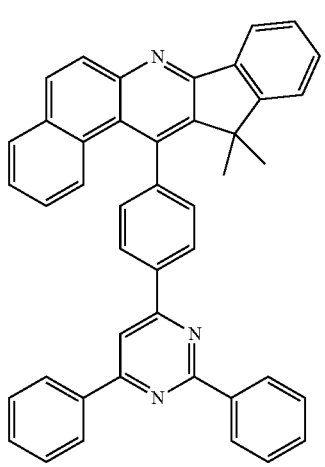
44
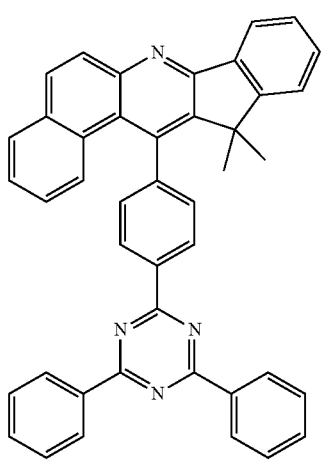

27
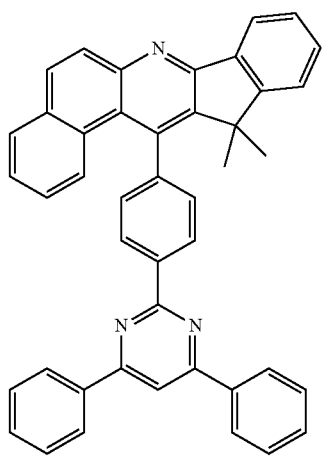
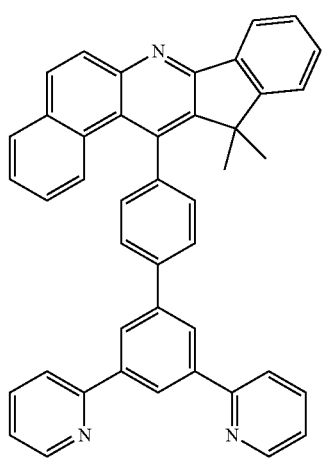
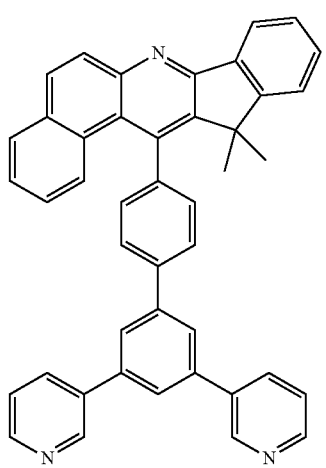
28
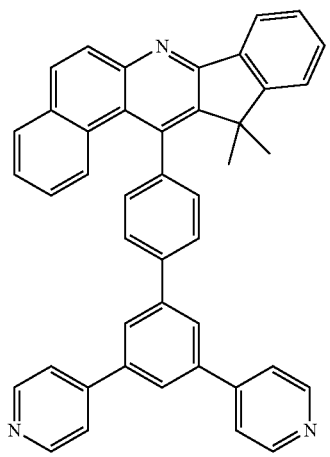
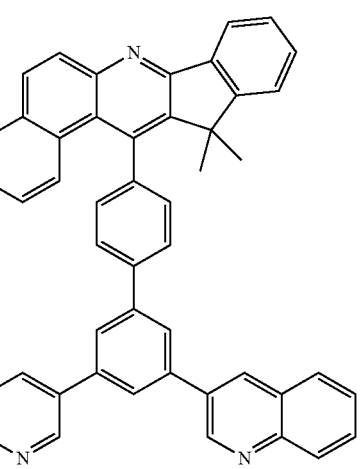
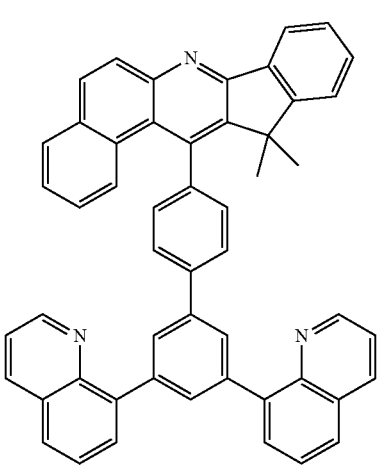

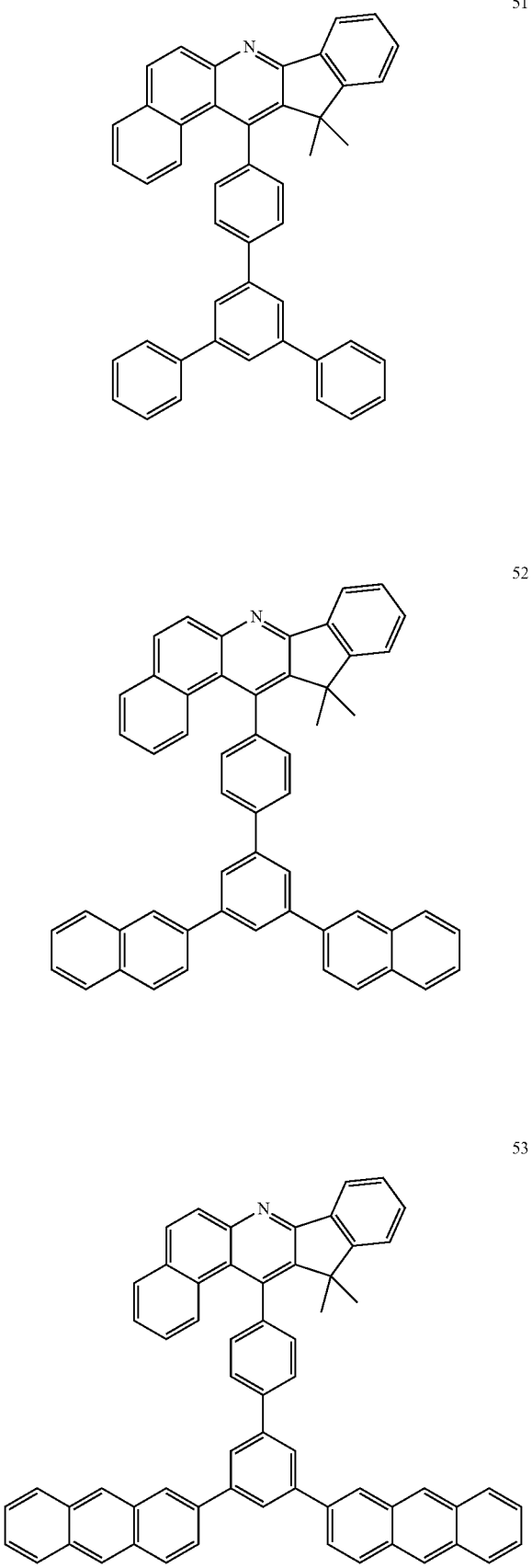
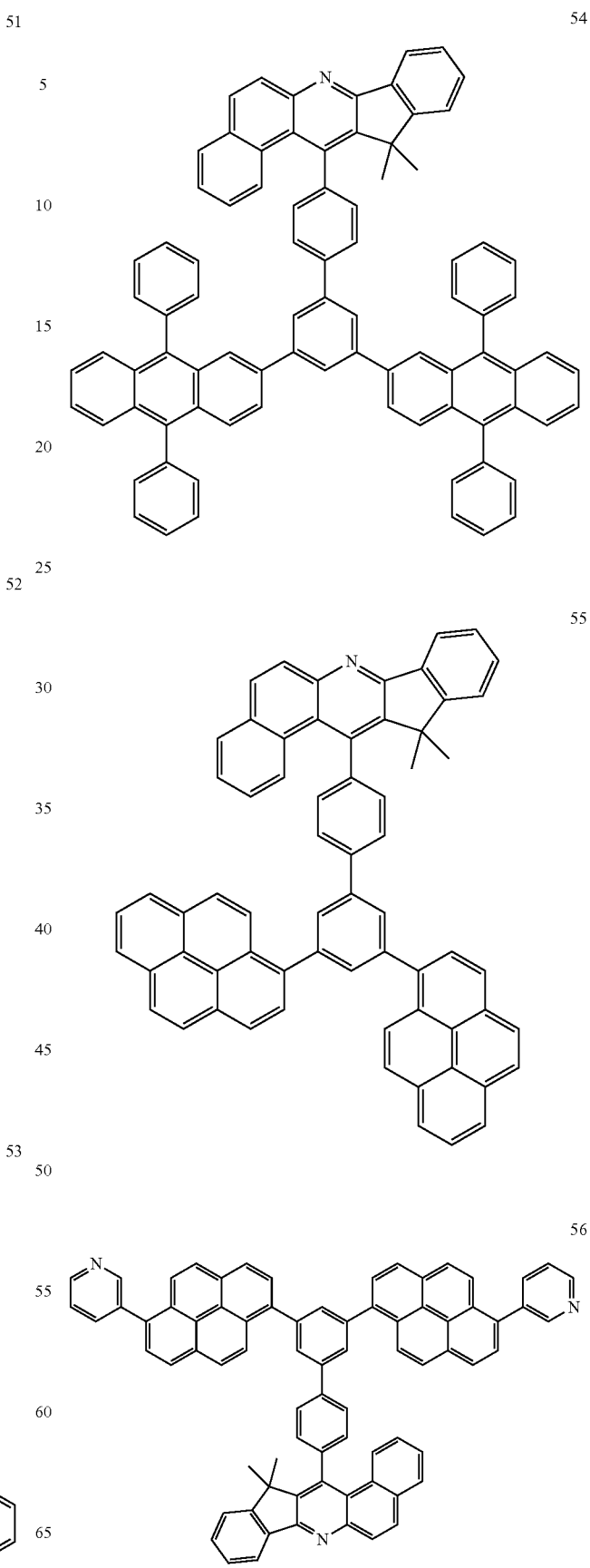

57
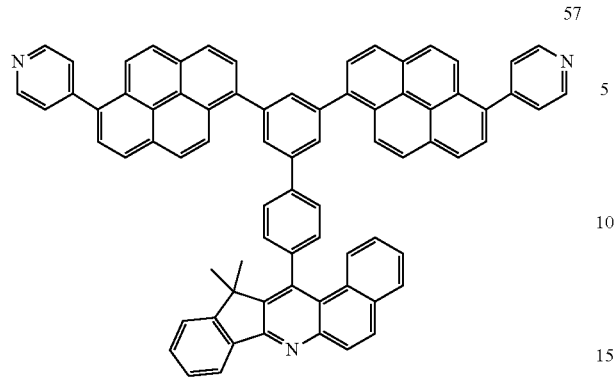
58
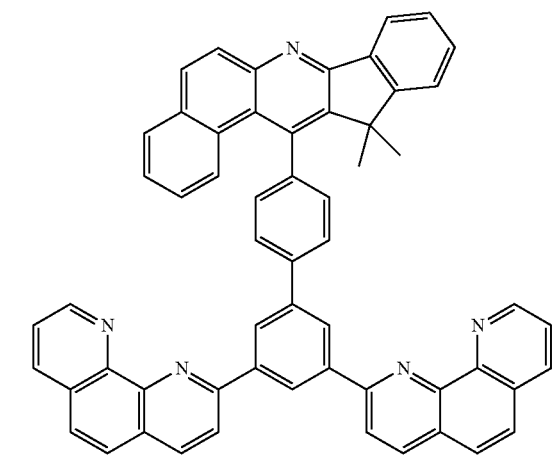
59
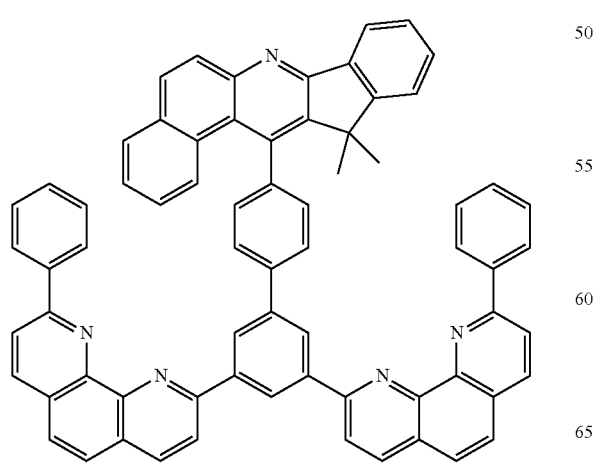
60
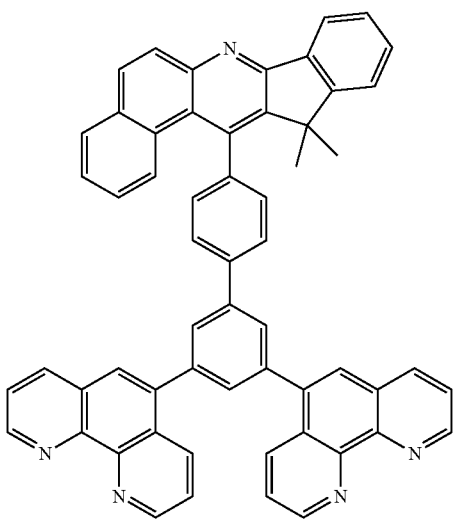
61
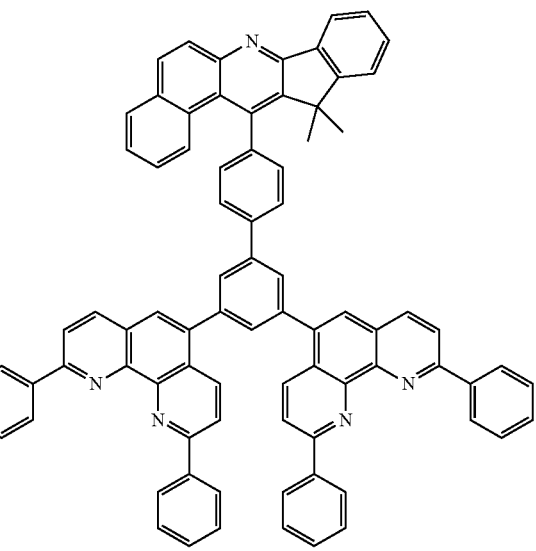
62
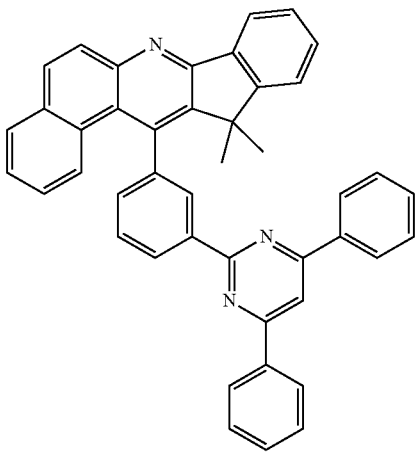

33  34
-continued  -continued
63  66
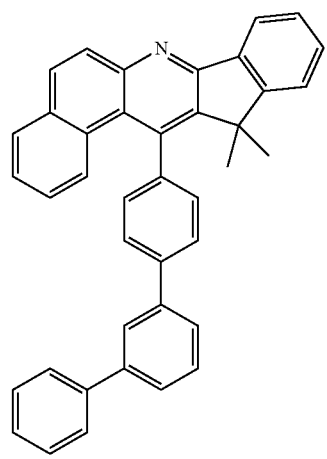  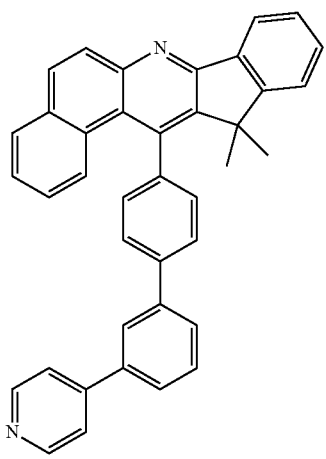
64  67
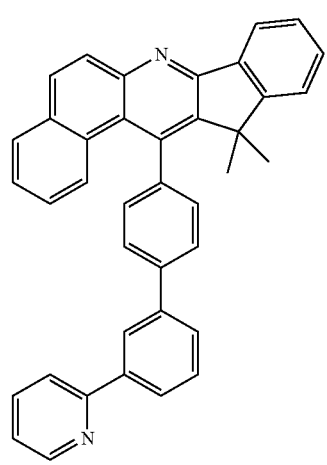  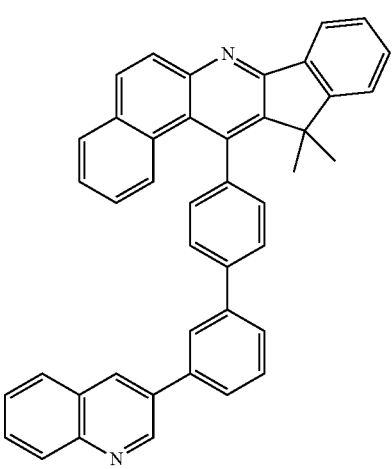
65  68
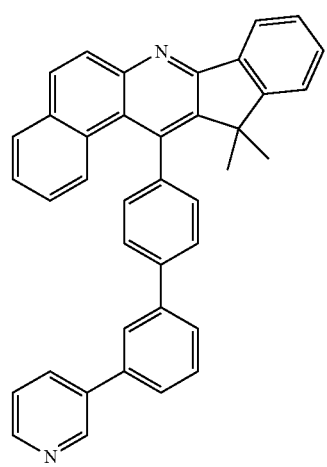  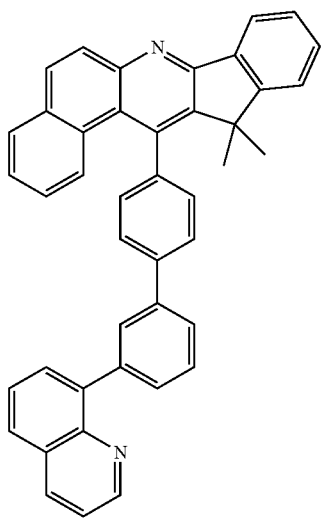

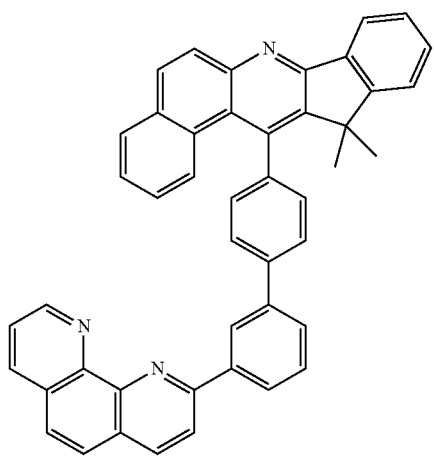
69
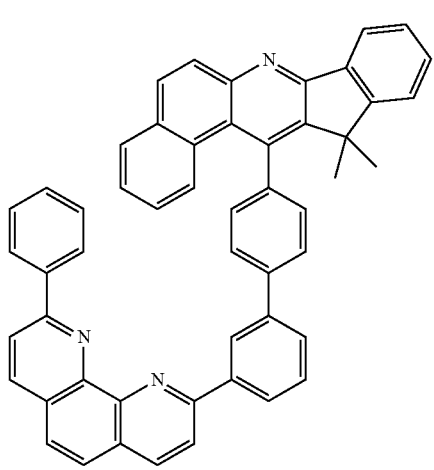
70
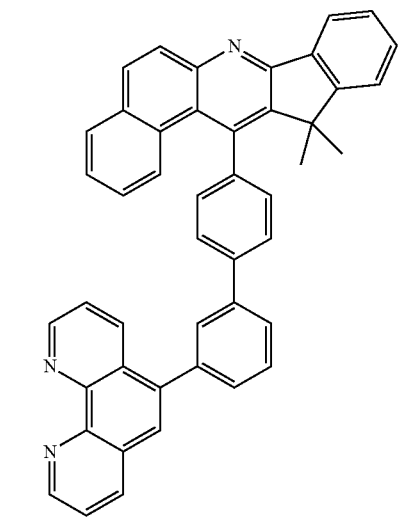
71
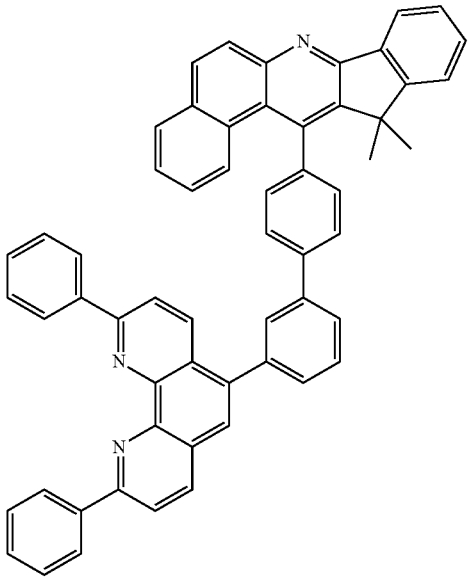
72
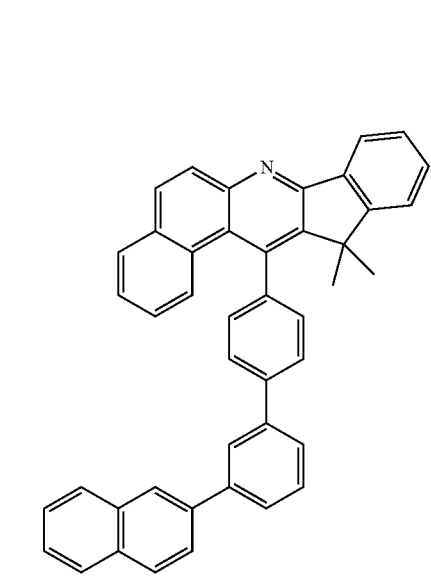
73
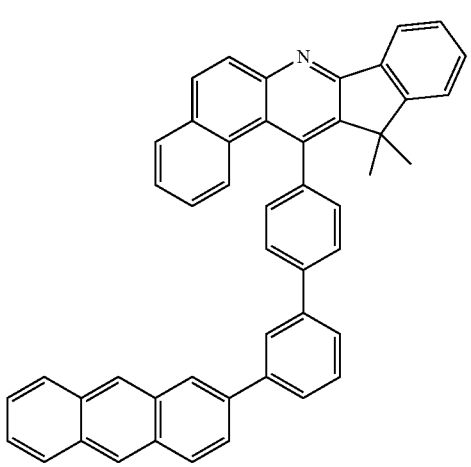
74

75
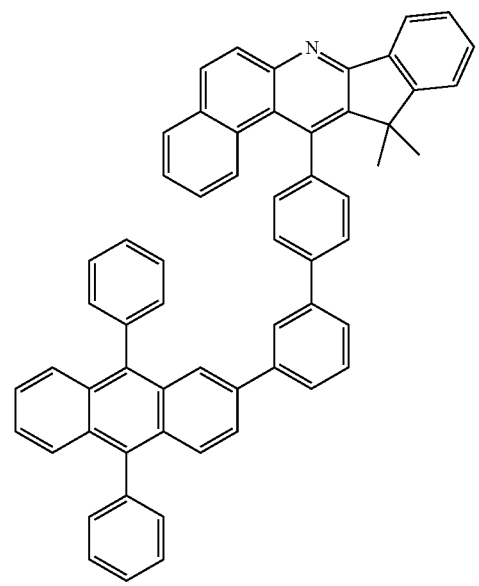
76
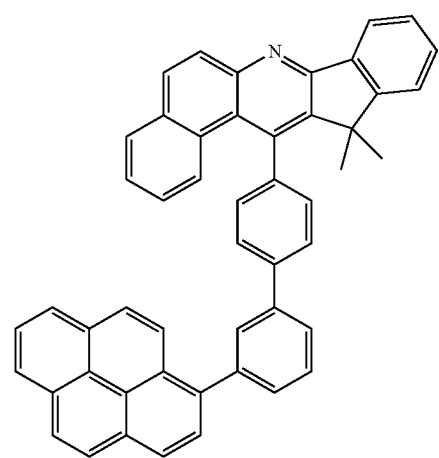
77
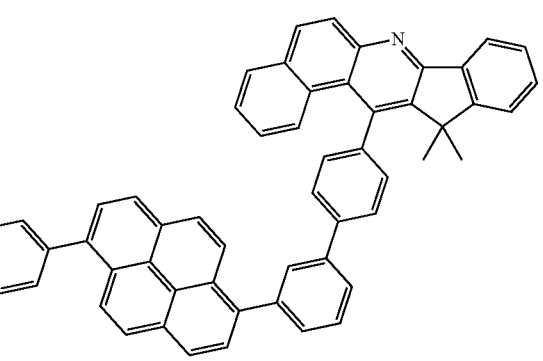
78
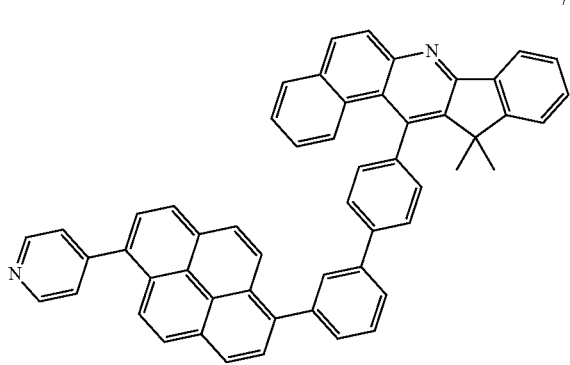
79
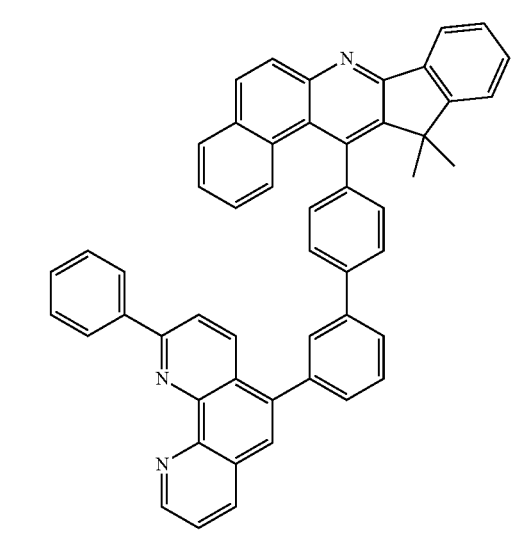
80
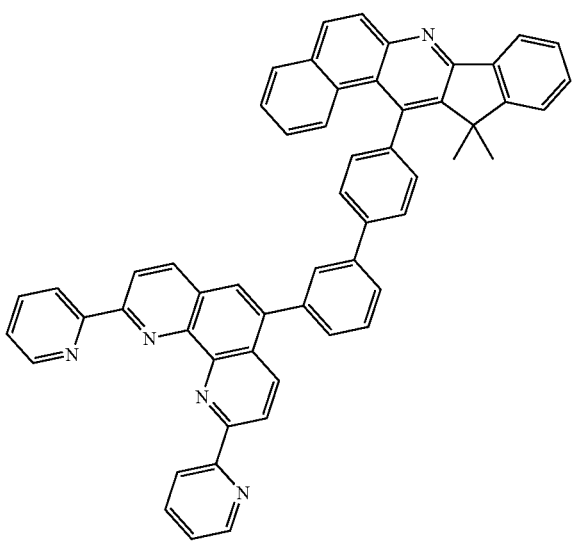

-continued
81
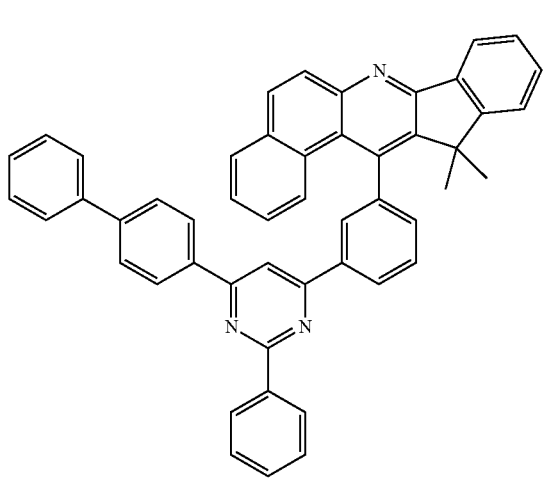
82
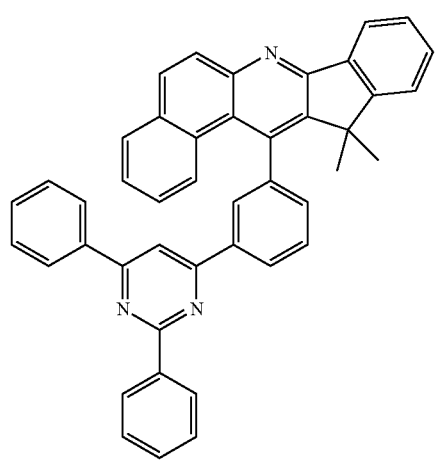
83
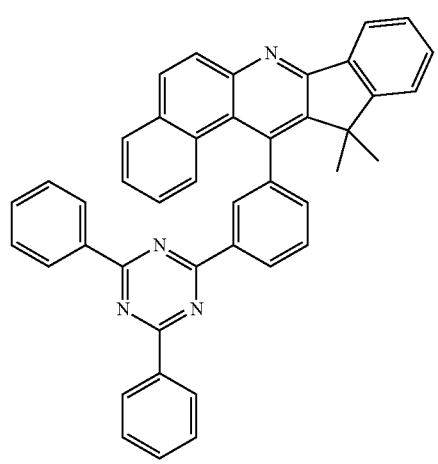
-continued
84
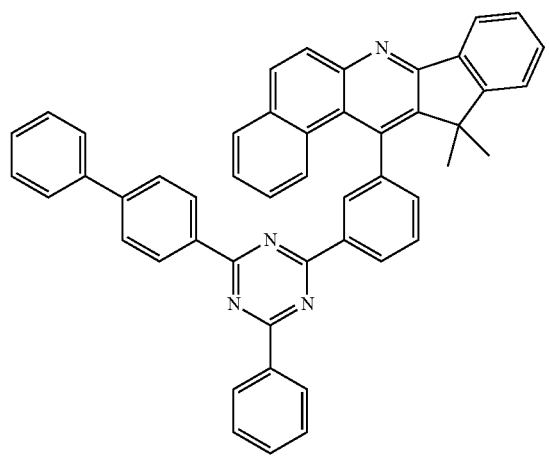
85
86
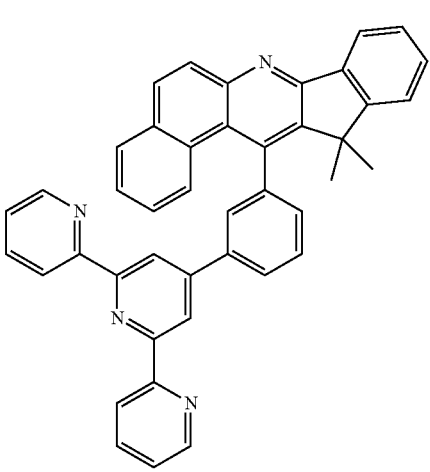

87
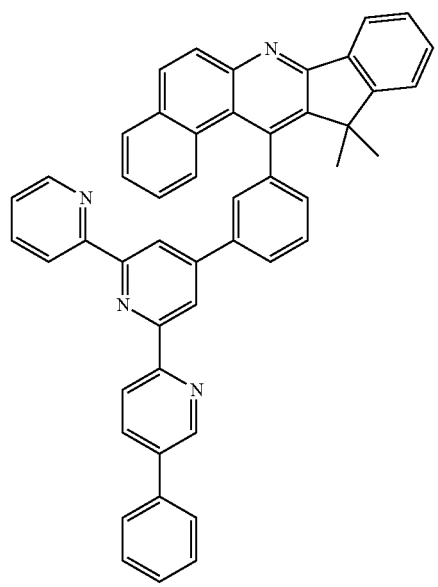
88
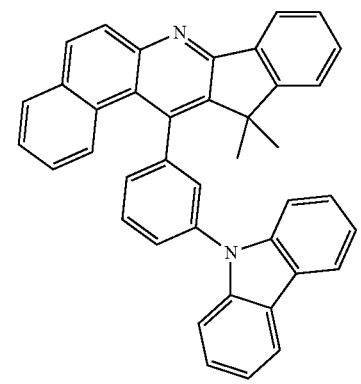
89
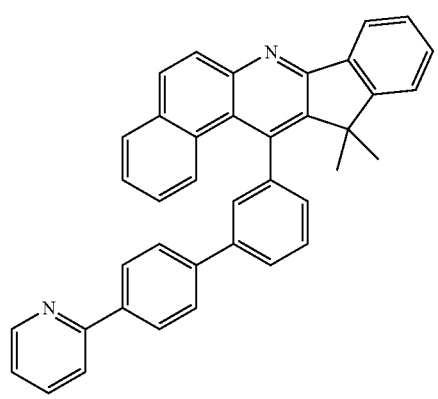
90
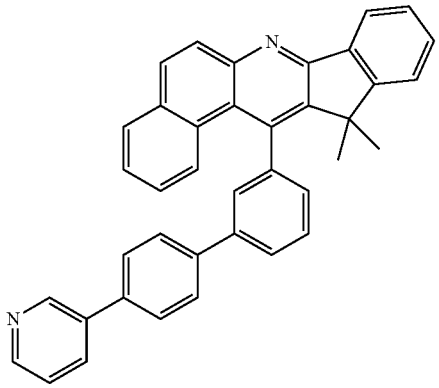
91
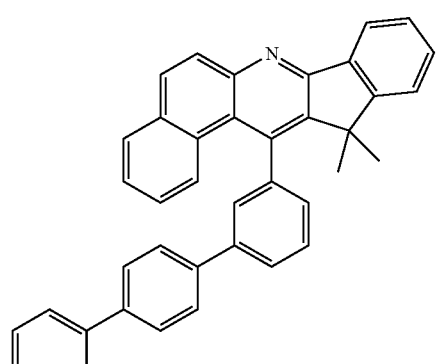
92
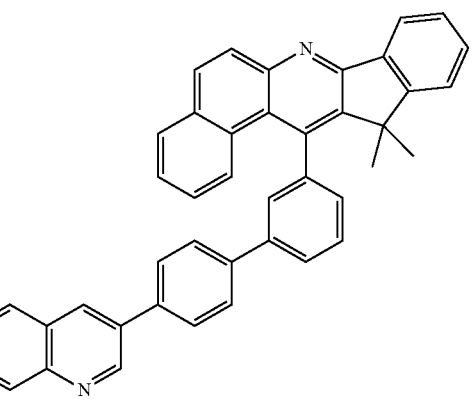
93
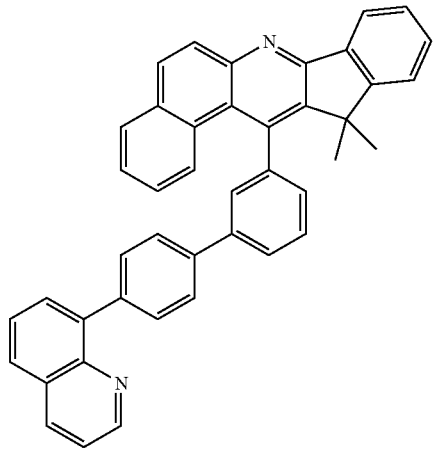

94
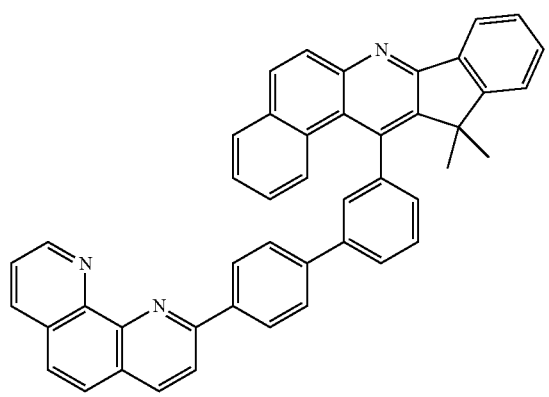
95
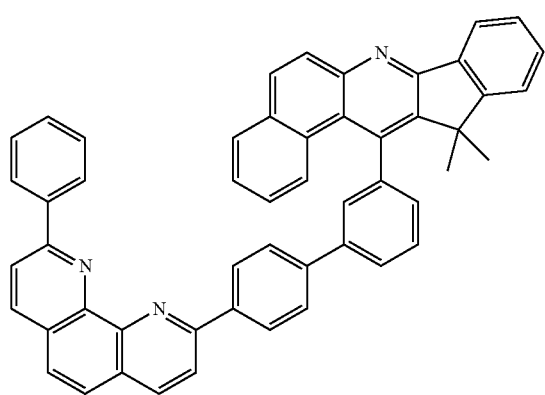
96
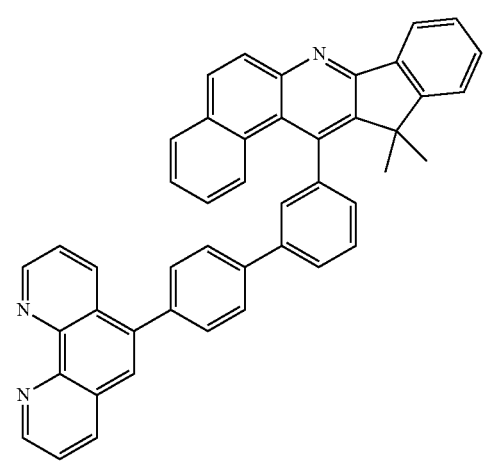
97
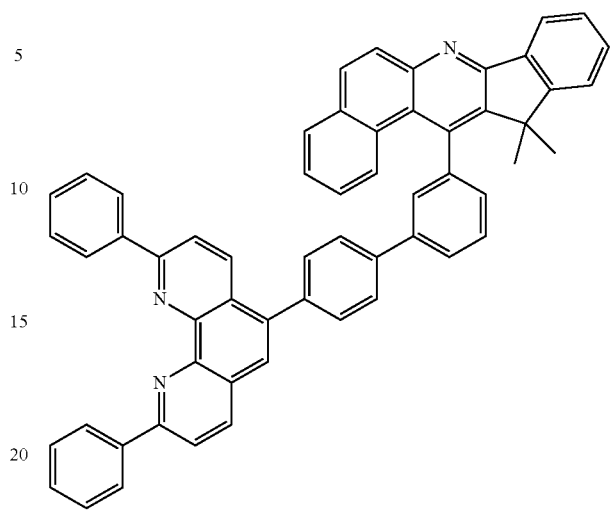
98
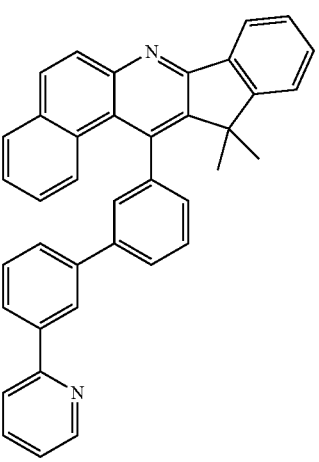
99

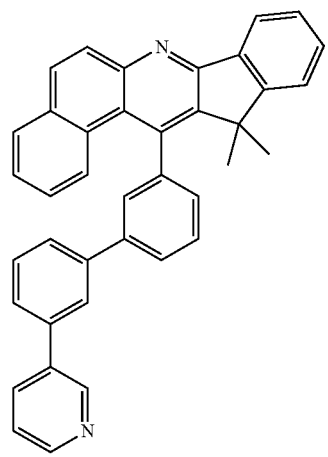
100
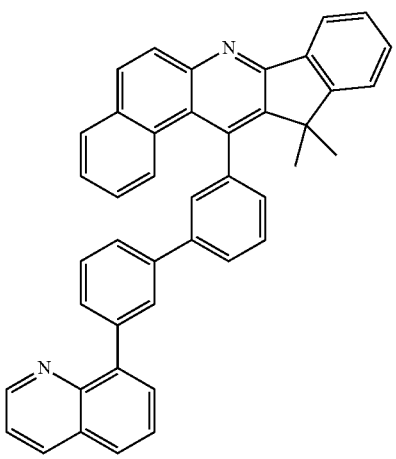
103
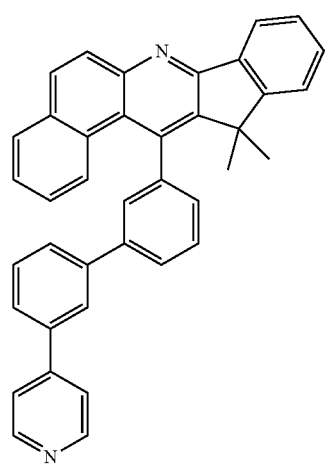
101
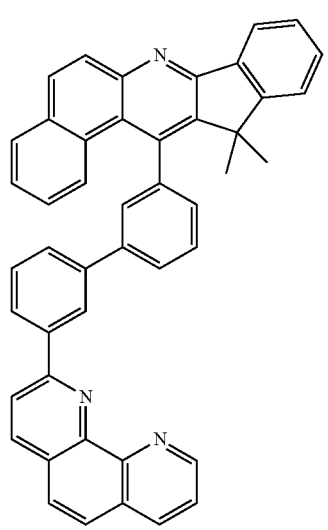
104
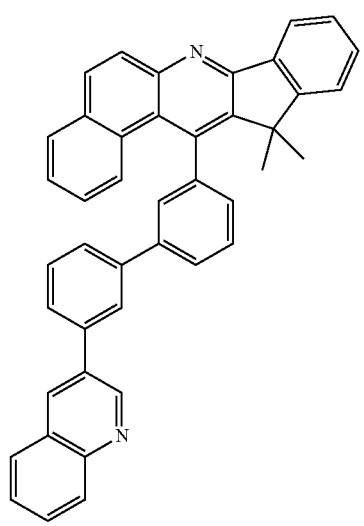
102
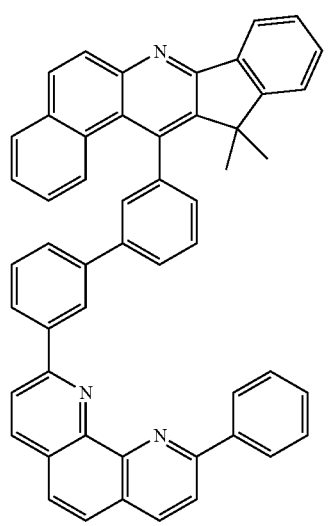
105

106 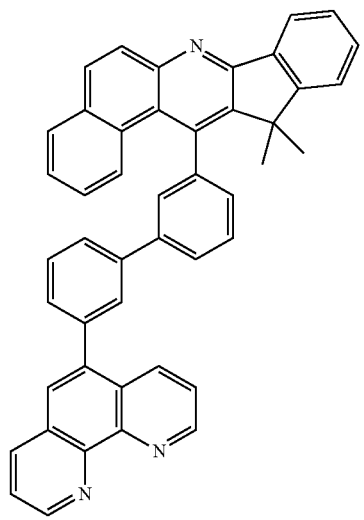
107 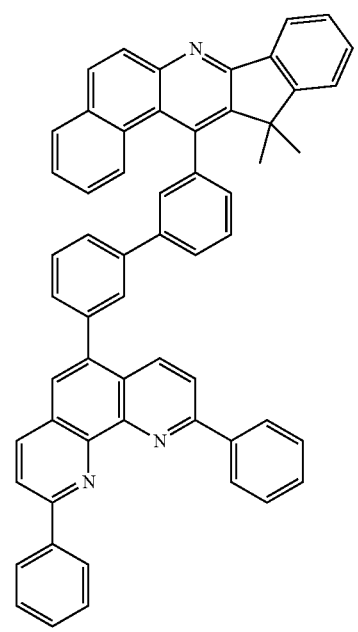
108 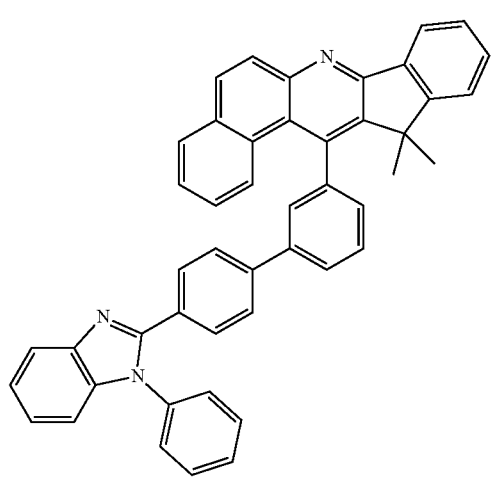
109 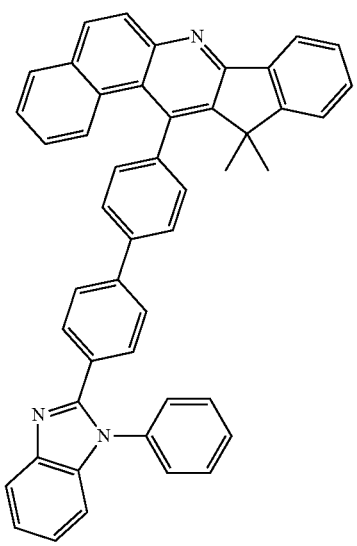
110 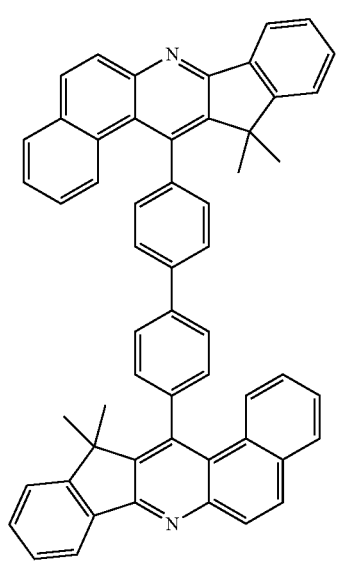
111 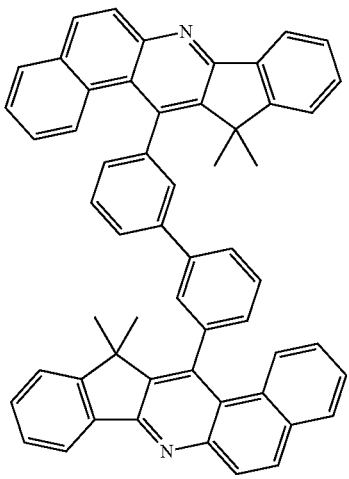

112
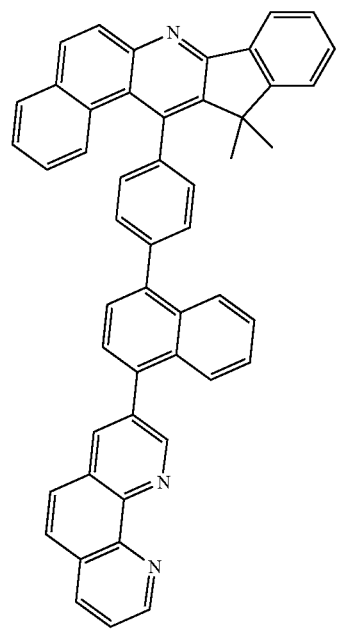
113
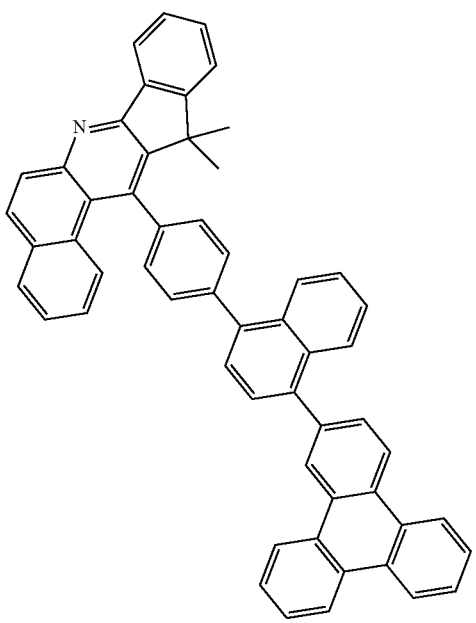
114
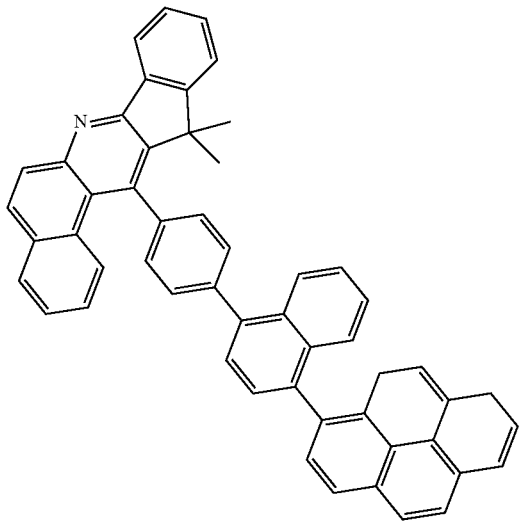
115
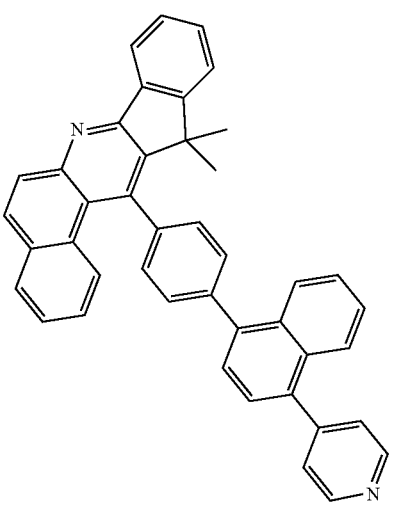
116
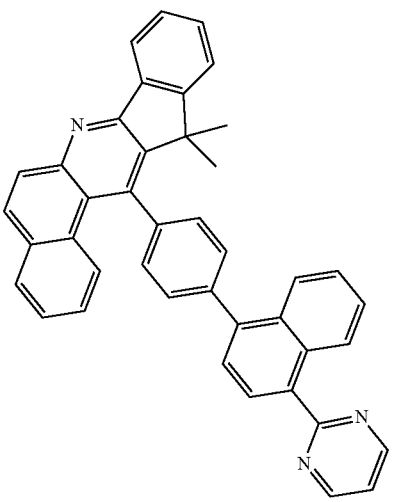

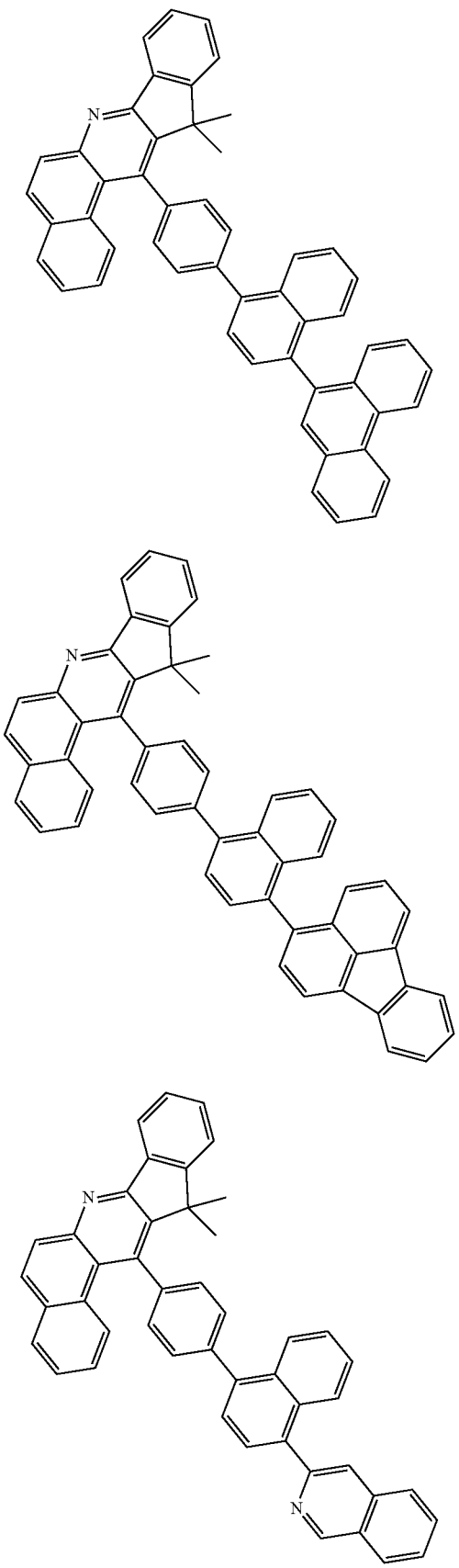
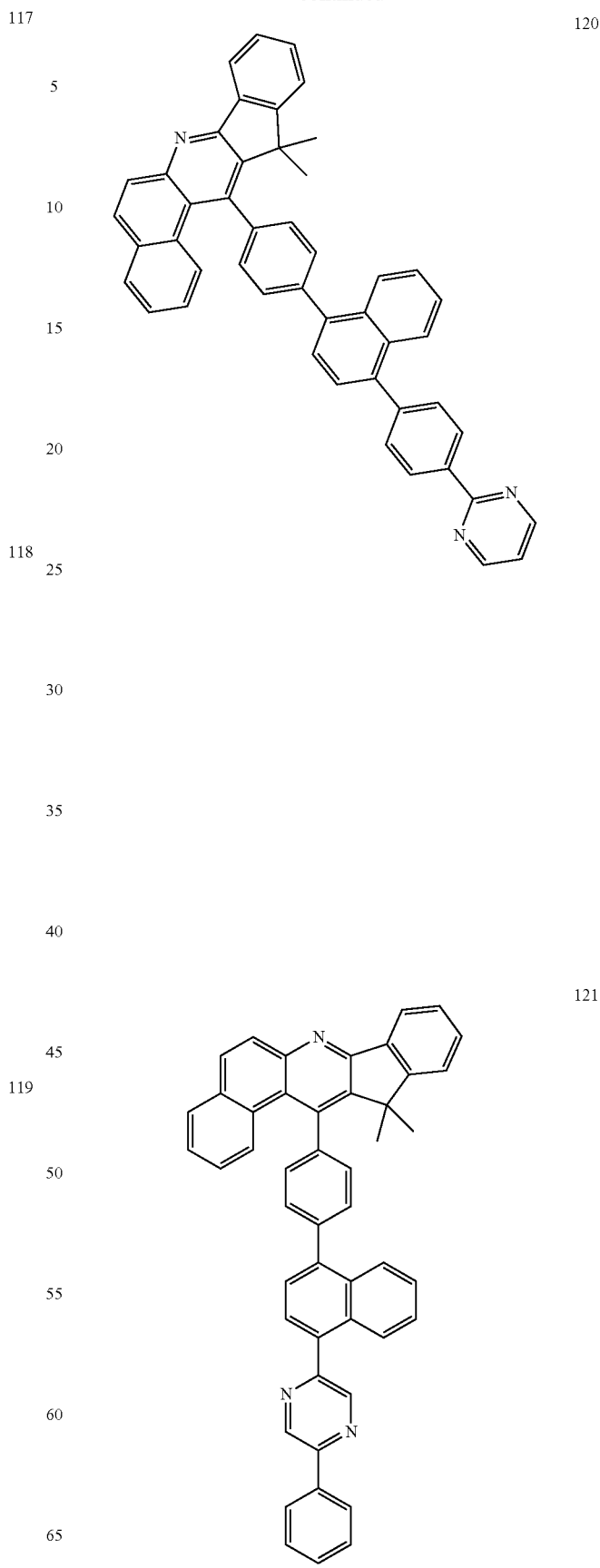

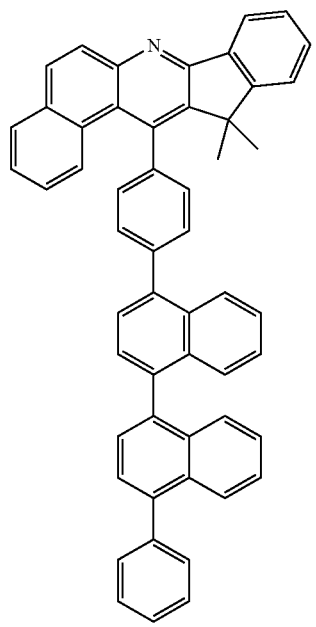
122
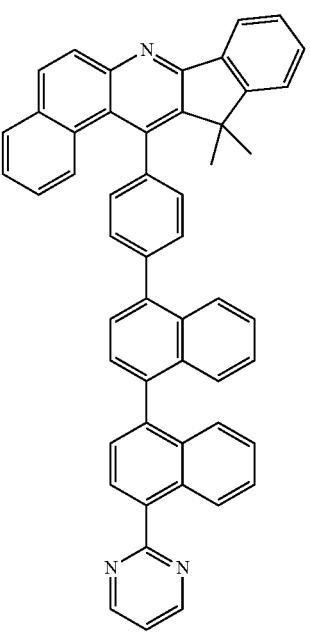
123
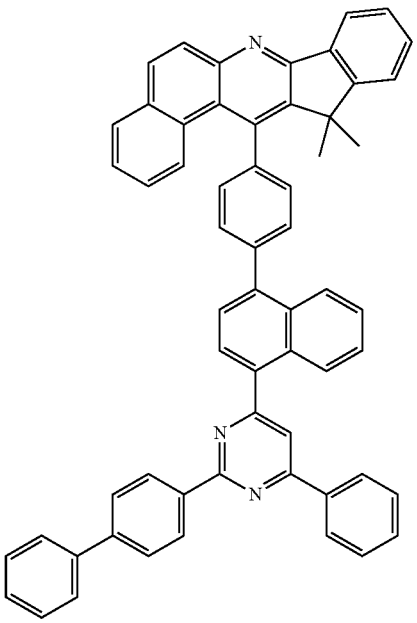
124
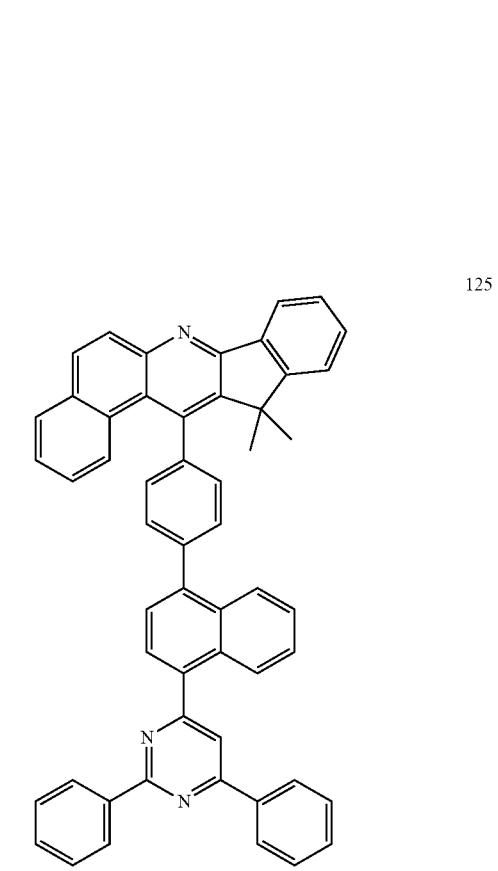
125

126
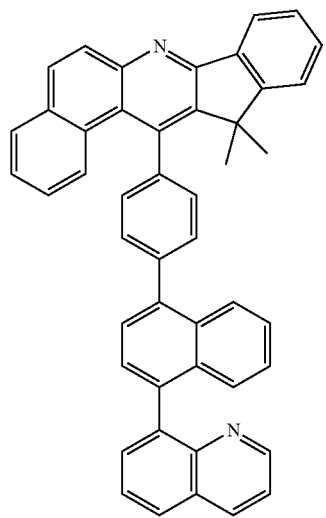
127
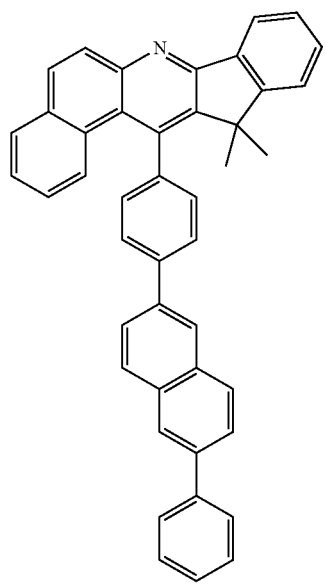
128
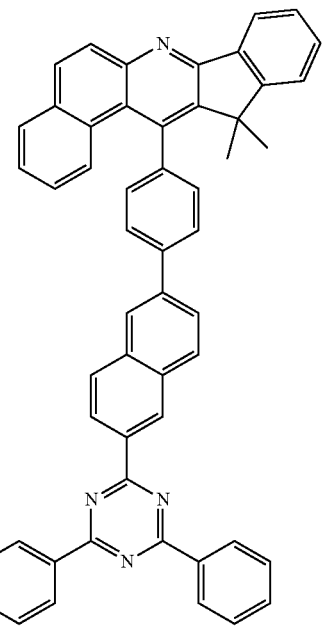
129
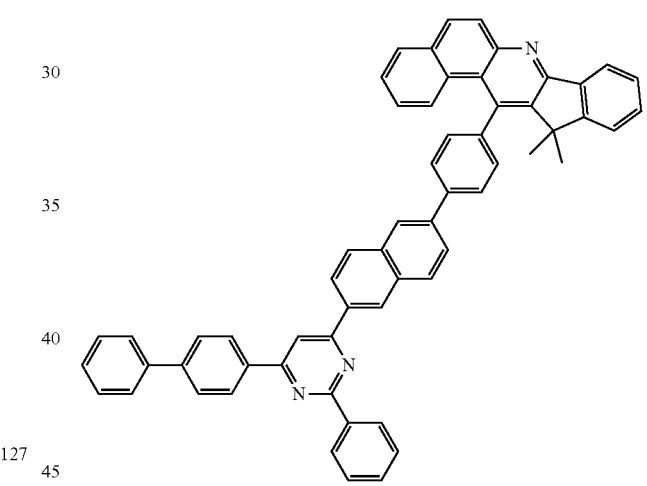
130
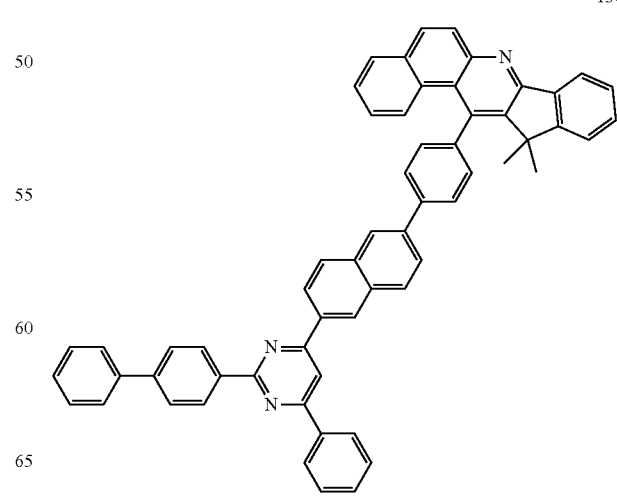

131
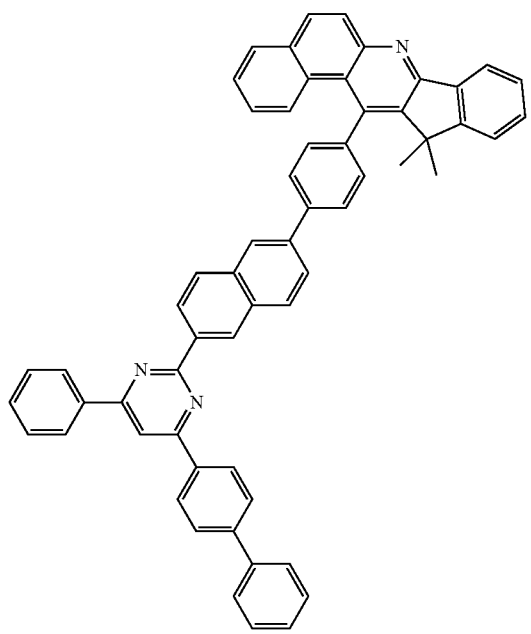
132
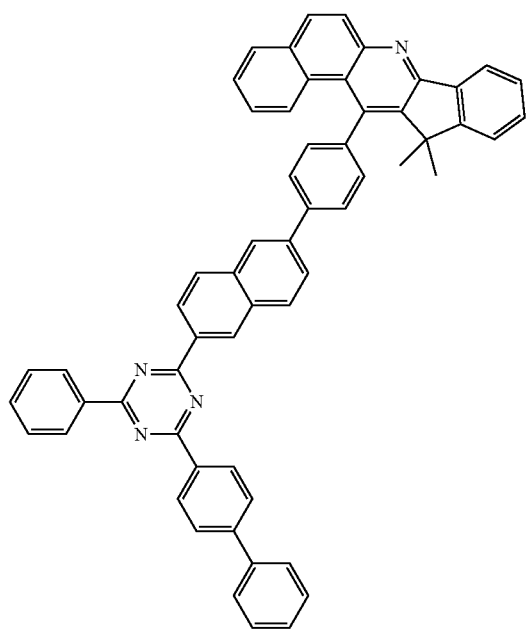
133
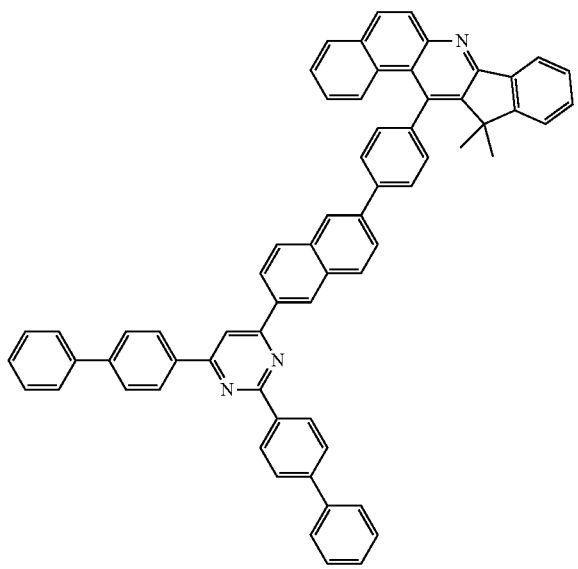
134
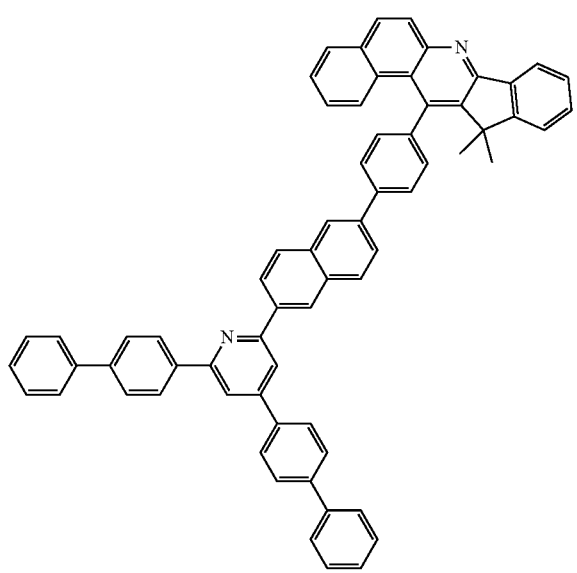

135
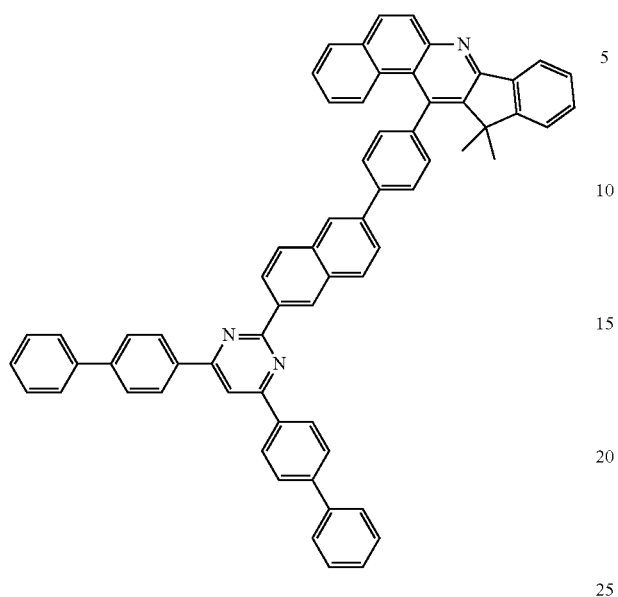
137
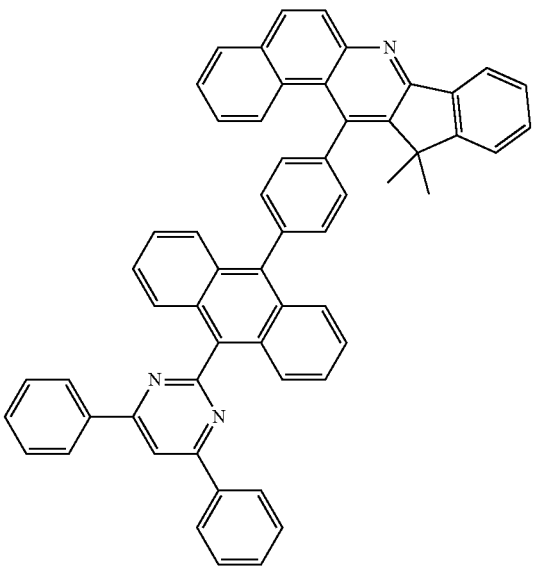
138
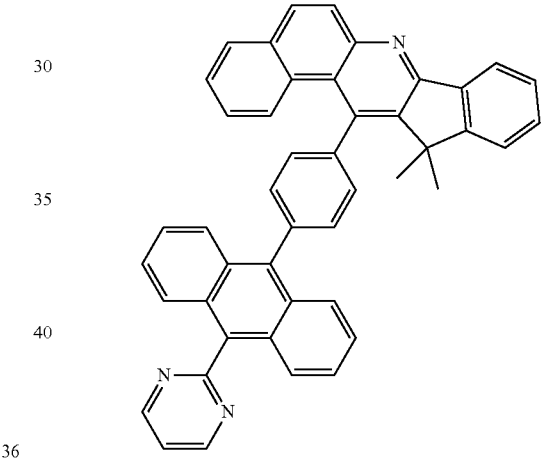
136
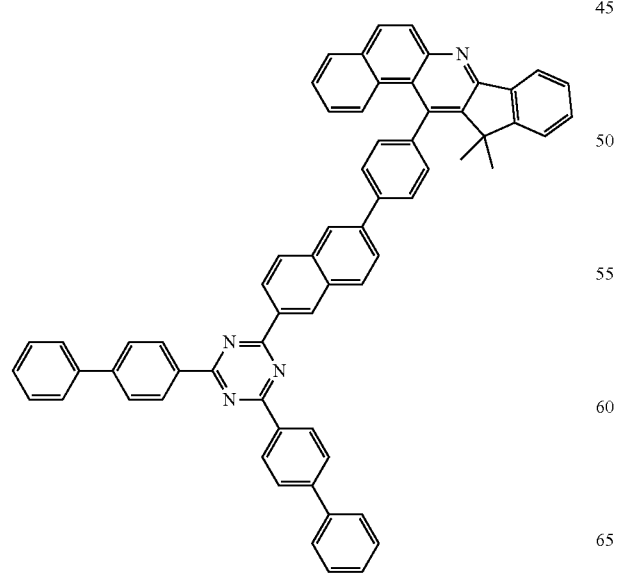
139
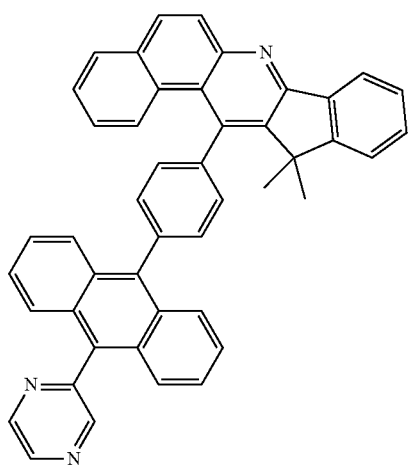

140
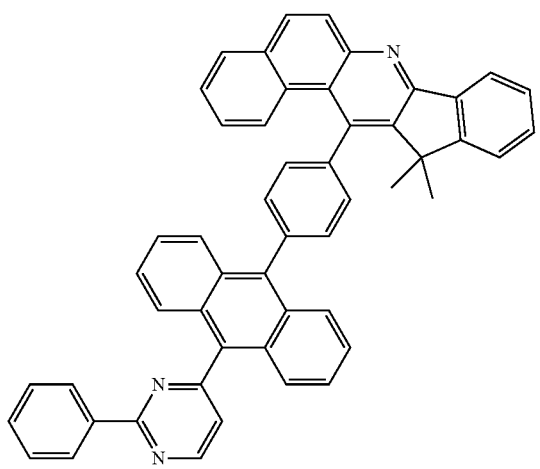
141
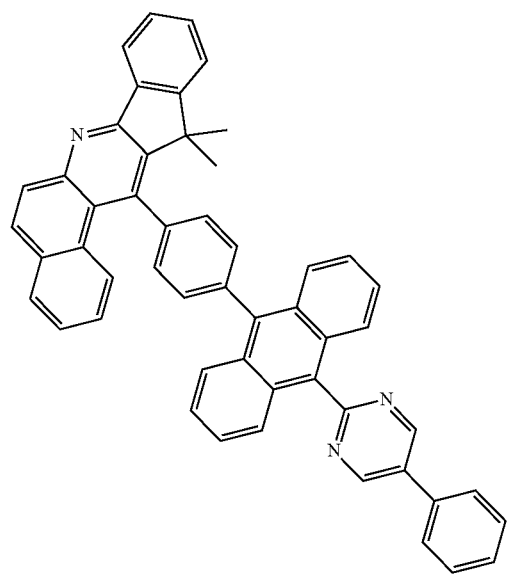
142
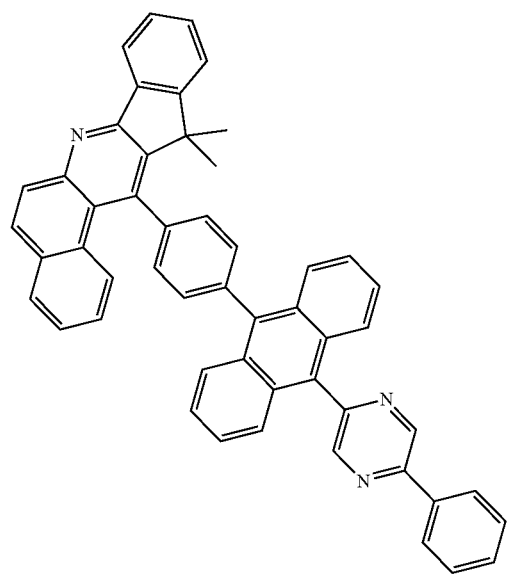
143
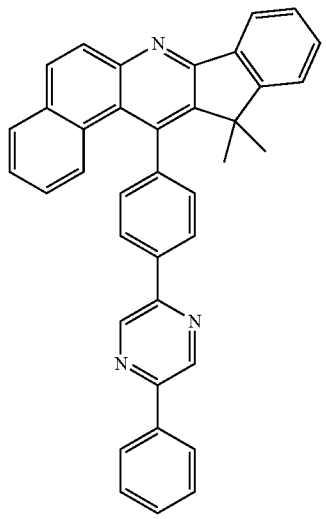
144
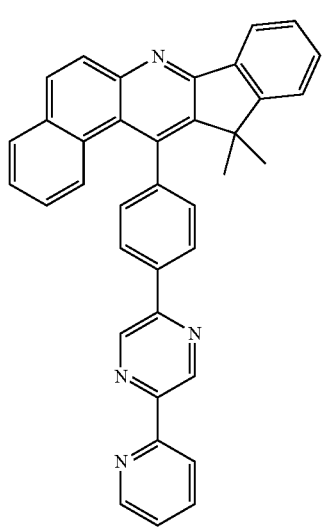
145
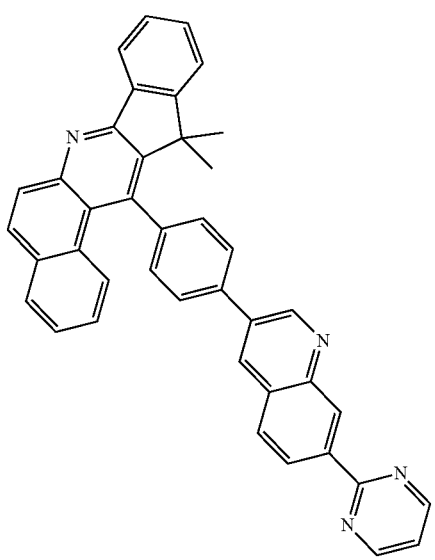

146
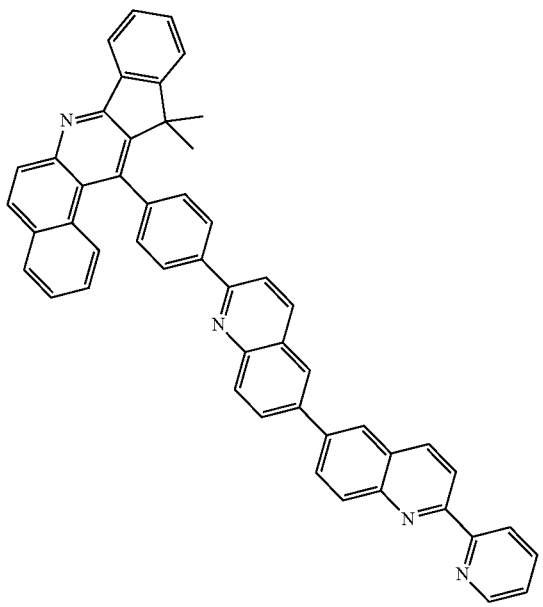
148
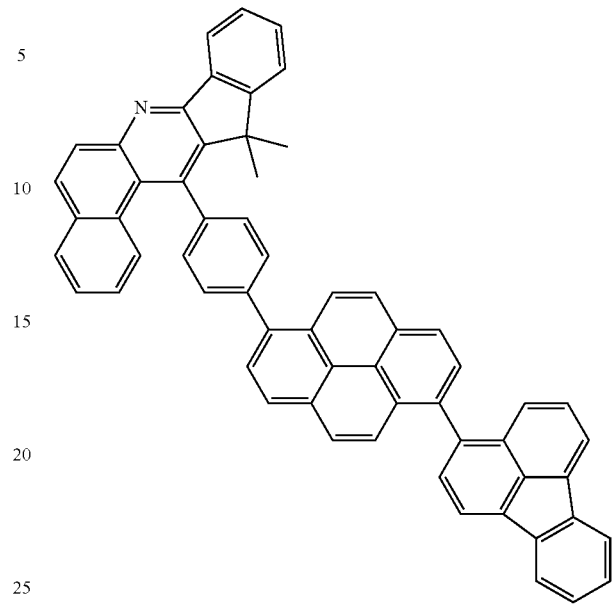
147
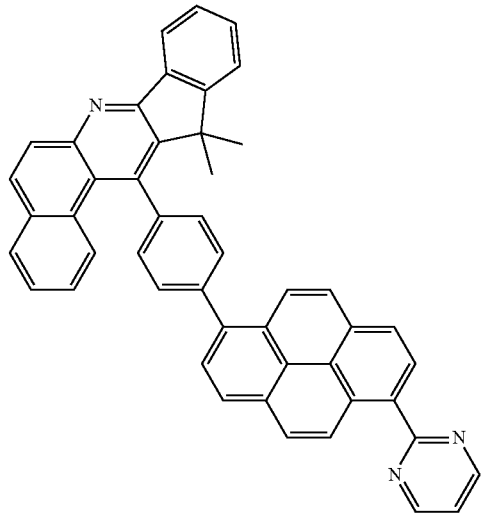
149
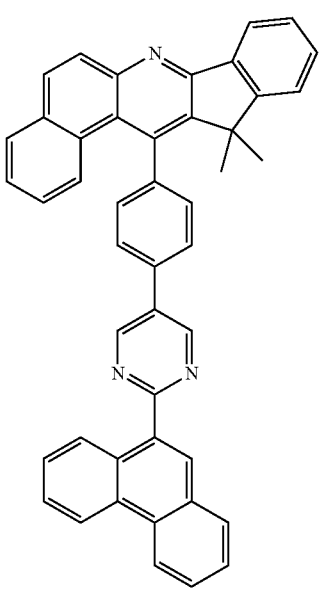

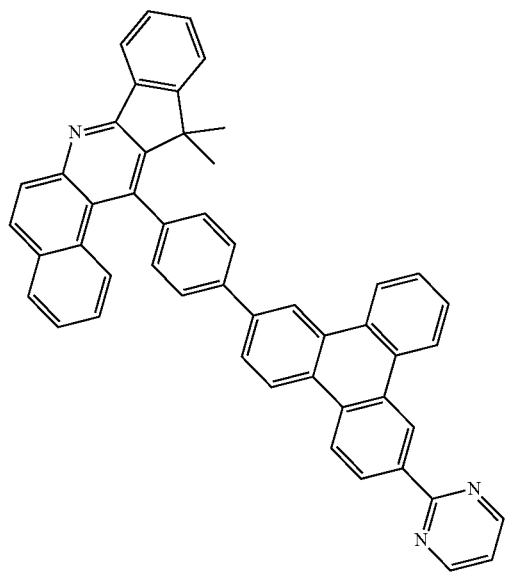
150
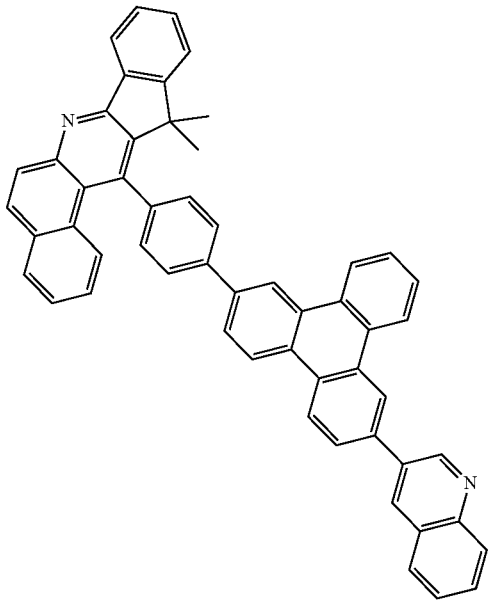
152
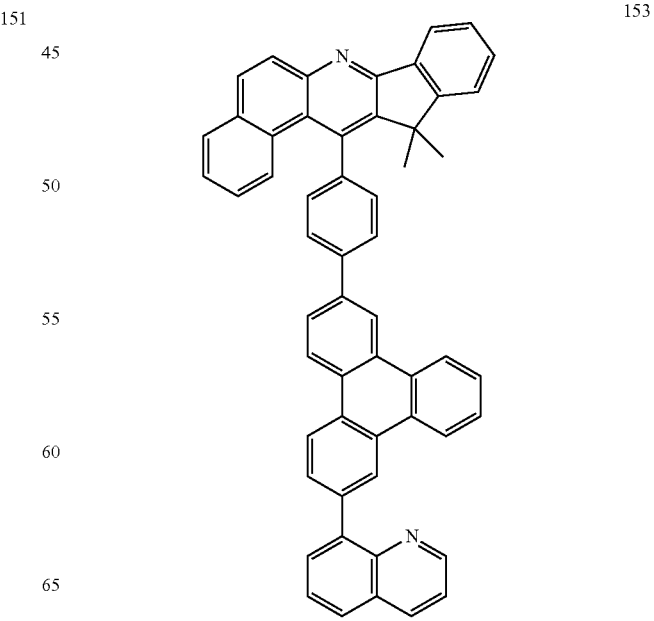
153

154
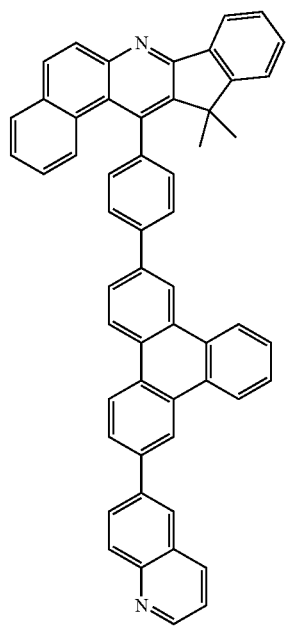
155
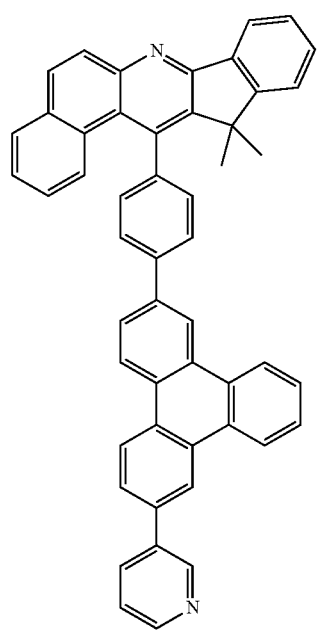
156
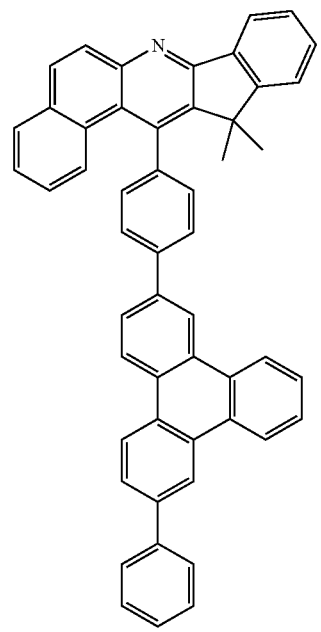
157
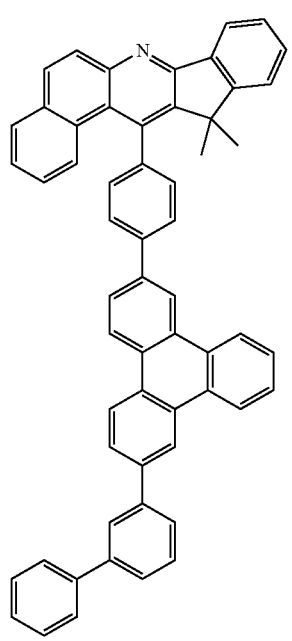

158
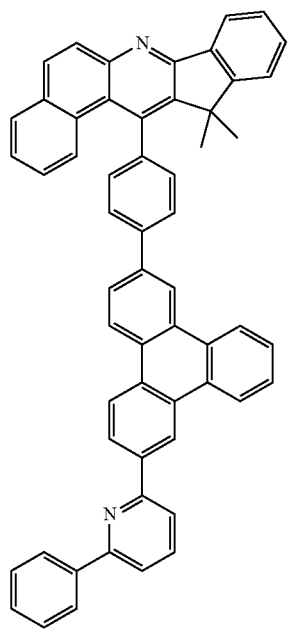
159
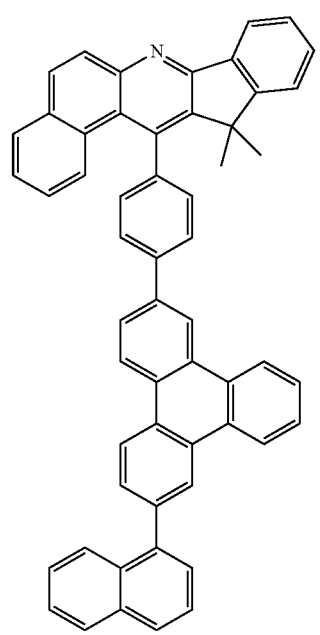
160
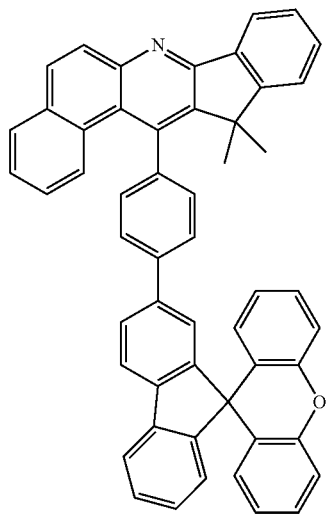
161
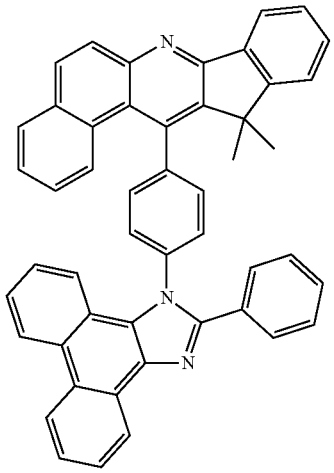
162

163 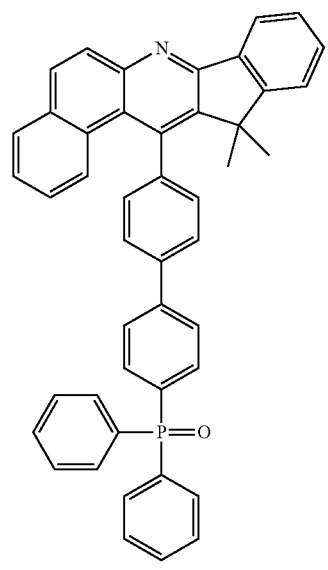
164 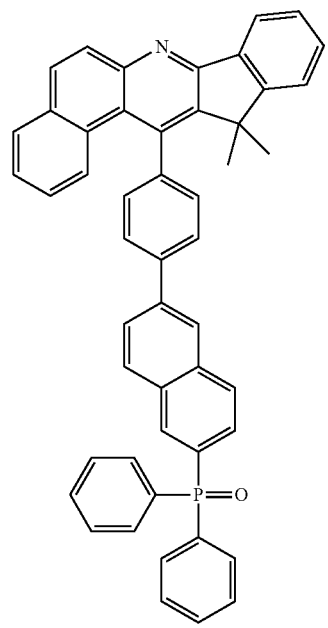
165 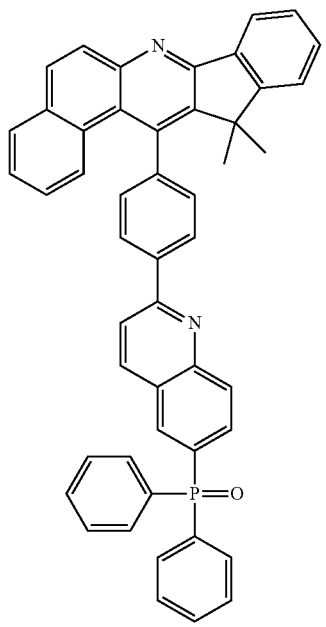
166 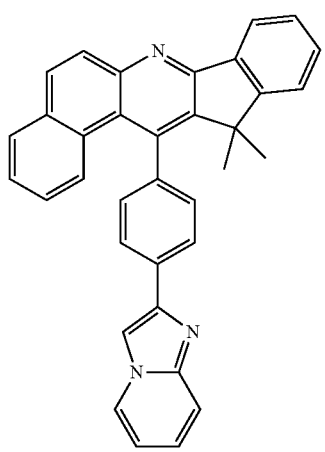
167 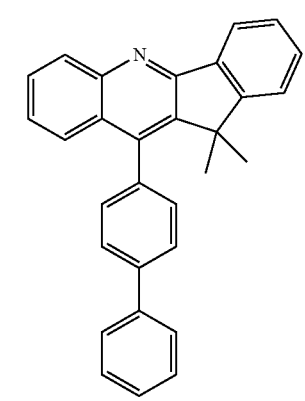

168
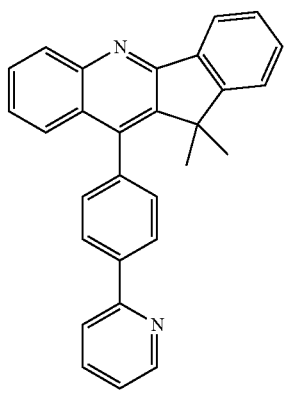
169
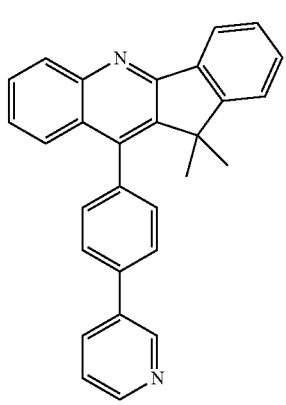
170
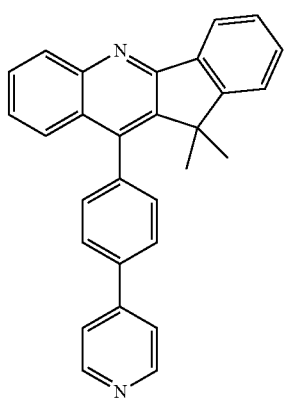
171
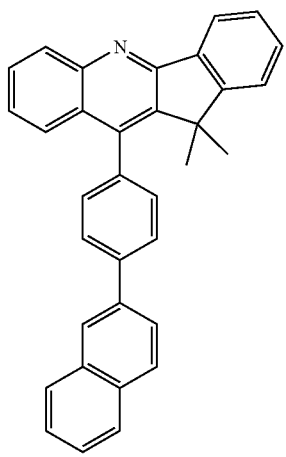
172
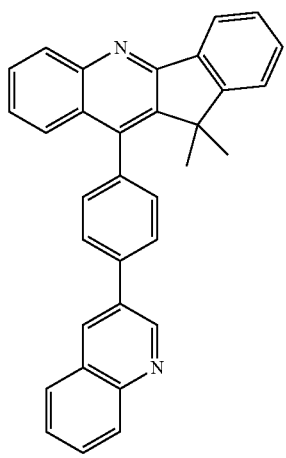
173
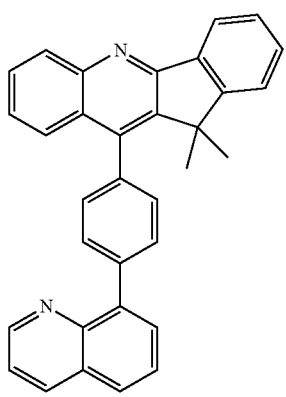
174
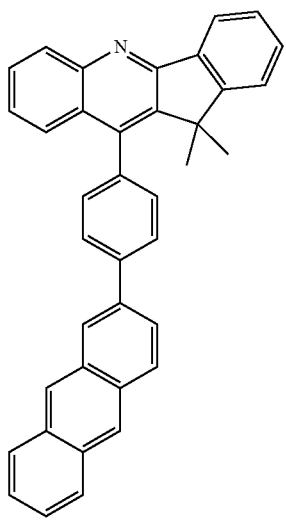

175
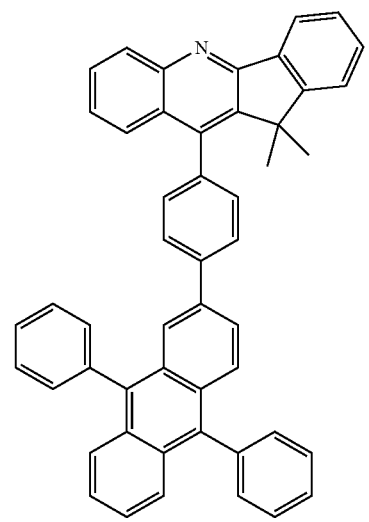
176
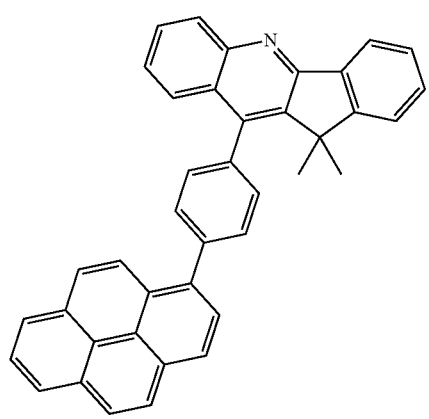
177
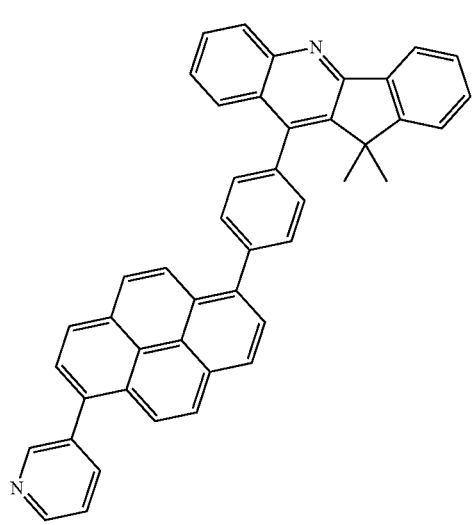
178
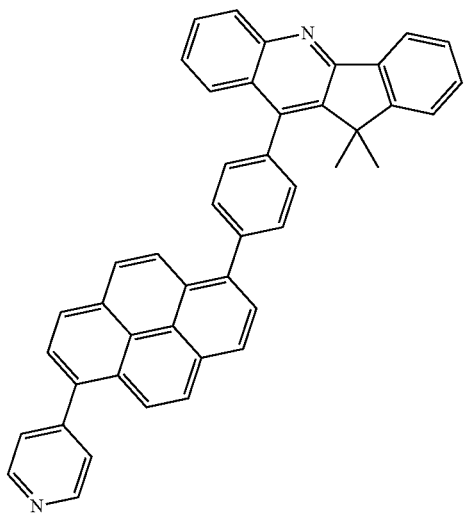
179
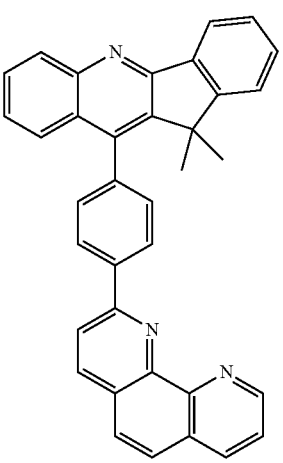
180
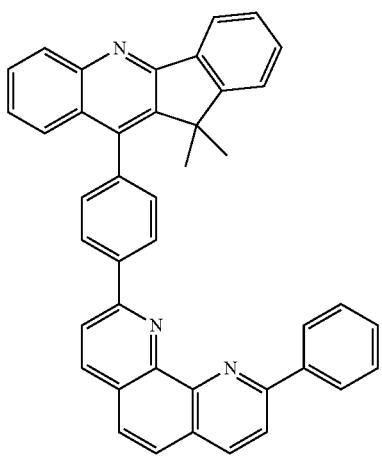

181
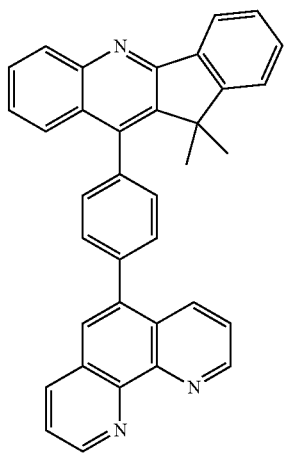
182
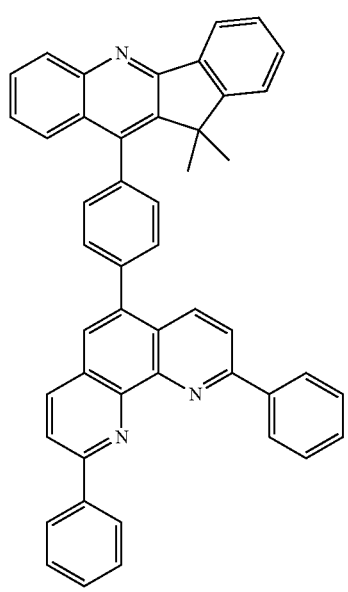
183
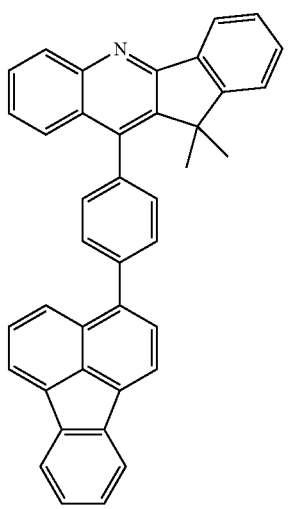
184
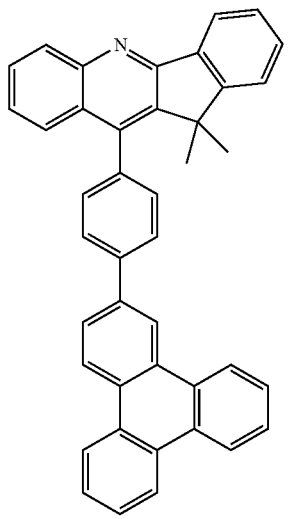
185
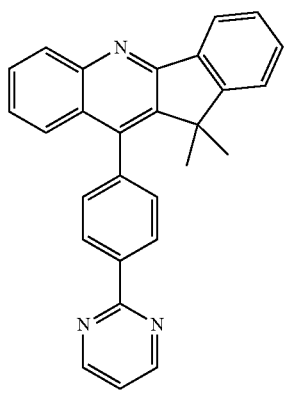
186
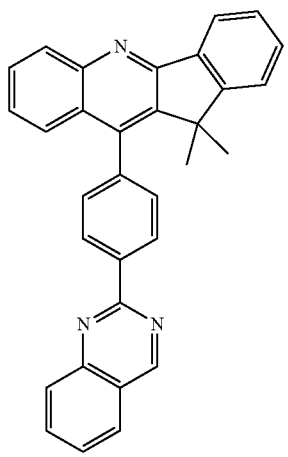

187
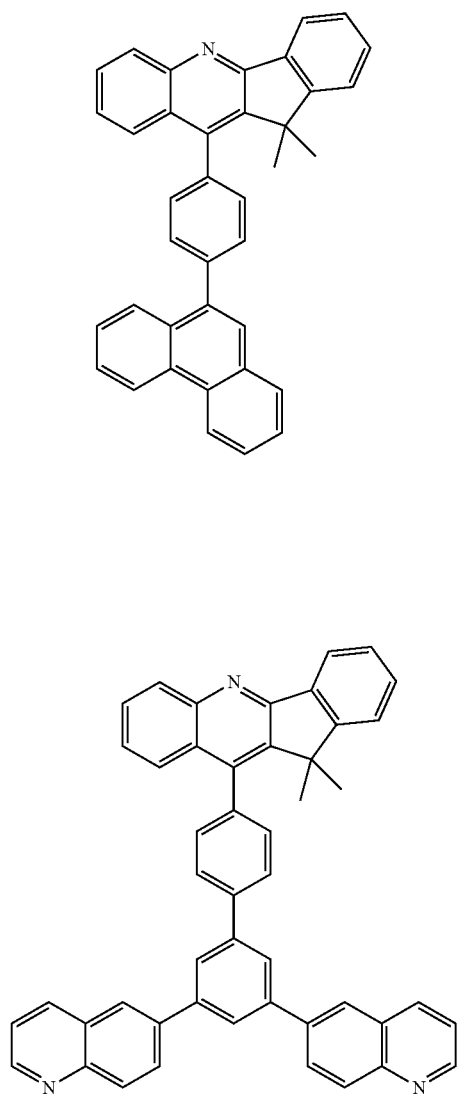
188
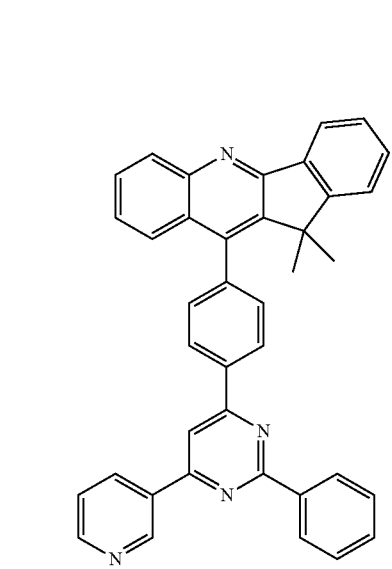
190
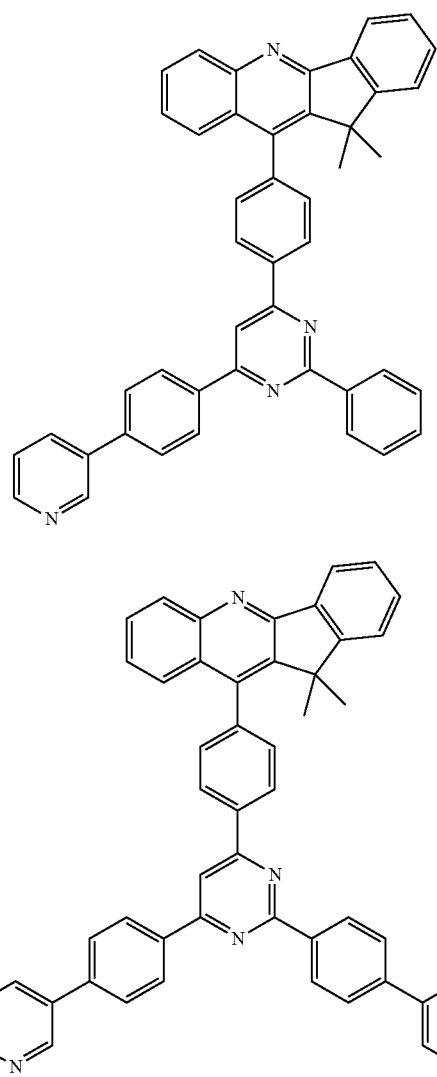
191
192
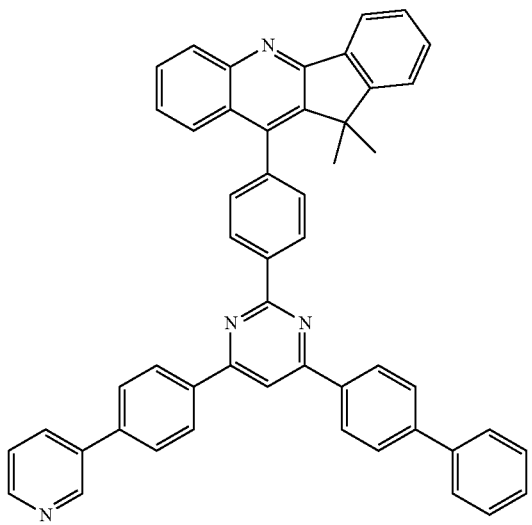
189

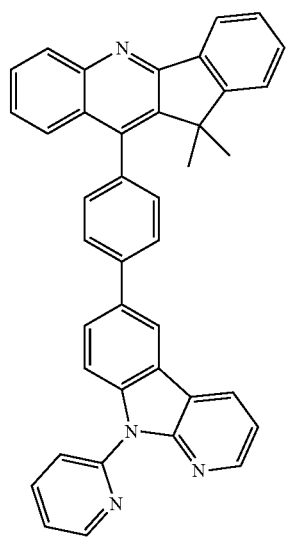
193
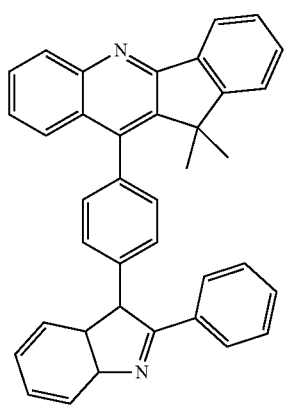
196
194
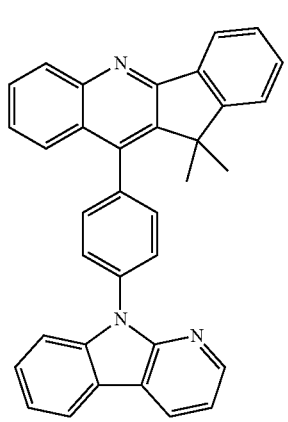
197
195
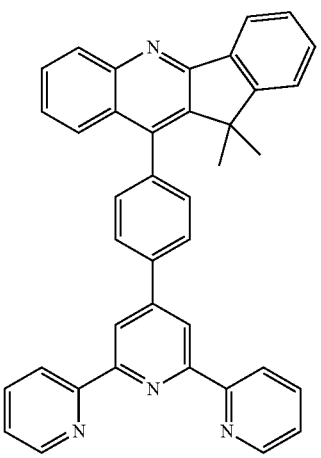
198

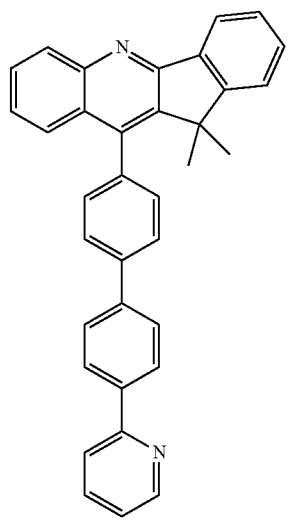
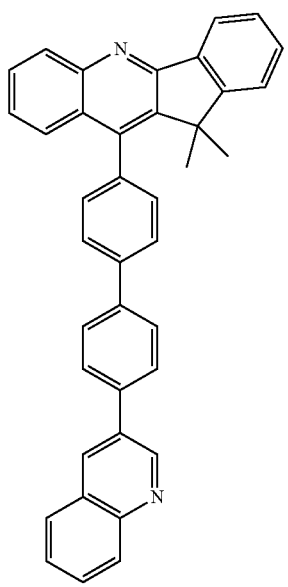

-continued
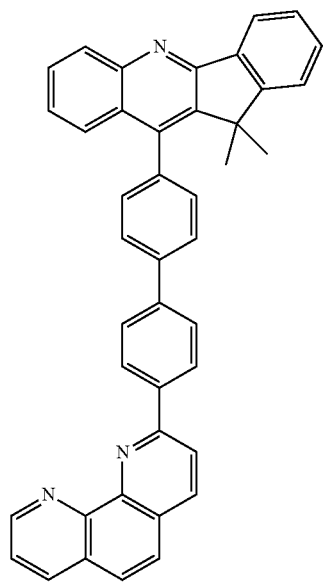
204
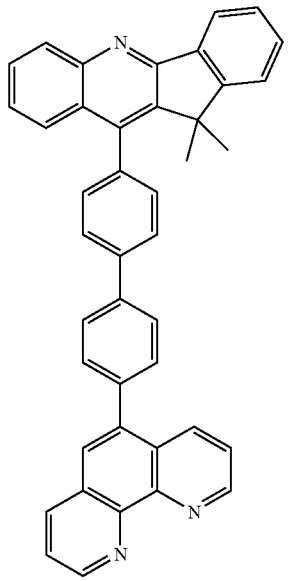
206
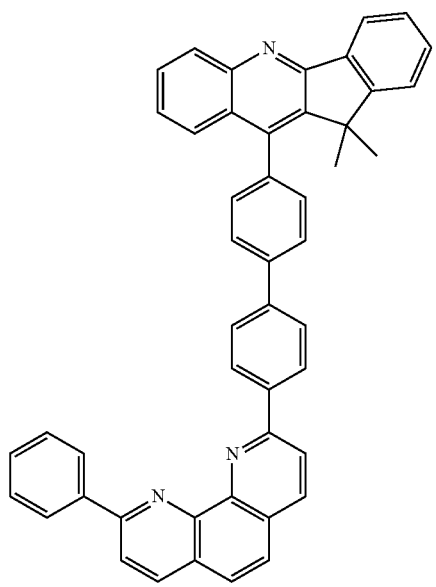
205
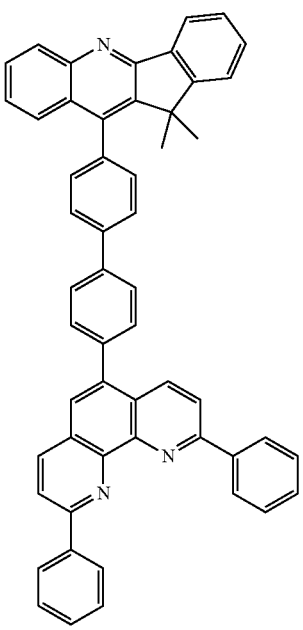
207

208
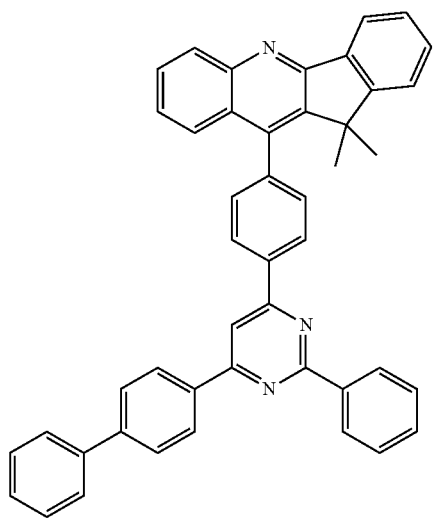
209
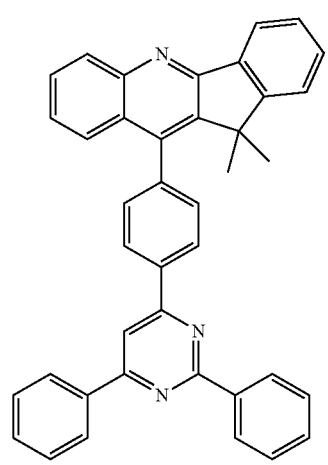
210
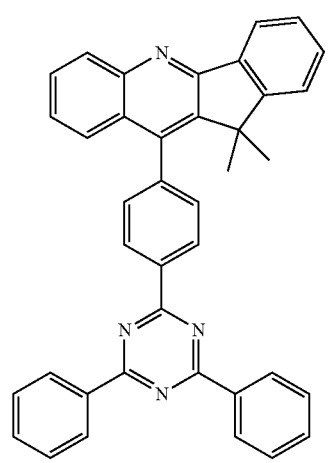
211
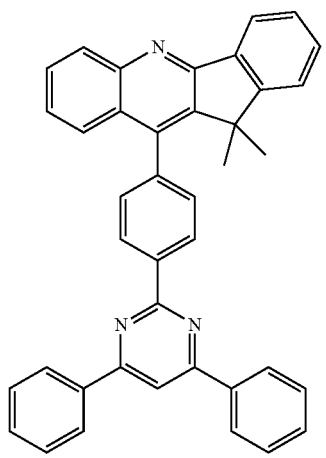
212
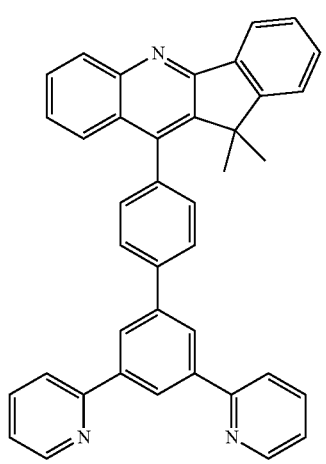
213
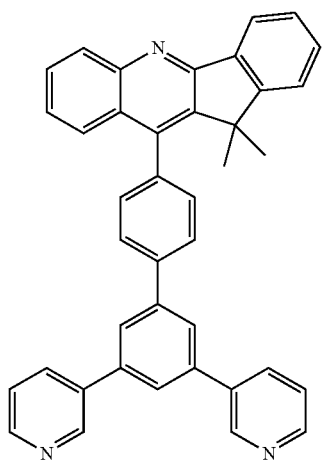

214
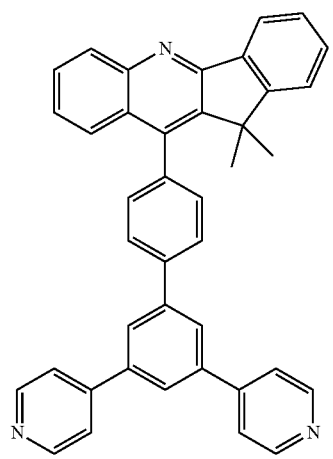
215
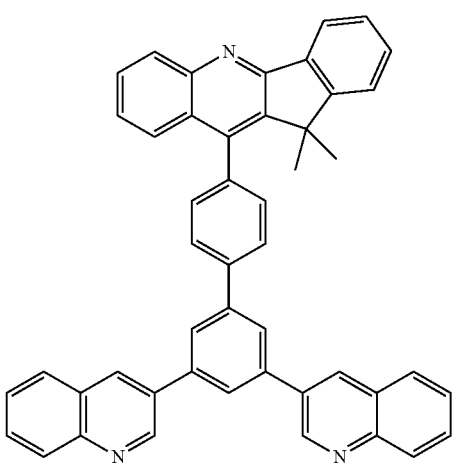
216
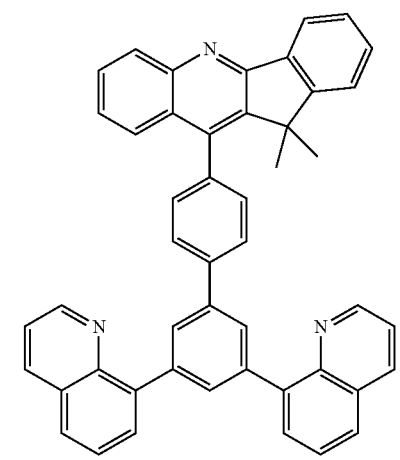
217
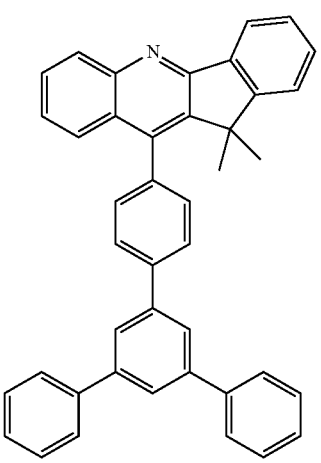
218
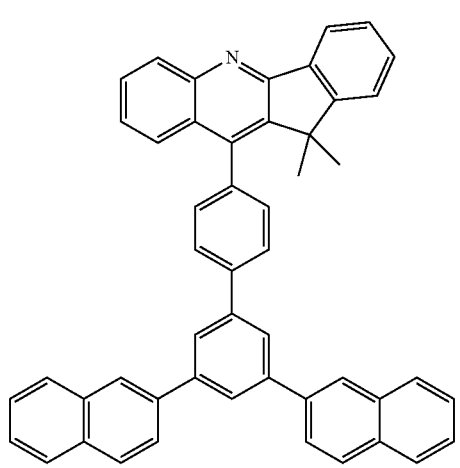
219
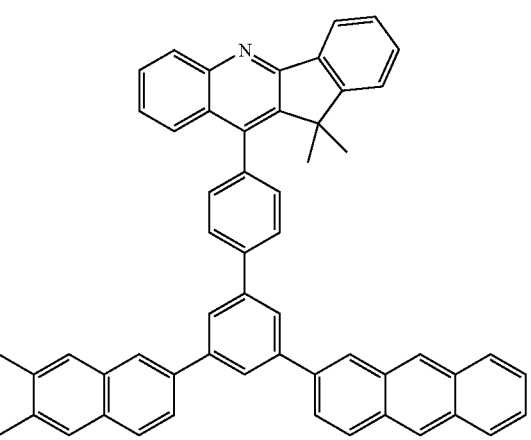

220
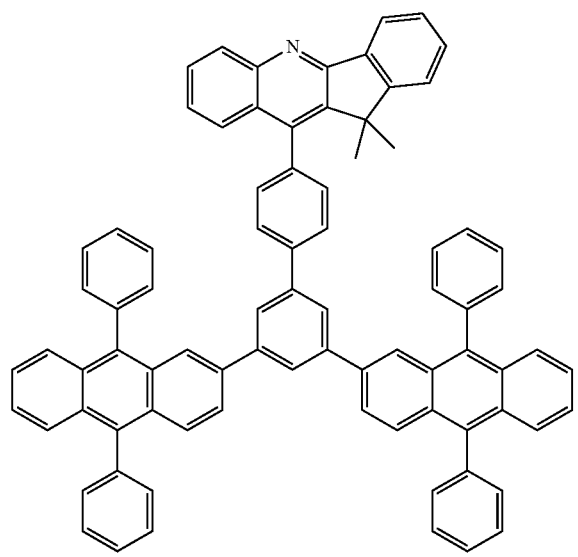
221
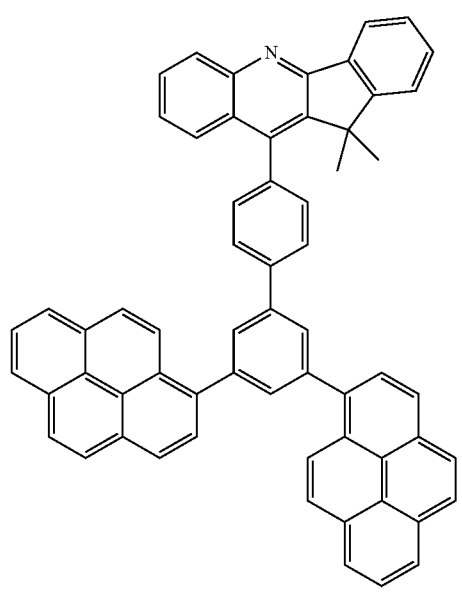
222
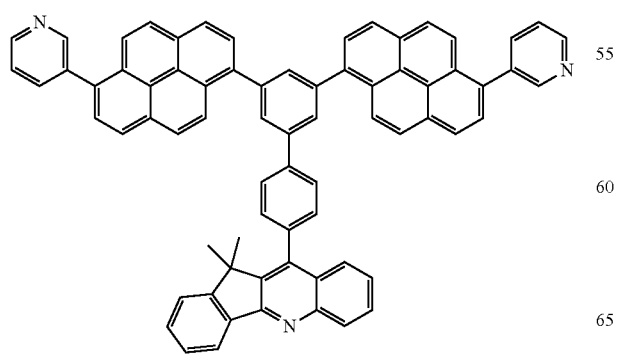
223
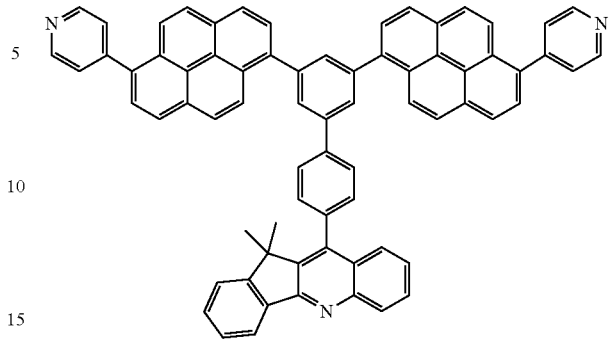
224
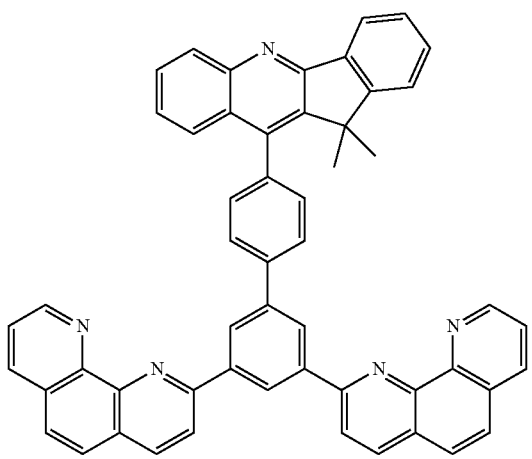
225
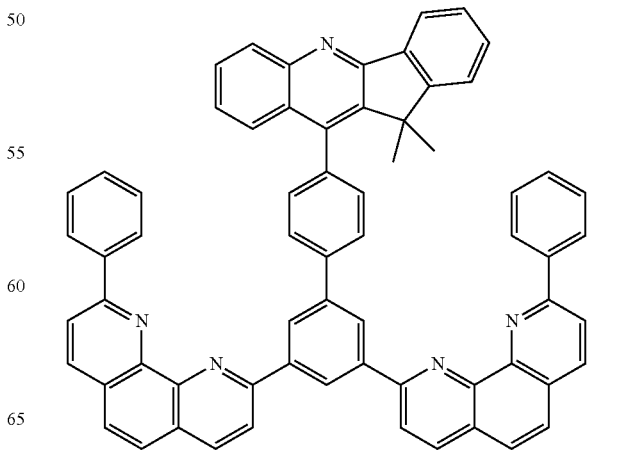

226 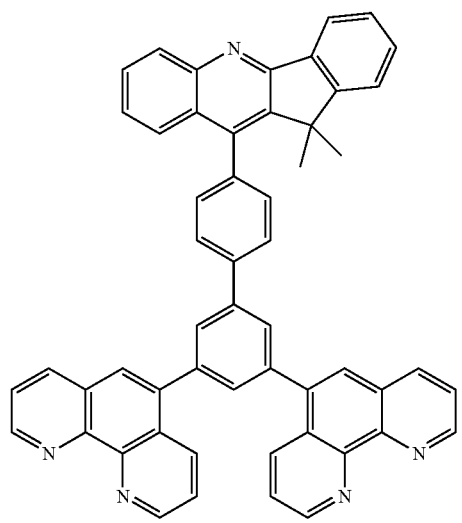
229 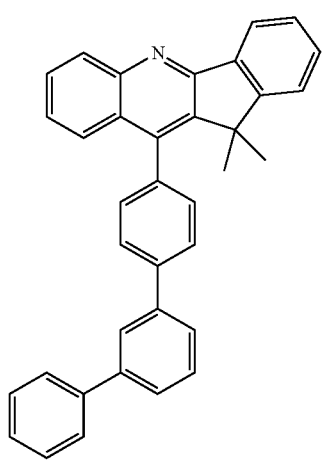
227 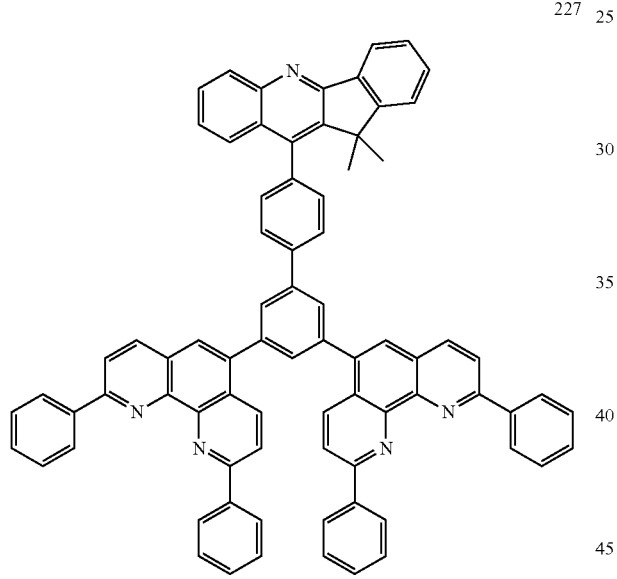
230 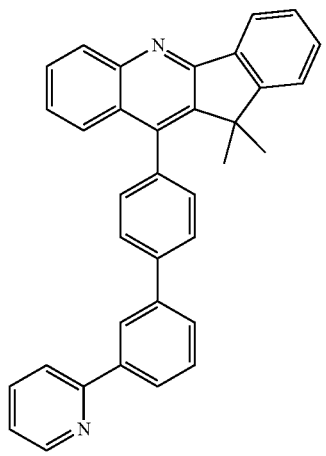
228 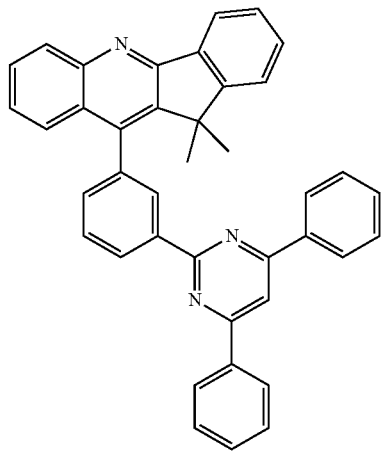
231 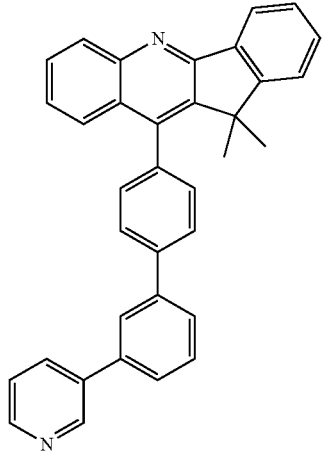

232
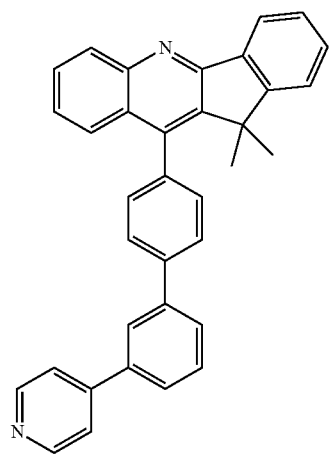
233
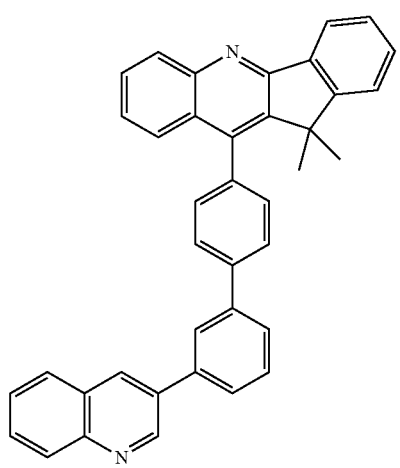
234
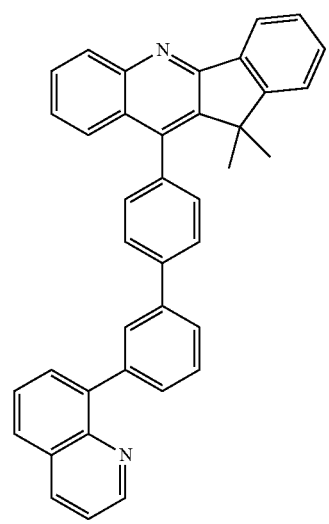
235
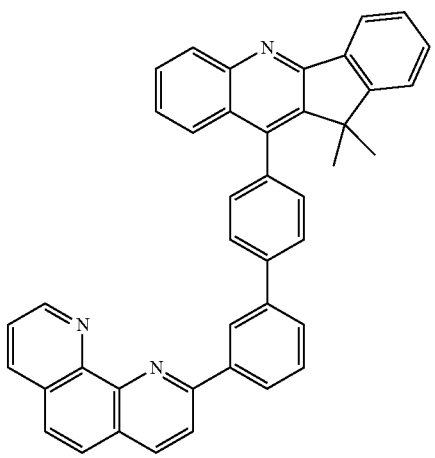
236
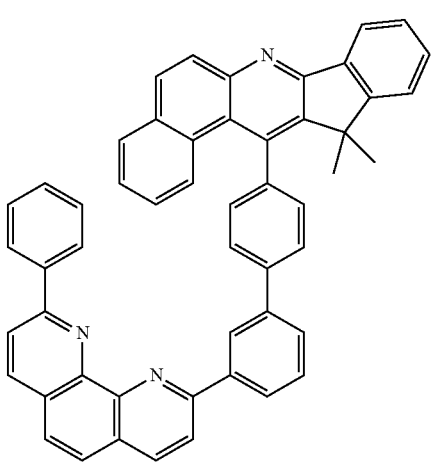
237
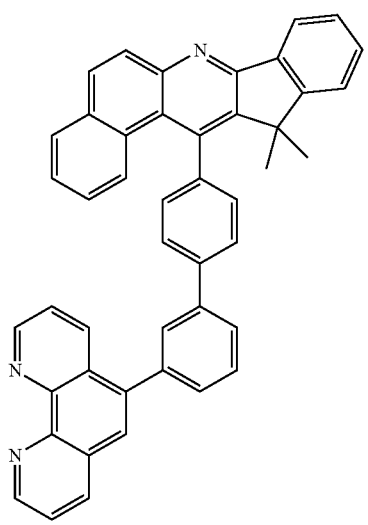

238
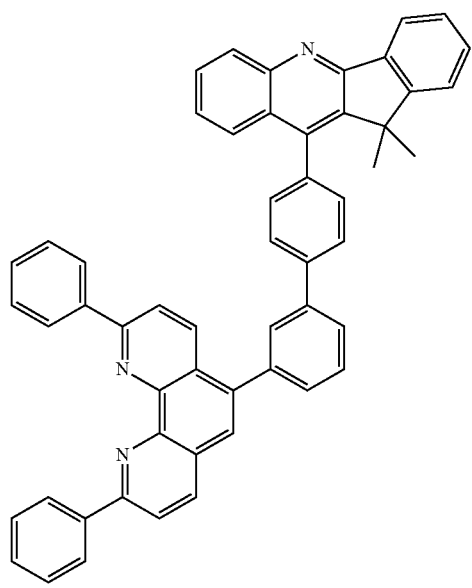
239
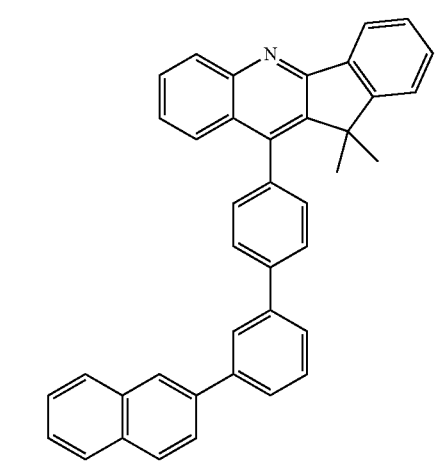
240
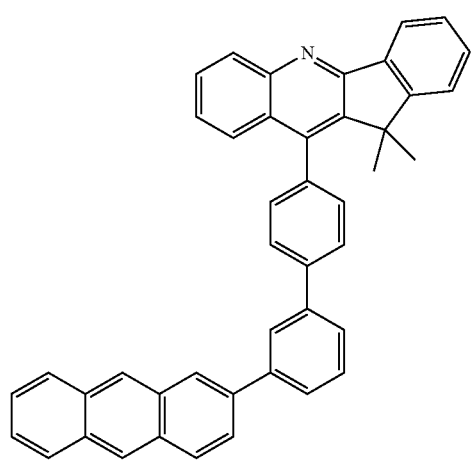
241
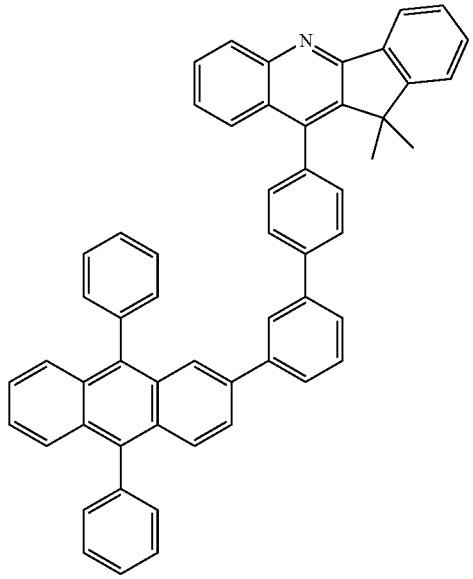
242
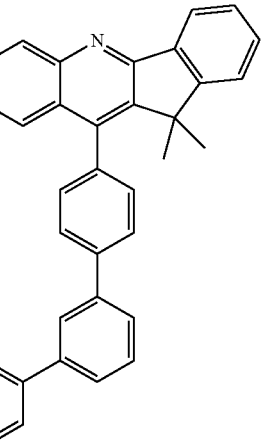
243
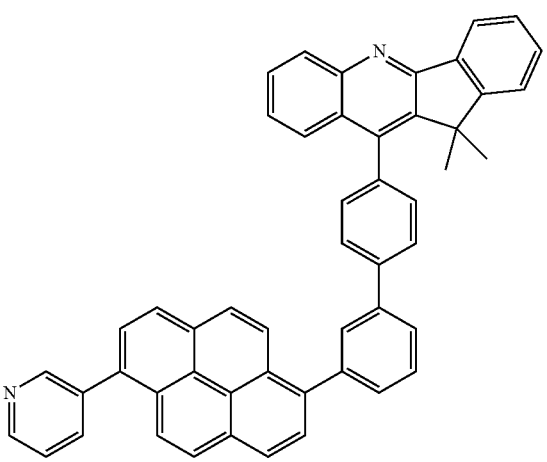

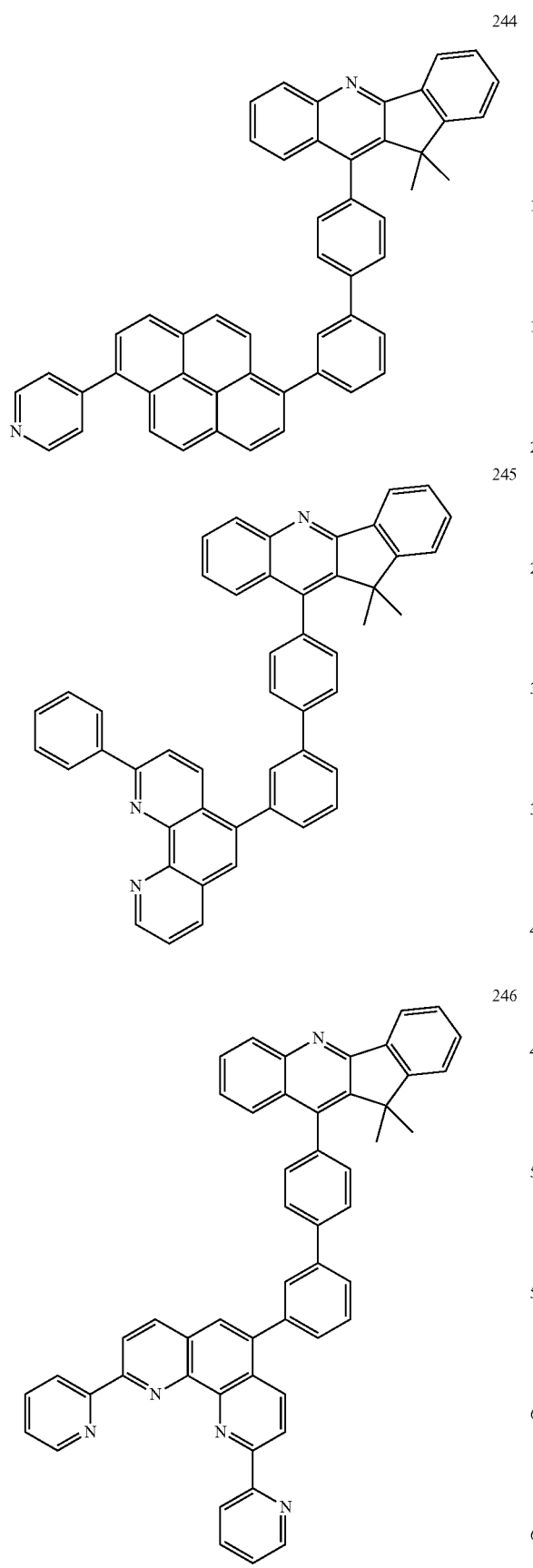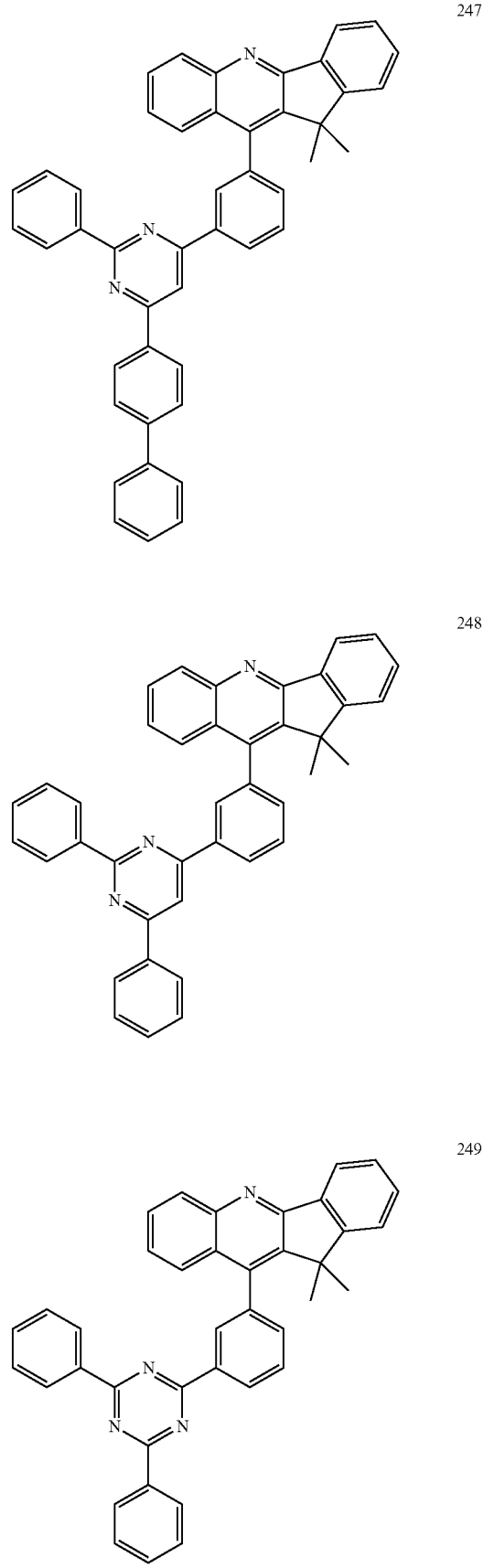

250
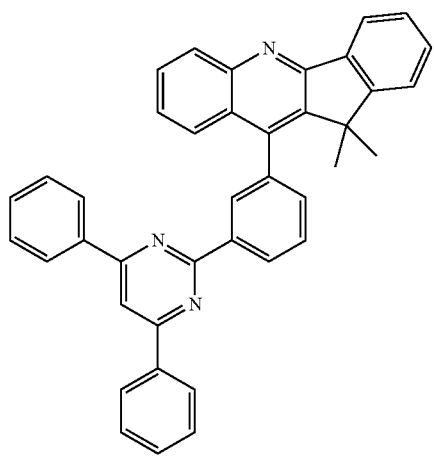
251
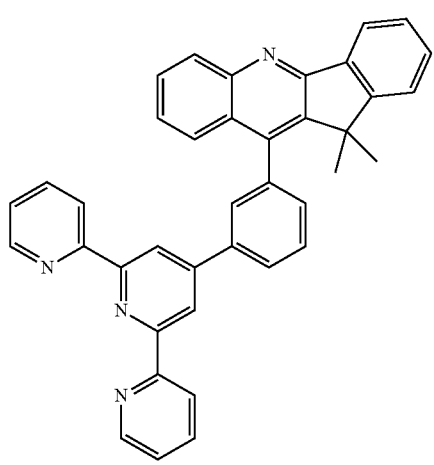
252
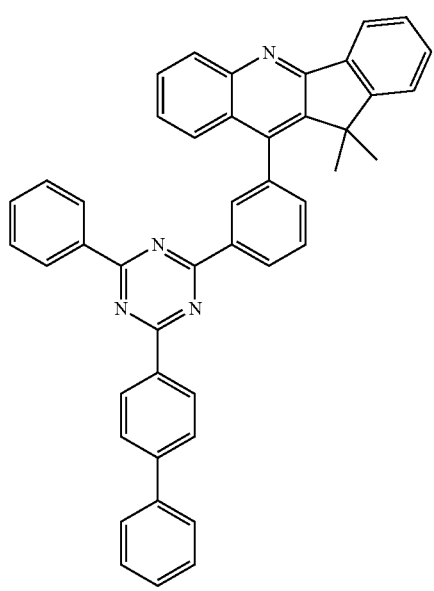
253
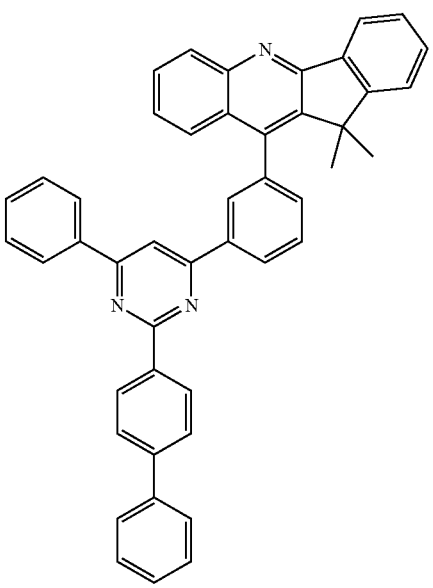
254
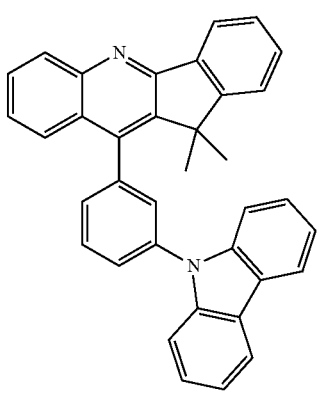
255
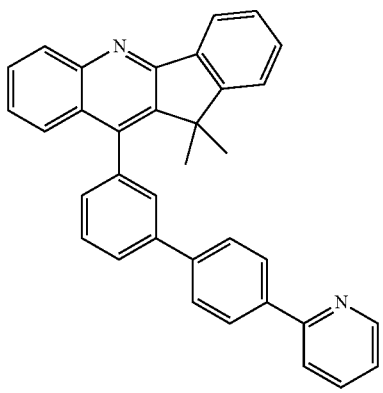

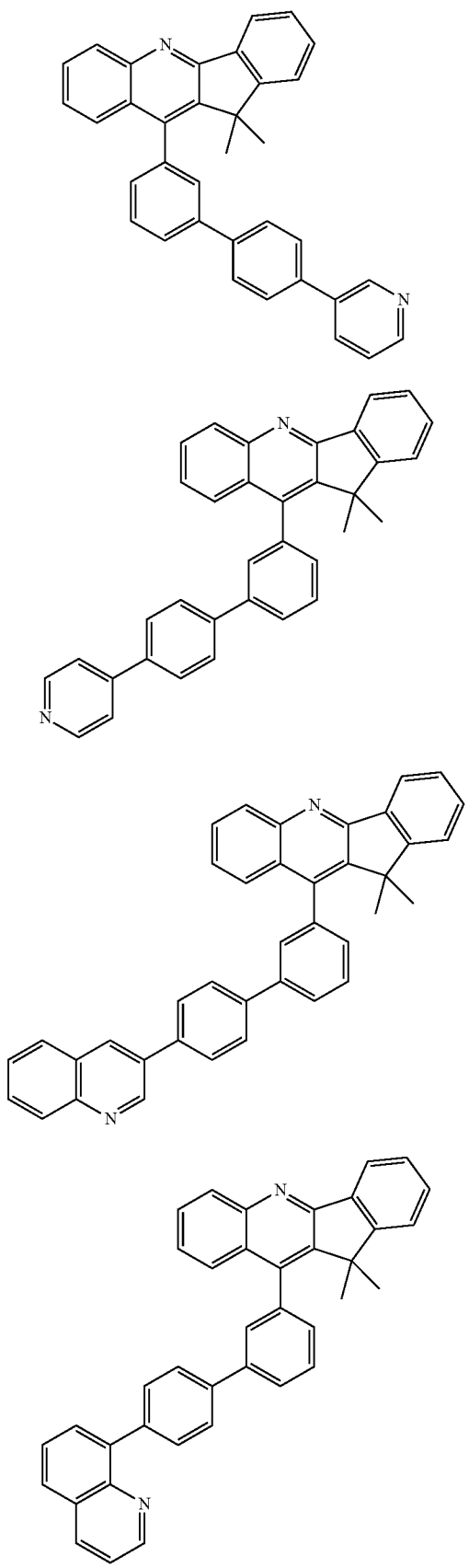
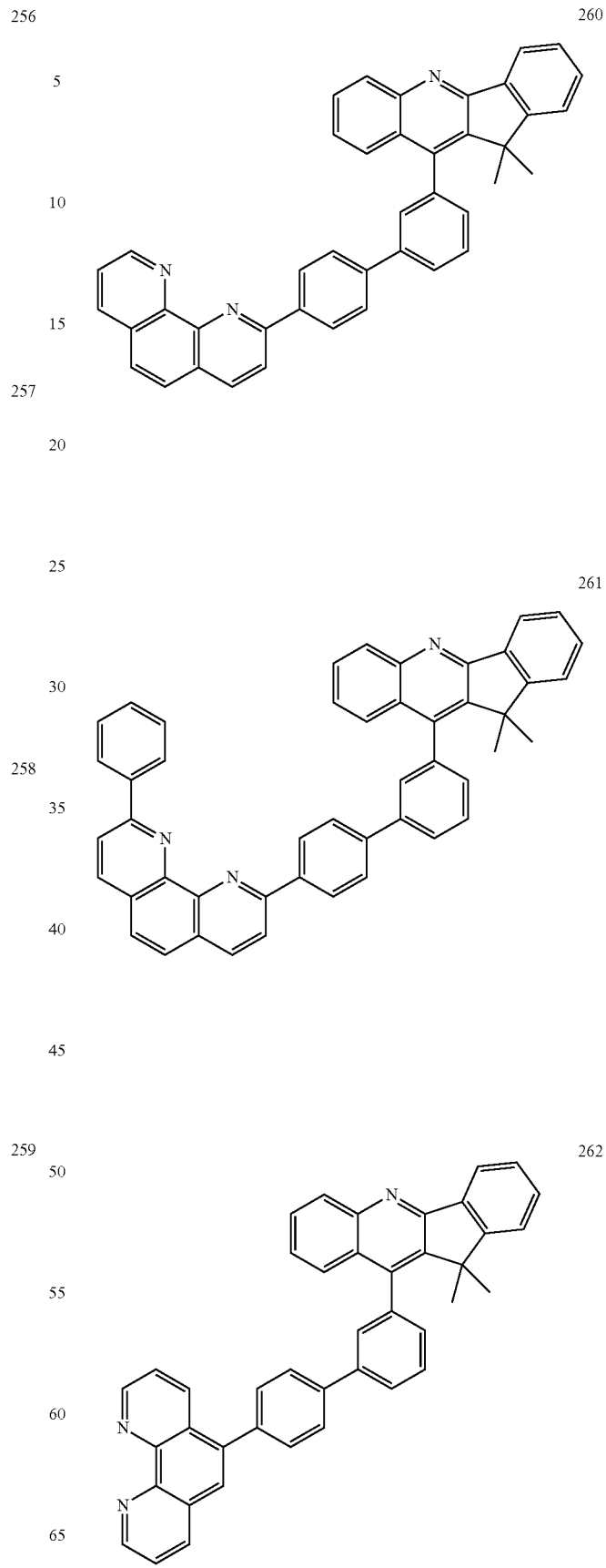

263
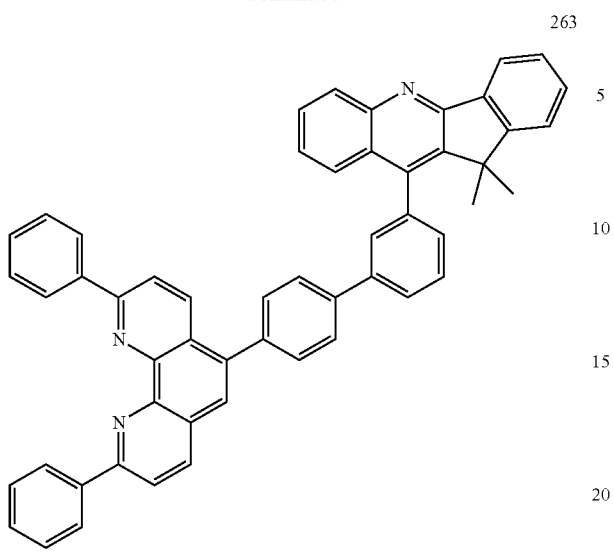
264
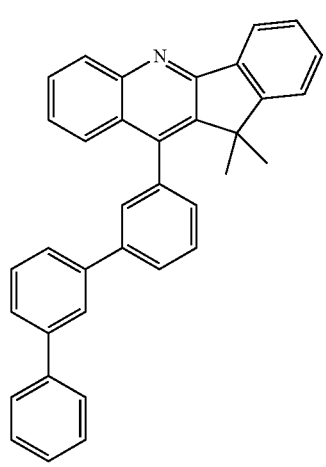
265
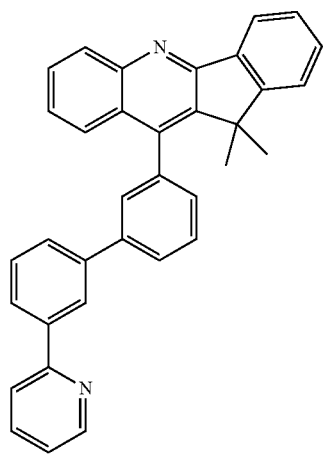
266
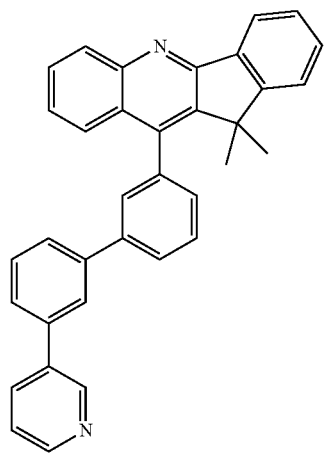
267
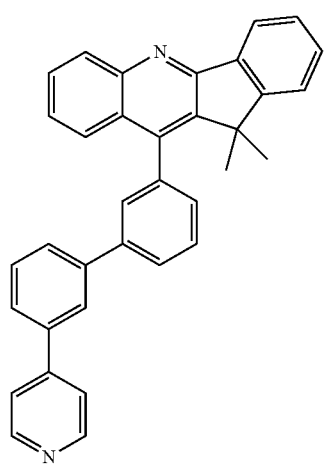
268
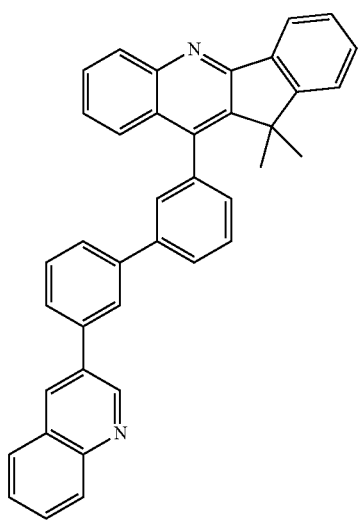

269 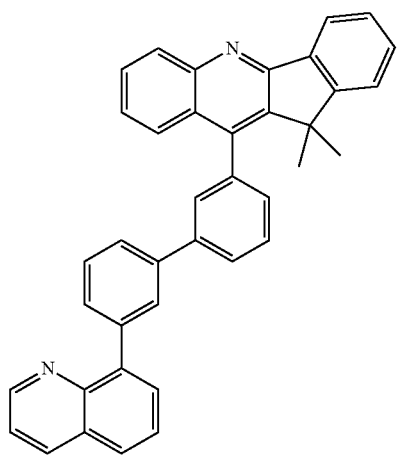
270 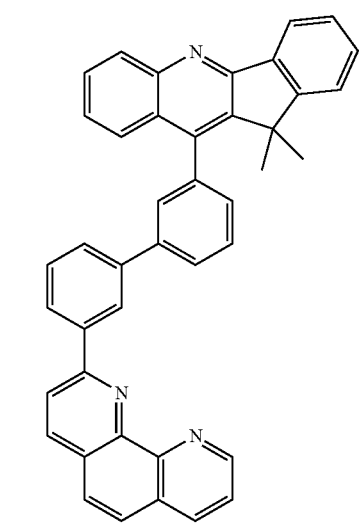
271 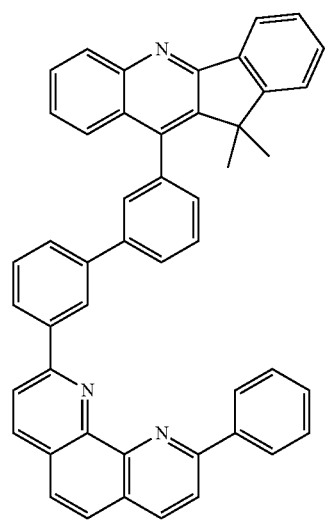
272 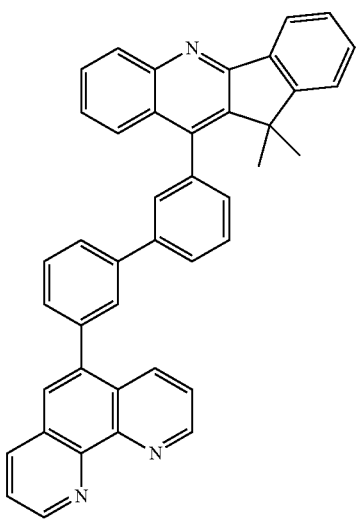
273 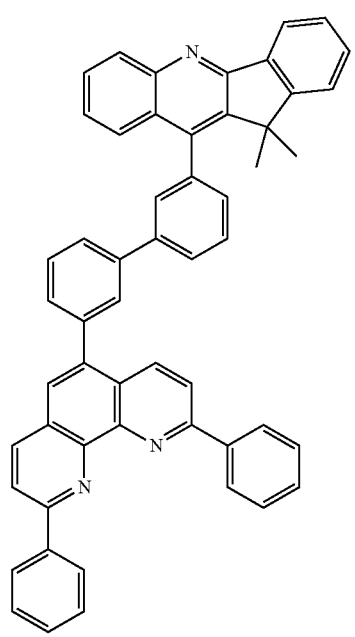
274 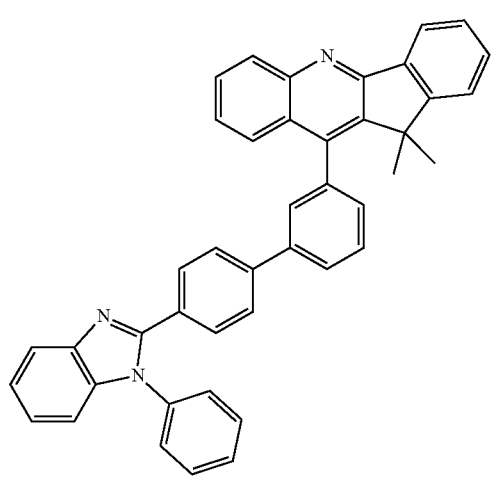

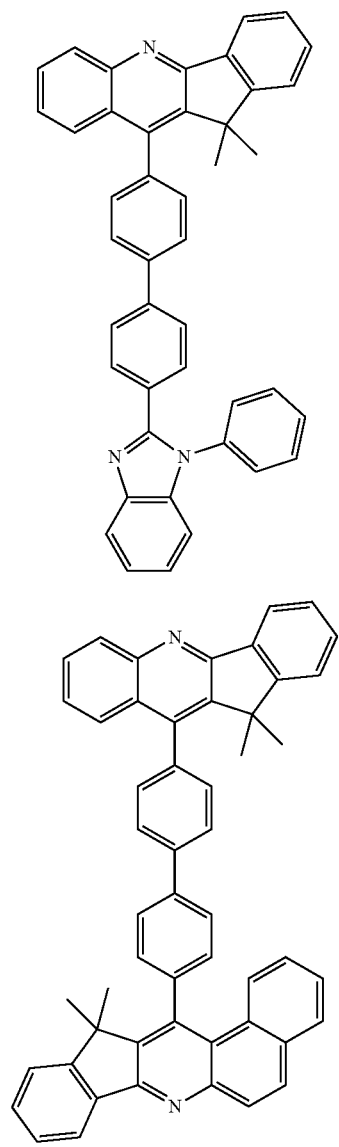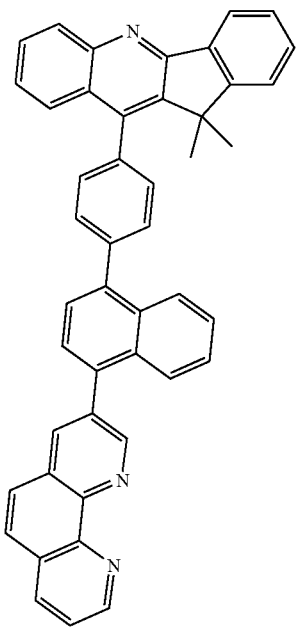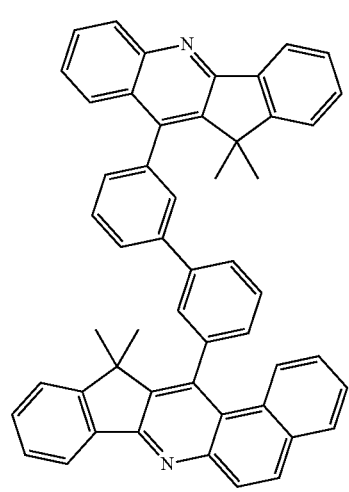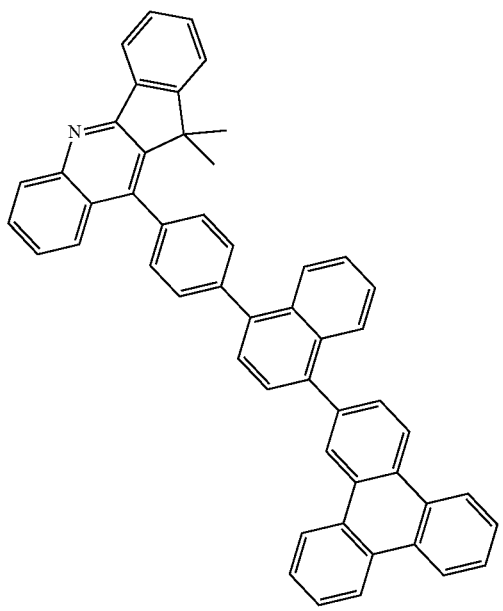

-continued
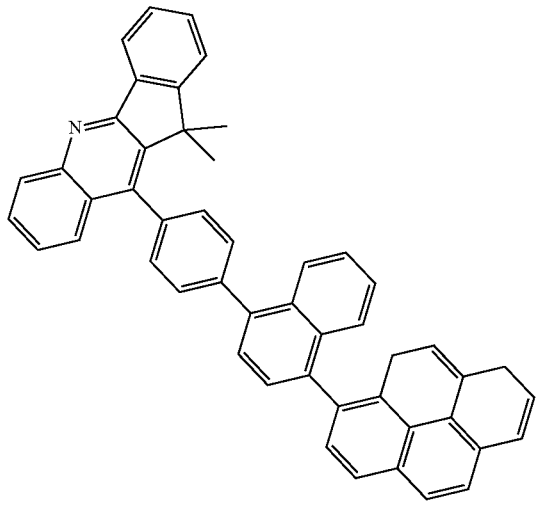
280
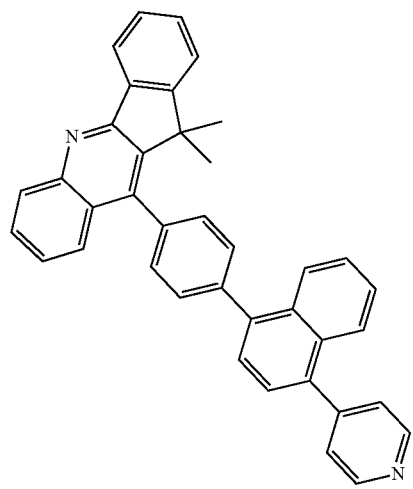
281
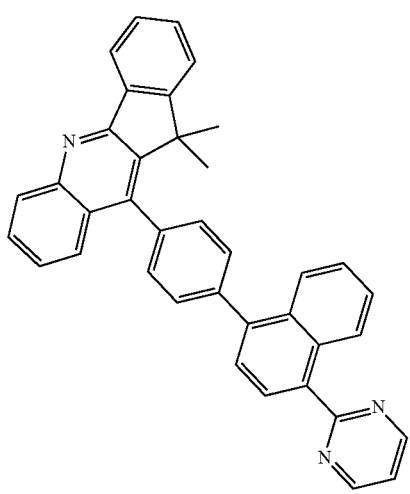
282
-continued
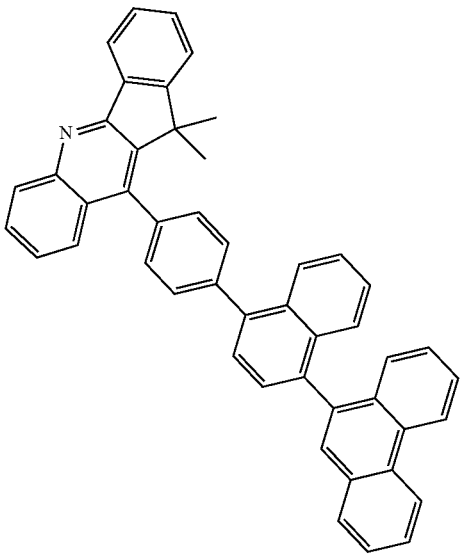
283
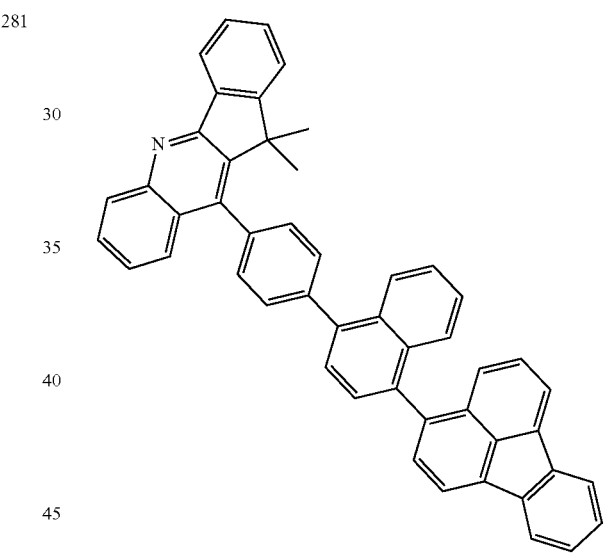
284
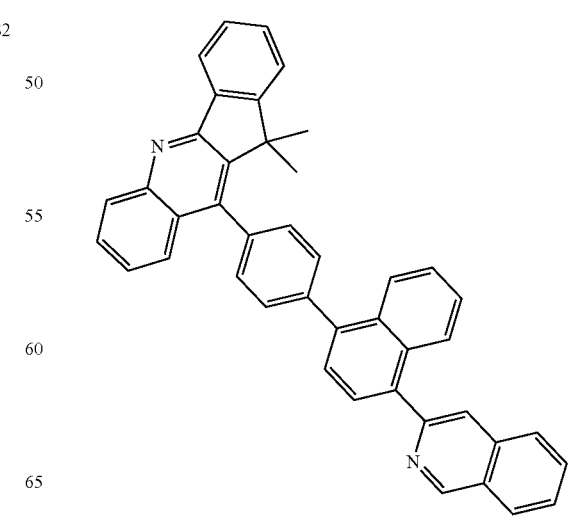
285

286
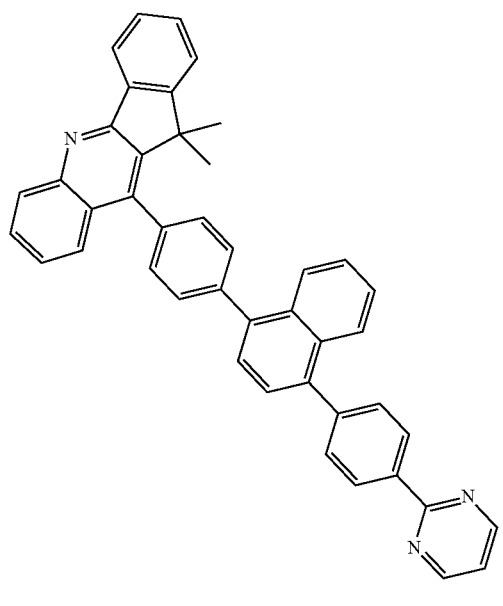
287
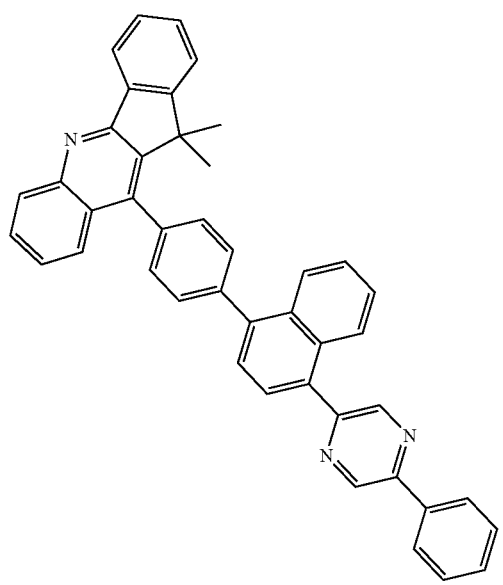
288
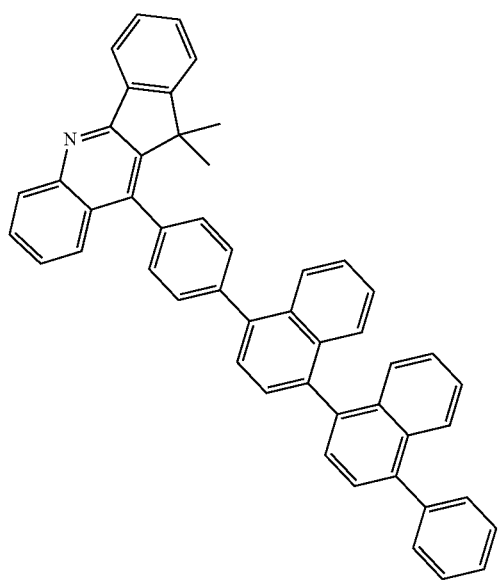
289
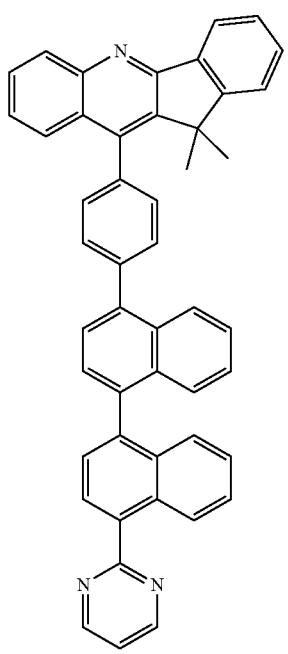

290
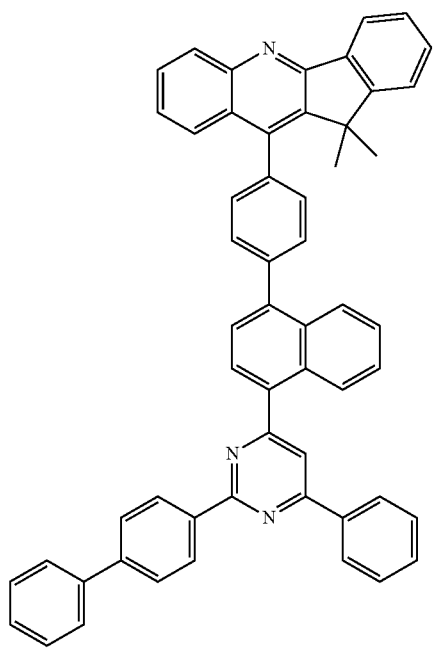
291
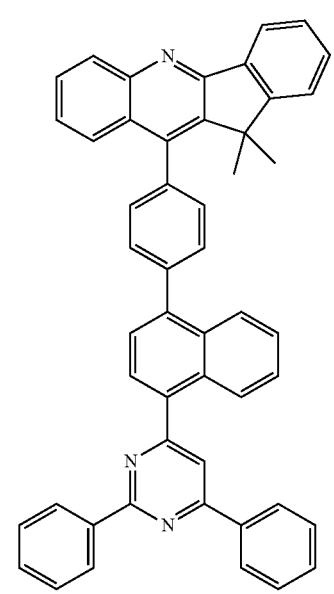
292
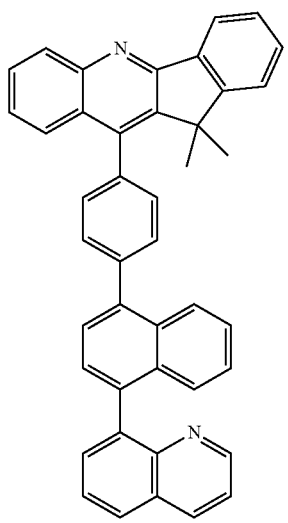
293
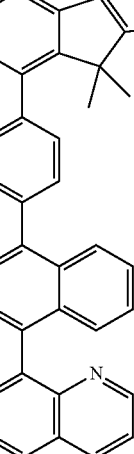

294
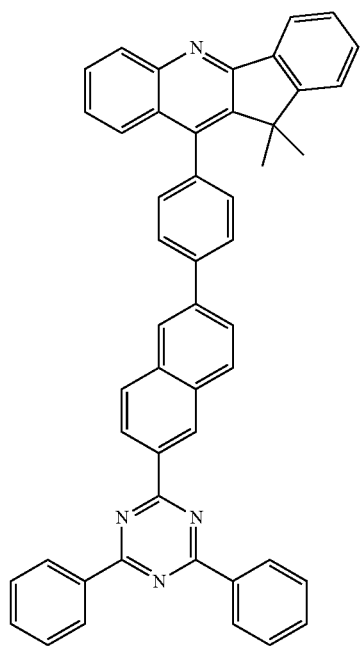
297
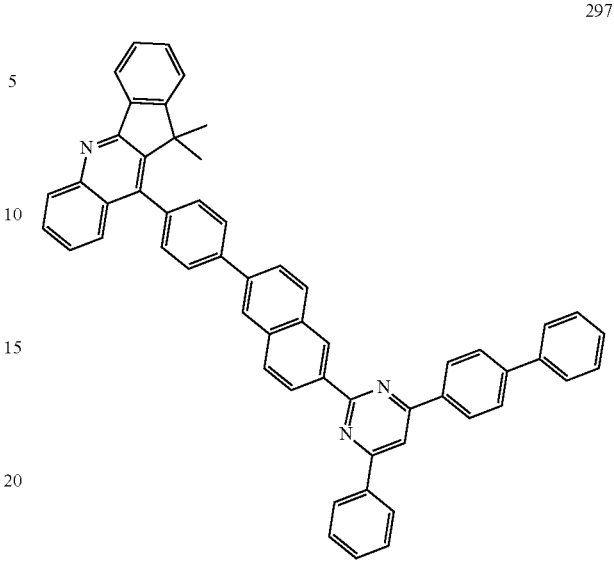
295
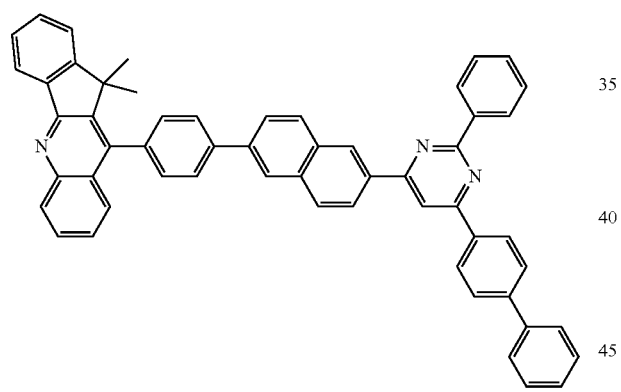
296
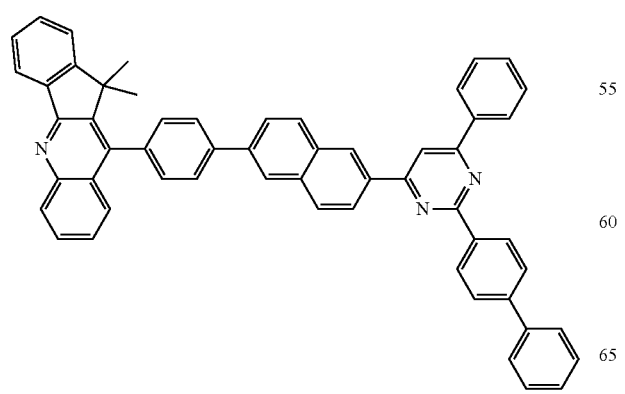
298
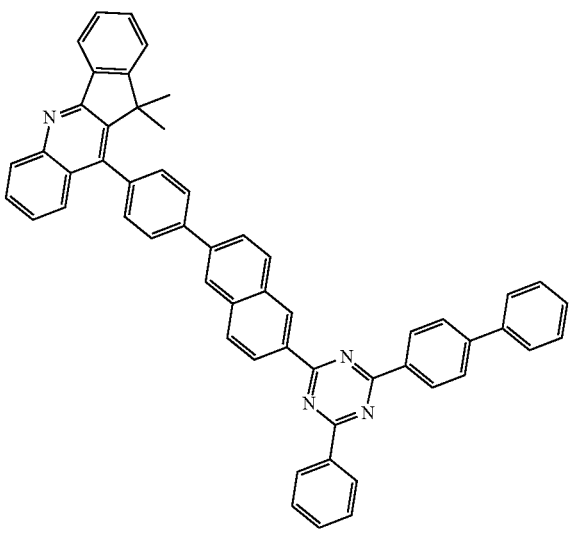

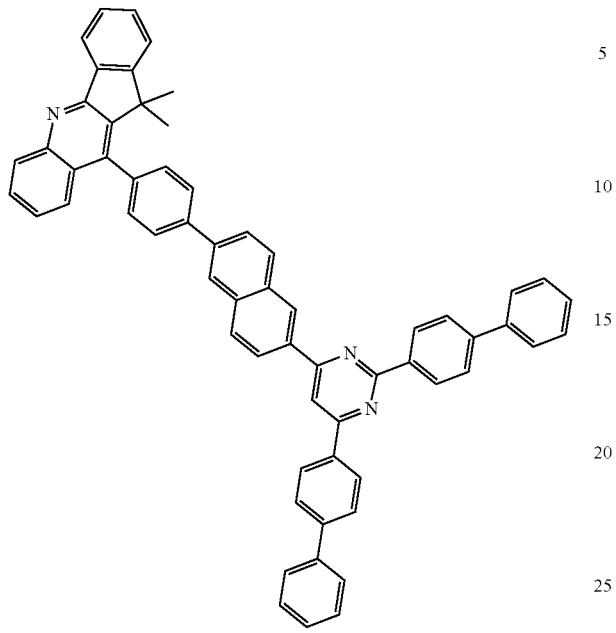
299
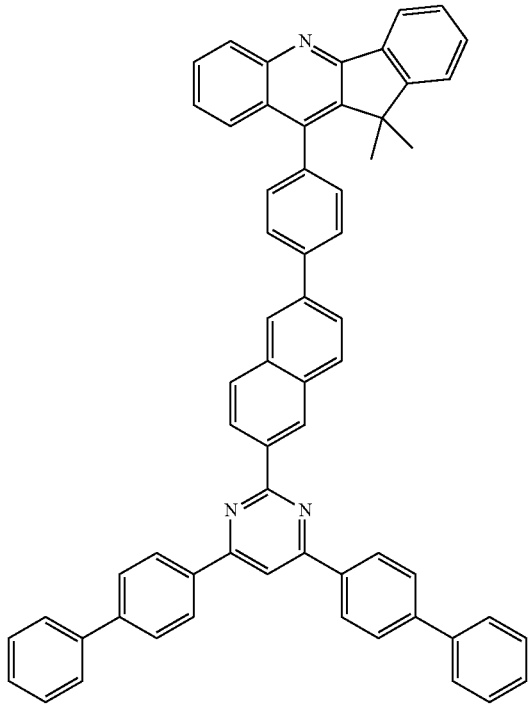
301
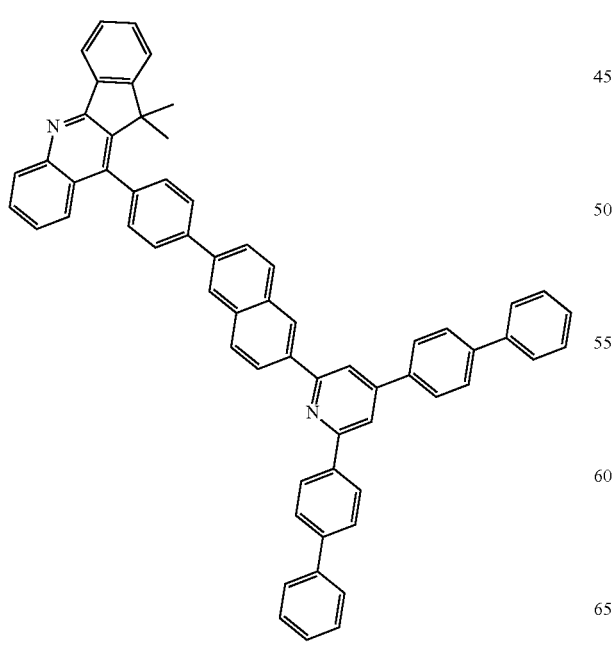
300
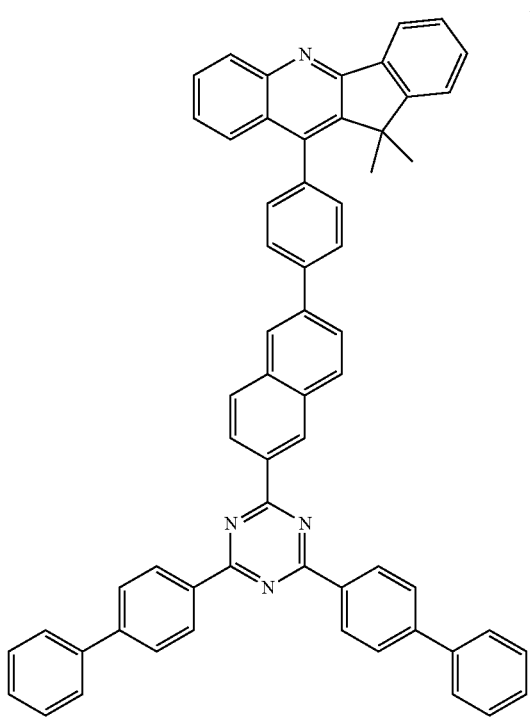
302

-continued
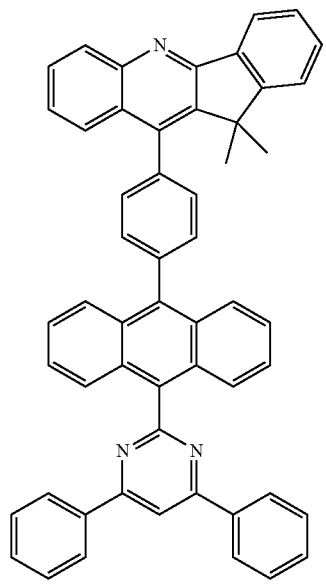
303
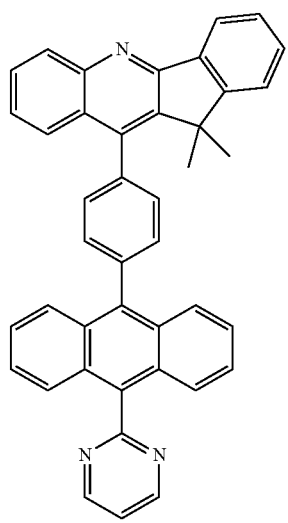
304
305
-continued
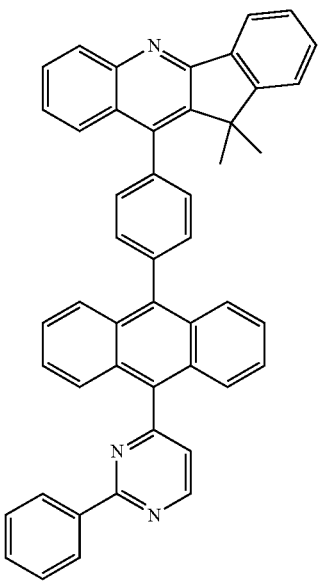
306
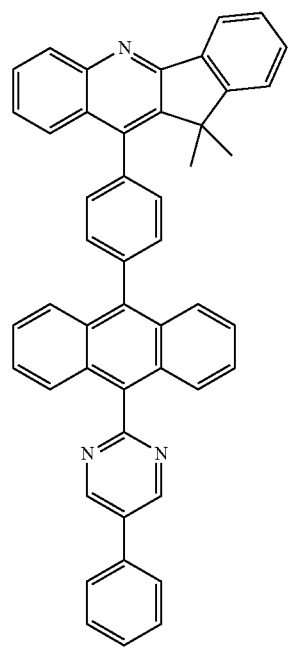
307

308
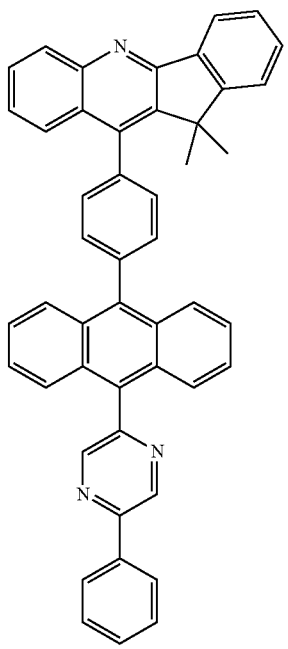
309
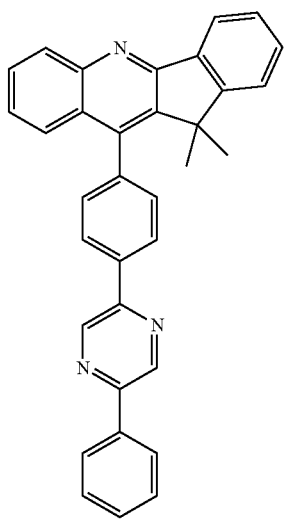
310
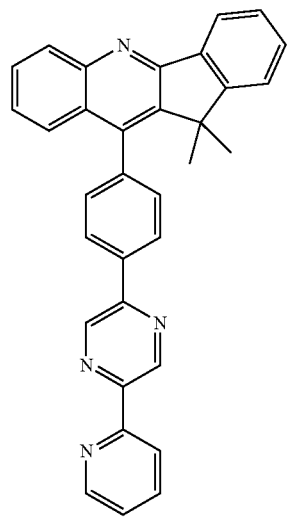
311
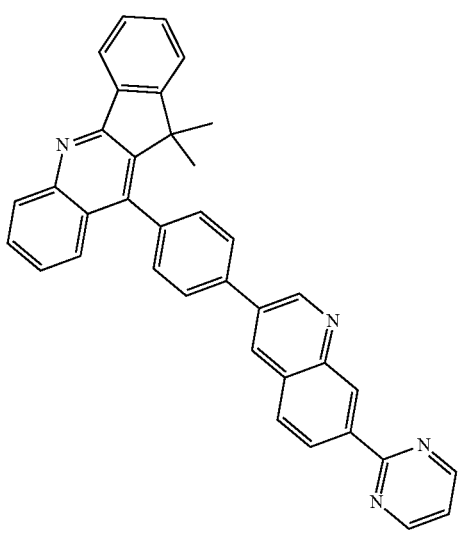
312

125
-continued
313
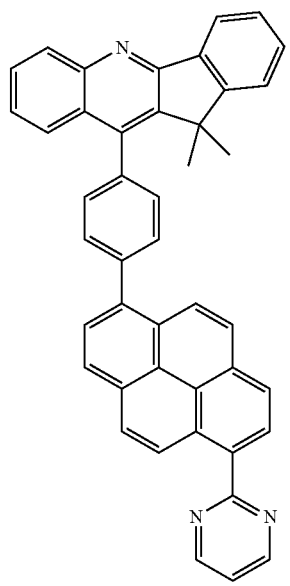
314
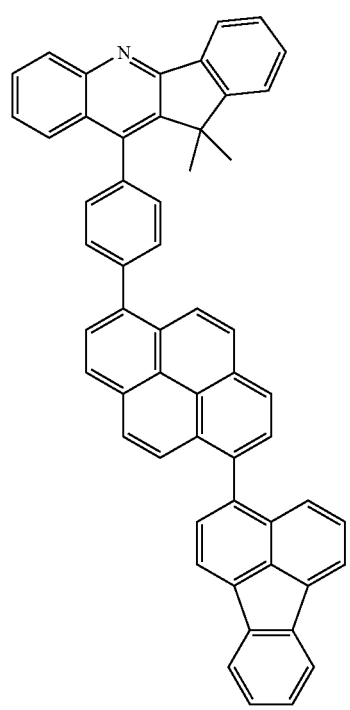
126
-continued
315
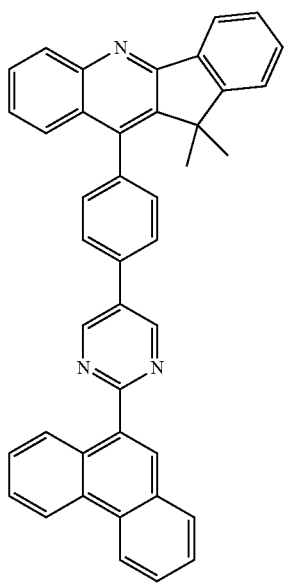
316
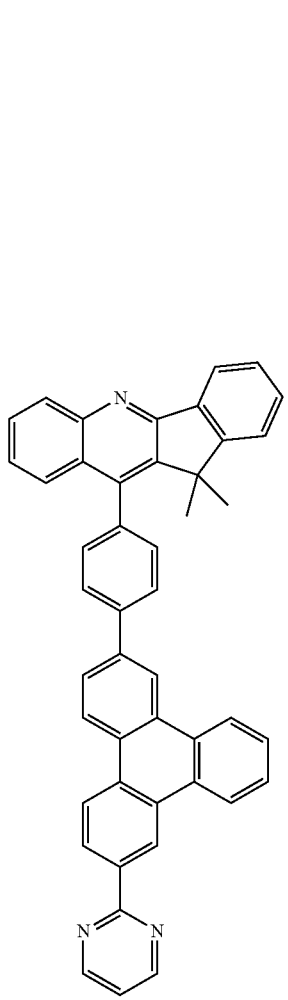

127
-continued
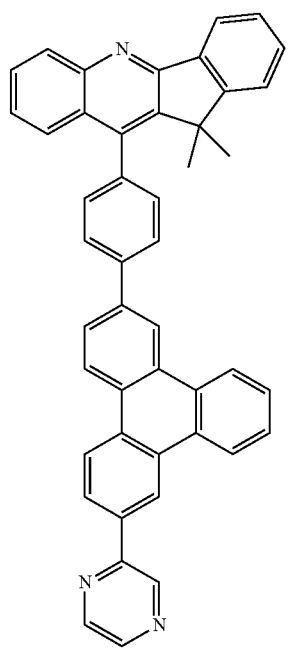
317
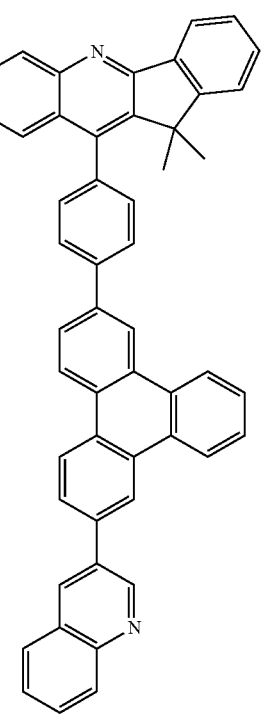
318
128
-continued
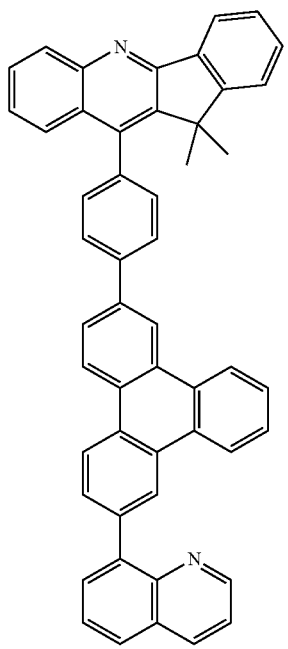
319
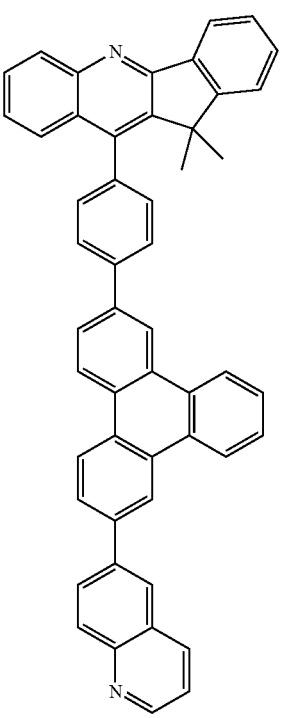
320

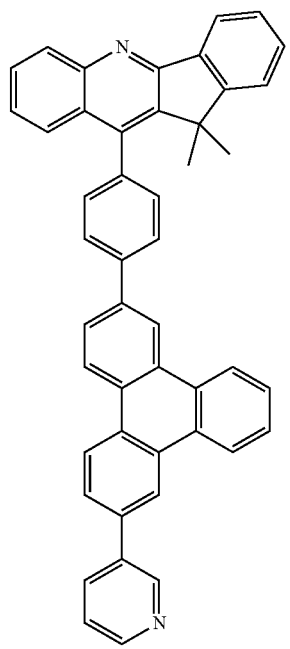
321
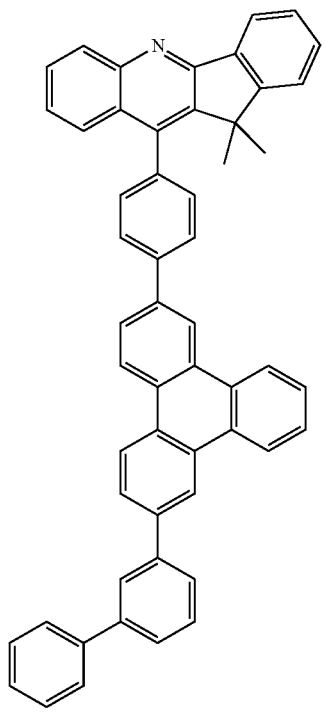
323
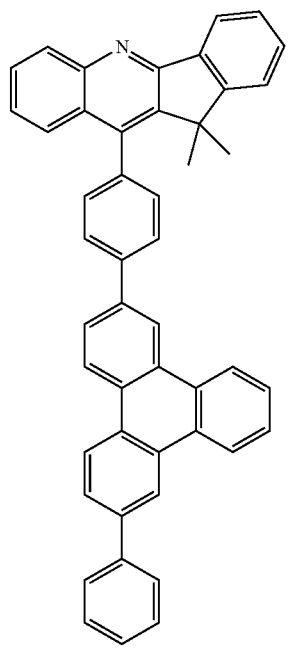
322
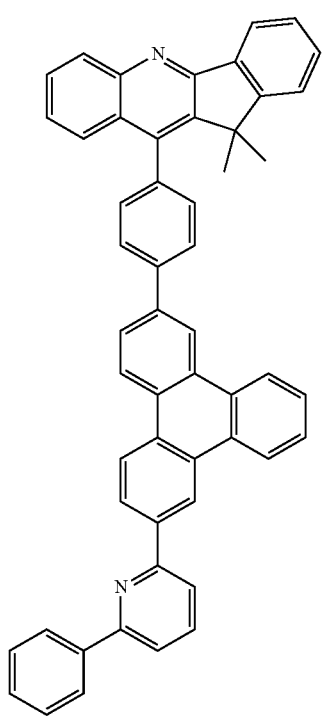
324

-continued
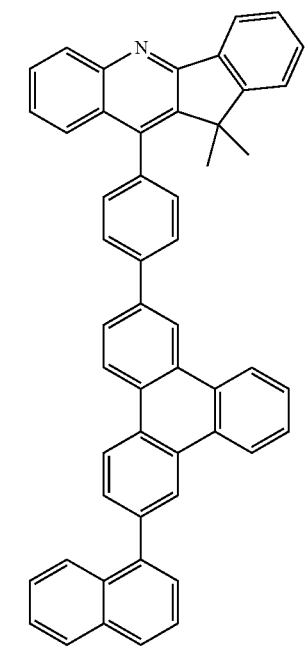
325
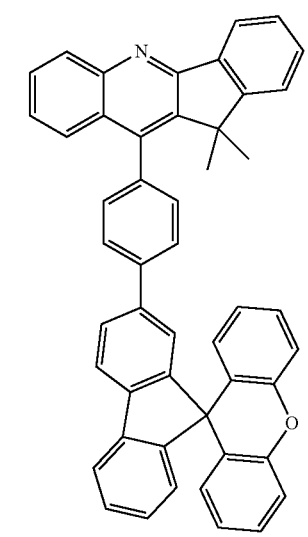
326
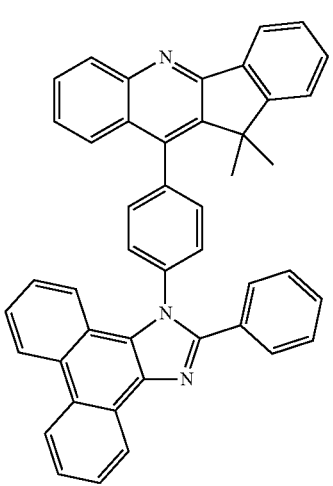
327
-continued
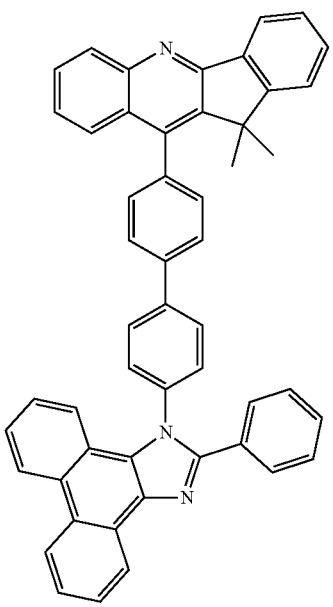
328
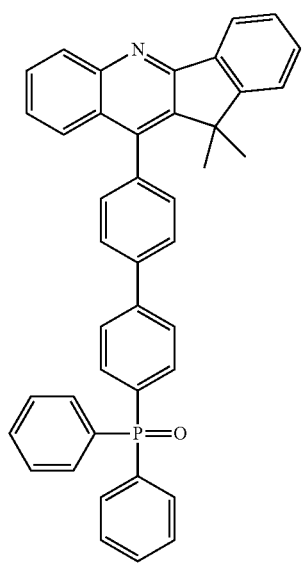
329

-continued
330
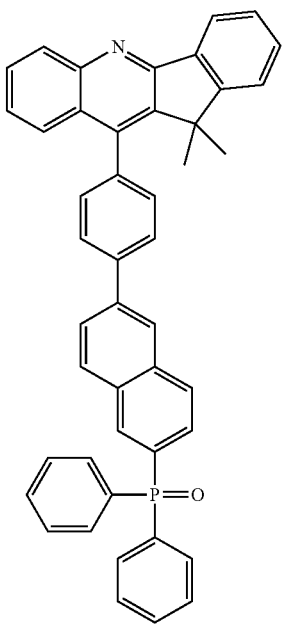
331
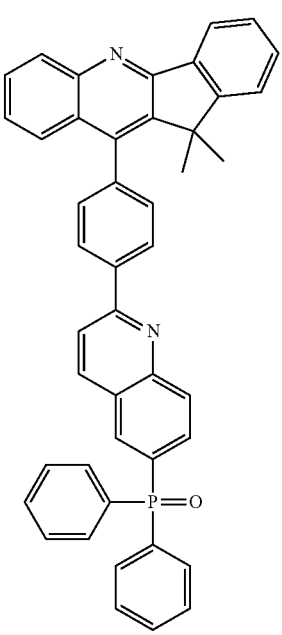
-continued
332
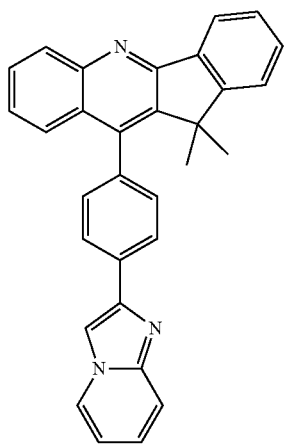
333
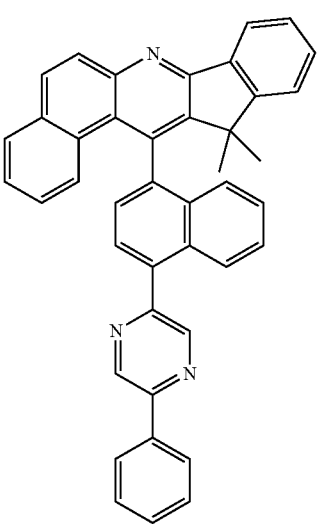
334
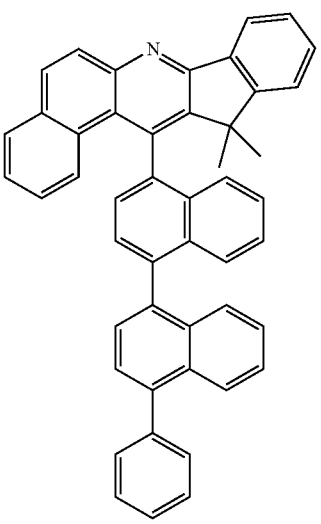

335
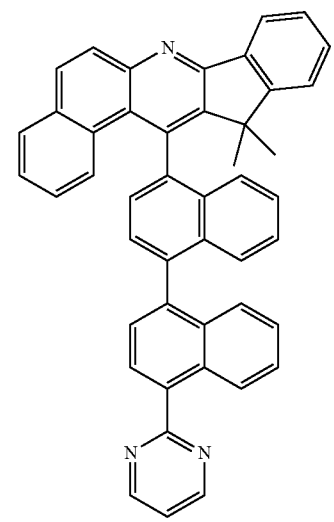
336
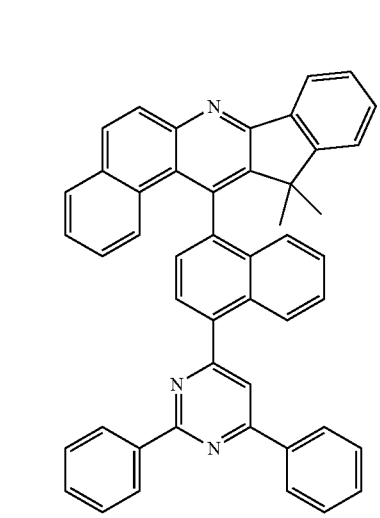
337
338
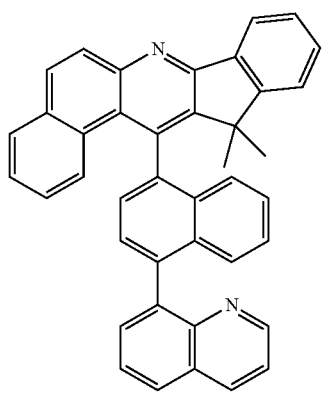
339
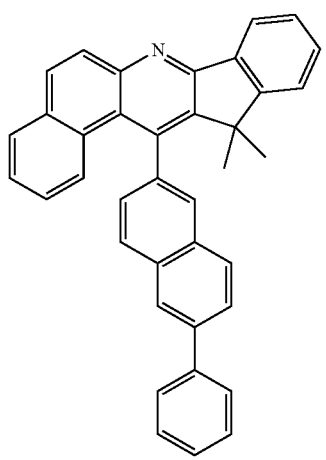
340
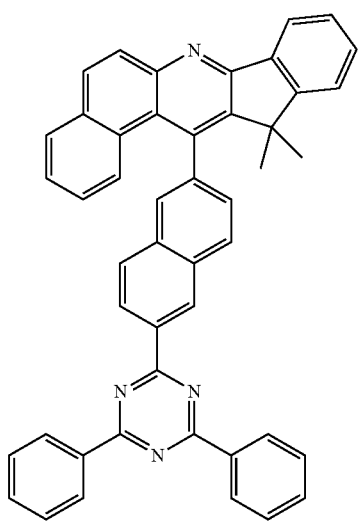

341
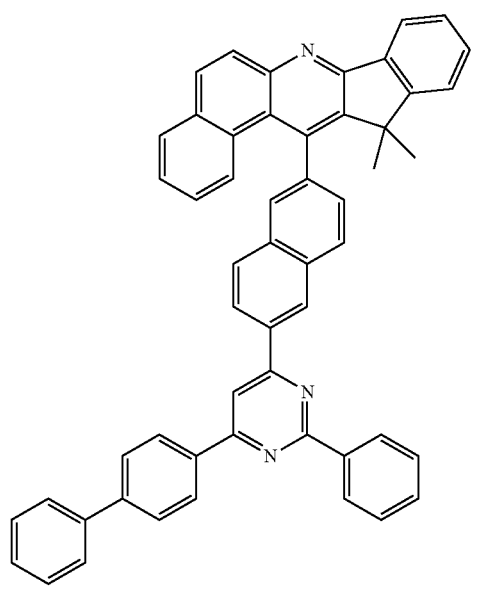
342
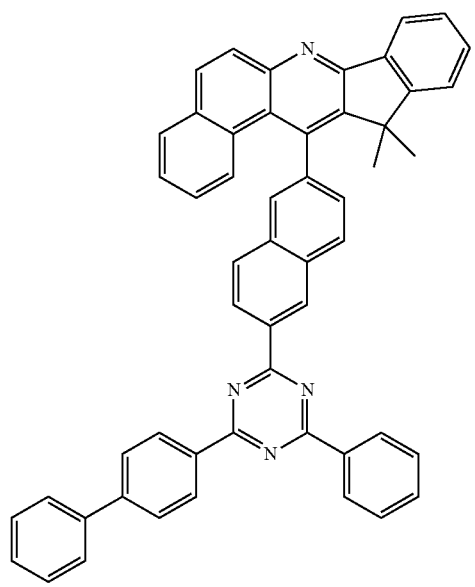
343
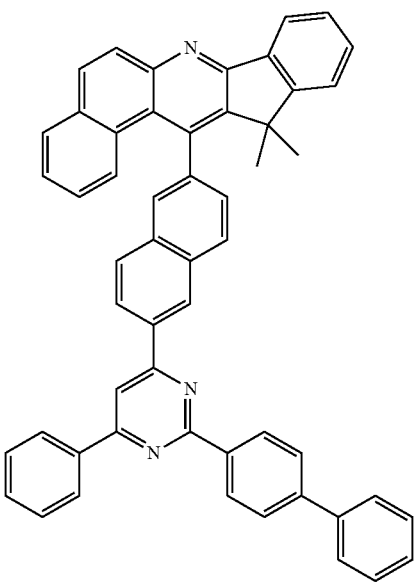
344
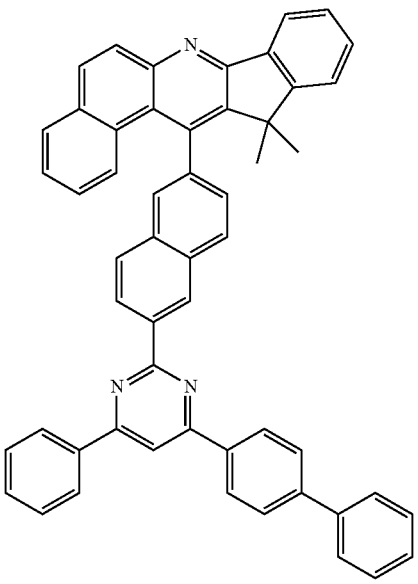

-continued
345
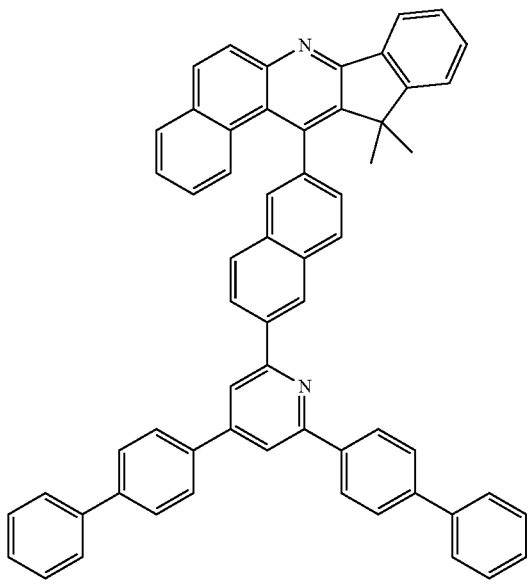
346
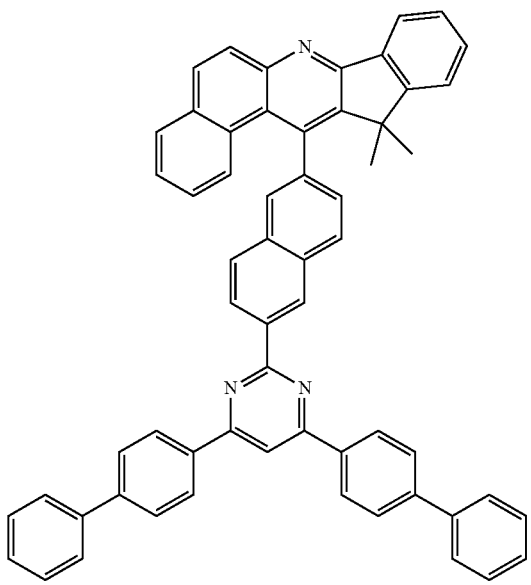
-continued
347
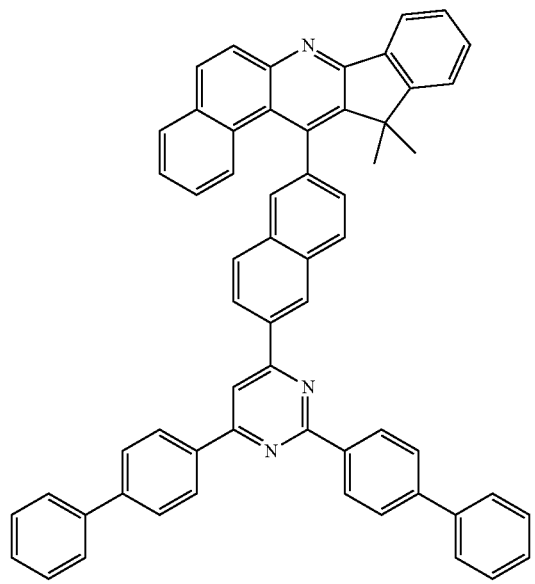
348
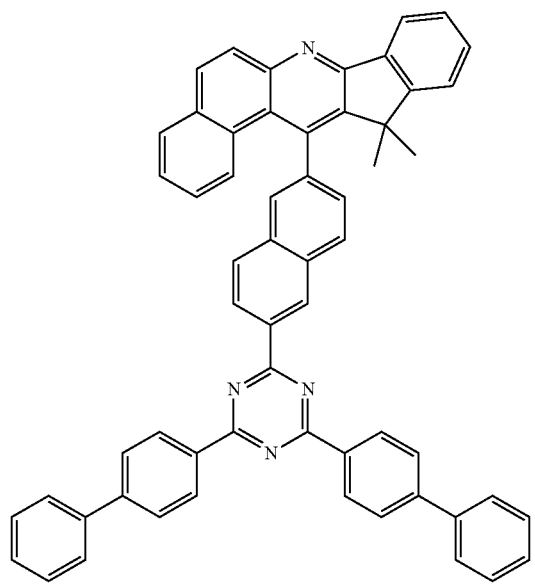

349 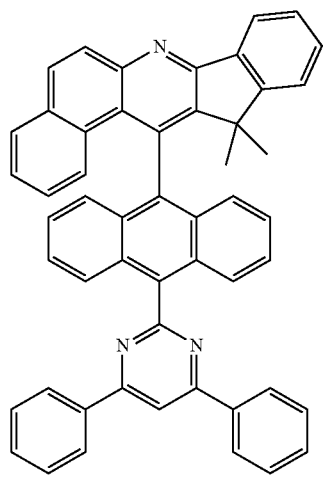
350 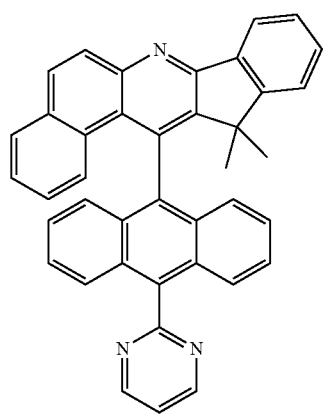
351 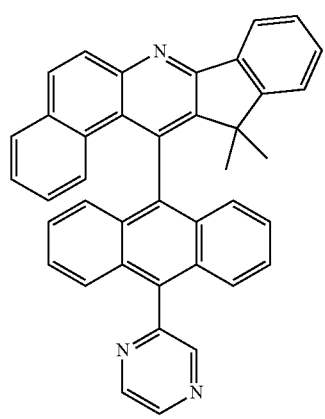
352 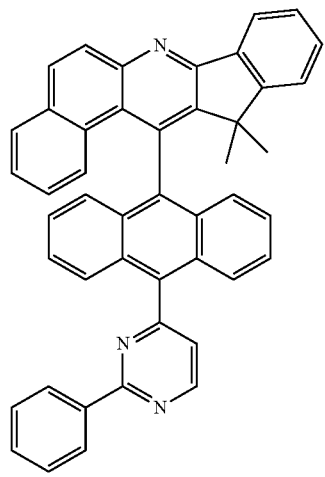
353 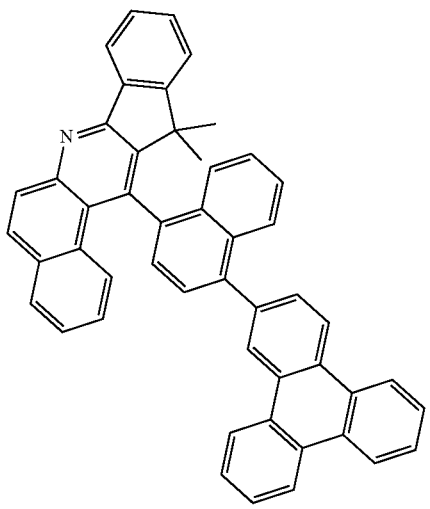
354 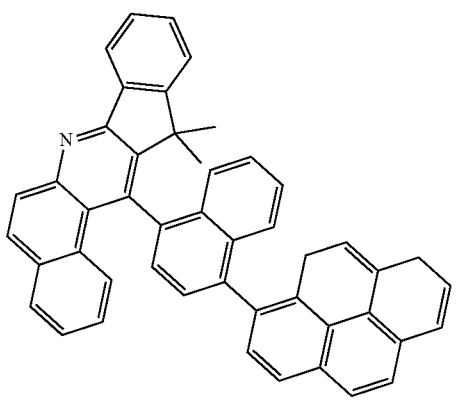

355 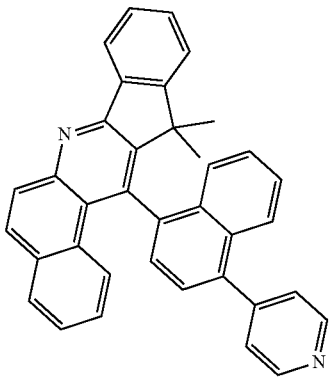
356 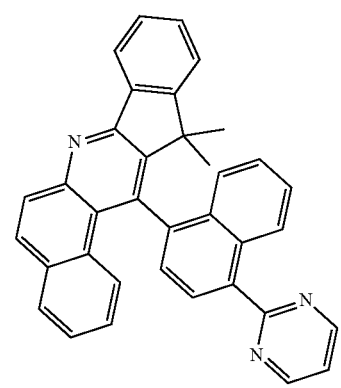
357 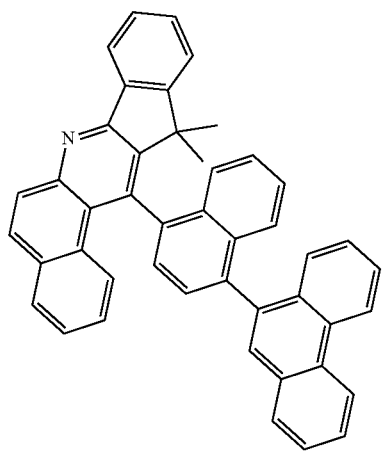
358 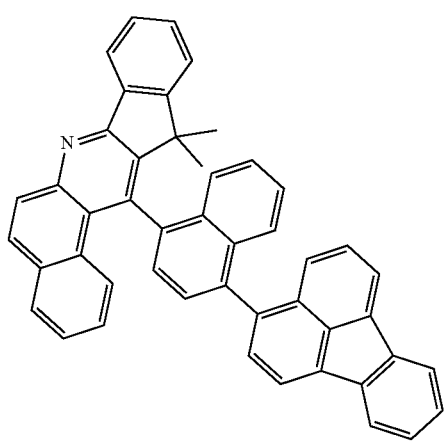
359 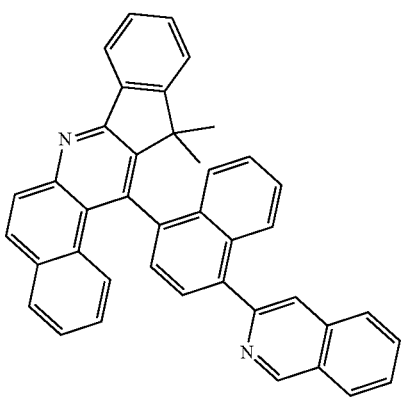
360 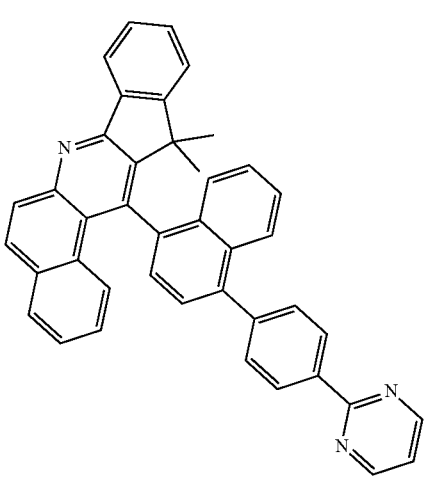
361 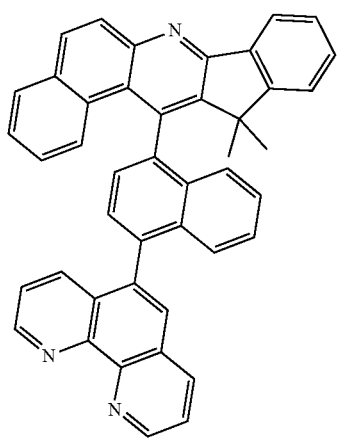

362
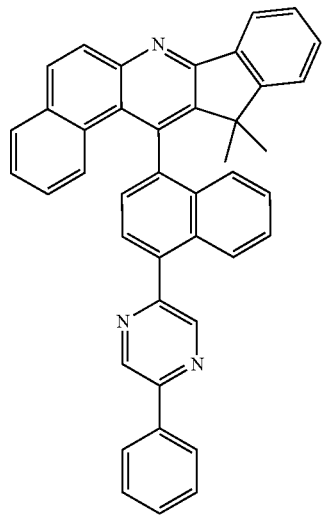
363
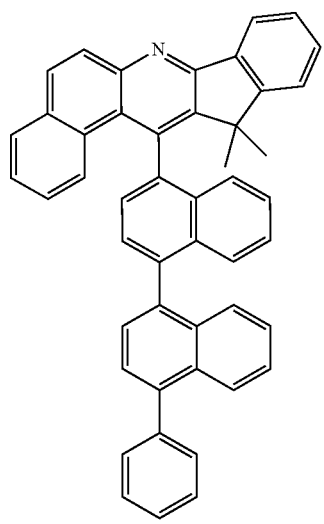
364
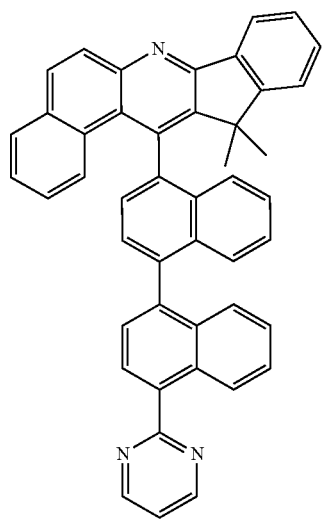
365
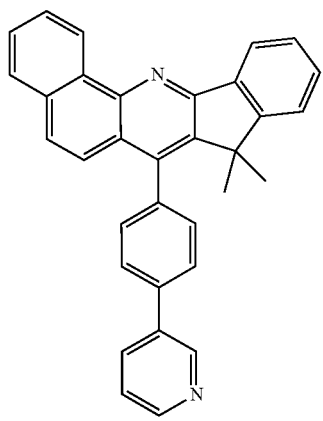
366
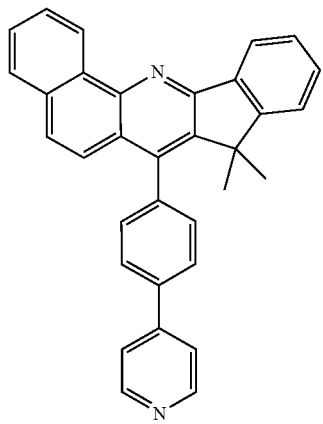
367
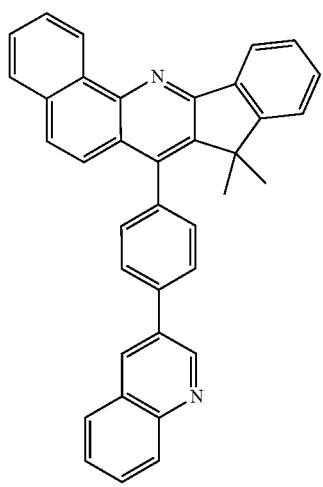

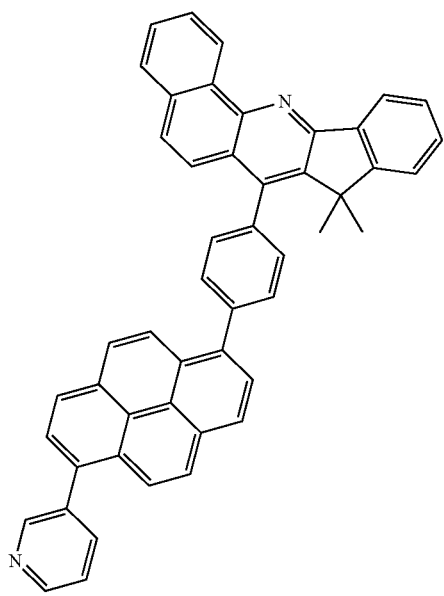
368
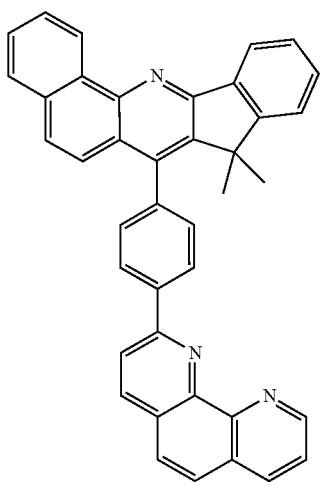
369
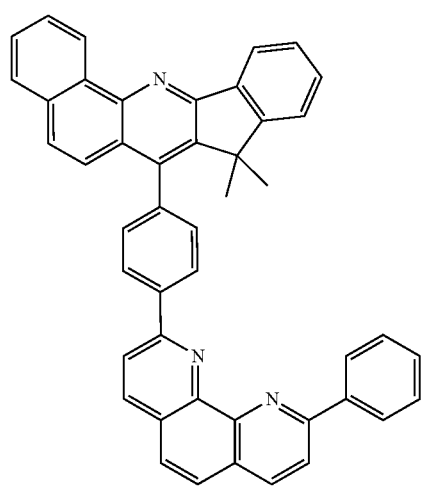
370
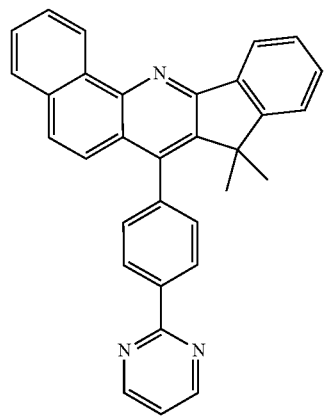
371
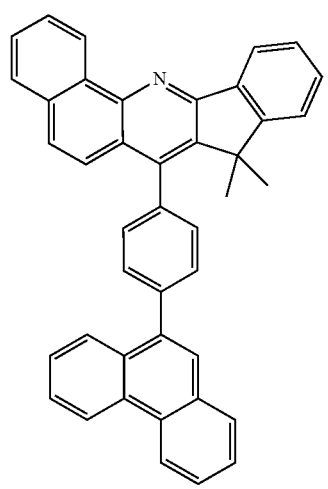
372
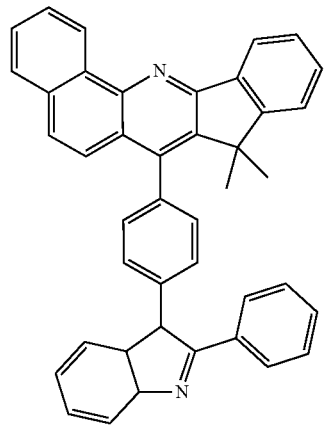
373

149
-continued
150
-continued
374
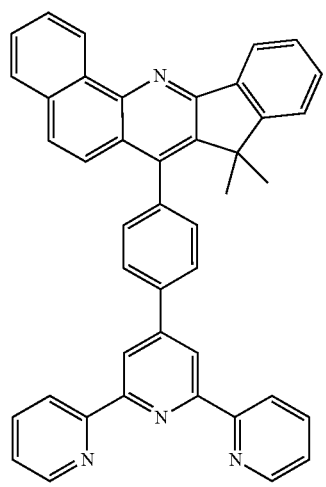
376
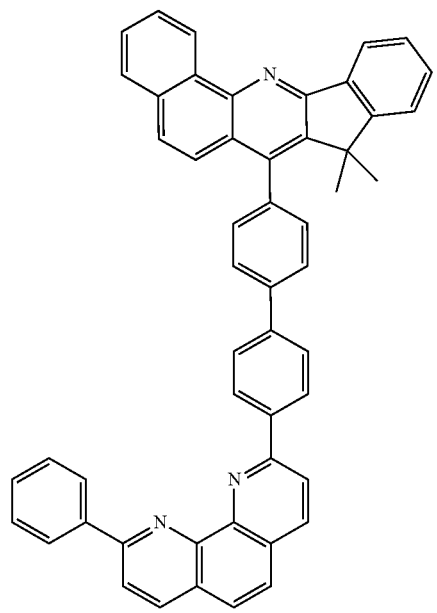
377
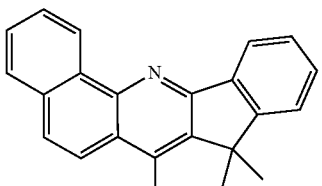
375
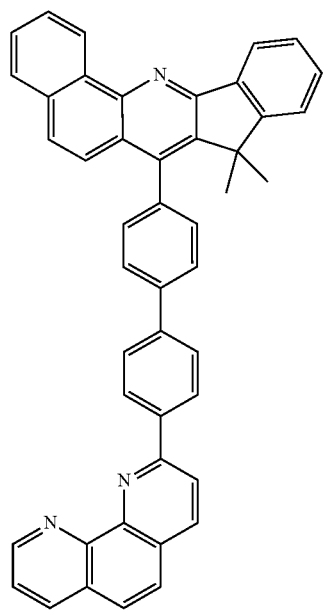
378
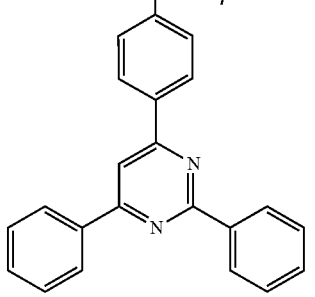
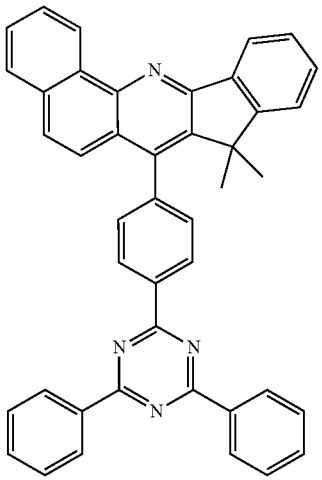

151
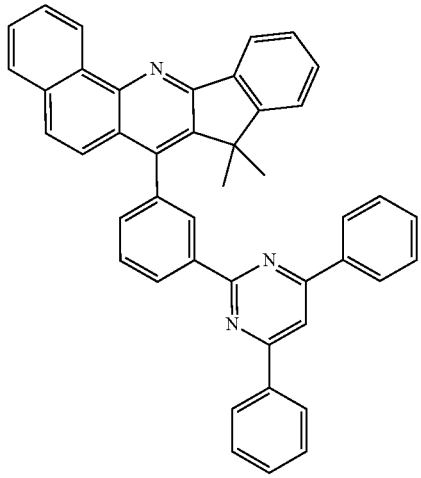
379
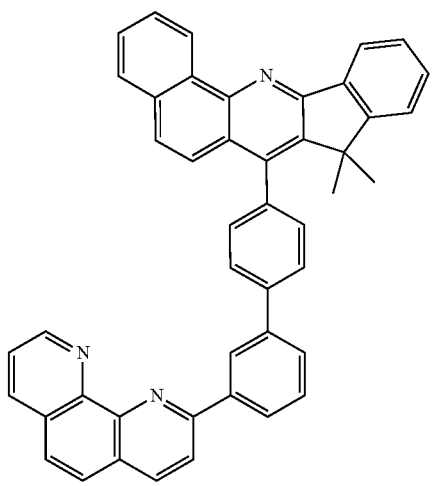
380
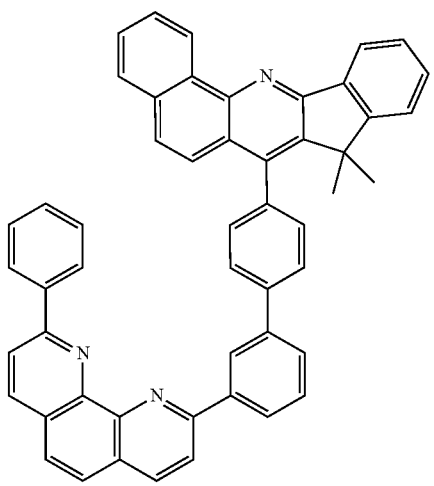
381
152
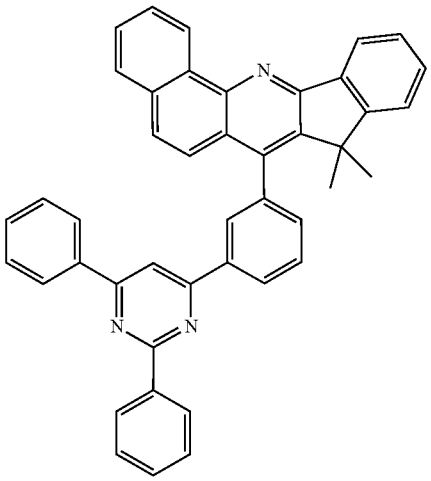
382
383
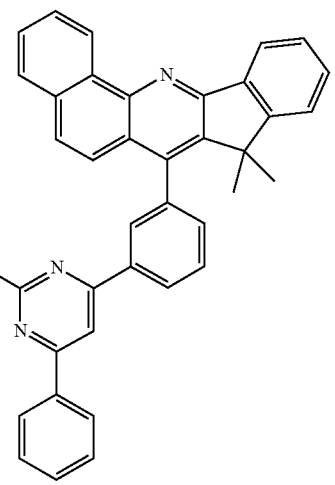
384

385
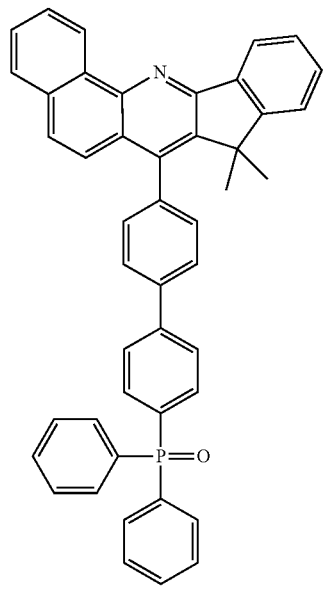
386
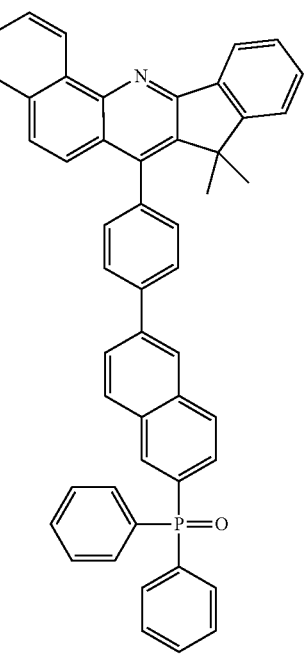
387
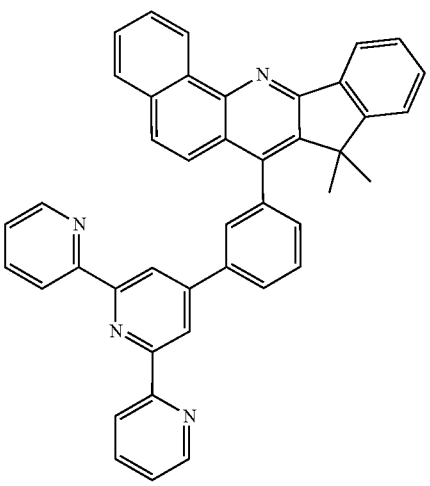
388
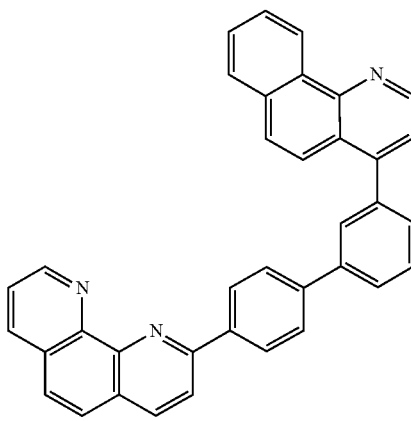
389
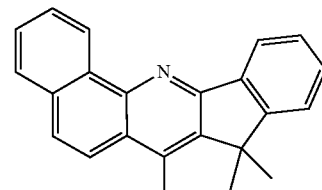

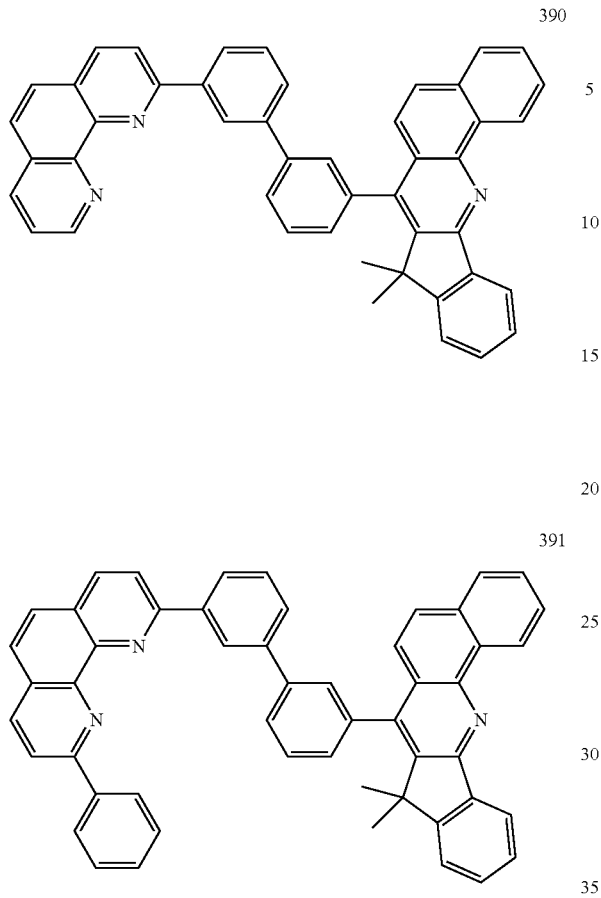
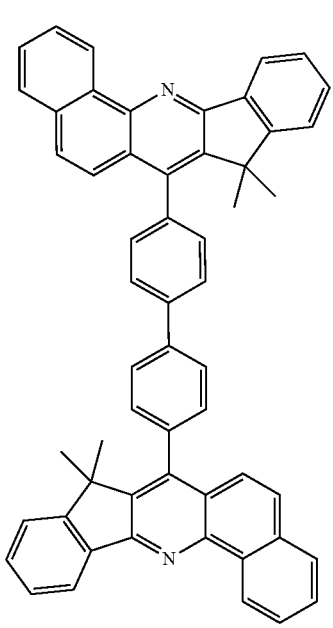
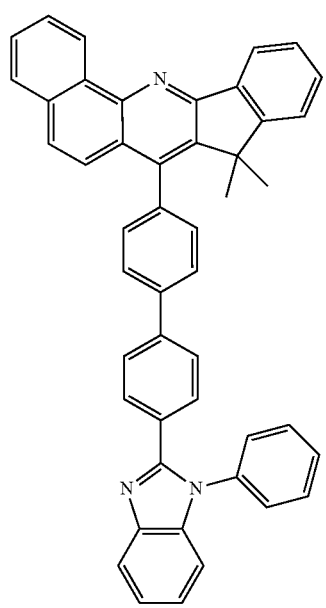
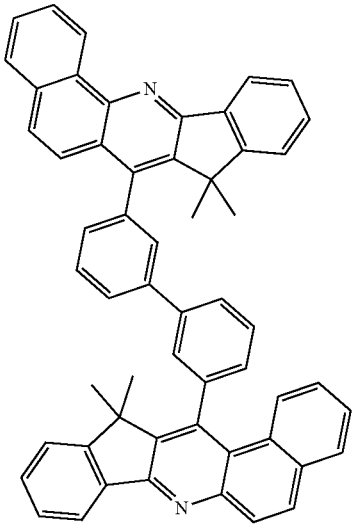

395
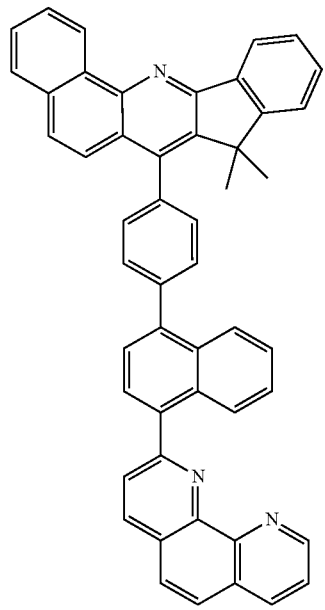
396
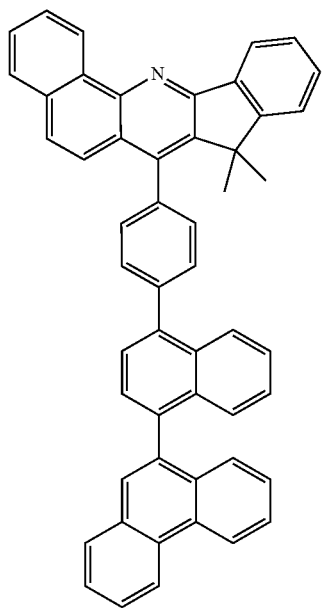
397
398
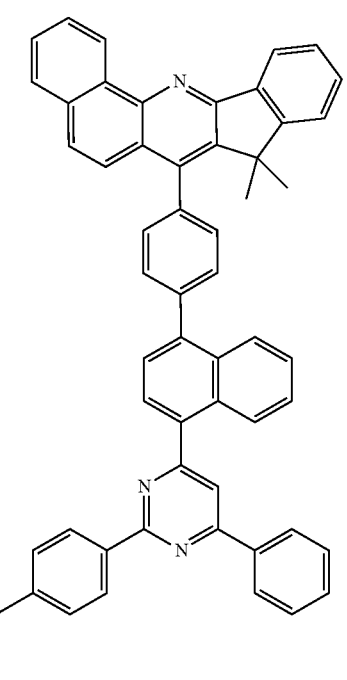

399

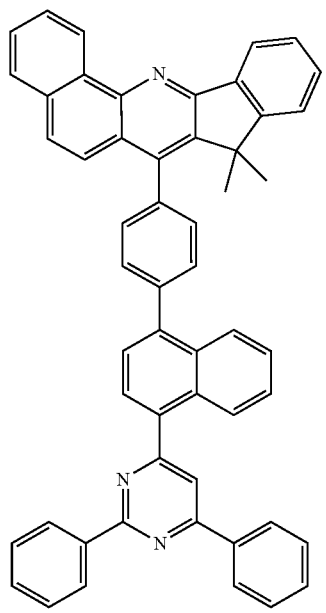

401

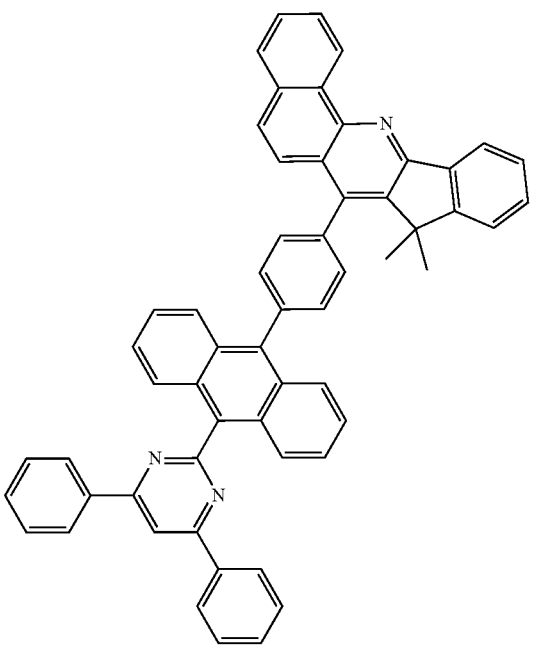

402

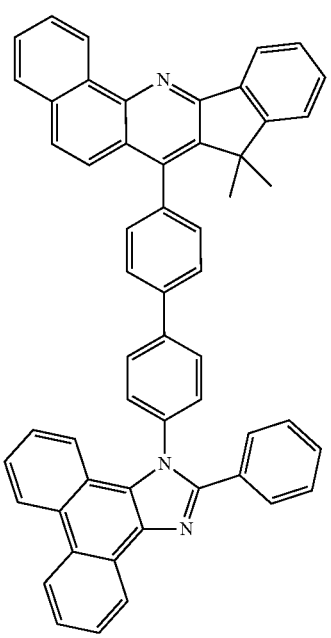

400

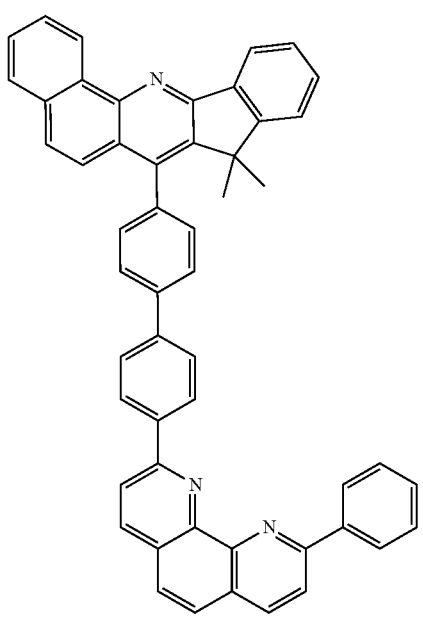

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the hetero-cyclic compound has excellent thermal stability with a high glass transition temperature (Tg). Such an increase in the thermal stability becomes an important factor in providing driving stability to a device.

The hetero-cyclic compound according to one embodiment of the present application may be prepared through a multistep chemical reaction. Some intermediate compounds are prepared first, and the compound of Chemical Formula 1 may be prepared from the intermediate compounds. More specifically, the hetero-cyclic compound according to one embodiment of the present application may be prepared based on preparation examples to be described below.

Another embodiment of the present application provides an organic light emitting device comprising the hetero-cyclic compound represented by Chemical Formula 1.

The organic light emitting device according to one embodiment of the present application may be manufactured using common organic light emitting device manufacturing methods and materials except that one or more organic material layers are formed using the hetero-cyclic compound described above.

The hetero-cyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

Specifically, the organic light emitting device according to one embodiment of the present application comprises an anode, a cathode, and one or more organic material layers provided between the anode and the cathode, wherein one or more layers of the organic material layers comprise the hetero-cyclic compound represented by Chemical Formula 1.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

In addition, the organic light emitting device according to one embodiment of the present application comprises an anode, a cathode, and two or more stacks provided between the anode and the cathode, wherein the two or more stacks each independently comprise a light emitting layer, a charge generation layer is included between the two or more stacks, and the charge generation layer comprises the hetero-cyclic compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the hetero-cyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the hetero-cyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first hole blocking layer, the second hole blocking layer and the like described in FIG. 4 may not be included in some cases.

The organic light emitting device according to the present specification may be manufactured using materials and methods known in the art except that one or more layers of the organic material layers comprise the hetero-cyclic compound represented by Chemical Formula 1.

The hetero-cyclic compound represented by Chemical Formula 1 may form one or more layers of the organic material layers of the organic light emitting device alone. However, as necessary, the hetero-cyclic compound represented by Chemical Formula 1 may be mixed with other materials to form the organic material layers.

The hetero-cyclic compound represented by Chemical Formula 1 may be used as a material of the charge generation layer in the organic light emitting device.

The hetero-cyclic compound represented by Chemical Formula 1 may be used as a material of the electron transfer layer, the hole blocking layer, the light emitting layer or the like in the organic light emitting device. As one example, the hetero-cyclic compound represented by Chemical Formula 1 may be used as a material of the electron transfer layer, the hole transfer layer or the light emitting layer in the organic light emitting device.

In addition, the hetero-cyclic compound represented by Chemical Formula 1 may be used as a material of the light emitting layer in the organic light emitting device. As one example, the hetero-cyclic compound represented by Chemical Formula 1 may be used as a phosphorescent host material of the light emitting layer in the organic light emitting device.

In the organic light emitting device according to one embodiment of the present application, materials other than the hetero-cyclic compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylcompound), poly[3,4-(ethylene-1,2-dioxy)compound](PEDT), polypyrrole and polyaniline, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. In addition, fluorescent materials may also be used as the light emitting material, however, phosphorescent materials may also be used.

As the light emitting material, materials emitting light by bonding electrons and holes injected from an anode and a cathode, respectively, may be used alone, however, materials having a host material and a dopant material involved in light emission together may also be used.

The organic light emitting device according to one embodiment of the present application may be a top-emission type, a bottom-emission type or a dual-emission type depending on the materials used.

The hetero-cyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

EXAMPLE

<Preparation Example 1> Preparation of Compound 10

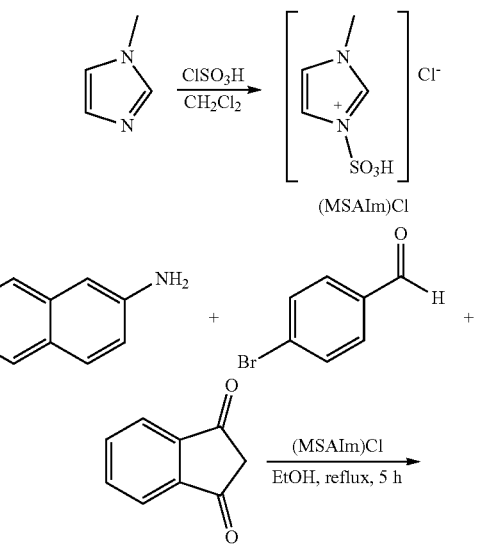

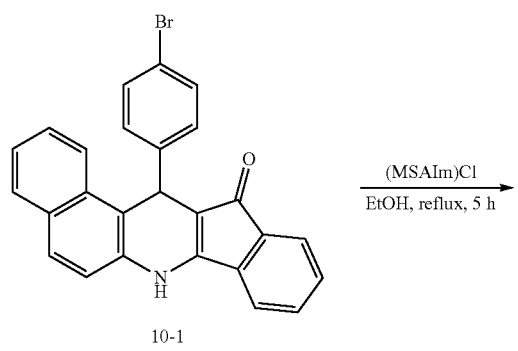

10-1

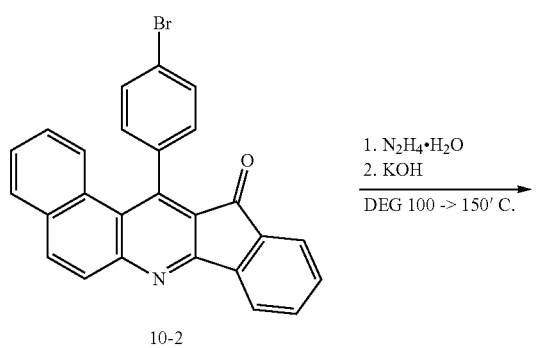

10-2

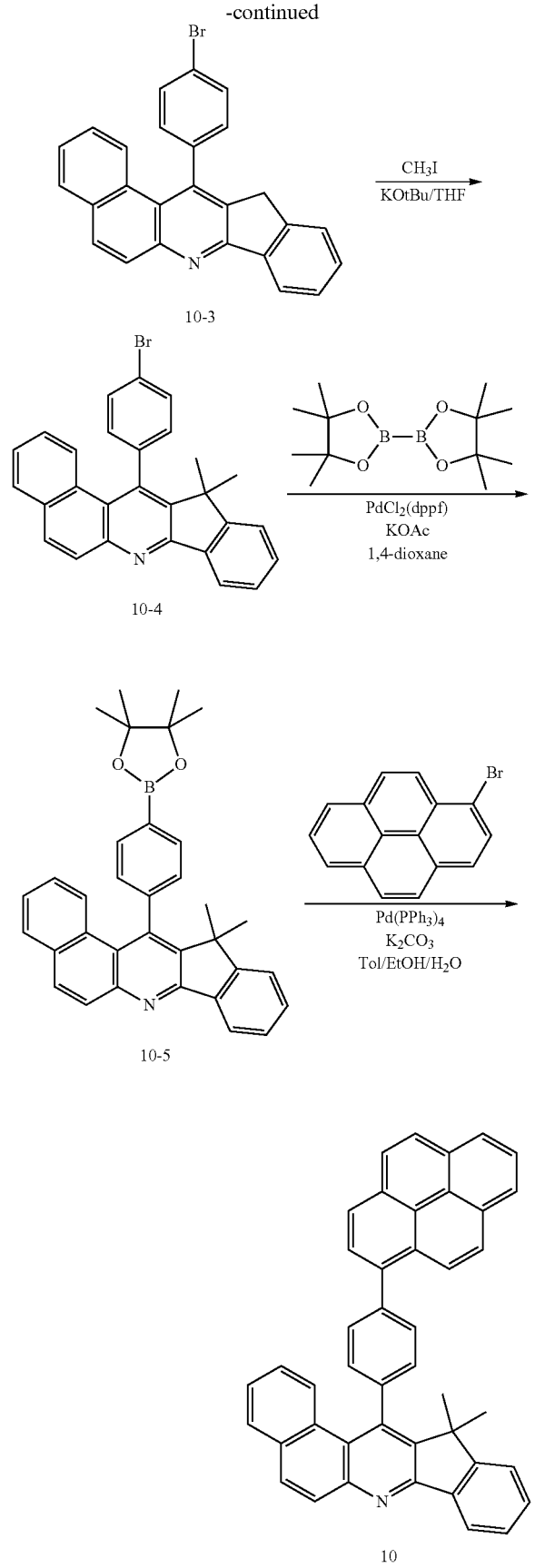

1) Preparation of (MSAIm)Cl

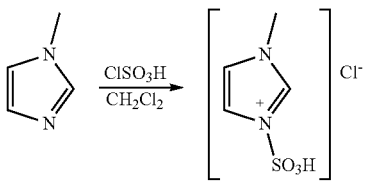

A 1-methyl-1H-imidazole compound (2 g, 24.36 mmol) was dissolved in 50 ml of MC. Chlorosulfonic acid (1.6 ml, 24.36 mmol) was added dropwise thereto at 0° C., the temperature was raised to room temperature, and the result was stirred for 1 hour. The reaction solution was washed twice with dichloromethane to obtain target Compound (MSAIm)Cl (3.2 g, 67%).

2) Preparation of Compound 10-1

After dissolving a naphtylamine compound (16.2 g, 112.91 mmol) in 200 ml of EtOH, 4-bromobenzaldehyde (19 g, 102.64 mmol), 1H-indene-1,3 (2H)-dione (15 g, 102.64 mmol) and (MSAIm)Cl (1 g, 5.13 mmol) were added thereto, and the result was stirred under reflux. Excess EtOH was added thereto, and the result was ultrasonic treated and filtered to obtain target Compound 10-1 (42 g, 85%).

3) Preparation of Compound 10-2

500 ml of MC was introduced to Compound 10-1 (42 g, 95.82 mmol) and dispersed. $MnO_2$ (142 g, 1633.31 mmol) was added thereto, and the result was stirred for 24 hours at room temperature. Solids were filtered, and the filtrate was concentrated and recrystallized with MC/MeOH to obtain target Compound 10-2 (13 g, 31%).

4) Preparation of Compound 10-3

After dissolving Compound 10-2 (13 g, 29.80 mmol) in 400 ml of DEG, hydrazine monohydrate (95.5 g, 2979.60 mmol) was added thereto, and the result was stirred under reflux. KOH (16.7 g, 297.96 mmol) dissolved in 80 ml of D.W was added dropwise thereto, and the result was stirred at 140° C. 1 L of D.W was added thereto for precipitation and the result was filtered, washed with D.W and MeOH, and then dried to obtain target Compound 10-3 (11.5 g, 91%).

5) Preparation of Compound 10-4

After dissolving Compound 10-3 (11 g, 26.05 mmol) in 150 ml of THF, KOt-Bu (8.8 g, 78.14 mmol) was added thereto at 0° C., and the result was stirred for 10 minutes. Iodomethane (11.1 g, 78.14 mmol) was added thereto, and the result was stirred at room temperature. D.W was added thereto, the result was extracted with MC, and the MC layer was dried with anhydrous $Na_2SO_4$.

The result was purified using column chromatography with EA and hexane as a developing solvent to obtain target Compound 10-4 (9 g, 77%).

6) Preparation of Compound 10-5

After dissolving Compound 10-4 (9.2 g, 20.43 mmol) in 200 ml of 1,4-dioxane, bis(pinacolato)diboron (7.8 g, 30.64 mmol), PdCl$_2$(dppf) (0.8 g, 1.02 mmol) and potassium acetate (8 g, 81.71 mmol) were added thereto, and the result was stirred under reflux. D.W was added thereto, the result was extracted with MC, and the MC layer was dried with anhydrous Na$_2$SO$_4$. The result was purified using column chromatography with EA and hexane as a developing solvent to obtain target Compound 10-5 (10 g, 98%).

7) Preparation of Compound 10

After introducing Compound 10-5 (11.2 g, 22.52 mmol) and 1-bromopyrene (5.7 g, 20.26 mmol) to 100 ml of toluene, 20 ml of EtOH and 20 ml of D.W, Pd(PPh$_3$)$_4$ (1.3 g, 1.13 mmol) and K$_2$CO$_3$ (6.2 g, 45.03 mmol) were added thereto, and the result was stirred under reflux. D.W was added thereto, the result was extracted with MC, and the MC layer was dried with anhydrous Na$_2$SO$_4$. After vacuum concentrating the solvent, MeOH was added thereto to recrystallize and obtain solids. The result was purified using column chromatography with EA and hexane as a developing solvent to obtain target Compound 10 (7.9 g, 61%).

Target Compound A was synthesized in the same manner as the preparation of Compound 10 except that, in Preparation Example 1, Intermediate A of the following Table 1 was used instead of 1-bromopyrene.

TABLE 1

| Compound Number | Intermediate A | Target Compound A | Yield |
|---|---|---|---|
| 1 | 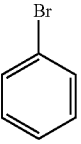 | 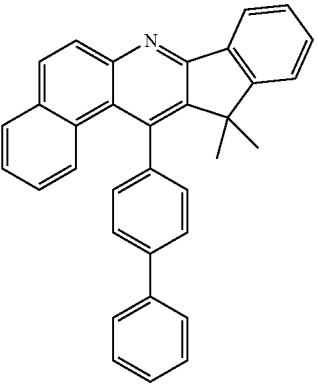 | 55% |
| 6 | 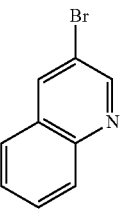 | 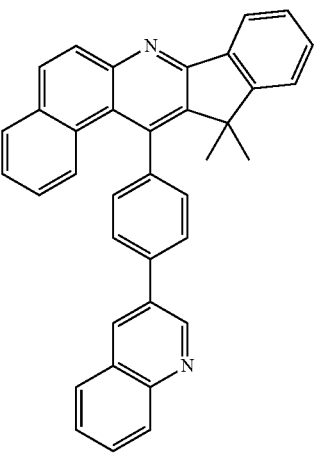 | 50% |

TABLE 1-continued

| Compound Number | Intermediate A | Target Compound A | Yield |
| --- | --- | --- | --- |
| 13 | | | 61% |
| 14 | | | 60% |
| 15 | | | 54% |

TABLE 1-continued
| Compound Number | Intermediate A | Target Compound A | Yield |
|---|---|---|---|
| 27 | 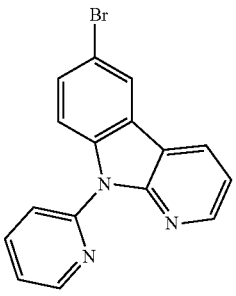 [SMILES: Brc1ccc2c(c1)c1cccnc1n2-c1ccccn1] | 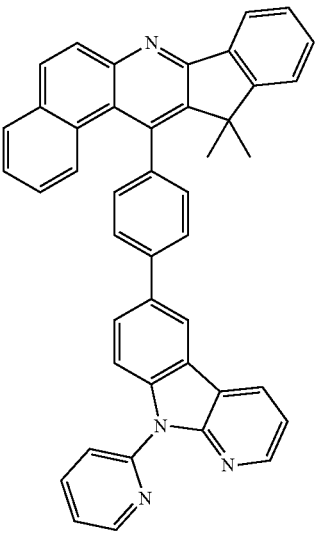 [SMILES: CC1(C)c2ccccc2-c2nc3ccc4ccccc4c3c(-c3ccc(-c4ccc5c(c4)c4cccnc4n5-c4ccccn4)cc3)c21] | 59% |
| 32 | 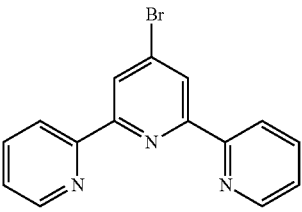 [SMILES: Brc1cc(-c2ccccn2)nc(-c2ccccn2)c1] | 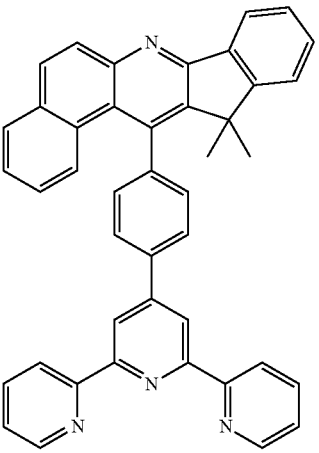 [SMILES: CC1(C)c2ccccc2-c2nc3ccc4ccccc4c3c(-c3ccc(-c4cc(-c5ccccn5)nc(-c5ccccn5)c4)cc3)c21] | 64% |
| 34 | 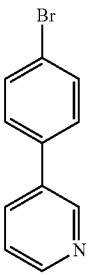 [SMILES: Brc1ccc(-c2cccnc2)cc1] | 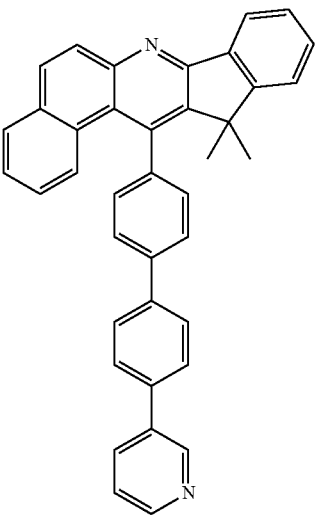 [SMILES: CC1(C)c2ccccc2-c2nc3ccc4ccccc4c3c(-c3ccc(-c4ccc(-c5cccnc5)cc4)cc3)c21] | 62% |

TABLE 1-continued

| Compound Number | Intermediate A | Target Compound A | Yield |
|---|---|---|---|
| 44 | | | 51% |
| 53 | | | 58% |
| 65 | | | 57% |

TABLE 1-continued

| Compound Number | Intermediate A | Target Compound A | Yield |
|---|---|---|---|
| 72 | | | 55% |
| 77 | | | 50% |
| 80 | | | 50% |

TABLE 1-continued
| Compound Number | Intermediate A | Target Compound A | Yield |
|---|---|---|---|
| 110 | 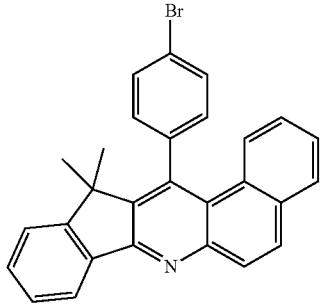 [SMILES: CC1(C)c2ccccc2-c2nc3ccc4ccccc4c3c(-c3ccc(Br)cc3)c21] | 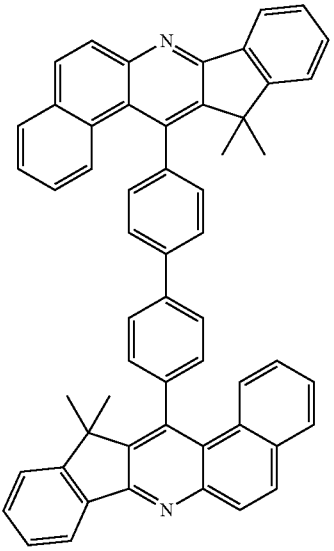 [SMILES: CC1(C)c2ccccc2-c2nc3ccc4ccccc4c3c(-c3ccc(-c4ccc(-c5c6c(nc7ccc8ccccc8c57)-c5ccccc5C6(C)C)cc4)cc3)c21] | 55% |
| 113 | 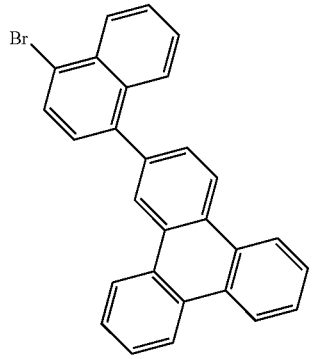 [SMILES: Brc1ccc(-c2ccc3c4ccccc4c4ccccc4c3c2)c2ccccc12] | 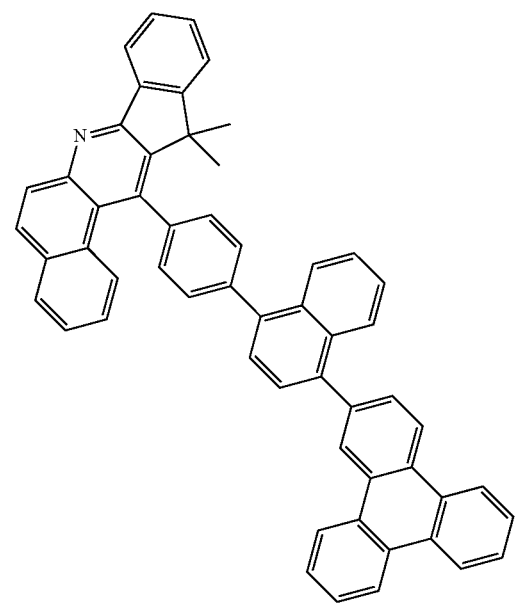 [SMILES: CC1(C)c2ccccc2-c2nc3ccc4ccccc4c3c(-c3ccc(-c4ccc(-c5ccc6c7ccccc7c7ccccc7c6c5)c5ccccc45)cc3)c21] | 51% |

TABLE 1-continued

| Compound Number | Intermediate A | Target Compound A | Yield |
|---|---|---|---|
| 117 | | | 57% |
| 120 | | | 61% |

TABLE 1-continued
| Compound Number | Intermediate A | Target Compound A | Yield |
|---|---|---|---|
| 124 | 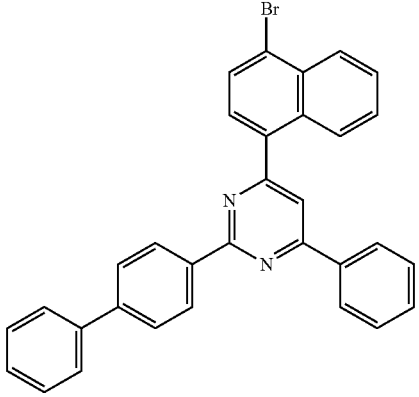 [SMILES: Brc1ccc(-c2cc(-c3ccccc3)nc(-c3ccc(-c4ccccc4)cc3)n2)c2ccccc12] | 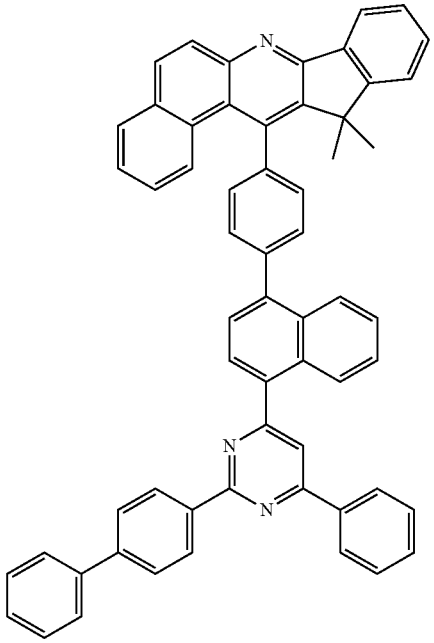 [SMILES: CC1(C)c2ccccc2-c2nc3ccc4ccccc4c3c(-c3ccc(-c4ccc(-c5cc(-c6ccccc6)nc(-c6ccc(-c7ccccc7)cc6)n5)c5ccccc45)cc3)c21] | 59% |
| 128 | 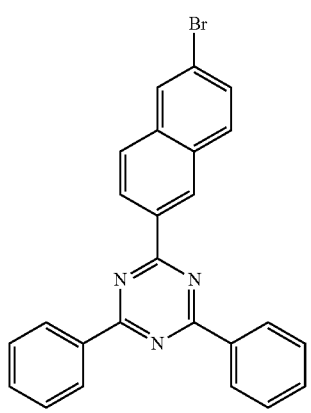 [SMILES: Brc1ccc2cc(-c3nc(-c4ccccc4)nc(-c4ccccc4)n3)ccc2c1] | 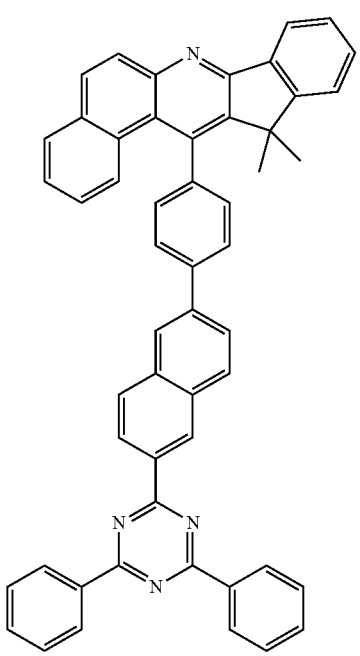 [SMILES: CC1(C)c2ccccc2-c2nc3ccc4ccccc4c3c(-c3ccc(-c4ccc5cc(-c6nc(-c7ccccc7)nc(-c7ccccc7)n6)ccc5c4)cc3)c21] | 53% |

TABLE 1-continued

| Compound Number | Intermediate A | Target Compound A | Yield |
|---|---|---|---|
| 130 | | | 63% |
| 138 | | | 51% |
| 146 | | | 50% |

TABLE 1-continued
| Compound Number | Intermediate A | Target Compound A | Yield |
|---|---|---|---|
| 155 | 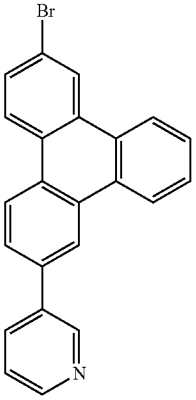 [SMILES: Brc1ccc2c3ccc(-c4cccnc4)cc3c3ccccc3c2c1] | 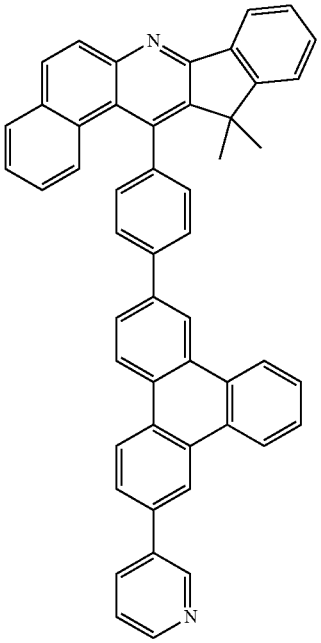 [SMILES: CC1(C)c2ccccc2-c2nc3ccc4ccccc4c3c(-c3ccc(-c4ccc5c6ccc(-c7cccnc7)cc6c6ccccc6c5c4)cc3)c21] | 54% |
| 160 | 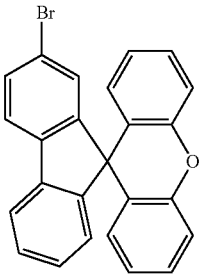 [SMILES: Brc1ccc2c(c1)C1(c3ccccc3Oc3ccccc31)c1ccccc1-2] | 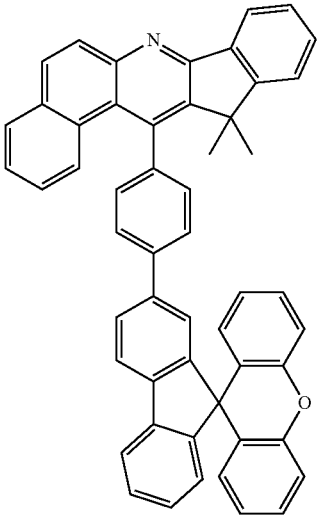 [SMILES: CC1(C)c2ccccc2-c2nc3ccc4ccccc4c3c(-c3ccc(-c4ccc5c(c4)C4(c6ccccc6Oc6ccccc64)c4ccccc4-5)cc3)c21] | 55% |

TABLE 1-continued

| Compound Number | Intermediate A | Target Compound A | Yield |
|---|---|---|---|
| 162 | | | 59% |
| 164 | | | 57% |

<Preparation Example 2> Preparation of Compound 179

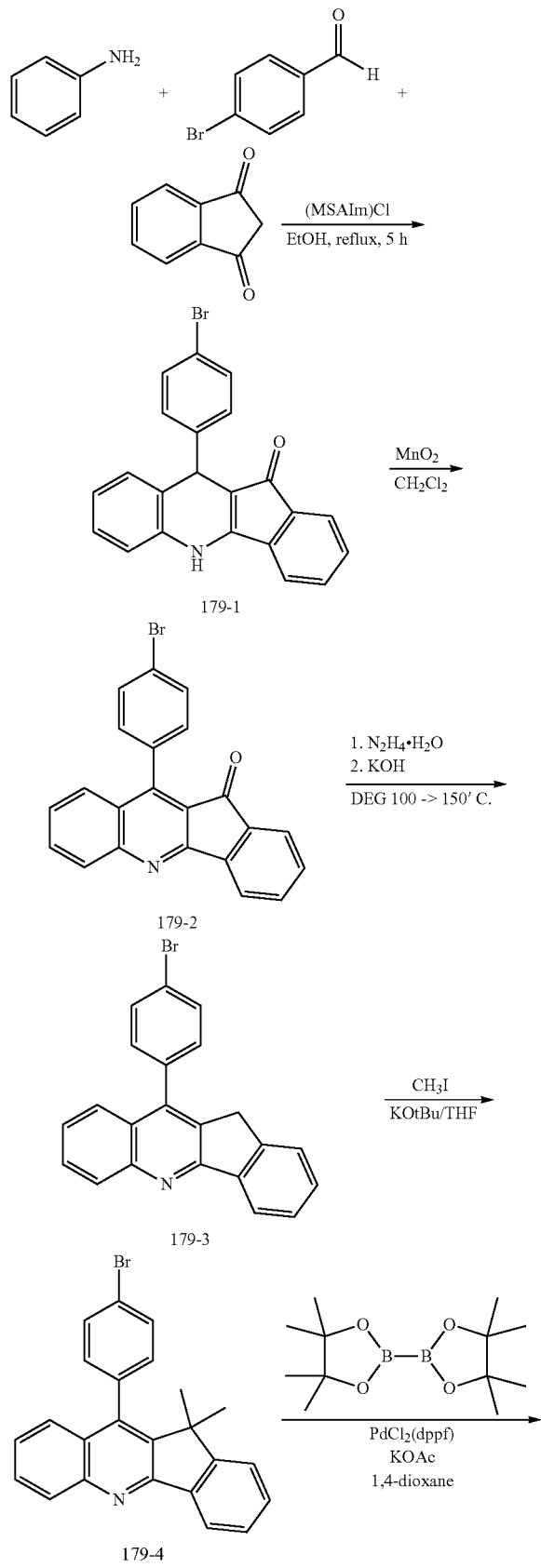

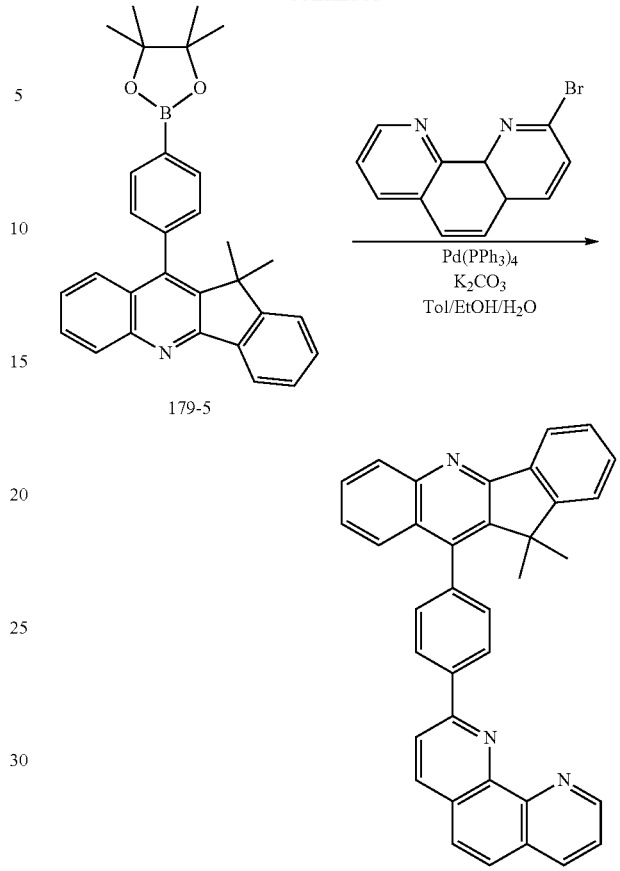

1) Preparation of Compound 179-1

After dissolving an aniline compound (10.4 g, 112.91 mmol) in 200 ml of EtOH, 4-bromobenzaldehyde (19 g, 102.64 mmol), 1H-indene-1,3(2H)-dione (15 g, 102.64 mmol) and (MSAIm)Cl (1 g, 5.13 mmol) were added thereto, and the result was stirred under reflux. Excess EtOH was added thereto, and the result was ultrasonic treated and filtered to obtain target Compound 179-1 (42 g, 85%).

2) Preparation of Compound 179-2

500 ml of MC was introduced to Compound 179-1 (37 g, 95.82 mmol) and dispersed. MnO₂ (142 g, 1633.31 mmol) was added thereto, and the result was stirred for 24 hours at room temperature. Solids were filtered, and the filtrate was concentrated and recrystallized with MC/MeOH to obtain target Compound 179-2 (13 g, 31%).

3) Preparation of Compound 179-3

After dissolving Compound 179-2 (11.5 g, 29.80 mmol) in 400 ml of DEG, hydrazine monohydrate (95.5 g, 2979.60 mmol) was added thereto, and the result was stirred under reflux. KOH (16.7 g, 297.96 mmol) dissolved in 80 ml of D.W was added dropwise thereto, and the result was stirred at 140° C. 1 L of D.W was added thereto for precipitation and the result was filtered, washed with D.W and MeOH, and then dried to obtain target Compound 179-3 (11.5 g, 91%).

4) Preparation of Compound 179-4

After dissolving Compound 179-3 (9.6 g, 26.05 mmol) in 150 ml of THF, KOt-Bu (8.8 g, 78.14 mmol) was added thereto at 0° C., and the result was stirred for 10 minutes. Iodomethane (11.1 g, 78.14 mmol) was added thereto, and the result was stirred at room temperature. D.W was added thereto, the result was extracted with MC, and the MC layer was dried with anhydrous $Na_2SO_4$.

The result was purified using column chromatography with EA and hexane as a developing solvent to obtain target Compound 179-4 (9 g, 77%).

5) Preparation of Compound 179-5

After dissolving Compound 179-4 (9.7 g, 20.43 mnmol) in 200 ml of 1,4-dioxane, bis(pinacolato)diboron (7.8 g, 30.64 mmol), $PdCl_2(dppf)$ (0.8 g, 1.02 mmol) and potassium acetate (8 g, 81.71 mmol) were added thereto, and the result was stirred under reflux. D.W was added thereto, the result was extracted with MC, and the MC layer was dried with anhydrous $Na_2SO_4$. The result was purified using column chromatography with EA and hexane as a developing solvent to obtain target Compound 179-5 (10 g, 98%).

6) Preparation of Compound 179

After introducing Compound 179-5 (11.2 g, 22.52 mmol) and 2-bromo-1,10-phenanthroline (5.3 g, 20.26 mmol) to 100 ml of toluene, 20 ml of EtOH and 20 ml of D.W, $Pd(PPh_3)_4$ (1.3 g, 1.13 mmol) and $K_2CO_3$ (6.2 g, 45.03 mmol) were added thereto, and the result was stirred under reflux. D.W was added thereto, the result was extracted with MC, and the MC layer was dried with anhydrous $Na_2SO_4$. After vacuum concentrating the solvent, MeOH was added thereto to recrystallize and obtain solids. The result was purified using column chromatography with EA and hexane as a developing solvent to obtain target Compound 179 (7.1 g, 57%).

Target Compound B was synthesized in the same manner as the preparation of Compound 179 except that, in Preparation Example 2, Intermediate B of the following Table 2 was used instead of 2-bromo-1,10-phenanthroline.

TABLE 2

| Compound Number | Intermediate B | Target Compound B | Yield |
|---|---|---|---|
| 171 | 2-bromonaphthalene | [structure] | 50% |
| 174 | 2-bromoanthracene | [structure] | 58% |

TABLE 2-continued

| Compound Number | Intermediate B | Target Compound B | Yield |
|---|---|---|---|
| 178 | | | 49% |
| 184 | | | 55% |
| 195 | | | 48% |

TABLE 2-continued
| Compound Number | Intermediate B | Target Compound B | Yield |
|---|---|---|---|
| 196 |  | 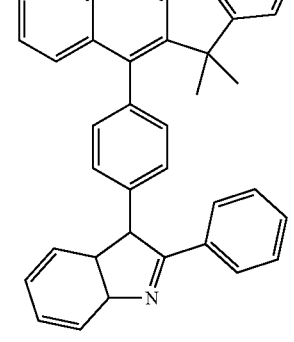 | 60% |
| 208 | 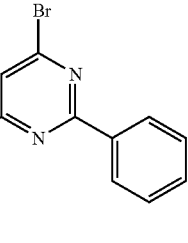 | 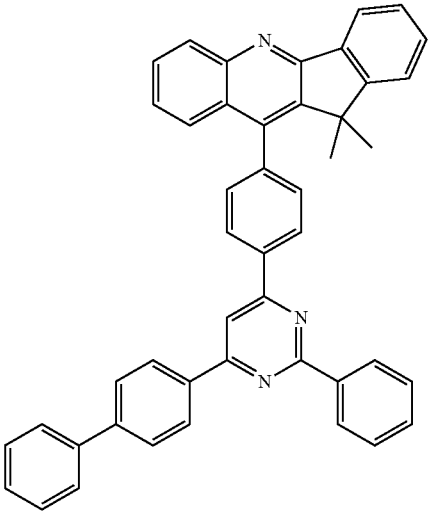 | 58% |
| 211 | 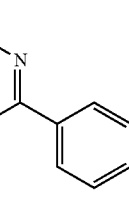 | 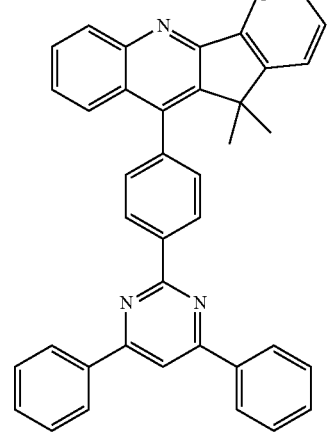 | 55% |

TABLE 2-continued

| Compound Number | Intermediate B | Target Compound B | Yield |
|---|---|---|---|
| 218 | | | 46% |
| 224 | | | 40% |
| 226 | | | 40% |

TABLE 2-continued

| Compound Number | Intermediate B | Target Compound B | Yield |
|---|---|---|---|
| 280 | | | 51% |
| 284 | | | 56% |
| 290 | | | 55% |

TABLE 2-continued
| Compound Number | Intermediate B | Target Compound B | Yield |
|---|---|---|---|
| 298 | 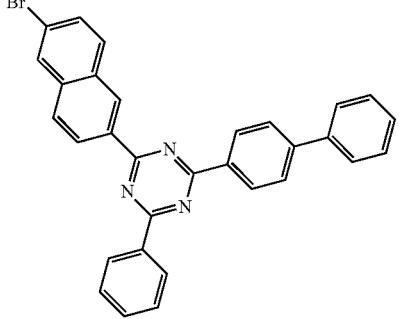 | 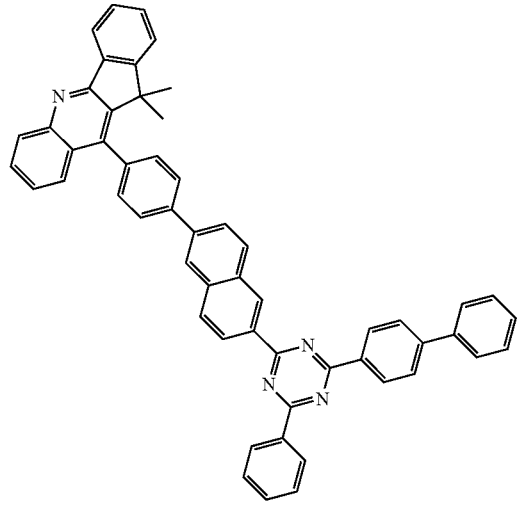 | 50% |
| 303 | 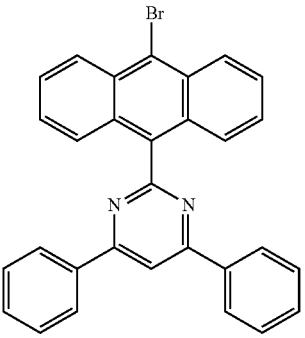 | 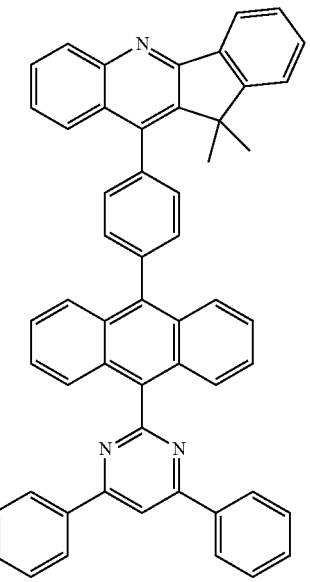 | 45% |

TABLE 2-continued
| Compound Number | Intermediate B | Target Compound B | Yield |
|---|---|---|---|
| 316 | 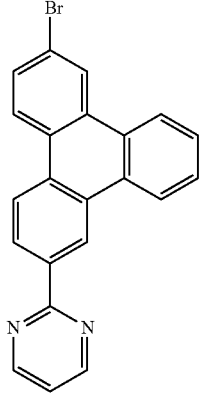 | 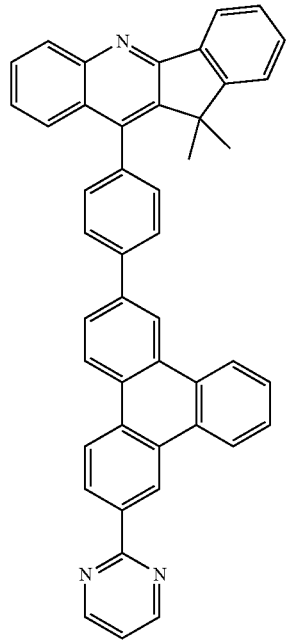 | 57% |
| 320 | 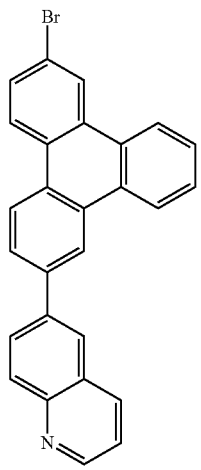 | 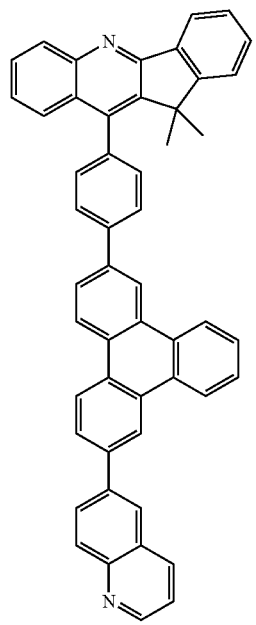 | 55% |

TABLE 2-continued
| Compound Number | Intermediate B | Target Compound B | Yield |
|---|---|---|---|
| 323 | 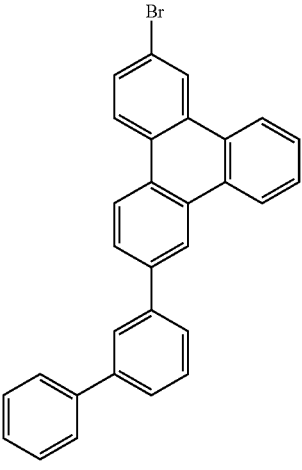 | 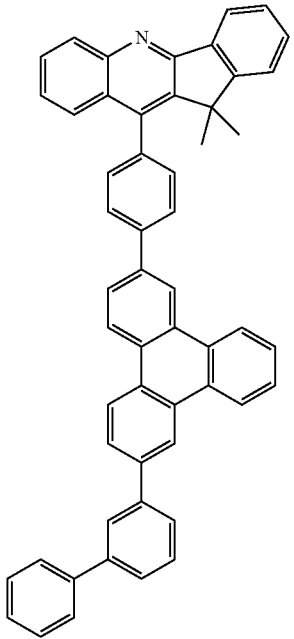 | 57% |
| 329 | 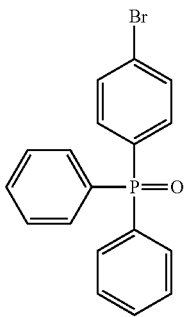 | 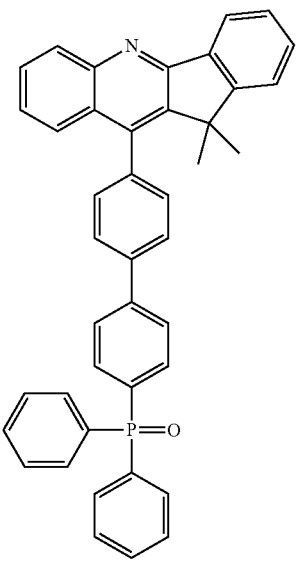 | 60% |

US 11,133,477 B2
207                                                                      208
TABLE 2-continued
| Compound Number | Intermediate B | Target Compound B | Yield |
|---|---|---|---|
| 332 | 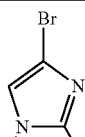 | 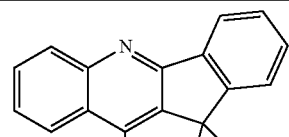 | 58% |
<Preparation Example 3> Preparation of Compound 337
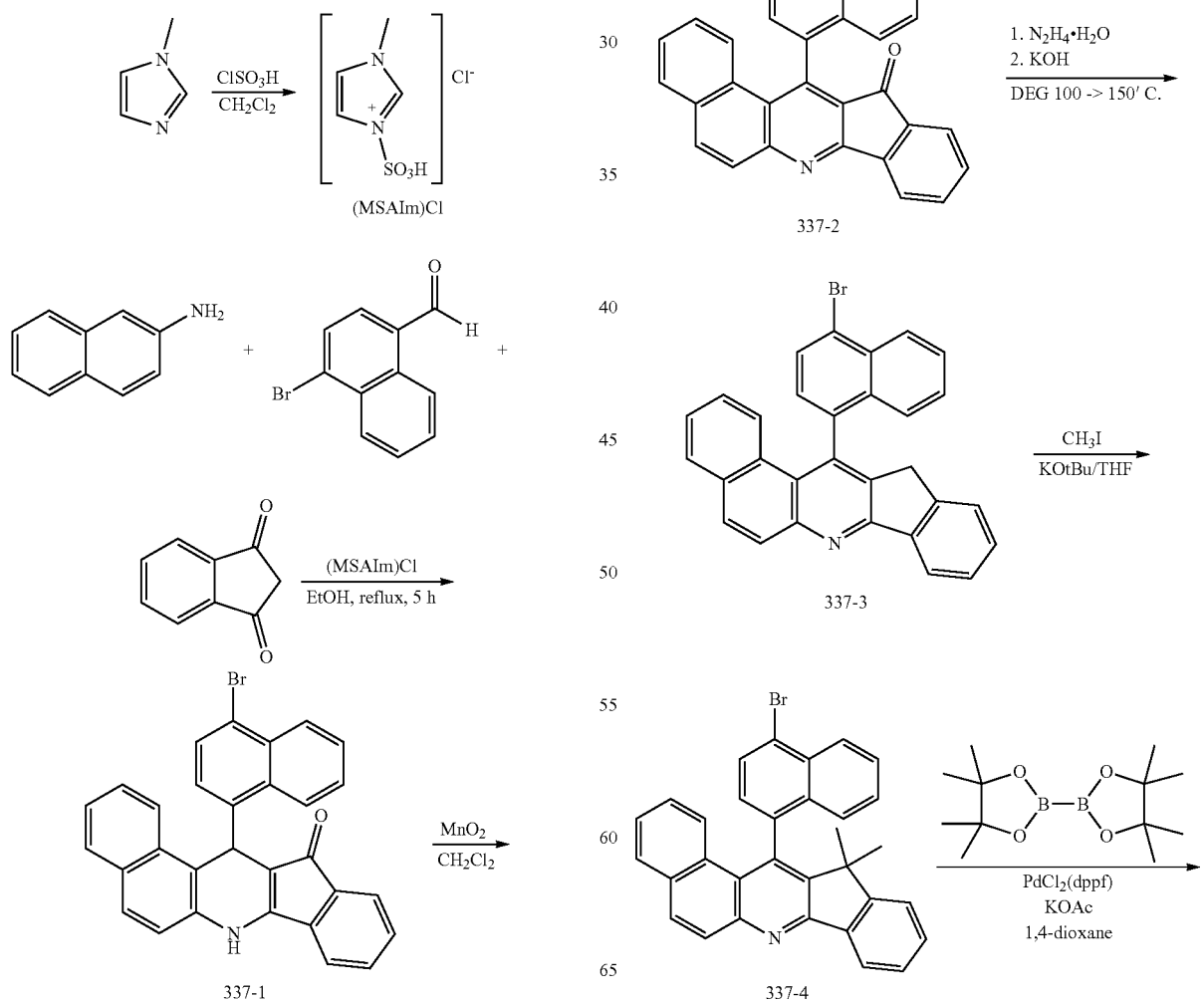

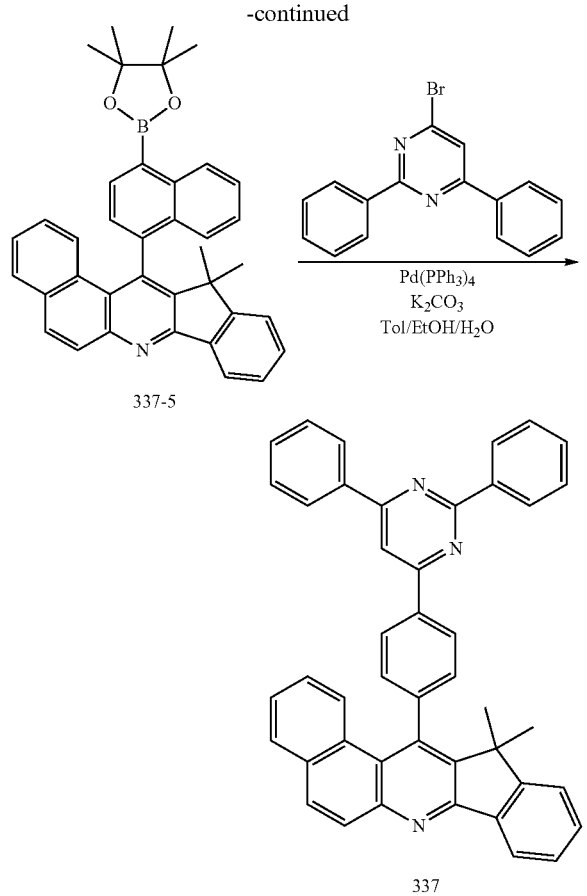

1) Preparation of Compound 337-1

After dissolving a naphthalen-2-amine compound (10.4 g, 112.91 mmol) in 200 ml of EtOH, 4-bromo-1-naphthaldehyde (23 g, 102.64 mmol), 1H-indene-1,3(2H)-dione (15 g, 102.64 mmol) and (MSAIm)Cl (1 g, 5.13 mmol) were added thereto, and the result was stirred under reflux. Excess EtOH was added thereto, and the result was ultrasonic treated and filtered to obtain target Compound 337-1 (42 g, 85%).

2) Preparation of Compound 337-2

500 ml of MC was introduced to Compound 337-1 (37 g, 95.82 mmol) and dispersed. $MnO_2$ (142 g, 1633.31 mmol) was added thereto, and the result was stirred for 24 hours at room temperature. Solids were filtered, and the filtrate was concentrated and recrystallized with MC/MeOH to obtain target Compound 337-2 (13 g, 31%).

3) Preparation of Compound 337-3

After dissolving Compound 337-2 (11.5 g, 29.80 mmol) in 400 ml of DEG, hydrazine monohydrate (95.5 g, 2979.60 mmol) was added thereto, and the result was stirred under reflux. KOH (16.7 g, 297.96 mmol) dissolved in 80 ml of D.W was added dropwise thereto, and the result was stirred at 140° C. 1 L of D.W was added thereto for precipitation and the result was filtered, washed with D.W and MeOH, and then dried to obtain target Compound 337-3 (11.5 g, 91%).

4) Preparation of Compound 337-4

After dissolving Compound 337-3 (9.6 g, 26.05 mmol) in 150 ml of THF, KOt-Bu (8.8 g, 78.14 mmol) was added thereto at 0° C., and the result was stirred for 10 minutes. Iodomethane (11.1 g, 78.14 mmol) was added thereto, and the result was stirred at room temperature. D.W was added thereto, the result was extracted with MC, and the MC layer was dried with anhydrous $Na_2SO_4$.

The result was purified using column chromatography with EA and hexane as a developing solvent to obtain target Compound 337-4 (9 g, 77%).

5) Preparation of Compound 337-5

After dissolving Compound 337-4 (9.7 g, 20.43 mmol) in 200 ml of 1,4-dioxane, bis(pinacolato)diboron (7.8 g, 30.64 mmol), $PdCl_2(dppf)$ (0.8 g, 1.02 mmol) and potassium acetate (8 g, 81.71 mmol) were added thereto, and the result was stirred under reflux. D.W was added thereto, the result was extracted with MC, and the MC layer was dried with anhydrous $Na_2SO_4$. The result was purified using column chromatography with EA and hexane as a developing solvent to obtain target Compound 337-5 (10 g, 98%).

6) Preparation of Compound 337

After introducing Compound 337-5 (11.2 g, 22.52 mmol) and 4-bromo-2,6-diphenylpyrimidine (6.3 g, 20.26 mmol) to 100 ml of toluene, 20 ml of EtOH and 20 ml of D.W, $Pd(PPh_3)_4$ (1.3 g, 1.13 mmol) and $K_2CO_3$ (6.2 g, 45.03 mmol) were added thereto, and the result was stirred under reflux. D.W was added thereto, the result was extracted with MC, and the MC layer was dried with anhydrous $Na_2SO_4$. After vacuum concentrating the solvent, MeOH was added thereto to recrystallize and obtain solids. The result was purified using column chromatography with EA and hexane as a developing solvent to obtain target Compound 337 (6.5 g, 68%).

Target Compound C was synthesized in the same manner as the preparation of Compound 337 except that, in Preparation Example 3, Intermediate C of the following Table 3 was used instead of 4-bromo-2,6-diphenylpyrimidine.

TABLE 3

| Compound Number | Intermediate C | Target Compound C | Yield |
| --- | --- | --- | --- |
| 357 | | | 50% |
| 360 | | | 58% |
| 361 | | | 49% |

Target Compound D was synthesized in the same manner as the preparation of Compound 337 except that, in the synthesis of 366-1 in Preparation Example 3, Synthesis Reagent D of the following Table 4 was used instead of the synthesis reagent 4-bromo-1-naphthaldehyde.

TABLE 4

| Compound Number | Synthesis Reagent D | Target Compound D | Yield |
|---|---|---|---|
| 341 | | | 55% |
| 349 | | | 49% |

<Preparation Example 4> Preparation of Compound 400
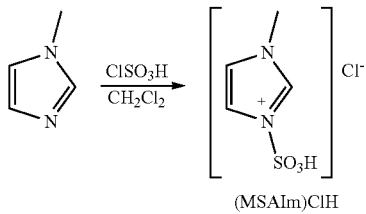
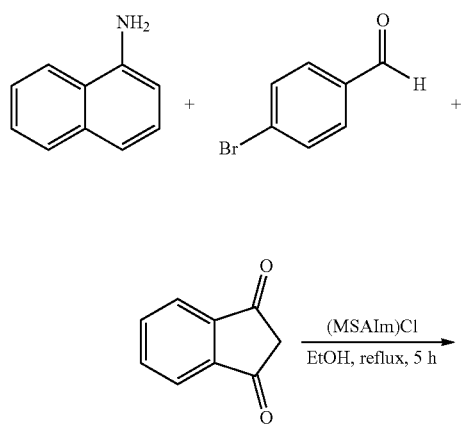
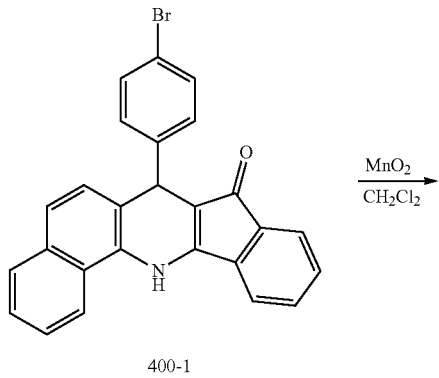
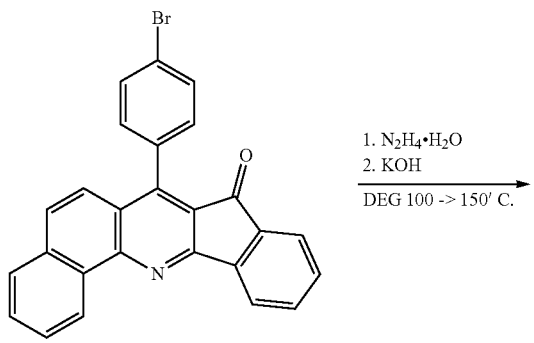
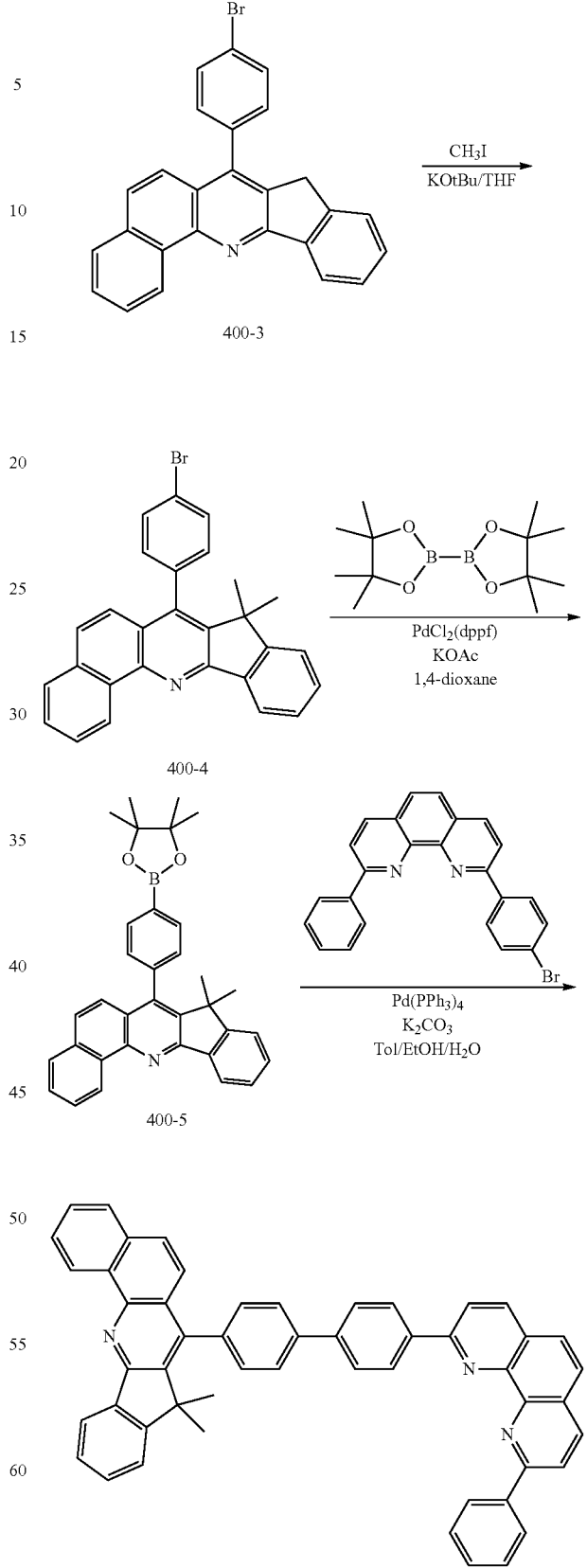

1) Preparation of Compound 400-1

After dissolving a naphthalen-1-amine compound (17.3 g, 112.91 mmol) in 200 ml of EtOH, 4-bromo-1-naphthaldehyde (23 g, 102.64 mmol), 1H-indene-1,3(2H)-dione (15 g, 102.64 mmol) and (MSAIm)Cl (1 g, 5.13 mmol) were added thereto, and the result was stirred under reflux. Excess EtOH was added thereto, and the result was ultrasonic treated and filtered to obtain target Compound 400-1 (42 g, 85%).

2) Preparation of Compound 400-2

500 ml of MC was introduced to Compound 400-1 (37 g, 95.82 mmol) and dispersed. $MnO_2$ (142 g, 1633.31 mmol) was added thereto, and the result was stirred for 24 hours at room temperature. Solids were filtered, and the filtrate was concentrated and recrystallized with MC/MeOH to obtain target Compound 400-2 (13 g, 31%).

3) Preparation of Compound 400-3

After dissolving Compound 400-2 (11.5 g, 29.80 mmol) in 400 ml of DEG, hydrazine monohydrate (95.5 g, 2979.60 mmol) was added thereto, and the result was stirred under reflux. KOH (16.7 g, 297.96 mmol) dissolved in 80 ml of D.W was added dropwise thereto, and the result was stirred at 140° C. 1 L of D.W was added thereto for precipitation and the result was filtered, washed with D.W and MeOH, and then dried to obtain target Compound 400-3 (11.5 g, 91%).

4) Preparation of Compound 400-4

After dissolving Compound 400-3 (9.6 g, 26.05 mmol) in 150 ml of THF, KOt-Bu (8.8 g, 78.14 mmol) was added thereto at 0° C., and the result was stirred for 10 minutes. Iodomethane (11.1 g, 78.14 mmol) was added thereto, and the result was stirred at room temperature. D.W was added thereto, the result was extracted with MC, and the MC layer was dried with anhydrous $Na_2SO_4$.

The result was purified using column chromatography with EA and hexane as a developing solvent to obtain target Compound 400-4 (9 g, 77%).

5) Preparation of Compound 400-5

After dissolving Compound 400-4 (9.7 g, 20.43 mmol) in 200 ml of 1,4-dioxane, bis(pinacolato)diboron (7.8 g, 30.64 mmol), $PdCl_2$(dppf) (0.8 g, 1.02 mmol) and potassium acetate (8 g, 81.71 mmol) were added thereto, and the result was stirred under reflux. D.W was added thereto, the result was extracted with MC, and the MC layer was dried with anhydrous $Na_2SO_4$. The result was purified using column chromatography with EA and hexane as a developing solvent to obtain target Compound 400-5 (10 g, 98%).

6) Preparation of Compound 400

After introducing Compound 400-5 (11.2 g, 22.52 mmol) and 2-(4-bromophenyl)-9-phenyl-1,10-phenanthroline (6.3 g, 20.26 mmol) to 100 ml of toluene, 20 ml of EtOH and 20 ml of D.W, $Pd(PPh_3)_4$ (1.3 g, 1.13 mmol) and $K_2CO_3$ (6.2 g, 45.03 mmol) were added thereto, and the result was stirred under reflux. D.W was added thereto, the result was extracted with MC, and the MC layer was dried with anhydrous $Na_2SO_4$. After vacuum concentrating the solvent, MeOH was added thereto to recrystallize and obtain solids. The result was purified using column chromatography with EA and hexane as a developing solvent to obtain target Compound 400 (7.1 g, 68%).

Target Compound E was synthesized in the same manner as the preparation of Compound 400 except that, in Preparation Example 4, Intermediate E of the following Table 5 was used instead of 2-(4-bromophenyl)-9-phenyl-1,10-phenanthroline.

TABLE 5

| Compound Number | Intermediate E | target Compound E | Yield |
|---|---|---|---|
| 392 | (structure) | (structure) | 50% |

TABLE 5-continued

| Compound Number | Intermediate E | target Compound E | Yield |
|---|---|---|---|
| 395 | | | 58% |
| 399 | | | 49% |

TABLE 5-continued

| Compound Number | Intermediate E | target Compound E | Yield |
|---|---|---|---|
| 401 | | | 44% |
| 402 | | | 38% |

Compounds were prepared in the same manner as in the preparation examples, and the synthesis identification results are shown in Table 6 and Table 7. Table 6 shows measurement values of $^1$H NMR (CDCl$_3$, 200 MHz), and Table 7 shows measurement values of field desorption mass spectrometry (FD-MS).

TABLE 6

| Example | $^1$H NMR (CDCl$_3$, 200 Mz) |
|---|---|
| 1 | δ = 8.54(d, 1H), 8.01-7.99(t, 3H), 7.86(d, 1H), 7.75(d, 2H), 7.61-7.37(m, 7H), 7.27(t, 1H), 7.25(m, 4H), 1.69(s, 6H) |
| 6 | δ = 8.54(d, 1H), 8.26(s, 1H), 8.20(s, 1H), 8.09~7.99(m, 5H), 7.86(d, 1H), 7.71(t, 1H), 7.61~7.53(m, 3H), 7.37(t, 2H), 7.27(t, 1H), 7.25(d, 4H), 1.69(s, 6H) |
| 10 | δ = 8.54(d, 1H), 8.31(d, 1H), 8.15(d, 1H), 8.08~7.86(m, 9H), 7.70(d, 1H), 7.61~7.53(m, 2H), 7.39~7.37(t, 2H), 7.27(t, 1H), 7.25(d, 4H), 1.69(s, 6H) |
| 13 | δ = 8.80(d, 1H), 8.71~8.69(d, 1H), 8.54(d, 1H), 8.45(d, 1H), 8.20(d, 1H), 8.01~7.99(d, 3H), 7.90~7.86(d, 2H), 7.61~7.53(m, 3H), 7.39~7.37(t, 2H), 7.29~2.25(m, 4H), 1.69(s, 6H) |
| 14 | δ = 8.71~8.69(d, 4H), 8.54(d, 1H), 8.33(d, 2H), 8.20(d, 1H), 8.01~7.99(t, 3H), 7.90~7.86(d, 2H), 7.61~7.49(m, 5H), 7.39~7.37(t, 2H), 7.29~7.25(m, 5H), 1.69(s, 6H) |
| 15 | δ = 8.80(d, 1H), 8.67(d, 1H), 8.54~8.44(m, 3H), 8.01~7.99(t, 3H), 7.86(d, 1H), 7.62~7.53(m, 4H), 7.39~7.27(m, 3H), 7.25(d, 4H), 1.69(s, 6H) |
| 27 | δ = 8.65(d, 1H), 8.54~8.51(t, 2H), 8.39(d, 1H), 8.30(d, 1H), 8.15~8.14(t, 2H), 8.01~7.99(m, 3H), 7.89~7.86(d, 2H), 7.61~7.53(m, 2H), 7.39~7.27(m, 4H), 7.25(d, 4H), 7.17(t, 1H), 1.69(s, 6H) |
| 32 | δ = 9.18(d, 2H), 9.14(s, 1H), 8.55~8.54(d, 3H), 8.01(m, 3H), 7.86(d, 1H), 7.74(t, 2H), 7.61~7.53(m, 2H), 7.39~7.37(m, 2H), 7.27~7.23(m, 6H), 1.69(s, 6H) |
| 34 | δ = 9.24(s, 1H), 8.70(d, 1H), 8.54(d, 1H), 8.42(d, 1H), 8.01~7.99(m, 3H), 7.86(d, 1H), 7.61~7.53(m, 3H), 7.39~7.37(m, 2H), 7.25(d, 8H), 1.69(s, 6H) |
| 44 | δ = 8.54(d, 2H), 8.36(d, 4H), 8.01~7.96(m, 5H), 7.86(d, 1H), 7.61~7.50(m, 8H), 7.39~7.37(t, 2H), 7.27~7.25(m, 3H), 1.69(s, 6H) |
| 53 | δ = 8.85(s, 2H), 8.67(s, 2H), 8.54~8.49(m, 3H), 8.39(d, 2H), 8.04~7.99(m, 10H), 7.86(d, 1H), 7.61~7.53(m, 8H), 7.39~7.31(t, 2H), 7.27~7.25(m, 5H), 1.69(s, 6H) |
| 65 | δ = 9.24(s, 1H), 8.70(d, 1H), 8.54(d, 1H), 8.42(d, 1H), 8.01~7.94(m, 4H), 7.86(d, 1H), 7.73(t, 1H), 7.61~7.53(m, 5H), 7.39~7.37(t, 2H), 7.27~7.20(m, 5H), 1.69(s, 6H) |
| 72 | δ = 8.69~8.71(d, 2H), 8.54(d, 1H), 8.33(d, 4H), 8.01~7.94(m, 4H), 7.86(d, 1H), 7.73(t, 1H), 7.61~7.22(m, 20H), 1.69(s, 6H) |
| 77 | δ = 9.24(s, 1H), 8.70(d, 1H), 8.54~8.52(d, 2H), 8.42(d, 1H), 8.28(d, 1H), 8.15(d, 2H), 8.01~7.86(m, 7H), 7.70~7.53(m, 8H), 7.39~7.37(t, 2H), 7.27~7.25(m, 5H), 1.69(s, 6H) |
| 80 | δ = 9.18(d, 2H), 8.54(d, 1H), 8.41~8.35(m, 3H), 8.01~7.94(m, 4H), 7.86(d, 1H), 7.74~7.71(m, 3H), 7.61~7.53(m, 4H), 7.39~7.23(m, 10H), 1.69(s, 6H) |
| 110 | δ = 8.54(d, 1H), 8.01~7.99(m, 6H), 7.86(d, 2H), 7.61~7.53(m, 4H), 7.39~7.37(m, 4H), 7.27~7.20(m, 10H), 1.69(s, 6H) |
| 113 | δ = 9.27(s, 1H), 9.00(d, 2H), 8.79(d, 1H), 8.54(d, 1H), 8.37~8.30(m, 4H), 8.01~7.99(m, 3H), 7.86(d, 1H), 7.70~7.53(m, 9H), 7.39~7.37(m, 4H), 7.27~7.25(m, 5H), 1.69(s, 6H) |
| 117 | δ = 9.08~9.00(d, 3H), 8.84~8.79(d, 2H), 8.25(d, 1H), 8.05~7.99(m, 4H), 7.90~7.86(d, 2H), 7.70~7.53(m, 8H), 7.39~7.37(m, 4H), 7.27~7.25(d,5H), 1.69(s, 6H) |
| 120 | δ = 9.00(d, 2H), 8.73(d, 2H), 8.54(d, 1H), 8.01~7.86(m, 5H), 7.86~7.83(d, 1H), 7.61~7.53(m, 4H), 7.39~7.7.35(m, 4H), 7.27~7.25(m, 8H), 1.69(s, 6H) |
| 124 | δ = 9.02~8.90(d, 2H), 8.54(d, 1H), 8.23(s, 1H), 8.01~7.84(m, 10H), 7.75~7.70(d, 2H), 7.61~7.37(m, 12H), 7.27~7.25(m, 7H), 1.69(s, 6H) |
| 128 | δ = 9.15(s, 1H), 8.54~8.51(d, 2H), 8.36~8.30(d, 4H), 8.01~7.86(m, 6H), 7.61~7.50(m, 9H), 7.39~7.37(t, 3H), 7.27~7.25(d, 5H), 1.69(s, 6H) |

TABLE 6-continued

| Example | $^1$H NMR (CDCl$_3$, 200 Mz) |
|---|---|
| 130 | δ = 8.54~8.52(d, 2H), 8.23(s, 1H), 8.01~7.86(m, 11H), 7.75(d, 2H), 7.61~7.39(m, 12H), 7.27~7.25(m, 7H), 1.69(s, 6H) |
| 138 | δ = 8.73~8.70(d, 2H), 8.54~8.50(d, 1H), 8.22~8.19(d, 4H), 8.01~7.99(t, 3H), 7.86(d, 1H), 7.61~7.37(m, 8H), 7.27~7.20(6H), 1.69(s, 6H) |
| 146 | δ = 9.18(d, 1H), 8.70~8.65(d, 3H), 8.54(d, 1H), 8.45~8.43(d, 1H), 8.35~8.31(t, 3H), 8.09~7.94(m, 6H), 7.88~7.86(d, 2H), 7.78~7.74(t, 1H), 7.61~7.53(t, 2H), 7.39~7.23(m, 7H), 1.69(s, 6H) |
| 155 | δ = 9.62~9.60(d, 1H), 9.27~9.24(d, 2H), 9.13~9.11(d, 1H), 8.81~8.79(d, 1H), 8.72~8.70(d, 1H), 8.54~8.51(d, 1H), 8.46~8.30(m, 5H), 8.01~7.99(d, 3H), 7.87~7.85(d, 1H), 7.70~7.53(m, 5H), 7.39~7.37(t, 2H), 7.25~7.22(d, 4H), 1.69(s, 6H) |
| 160 | δ = 8.54~8.51(d, 1H), 8.10~8.08(d, 1H), 8.01~7.99(d, 3H), 7.90~7.86(d, 3H), 7.79~7.77(d, 1H), 7.61~7.53(m, 3H), 7.38~7.14(m, 15H), 7.03~7.00(t, 2H), 1.69(s, 6H) |
| 171 | δ = 8.09~7.99(m, 5H), 7.89~7.86(d, 1H), 7.63~7.51(m, 5H), 7.39~7.37(t, 3H), 7.27~2.25(m, 5H), 1.69(s, 6H) |
| 174 | δ = 8.85(s, 1H), 8.67(s, 1H), 8.49(s, 1H), 8.39~8.87(d, 1H), 8.08~8.01(d, 4H), 7.89~7.86(d, 1H), 7.62~7.51(m, 5H), 7.39~7.37(t, 2H), 7.27~7.25(d, 5H), 1.69(s, 6H) |
| 178 | δ = 8.71~8.69(d, 2H), 8.52~8.50(d, 1H), 8.28~8.26(d, 1H), 8.15~7.87(m, 9H), 7.70~7.62(m, 3H), 7.51~7.49(t, 1H), 7.39~7.37(t, 2H), 7.27~7.25(d, 5H), 1.69(s, 6H) |
| 179 | δ = 8.80~8.79(d, 1H), 8.71~8.69(t, 3H), 8.45~8.42(d, 1H), 8.20~8.18(d, 1H), 8.08~8.01(d, 2H), 7.90~7.87(d, 2H), 7.62~7.51(m, 3H), 7.39~7.37(t, 2H), 7.29~7.25(t, 4H), 1.69(s, 6H) |
| 184 | δ = 9.27(s, 1H), 8.79~8.77(d, 1H), 8.37~8.33(m, 4H), 8.08~8.01(d, 2H), 7.87~7.85(d, 1H), 7.70~7.62(m, 5H), 7.52~7.50(t, 2H), 7.39~7.34(t, 2H), 7.27~7.25(d, 5H), 1.69(s, 6H) |
| 195 | δ = 8.09~8.08(d, 2H), 8.01~8.00(d, 1H), 7.90~7.87(t, 5H), 7.78~7.86(d, 1H), 7.62~7.37(m, 8H), 7.28~7.19(m, 10H), 1.69(s, 6H) |
| 196 | δ = 8.08~8.06(d, 1H), 8.01~7.87(m, 4H), 7.63~7.51(m, 7H), 7.39~7.27(m, 6H), 6.5~6.62(t, 1H), 5.83~5.79(d, 2H), 3.69(t, 1H), 3.16(d, 1H), 2.5(d 1H), 1.69(s, 6H) |
| 208 | δ = 8.35~8.28(m, 6H), 8.23(s, 1H), 8.08~8.01(d, 2H), 7.87~7.82(d, 3H), 7.75~7.70(d, 2H), 7.62~7.58(t, 1H), 7.51~7.37(m, 9H), 7.27~7.20(t, 3H), 1.69(s, 6H) |
| 211 | δ = 8.23(s, 1H), 8.08~7.87(m, 9H), 7.62~7.49(m, 8H), 7.39~7.30(t, 2H), 7.27~7.20(t, 3H), 1.69(s, 6H) |
| 218 | δ = 8.09~7.99(m, 11H), 7.87~7.84(m, 1H), 7.63~7.51(m, 8H), 7.39~7.30(t, 4H), 7.27~7.2 0(m, 5H), 1.69(s, 6H) |
| 224 | δ = 8.82(s, 1H), 8.80(d, 2H), 8.71~8.68(d, 2H), 8.45~8.40(t, 4H), 8.20~8.15(d, 2H), 8.08~8.01(d, 2H), 7.87~7.84(d, 1H), 7.62~7.51(m, 4H), 7.39~7.34(t, 2H), 7.27~7.10(m, 5H), 1.69(s, 6H) |
| 226 | δ = 8.81~8.79(d, 1H), 8.67~8.64(d, 2H), 8.50~8.40(m, 4H), 8.08~8.05(d, 1H), 8.02(s, 3H), 8.01~7.98(d, 1H), 7.87~7.84(d, 1H), 7.62~7.51(m, 6H), 7.39~7.25(m, 9H), 1.69(s, 6H) |
| 280 | δ = 9.00~8.95(d, 2H), 8.52~8.49(d, 1H), 8.31~8.28(d, 1H), 8.15~8.01(m, 7H), 7.92~7.87(d, 2H), 7.70~7.61(m, 4H), 7.51~7.48(t, 1H), 7.39~7.33(m, 4H), 1.69(s, 6H) |
| 284 | δ = 9.00~8.95(d, 2H), 8.42~8.39(d, 2H), 8.10~8.01(m, 4H), 7.87~7.83(d, 1H), 7.76~7.73(d, 1H), 7.67~7.58(t, 5H), 7.51~7.48(t, 2H), 7.39~7.31(m, 5H), 7.27~7.25(d, 5H), 1.69(s, 6H) |
| 298 | δ = 9.02~8.99(d, 1H), 8.95~8.92(d, 1H), 8.23(s, 1H), 8.08~7.87(m, 9H), 7.75~7.70(d, 2H), 7.62~7.37(m, 12H), 7.27~7.20(m, 7H), 1.69(s, 6H) |
| 303 | δ = 8.23(s, 1H), 8.22~8.19(d, 4H), 8.08~7.87(m, 7H), 7.62~7.37(m, 14H), 7.27~7.20(m, 5H), 1.69(s, 6H) |
| 316 | δ = 9.60~9.57(d, 1H), 9.27(s, 1H), 9.11~9.07(d, 1H), 8.79~8.71(d, 3H), 8.46~8.43(d, 2H), 8.30~8.26(d, 1H), 8.15~8.01(m, 3H), 7.87~7.83(d, 1H), 7.70~7.62(t, 3H), 7.51~7.49(d, 1H), 7.39~7.34(t, 2H), 7.27~7.22(d, 6H), 1.69(s, 6H) |
| 320 | δ = 9.90~9.88(d, 1H), 9.27(s, 1H), 9.11~9.08(d, 1H), 8.91~8.88(d, 1H), 8.79~8.72(d, 1H), 8.48~8.33(m, 6H), 8.08~8.01(d, 3H), 7.88~7.82(d, 2H), 7.70~7.51(m, 5H), 7.39~7.24(m, 6H), 1.69(s, 6H) |

TABLE 6-continued

| Example | ¹H NMR (CDCl₃, 200 Mz) |
|---|---|
| 323 | δ = 9.60~9.57(d, 1H), 9.27(s, 1H), 9.11~9.08(d, 1H), 8.79~7.74(d, 1H), 8.46~8.30(m, 4H), 8.08~8.00(d, 2H), 7.94(s, 1H), 7.87~7.84(d, 1H), 7.75~7.60(m, 8H), 7.51~7.30(m, 6H), 7.27~7.22(d, 5H), 1.69(s, 6H) |
| 329 | δ = 8.08~8.02(d, 1H), 8.01~7.90(m, 5H), 7.87~7.80(d, 1H), 7.77~7.70(d, 4H), 7.62~7.56(t, 1H), 7.51~7.40(m, 7H), 7.39~7.30(t, 2H), 7.27~7.20(m, 5H), 1.69(s, 6H) |
| 332 | δ = 8.48~8.40(d, 1H), 8.30~8.20(t, 3H), 8.08~7.97(d, 2H), 7.87~7.80(d, 1H), 7.62~7.48(t, 3H), 7.39~7.30(d, 2H), 7.27~7.15(t, 4H), 6.86~6.79(t, 1H), 1.69(s, 6H) |
| 337 | δ = 8.97(d, 2H), 8.29(d, 1H), 8.35(d, 2H), 8.29(d, 2H), 8.23(s, 1H), 8.01~7.94(m, 5H), 7.86(d, 1H), 7.61~7.49(m, 10H), 7.39(t, 2H), 7.27(t, 1H), 1.69(s, 6H) |
| 341 | δ = 8.54(d, 1H), 8.46(s, 1H), 8.35~8.30(d, 4H), 8.23(s, 1H), 8.01~7.85(m, 9H), 7.75~7.54(m, 4H), 7.53~7.37(m, 10H), 7.27(t, 1H), 1.69(s, 6H) |
| 349 | δ = 8.54(d, 1H), 8.20(d, 4H), 8.01~7.86(m, 8H), 7.61~7.49(m, 14H), 7.27(t, 1H), 1.69(s, 6H) |
| 357 | δ = 9.08~8.79(t, 3H), 8.95~8.70(t, 2H), 8.06(d, 1H), 8.05~7.99(m, 5H), 7.90~7.80(d, 3H), 7.68~7.30(m, 10H), 7.20(t,1H), 1.69(s, 6H) |
| 360 | δ = 9.02(d, 1H), 8.95(d, 1H), 8.73(d, 2H), 8.54(d, 1H), 8.06~7.88(m, 6H), 7.86~7.80(d, 2H), 7.53~7.37(m, 6H), 7.27~7.20(m, 5H), 1.69(s, 6H) |
| 361 | δ = 9.02~8.95(d, 2H), 8.80(d, 1H), 8.67(d, 1H), 8.50~8.44(d, 3H), 8.06~7.99(m, 4H), 7.86~7.77(d, 2H), 7.62~7.27(m, 10H), 1.69(s, 6H) |
| 392 | δ = 8.56~8.51(d, 2H), 8.11~7.90(m, 5H), 7.81(d, 1H), 7.72~7.37(m, 11H), 7.27~7.20(m, 8H), 1.69(s, 6H) |
| 395 | δ = 9.02(d, 1H), 8.95(d, 1H), 8.80(d, 1H), 8.71(d, 1H), 8.51(d, 1H), 8.45(d, 2H), 8.20(d, 1H), 8.11~8.01(t, 3H), 7.90(d, 1H), 7.84(d, 1H), 7.72~7.60(m, 3H), 7.56(t, 1H), 7.52~7.39(m, 4H), 7.29~7.27(t, 2H), 7.25(d, 4H), 1.69(s, 6H) |
| 399 | δ = 9.02(d, 1H), 8.95(d, 1H), 8.51(d, 1H), 8.35(d, 2H), 8.23(s, 1H), 8.11~7.94(m, 6H), 7.84(d, 1H), 7.72~7.61(t, 3H), 7. |
| 400 | δ = 9.26(s, 2H), 9.08(d, 1H), 8.84(d, 1H), 8.51(d, 1H), 8.17(d, 1H), 8.11(d, 1H), 8.08~8.01(t, 3H), 7.90(d, 1H), 7.72~7.62(m, 8H), 7.39(t, 2H), 7.27(t, 1H), 7.25(d, 4H), 1.69(s, 6H) |
| 401 | δ = 9.02(d, 1H), 8.95(d, 1H), 8.51(d, 1H), 8.35(d, 2H), 8.23(s, 1H), 8.11~7.94(m, 6H), 7.84(d, 1H), 7.72~7.63(t, 3H), 7.55~7.37(m, 10H), 7.27~7.25(d, 5H), 1.69(s, 6H) |
| 402 | δ = 9.26(s, 2H), 9.08(d, 1H), 8.84(d, 1H), 8.51(d, 1H), 8.17~8.05(m, 5H), 7.90(d, 1H), 7.72~7.62(m, 7H), 7.39~7.30(m, 2H), 7.27(t, 1H), 7.25(d, 4H), 1.69(s, 6H) |

TABLE 7

| Compound | FD-Mass | Compound | FD-Mass |
|---|---|---|---|
| 1 | m/z = 447.58(C34H25N = 447.21) | 2 | m/z = 448.56(C33H24N2 = 448.44) |
| 3 | m/z = 448.56(C33H24N2 = 448.32) | 4 | m/z = 448.56(C33H24N2 = 448.51) |
| 5 | m/z = 497.64(C38H27N = 497.51) | 6 | m/z = 498.62(C37H26N2 = 498.59) |
| 7 | m/z = 498.62(C37H26N2 = 498.54) | 8 | m/z = 547.70(C42H29N = 547.51) |
| 9 | m/z = 699.89(C54H37N = 699.81) | 10 | m/z = 571.73(C44H29N = 571.70) |
| 11 | m/z = 648.80(C49H32N2 = 648.77) | 12 | m/z = 648.80(C49H32N2 = 648.65) |
| 13 | m/z = 549.67(C40H27N3 = 549.44) | 14 | m/z = 625.77(C40H31N3 = 625.31) |
| 15 | m/z = 549.67(C40H27N3 = 549.45) | 16 | m/z = 701.87(C52H35N3 = 701.66) |
| 17 | m/z = 571.72(C44H29N = 571.21) | 18 | m/z = 597.76(C46H31N = 597.44) |
| 19 | m/z = 449.55(C32H23N3 = 449.31) | 20 | m/z = 498.62(C37H26N2 = 498.55) |
| 21 | m/z = 547.70(C42H29N = 547.49) | 22 | m/z = 701.87(C52H35N3 = 701.28) |
| 23 | m/z = 602.74(C43H30N4 = 602.24) | 24 | m/z = 678.83(C49H34N4 = 678.27) |
| 25 | m/z = 754.93(C55H38N4 = 754.30) | 26 | m/z = 754.93(C55H38N4 = 754.31) |
| 27 | m/z = 614.75(C44H30N4 = 614.24) | 28 | m/z = 687.88(C53H37N = 687.29) |
| 29 | m/z = 685.87(C53H35N = 685.27) | 30 | m/z = 564.73(C42H32N2 = 564.21) |
| 31 | m/z = 537.66(C39H27N3 = 537.22) | 32 | m/z = 602.74(C43H30N4 = 602.40) |
| 33 | m/z = 524.66(C39H28N2 = 524.21) | 34 | m/z = 524.68(C39H28N2 = 524.31) |
| 35 | m/z = 524.66(C39H28N2 = 524.33) | 36 | m/z = 574.72(C43H30N2 = 574.61) |
| 37 | m/z = 574.72(C43H30N2 = 574.55) | 38 | m/z = 625.77(C46H31N3 = 625.49) |
| 39 | m/z = 701.87(C52H35N3 = 701.68) | 40 | m/z = 625.77(C46H31N3 = 625.51) |
| 41 | m/z = 777.99(C58H39N3 = 777.88) | 42 | m/z = 677.85(C50H85N3 = 677.53) |
| 43 | m/z = 601.75(C44H31N3 = 601.59) | 44 | m/z = 602.74(C43H30N4 = 602.60) |
| 45 | m/z = 601.75(C44H31N3 = 602.64) | 46 | m/z = 601.75(C44H31N3 = 601.43) |
| 47 | m/z = 601.75(C44H31N3 = 601.21) | 48 | m/z = 601.75(C44H31N3 = 601.39) |
| 49 | m/z = 701.87(C52H35N3 = 701.44) | 50 | m/z = 701.87(C52H35N3 = 701.52) |
| 51 | m/z = 599.77(C46H33N = 599.64) | 52 | m/z = 699.89(C54H37N = 699.82) |
| 53 | m/z = 800.01(C62H41N = 800.00) | 54 | m/z = 1104.40(C86H57N = 1104.21) |
| 55 | m/z = 848.06(C66H41N = 848.01) | 56 | m/z = 1002.23(C76H47N = 1002.11) |
| 57 | m/z = 1002.23(C76H47N3 = 1002.10) | 58 | m/z = 803.96(C58H37N5 = 803.21) |
| 59 | m/z = 956.16(C70H45N5 = 956.01) | 60 | m/z = 803.96(C58H37N5 = 803.77) |
| 61 | m/z = 1108.36(C82H53N5 = 1108.19) | 62 | m/z = 601.75(C44H31N3 = 601.22) |
| 63 | m/z = 523.67(C40H29N = 523.41) | 64 | m/z = 524.66(C39H28N2 = 524.39) |
| 65 | m/z = 524.66(C39H28N2 = 524.52) | 66 | m/z = 524.66(C39H28N2 = 524.38) |
| 67 | m/z = 574.72(C43H30N2 = 574.11) | 68 | m/z = 574.72(C43H30N2 = 574.69) |
| 69 | m/z = 625.77(C46H31N3 = 625.47) | 70 | m/z = 701.87(C52H35N3 = 701.55) |
| 71 | m/z = 625.77(C46H31N3 = 625.28) | 72 | m/z = 777.97(C58H39N3 = 777.85) |
| 73 | m/z = 573.73(C44H31N = 573.64) | 74 | m/z = 623.79(C48H33N = 623.40) |
| 75 | m/z = 775.99(C60H41N = 775.85) | 76 | m/z = 647.82(C50H33N = 647.77) |
| 77 | m/z = 724.90(C55H36N2 = 724.60) | 78 | m/z = 724.90(C55H36N2 = 724.88) |
| 79 | m/z = 701.87(C52H35N3 = 775.81) | 80 | m/z = 779.94(C56H37N5 = 779.30) |
| 81 | m/z = 677.85(C50H35N3 = 677.43) | 82 | m/z = 601.75(C44H31N3 = 601.47) |
| 83 | m/z = 602.74(C43H30N4 = 602.22) | 84 | m/z = 678.83(C49H34N4 = 678.27) |
| 85 | m/z = 677.85(C50H35N3 = 677.68) | 86 | m/z = 602.74(C43H30N4 = 601.30) |
| 87 | m/z = 678.83(C39H34N4 = 678.27) | 88 | m/z = 536.67(C40H28N2 = 536.47) |
| 89 | m/z = 524.66(C39H28N2 = 524.51) | 90 | m/z = 524.66(C39H28N2 = 524.25) |
| 91 | m/z = 524.66(C39H28N2 = 524.33) | 92 | m/z = 574.72(C43H30N2 = 574.40) |

TABLE 7-continued

| Compound | FD-Mass | Compound | FD-Mass |
|---|---|---|---|
| 93 | m/z = 574.72(C43H30N2 = 574.61) | 94 | m/z = 625.77(C46H31N3 = 625.28) |
| 95 | m/z = 701.87(C52H35N3 = 701.39) | 96 | m/z = 625.77(C46H31N3 = 625.44) |
| 97 | m/z = 777.97(C58H39N3 = 777.31) | 98 | m/z = 523.67(C40H29N = 523.58) |
| 99 | m/z = 524.66(C39H28N2 = 524.20) | 100 | m/z = 524.66(C39H28N2 = 524.29) |
| 101 | m/z = 524.66(C39H28N2 = 524.38) | 102 | m/z = 574.72(C43H30N2 = 574.19) |
| 103 | m/z = 574.72(C43H30N2 = 574.10) | 104 | m/z = 625.77(C46H31N3 = 625.70) |
| 105 | m/z = 701.87(C52H35N3 = 701.24) | 106 | m/z = 625.77(C46H31N3 = 625.44) |
| 107 | m/z = 777.97(C58H39N3 = 777.87) | 108 | m/z = 639.80(C47H33N3 = 639.25) |
| 109 | m/z = 639.80(C47H33N3 = 639.42) | 110 | m/z = 740.95(C56H40N2 = 740.48) |
| 111 | m/z = 740.95(C56H40N2 = 740.89) | 112 | m/z = 675.83(C50H33N3 = 675.26) |
| 113 | m/z = 723.91(C56H37N = 723.29) | 114 | m/z = 699.89(C54H37N = 699.29) |
| 115 | m/z = 574.72(C43H30N2 = 574.24) | 116 | m/z = 575.71(C42H29N3 = 575.23) |
| 117 | m/z = 673.85(C52H35N = 673.27) | 118 | m/z = 697.88(C54H35N = 697.27) |
| 119 | m/z = 624.78(C47H32N2 = 624.25) | 120 | m/z = 651.81(C48H33N3 = 651.26) |
| 121 | m/z = 651.81(C48H33N3 = 651.26) | 122 | m/z = 699.89(C54H37N = 699.29) |
| 123 | m/z = 701.87(C52H35N3 = 701.28) | 124 | m/z = 804.00(C60H41N3 = 803.33) |
| 125 | m/z = 727.91(C54H37N3 = 727.29) | 126 | m/z = 624.78(C47H32N2 = 624.25) |
| 127 | m/z = 573.73(C44H31N = 573.24) | 128 | m/z = 728.89(C53H36N4 = 728.29) |
| 129 | m/z = 804.00(C60H41N3 = 803.33) | 130 | m/z = 804.00(C60H41N3 = 803.33) |
| 131 | m/z = 7804.00(C60H41N3 = 803.33) | 132 | m/z = 804.99(C59H40N4 = 804.32) |
| 133 | m/z = 880.10(C66H45N3 = 879.36) | 134 | m/z = 879.11(C67H46N2 = 878.36) |
| 135 | m/z = 880.10(C66H45N3 = 879.36) | 136 | m/z = 881.09(C65H44N4 = 880.35) |
| 137 | m/z = 777.98(C58H39N3 = 777.31) | 138 | m/z = 625.77(C48H31N3 = 625.25) |
| 139 | m/z = 625.77(C46H31N3 = 625.25) | 140 | m/z = 701.87(C52H35N3 = 701.28) |
| 141 | m/z = 701.87(C52H35N3 = 701.28) | 142 | m/z = 701.87(C52H35N3 = 701.28) |
| 143 | m/z = 625.77(C46H31N3 = 625.25) | 144 | m/z = 525.65(C38H27N3 = 525.22) |
| 145 | m/z = 576.70(C41H28N4 = 576.23) | 146 | m/z = 702.86(C51H34N3 = 702.27) |
| 147 | m/z = 649.79(C48H31N3 = 649.25) | 148 | m/z = 771.96(C60H37N = 771.29) |
| 149 | m/z = 625.77(C46H31N3 = 625.25) | 150 | m/z = 675.83(C50H33N3 = 675.26) |
| 151 | m/z = 675.83(C50H33N3 = 675.26) | 152 | m/z = 724.90(C55H36N2 = 724.28) |
| 153 | m/z = 724.90(C55H36N2 = 724.28) | 154 | m/z = 724.90(C55H36N2 = 724.28) |
| 155 | m/z = 674.82(C51H34N2 = 674.27) | 156 | m/z = 673.85(C52H35N = 673.27) |
| 157 | m/z = 749.95(C58H39N = 749.30) | 158 | m/z = 750.94(C57H38N2 = 750.30) |
| 159 | m/z = 723.91(C56H37N = 723.29) | 160 | m/z = 701.86(C53H35NO = 701.27) |
| 161 | m/z = 663.82(C49H33N3 = 663.26) | 162 | m/z = 739.92(C55H37N3 = 739.29) |
| 163 | m/z = 647.75(C46H34NOP = 647.23) | 164 | m/z = 697.81(C50H36NOP = 697.25) |
| 165 | m/z = 698.80(C49H35N2OP = 698.24) | 166 | m/z = 487.60(C35H25N3 = 487.20) |
| 167 | m/z = 397.52(C30H23N = 397.18) | 168 | m/z = 398.50(C29H22N2 = 398.17) |
| 169 | m/z = 398.50(C29H22N2 = 398.17) | 170 | m/z = 398.50(C29H22N2 = 398.17) |
| 171 | m/z = 447.58(C34H25N = 447.19) | 172 | m/z = 448.56(C33H24N2 = 448.19) |
| 173 | m/z = 448.56(C33H24N2 = 448.19) | 174 | m/z = 497.64(C38H27N = 497.21) |
| 175 | m/z = 649.83(C50H35N = 649.27) | 176 | m/z = 521.66(C40H27N = 521.21) |
| 177 | m/z = 598.74(C45H30N2 = 598.24) | 178 | m/z = 598.74(C45H30N2 = 598.24) |
| 179 | m/z = 499.61(C36H25N3 = 499.20) | 180 | m/z = 575.71(C45H29N3 = 575.23) |
| 181 | m/z = 499.61(C36H25N3 = 499.20) | 182 | m/z = 651.81(C48H33N3 = 651.26) |
| 183 | m/z = 521.66(C40H27N = 521.21) | 184 | m/z = 547.70(C42H29N = 547.23) |
| 185 | m/z = 399.49(C28H21N3 = 399.17) | 186 | m/z = 448.56(C33H24N3 = 448.19) |
| 187 | m/z = 497.64(C38H27N = 497.21) | 188 | m/z = 651.81(C48H33N3 = 651.26) |
| 189 | m/z = 552.68(C39H28N4 = 552.23) | 190 | m/z = 628.77(C45H32N4 = 628.26) |
| 191 | m/z = 704.87(C51H36N4 = 704.29) | 192 | m/z = 704.87(C51H36N4 = 704.29) |
| 193 | m/z = 564.69(C40H28N4 = 564.23) | 194 | m/z = 637.82(C49H35N = 637.27) |
| 195 | m/z = 635.81(C49H33N = 635.26) | 196 | m/z = 514.67(C38H30N2 = 514.24) |
| 197 | m/z = 487.60(C35H25N3 = 487.20) | 198 | m/z = 552.68(C39H28N4 = 552.23) |
| 199 | m/z = 474.60(C35H26N2 = 474.21) | 200 | m/z = 474.60(C35H26N2 = 474.21) |
| 201 | m/z = 474.60(C35H26N2 = 474.21) | 202 | m/z = 524.66(C39H28N2 = 524.22) |
| 203 | m/z = 524.66(C39H28N2 = 524.22) | 204 | m/z = 575.71(C42H29N3 = 575.23) |
| 205 | m/z = 651.81(C48H33N3 = 651.26) | 206 | m/z = 575.71(C42H29N3 = 575.23) |
| 207 | m/z = 727.91(C54H37N3 = 727.29) | 208 | m/z = 627.79(C46H33N3 = 627.26) |
| 209 | m/z = 551.69(C40H29N3 = 551.23) | 210 | m/z = 552.68(C39H28N4 = 552.23) |
| 211 | m/z = 551.69(C40H29N3 = 551.23) | 212 | m/z = 551.69(C40H29N3 = 551.23) |
| 213 | m/z = 551.69(C40H29N3 = 551.23) | 214 | m/z = 551.69(C40H29N3 = 551.23) |
| 215 | m/z = 651.81(C48H33N3 = 651.26) | 216 | m/z = 651.81(C48H33N3 = 651.26) |
| 217 | m/z = 549.71(C42H31N = 549.24) | 218 | m/z = 649.83(C50H35N = 649.27) |
| 219 | m/z = 749.95(C58H39N = 749.30) | 220 | m/z = 1054.34(C82H55N = 1053.43) |
| 221 | m/z = 798.00(C62H39N = 797.30) | 222 | m/z = 952.17(C72H45N3 = 951.26) |
| 223 | m/z = 952.17(C72H45N3 = 952.36) | 224 | m/z = 753.90(C54H35N5 = 753.28) |
| 225 | m/z = 906.10(C66H43N5 = 905.35) | 226 | m/z = 753.90(C54H35N5 = 753.28) |
| 227 | m/z = 1058.30(C78H51N5 = 1057.41) | 228 | m/z = 551.69(C40H29N3 = 551.23) |
| 229 | m/z = 473.61(C36H27N = 473.21) | 230 | m/z = 474.60(C35H26N2 = 474.21) |
| 231 | m/z = 474.60(C35H26N2 = 474.21) | 232 | m/z = 474.60(C35H26N2 = 474.21) |
| 233 | m/z = 524.66(C39H28N2 = 524.22) | 234 | m/z = 524.66(C39H28N2 = 524.22) |
| 235 | m/z = 575.71(C42H29N3 = 575.23) | 236 | m/z = 701.87(C52H35N3 = 701.28) |
| 237 | m/z = 625.77(C46H31N3 = 625.25) | 238 | m/z = 727.91(C54H37N3 = 727.29) |
| 239 | m/z = 523.67(C40H29N = 523.23) | 240 | m/z = 573.73(C44H31N = 573.24) |
| 241 | m/z = 725.93(C56H39N = 725.30) | 242 | m/z = 597.76(C46H31N = 597.24) |
| 243 | m/z = 674.84(C51H34N2 = 674.27) | 244 | m/z = 674.84(C51H34N2 = 674.27) |
| 245 | m/z = 651.83(C48H33N3 = 651.81) | 246 | m/z = 729.88(C52H35N5 = 729.28) |
| 247 | m/z = 627.79(C46H33N3 = 627.26) | 248 | m/z = 551.69(C40H29N3 = 551.23) |

TABLE 7-continued

| Compound | FD-Mass | Compound | FD-Mass |
|---|---|---|---|
| 249 | m/z = 552.68(C39H28N4 = 552.23) | 250 | m/z = 551.69(C40H29N3 = 551.23) |
| 251 | m/z = 602.74(C43H30N4 = 602.24) | 252 | m/z = 628.77(C45H32N4 = 628.26) |
| 253 | m/z = 627.79(C46H33N3 = 627.26) | 254 | m/z = 486.61(C36H26N2 = 486.21) |
| 255 | m/z = 474.60(C35H26N2 = 474.21) | 256 | m/z = 474.60(C35H26N2 = 474.21) |
| 257 | m/z = 474.60(C35H26N2 = 474.21) | 258 | m/z = 524.66(C39H28N2 = 524.22) |
| 259 | m/z = 524.66(C39H28N2 = 524.22) | 260 | m/z = 575.71(C42H29N3 = 575.23) |
| 261 | m/z = 651.81(C48H33N3 = 651.26) | 262 | m/z = 575.71(C42H29N3 = 575.23) |
| 263 | m/z = 727.91(C54H37N3 = 727.29) | 264 | m/z = 473.61(C36H27N = 473.21) |
| 265 | m/z = 474.60(C35H26N2 = 474.21) | 266 | m/z = 474.60(C35H26N2 = 474.21) |
| 267 | m/z = 474.60(C35H26N2 = 474.21) | 268 | m/z = 524.66(C39H28N2 = 524.22) |
| 269 | m/z = 524.66(C39H28N2 = 524.22) | 270 | m/z = 575.71(C42H29N3 = 575.23) |
| 271 | m/z = 651.81(C48H33N3 = 651.26) | 272 | m/z = 575.71(C42H29N3 = 575.23) |
| 273 | m/z = 727.91(C54H37N3 = 727.29) | 274 | m/z = 589.74(C43H31N3 = 589.25) |
| 275 | m/z = 589.74(C43H31N3 = 589.25) | 276 | m/z = 690.89(C52H38N2 = 690.30) |
| 277 | m/z = 690.89(C52H38N2 = 690.30) | 278 | m/z = 625.77(C46H31N3 = 625.25) |
| 279 | m/z = 673.85(C52H35N = 673.27) | 280 | m/z = 649.83(C50H35N = 649.27) |
| 281 | m/z = 524.66(C39H28N2 = 524.22) | 282 | m/z = 525.65(C38H27N3 = 525.22) |
| 283 | m/z = 623.79(C48H33N = 623.26) | 284 | m/z = 647.82(C50H33N = 647.26) |
| 285 | m/z = 574.74(C43H30N2 = 574.24) | 286 | m/z = 601.75(C44H31N3 = 601.25) |
| 287 | m/z = 601.75(C44H31N3 = 601.25) | 288 | m/z = 649.83(C50H35N = 649.27) |
| 289 | m/z = 651.81(C48H33N3 = 651.26) | 290 | m/z = 753.94(C56H39N3 = 753.31) |
| 291 | m/z = 677.85(C50H35N3 = 677.28) | 292 | m/z = 574.24(C43H30N2 = 574.24) |
| 293 | m/z = 523.67(C40H29N = 523.23) | 294 | m/z = 678.83(C49H34N4 = 678.27) |
| 295 | m/z = 753.94(C56H39N3 = 753.31) | 296 | m/z = 753.94(C56H39N3 = 753.31) |
| 297 | m/z = 753.94(C56H39N3 = 753.31) | 298 | m/z = 754.93(C55H38N4 = 754.31) |
| 299 | m/z = 830.04(C62H43N3 = 829.34) | 300 | m/z = 829.05(C63H44N2 = 828.35) |
| 301 | m/z = 830.04(C62H43N3 = 829.34) | 302 | m/z = 831.03(C61H42N4 = 830.34) |
| 303 | m/z = 727.91(C54H37N3 = 727.29) | 304 | m/z = 575.71(C42H29N3 = 575.23) |
| 305 | m/z = 575.71(C42H29N3 = 575.23) | 306 | m/z = 651.81(C48H33N3 = 651.26) |
| 307 | m/z = 651.81(C48H33N3 = 651.26) | 308 | m/z = 651.81(C48H33N3 = 651.26) |
| 309 | m/z = 475.59(C34H25N3 = 475.20) | 310 | m/z = 476.58(C33H24N4 = 476.20) |
| 311 | m/z = 526.64(C37H26N4 = 526.21) | 312 | m/z = 652.80(C47H32N4 = 652.26) |
| 313 | m/z = 599.73(C44H29N3 = 599.23) | 314 | m/z = 721.90(C56H35N = 721.27) |
| 315 | m/z = 575.71(C42H29N3 = 575.23) | 316 | m/z = 625.77(C46H31N3 = 625.25) |
| 317 | m/z = 625.77(C46H31N3 = 625.25) | 318 | m/z = 674.84(C51H34N2 = 674.27) |
| 319 | m/z = 674.84(C51H34N2 = 674.27) | 320 | m/z = 674.84(C51H34N2 = 674.27) |
| 321 | m/z = 624.78(C47H32N2 = 624.25) | 322 | m/z = 623.79(C48H33N = 623.26) |
| 323 | m/z = 699.89(C54H37N = 699.29) | 324 | m/z = 700.88(C53H36N2 = 700.28) |
| 325 | m/z = 673.85(C52H35N = 673.27) | 326 | m/z = 651.80(C49H33NO = 651.25) |
| 327 | m/z = 613.76(C45H31N3 = 613.25) | 328 | m/z = 689.86(C51H35N3 = 689.28) |
| 329 | m/z = 597.69(C42H32NOP = 597.22) | 330 | m/z = 647.75(C46H34NOP = 647.23) |
| 331 | m/z = 648.74(C45H33N2OP = 648.23) | 332 | m/z = 437.54(C31H23N3 = 437.18) |
| 333 | m/z = 575.71(C42H29N3 = 575.23) | 334 | m/z = 623.79(C48H33N = 623.26) |
| 335 | m/z = 625.77(C46H31N3 = 625.25) | 336 | m/z = 727.91(C54H37N3 = 727.29) |
| 337 | m/z = 651.81(C48H33N3 = 651.26) | 338 | m/z = 548.68(C41H28N2 = 548.22) |
| 339 | m/z = 497.64(C38H27N = 497.21) | 340 | m/z = 652.80(C47H32N4 = 652.26) |
| 341 | m/z = 727.91(C54H37N3 = 727.29) | 342 | m/z = 728.89(C53H36N4 = 728.29) |
| 343 | m/z = 727.91(C54H37N3 = 727.29) | 344 | m/z = 727.91(C54H37N3 = 717.29) |
| 345 | m/z = 801.02(C61H42N2 = 802.33) | 346 | m/z = 804.00(C60H41N3 = 803.33) |
| 347 | m/z = 804.00(C60H41N4 = 803.33) | 348 | m/z = 804.99(C59H40N4 = 804.32) |
| 349 | m/z = 701.87(C52H35N3 = 701.28) | 350 | m/z = 549.67(C40H27N3 = 549.22) |
| 351 | m/z = 549.67(C40H27N3 = 549.22) | 352 | m/z = 625.77(C46H31N3 = 625.25) |
| 353 | m/z = 647.82(C50H33N = 647.26) | 354 | m/z = 623.79(C48H33N = 623.26) |
| 355 | m/z = 498.62(C37H26N2 = 492.21) | 356 | m/z = 499.61(C36H25N3 = 499.20) |
| 357 | m/z = 597.76(C46H31N = 597.24) | 358 | m/z = 621.78(C48H31N = 621.24) |
| 359 | m/z = 548.68(C41H28N2 = 548.22) | 360 | m/z = 575.71(C42H29N3 = 575.23) |
| 361 | m/z = 599.73(C44H29N3 = 599.23) | 362 | m/z = 575.71(C42H29N3 = 575.23) |
| 363 | m/z = 623.79(C48H33N = 623.26) | 364 | m/z = 625.77(C46H31N3 = 625.25) |
| 365 | m/z = 448.56(C33H24N2 = 488.19) | 366 | m/z = 448.46(C33H24N2 = 448.19) |
| 367 | m/z = 498.62(C37H26N2 = 498.21) | 368 | m/z = 648.80(C49H32N2 = 648.25) |
| 369 | m/z = 549.67(C40H27N3 = 549.22) | 370 | m/z = 625.77(C46H31N3 = 625.25) |
| 371 | m/z = 449.55(C32H23N3 = 449.18) | 372 | m/z = 547.70(C42H29N = 547.23) |
| 373 | m/z = 564.73(C42H32N2 = 564.25) | 374 | m/z = 602.74(C43H30N4 = 602.24) |
| 375 | m/z = 625.77(C46H31N3 = 625.25) | 376 | m/z = 701.87(C5235N3 = 701.28) |
| 377 | m/z = 601.75(C44H31N3 = 601.25) | 378 | m/z = 602.74(C43H30N4 = 602.24) |
| 379 | m/z = 601.75(C44H31N3 = 601.25) | 380 | m/z = 625.77(C46H31N3 = 635.25) |
| 381 | m/z = 701.87(C52H35N3 = 701.28) | 382 | m/z = 601.75(C44H31N3 = 601.25) |
| 383 | m/z = 602.74(C43H30N4 = 602.24) | 384 | m/z = 677.85(C50H35N3 = 677.28) |
| 385 | m/z = 647.75(C46H34NOP = 647.23) | 386 | m/z = 697.81(C50H36NOP = 697.25) |
| 387 | m/z = 602.74(C43H30N4 = 602.24) | 388 | m/z = 625.77(C46H31N3 = 625.25) |
| 389 | m/z = 701.87(C52H35N3 = 701.28) | 390 | m/z = 625.77(C46H31N3 = 625.25) |
| 391 | m/z = 602.74(C43H30N4 = 602.24) | 392 | m/z = 639.80(C47H33N3 = 639.26) |
| 393 | m/z = 740.95(C56H40N2 = 740.31) | 394 | m/z = 740.95(C56H40N2 = 740.31) |
| 395 | m/z = 675.83(C50H33N3 = 675.26) | 396 | m/z = 575.71(C42H29N3 = 575.23) |
| 397 | m/z = 673.85(C52H35N = 673.27) | 398 | m/z = 804.00(C60H41N3 = 803.33) |
| 399 | m/z = 727.91(C54H37N3 = 727.29) | 400 | m/z = 625.77(C46H31N3 = 625.25) |
| 401 | m/z = 777.97(C58H39N3 = 777.31) | 402 | m/z = 739.92(C55H37N3 = 739.29) |

Experimental Example

Experimental Example 1

1) Manufacture of Organic Light Emitting Device

A glass substrate on which ITO was coated as a thin film to a thickness of 1500 Å was cleaned with distilled water and ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for removing ITO work function and remaining film, and the substrate was transferred to a thermal deposition apparatus for organic deposition.

On the ITO transparent electrode (anode), organic materials were formed in a two-stack white organic light emitting diode (WOLED) structure. As for the first stack, a hole transfer layer was formed first by thermal vacuum depositing TAPC to a thickness of 300 Å. After forming the hole transfer layer, a light emitting layer was thermal vacuum deposited thereon as follows. The light emitting layer was deposited to 300 Å by doping FIrpic in 8% as a blue phosphorescent dopant to TCzl, a host. An electron transfer layer was formed to 400 Å using TmPyPB, and then a charge generation layer was formed to 100 Å by doping $Cs_2CO_3$ in 20% to a compound described in the following Table 8.

As for the second stack, a hole injection layer was formed first by thermal vacuum depositing $MoO_3$ to a thickness of 50 Å. A hole transfer layer, a common layer, was formed by doping $MoO_3$ to TAPC in 20% and forming to 100 Å, and then depositing TAPC to 300 Å. After depositing a light emitting layer to 300 Å thereon by doping Ir(ppy)$_3$, a green phosphorescent dopant, in 8% to TCzl, a host, an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic electroluminescent device.

Meanwhile, all the organic compounds required to manufacture the OLED device were vacuum sublimation purified under $10^{-6}$ torr to $10^{-8}$ torr by each material to be used in the OLED manufacture.

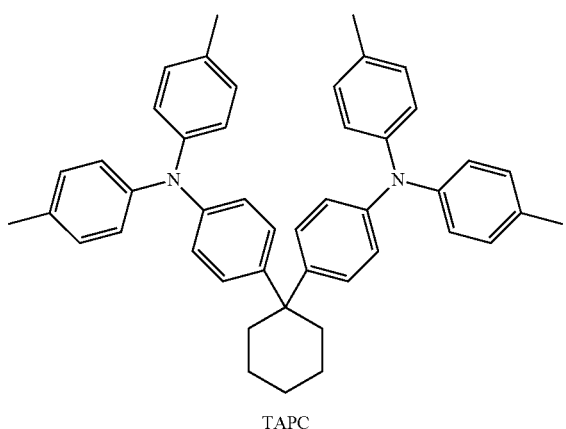

TAPC

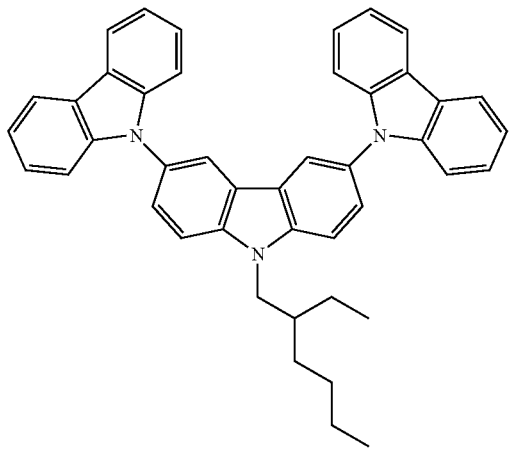

TCzl

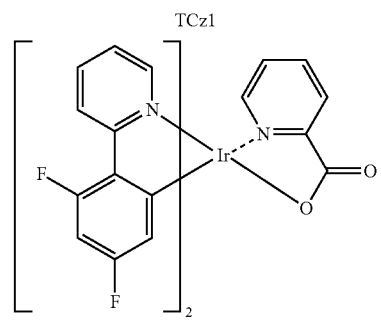

FIrpic

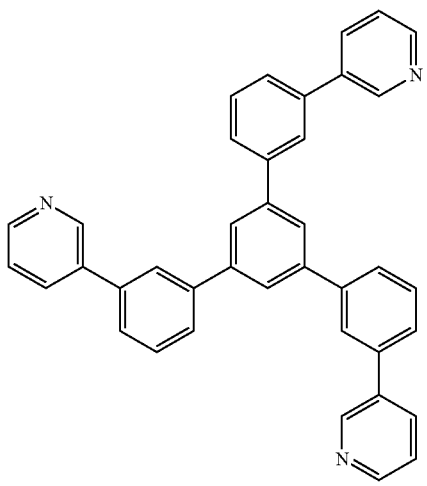

TmPyPB

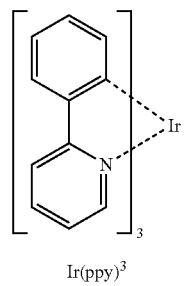

Ir(ppy)$^3$

2) Driving Voltage and Light Emission Efficiency of Organic Electroluminescent Device For the organic electroluminescent devices manufactured as above, electroluminescent light emission (EL) characteristics were measured using M7000 manufactured by McScience Inc., and with the measurement results, $T_{95}$ when standard luminance was 3,500 cd/m² was measured using a lifetime test system (M6000) manufactured by McScience Inc. Results of measuring a driving voltage, light emission efficiency, external quantum efficiency and a color coordinate (CIE) of the white organic electroluminescent devices manufactured according to the present disclosure are as shown in Table 8.

TABLE 8

| | Compound | Driving Voltage (V) | Light Emission Efficiency (cd/A) | CIE (x, y) | Lifespan (T95) |
|---|---|---|---|---|---|
| Example 1 | 1 | 8.13 | 60.17 | (0.211, 0.434) | 27 |
| Example 2 | 6 | 7.41 | 64.86 | (0.220, 0.480) | 33 |
| Example 3 | 9 | 8.71 | 58.11 | (0.223, 0.470) | 21 |
| Example 4 | 10 | 8.03 | 62.27 | (0.210, 0.424) | 25 |
| Example 5 | 13 | 7.08 | 68.92 | (0.208, 0.420) | 45 |
| Example 6 | 14 | 7.18 | 69.91 | (0.207, 0.421) | 46 |
| Example 7 | 15 | 7.01 | 69.32 | (0.206, 0.419) | 45 |
| Example 8 | 27 | 7.28 | 68.83 | (0.205, 0.411) | 43 |
| Example 9 | 32 | 7.05 | 68.52 | (0.201, 0.416) | 42 |
| Example 10 | 34 | 8.03 | 69.08 | (0.215, 0.425) | 34 |
| Example 11 | 39 | 8.69 | 51.00 | (0.212, 0.421) | 23 |
| Example 12 | 44 | 7.63 | 66.13 | (0.211, 0.427) | 32 |
| Example 13 | 53 | 8.25 | 55.92 | (0.212, 0.391) | 25 |
| Example 14 | 65 | 7.93 | 62.05 | (0.234, 0.445) | 36 |
| Example 15 | 70 | 8.30 | 52.00 | (0.213, 0.421) | 42 |
| Example 16 | 72 | 7.12 | 67.56 | (0.209, 0.415) | 44 |
| Example 17 | 77 | 7.86 | 61.19 | (0.232, 0.443) | 22 |
| Example 18 | 80 | 7.01 | 69.94 | (0.209, 0.418) | 41 |
| Example 19 | 82 | 7.31 | 50.11 | (0.212, 0.421) | 23 |
| Example 20 | 86 | 8.58 | 50.11 | (0.211, 0.417) | 25 |
| Example 21 | 95 | 8.89 | 61.73 | (0.209, 0.414) | 27 |
| Example 22 | 104 | 8.79 | 57.33 | (0.212, 0.423) | 28 |
| Example 23 | 105 | 8.67 | 58.91 | (0.222, 0.413) | 29 |
| Example 24 | 110 | 7.55 | 66.48 | (0.208, 0.419) | 33 |
| Example 25 | 113 | 7.87 | 62.86 | (0.229, 0.452) | 24 |
| Example 26 | 117 | 7.74 | 62.25 | (0.218, 0.443) | 25 |
| Example 27 | 120 | 8.12 | 59.34 | (0.216, 0.483) | 24 |
| Example 28 | 124 | 7.44 | 65.32 | (0.207, 0.423) | 33 |
| Example 29 | 125 | 8.89 | 57.91 | (0.200, 0.423) | 35 |
| Example 30 | 128 | 7.34 | 65.77 | (0.208, 0.418) | 31 |
| Example 31 | 130 | 7.52 | 64.82 | (0.210, 0.422) | 31 |
| Example 32 | 138 | 7.53 | 66.12 | (0.212, 0.429) | 30 |
| Example 33 | 146 | 7.24 | 68.88 | (0.212, 0.423) | 40 |
| Example 34 | 149 | 8.11 | 54.11 | (0.212, 0.433) | 39 |
| Example 35 | 155 | 7.91 | 61.34 | (0.211, 0.423) | 26 |
| Example 36 | 160 | 7.72 | 64.31 | (0.202, 0.422) | 26 |
| Example 37 | 171 | 7.92 | 61.87 | (0.222, 0.445) | 24 |
| Example 38 | 174 | 7.94 | 66.16 | (0.229, 0.465) | 28 |
| Example 39 | 176 | 8.42 | 51.84 | (0.211, 0.413) | 22 |
| Example 40 | 178 | 7.87 | 63.32 | (0.206, 0.428) | 26 |
| Example 41 | 179 | 7.21 | 69.93 | (0.209, 0.416) | 39 |
| Example 42 | 184 | 8.08 | 62.24 | (0.209, 0.423) | 25 |
| Example 43 | 187 | 7.91 | 58.99 | (0.219, 0.421) | 33 |
| Example 44 | 195 | 7.98 | 63.43 | (0.209, 0.420) | 26 |
| Example 45 | 196 | 7.86 | 61.81 | (0.222, 0.434) | 25 |
| Example 46 | 198 | 8.00 | 56.99 | (0.217, 0.411) | 32 |
| Example 47 | 208 | 7.63 | 66.12 | (0.212, 0.419) | 30 |
| Example 48 | 209 | 8.21 | 59.00 | (0.213, 0.423) | 27 |
| Example 49 | 211 | 7.57 | 65.66 | (0.214, 0.426) | 29 |
| Example 50 | 218 | 7.88 | 59.71 | (0.207, 0.421) | 25 |
| Example 51 | 224 | 7.21 | 69.02 | (0.208, 0.427) | 41 |
| Example 52 | 226 | 7.05 | 68.22 | (0.208, 0.421) | 43 |
| Example 53 | 236 | 7.98 | 52.11 | (0.212, 0.423) | 26 |
| Example 54 | 248 | 7.11 | 51.48 | (0.221, 0.411) | 25 |
| Example 55 | 261 | 8.22 | 50.95 | (0.213, 0.413) | 22 |
| Example 56 | 271 | 8.21 | 56.71 | (0.211, 0.4033) | 28 |
| Example 57 | 280 | 8.11 | 64.99 | (0.201, 0.421) | 26 |
| Example 58 | 284 | 7.96 | 50.09 | (0.217, 0.430) | 27 |
| Example 59 | 291 | 8.21 | 51.22 | (0.202, 0.411) | 25 |
| Example 60 | 298 | 7.51 | 66.10 | (0.208, 0.418) | 28 |
| Example 61 | 303 | 7.44 | 65.99 | (0.211, 0.422) | 29 |
| Example 62 | 316 | 7.97 | 64.00 | (0.228, 0.437) | 27 |
| Example 63 | 320 | 8.01 | 60.11 | (0.232, 0.441) | 25 |
| Example 64 | 323 | 8.32 | 57.99 | (0.210, 0.449) | 26 |
| Example 65 | 328 | 7.38 | 59.31 | (0.211, 0.419) | 26 |

TABLE 8-continued

| | Compound | Driving Voltage (V) | Light Emission Efficiency (cd/A) | CIE (x, y) | Lifespan (T95) |
|---|---|---|---|---|---|
| Example 66 | 329 | 8.21 | 59.77 | (0.219, 0.426) | 27 |
| Example 67 | 332 | 7.44 | 65.33 | (0.211, 0.429) | 32 |
| Example 68 | 337 | 7.05 | 51.11 | (0.221, 0.433) | 26 |
| Example 69 | 341 | 8.01 | 51.02 | (0.211, 0.421) | 24 |
| Example 70 | 349 | 8.89 | 60.12 | (0.222, 0.427) | 27 |
| Example 71 | 357 | 8.88 | 56.26 | (0.218, 0.421) | 28 |
| Example 72 | 360 | 8.91 | 52.23 | (0.211, 0.411) | 24 |
| Example 73 | 361 | 8.11 | 58.22 | (0.218, 0.422) | 31 |
| Example 74 | 392 | 8.60 | 51.90 | (0.208, 0.429) | 25 |
| Example 75 | 395 | 7.89 | 63.28 | (0.209, 0.431) | 30 |
| Example 76 | 399 | 8.11 | 56.90 | (0.201, 0.429) | 21 |
| Example 77 | 400 | 8.21 | 55.33 | (0.217, 0.423) | 33 |
| Example 78 | 401 | 8.67 | 51.22 | (0.209, 0.411) | 26 |
| Example 79 | 402 | 8.55 | 50.11 | (0.210, 0.429) | 21 |
| Comparative Example 1 | TmPyPB | 8.58 | 53.95 | (0.212, 0.433) | 23 |

As shown from the results of Table 8, the organic electroluminescent devices using the charge generation layer material of the 2-stack white organic electroluminescent device of the present disclosure had a low driving voltage and improved light emission efficiency compared to Comparative Example 1. Particularly, it was identified that Compounds 13, 14, 15, 27, 32, 72, 80, 146, 179, 224, 226, 361 and 395 were significantly excellent in all of driving, efficiency and lifespan.

The presumed reason for such results is that the compound of the present disclosure used as an N-type charge generation layer formed with an invented skeleton having proper length, strength and flat property and a proper heterocompound capable of binding with metals is doped with an alkali metal or an alkali-earth metal to form a gap state within the N-type charge generation layer, and electrons produced from a P-type charge generation layer are readily injected to the electron transfer layer through the gap state produced within the N-type charge generation layer. Accordingly, the P-type charge generation layer favorably carried out electron injection and electron transfer to the N-type charge generation layer, and as a result, it is considered that a driving voltage of the organic light emitting device decreased, and efficiency and lifespan were improved.

Experimental Example 2

1) Manufacture of Organic Light Emitting Device

A glass substrate on which ITO was coated as a thin film to a thickness of 1500 Å was cleaned with distilled water and ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for removing ITO work function and remaining film, and the substrate was transferred to a thermal deposition apparatus for organic deposition. On the ITO transparent electrode (anode), organic materials were formed in a single-stack structure. As a hole injection layer, HAT-CN was deposited to a thickness of 50 Å, and subsequently, a hole transfer layer was formed by doping DNTPD within 10% to NPD, depositing the result to a thickness of 1500 Å, and continuously depositing TCTA to a thickness of 200 Å. Subsequently, a light emitting layer comprising a t-Bu-perylene dopant in an ADN host was formed to a thickness of 250 Å. Next, $Alq_3$, an electron transfer layer, was formed to a thickness of 250 Å, and an N-type charge transfer layer was formed to a thickness of 100 Å by doping Li, an alkali metal, to a compound described in the following Table 9, and Al, a cathode, was formed to a thickness of approximately 1,000 Å to manufacture an organic electroluminescent device.

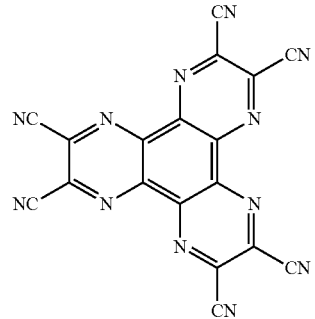

HAT-CN

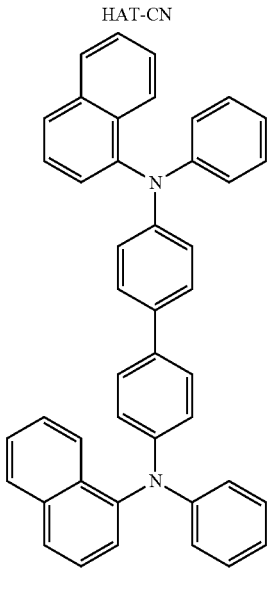

NPD

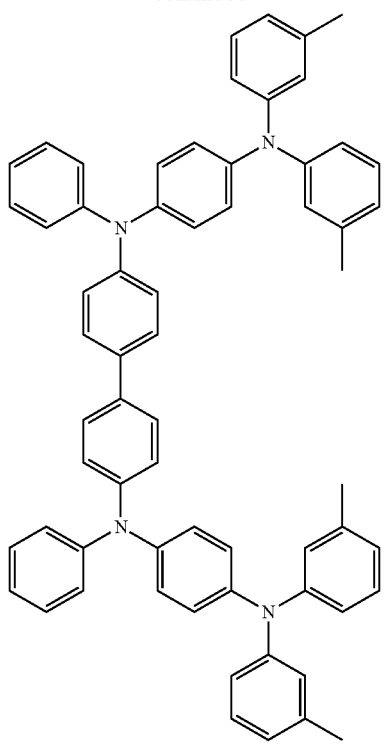

DNTPD

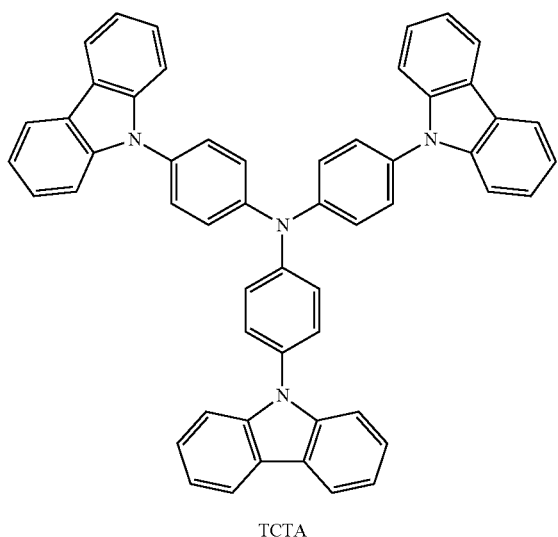

TCTA

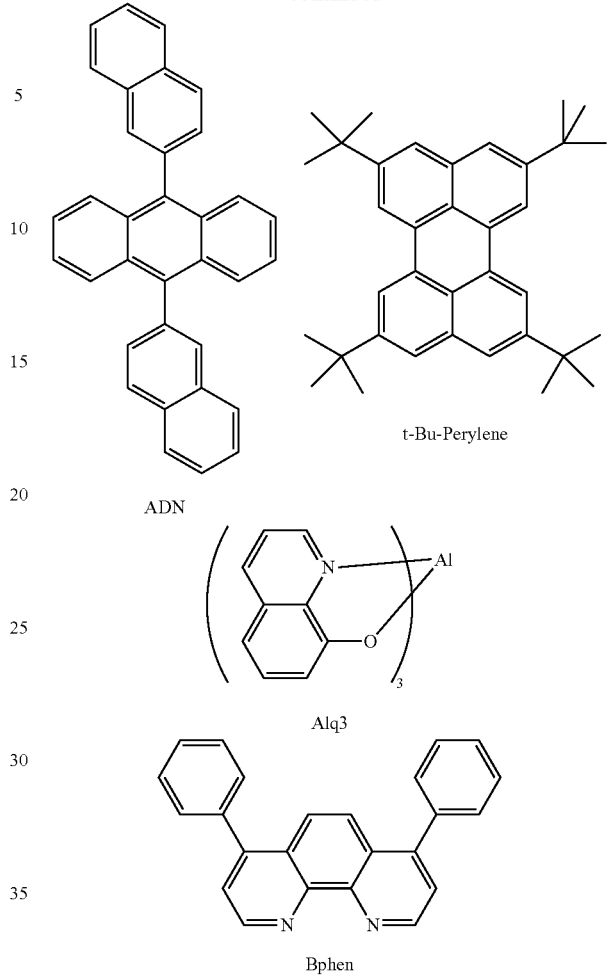

ADN t-Bu-Perylene

Alq3

Bphen

2) Driving Voltage and Light Emission Efficiency of Organic Electroluminescent Device For the organic electroluminescent devices manufactured as above, electroluminescent light emission (EL) characteristics were measured using M7000 manufactured by McScience Inc., and with the measurement results, $T_{95}$ when standard luminance was 750 cd/m² was measured using a lifetime test system (M6000) manufactured by McScience Inc. Results of measuring a driving voltage, light emission efficiency, external quantum efficiency and a color coordinate (CIE) of the white organic electroluminescent devices manufactured according to the present disclosure are as shown in Table 9.

TABLE 9

| | Compound | Driving Voltage (V) | Light Emission Efficiency (cd/A) | CIE (x, y) | Lifespan (T95) |
|---|---|---|---|---|---|
| Example 80 | 1 | 5.89 | 6.12 | (0.134, 0.108) | 26 |
| Example 81 | 6 | 4.99 | 6.53 | (0.134, 0.102) | 31 |
| Example 82 | 9 | 6.01 | 6.12 | (0.134, 0.101) | 26 |

TABLE 9-continued

| | Compound | Driving Voltage (V) | Light Emission Efficiency (cd/A) | CIE (x, y) | Lifespan (T95) |
|---|---|---|---|---|---|
| Example 83 | 10 | 5.99 | 6.00 | (0.134, 0.108) | 24 |
| Example 84 | 13 | 4.48 | 6.99 | (0.134, 0.099) | 44 |
| Example 85 | 14 | 4.50 | 6.87 | (0.134, 0.099) | 46 |
| Example 86 | 15 | 4.61 | 6.88 | (0.134, 0.098) | 45 |
| Example 87 | 27 | 4.55 | 6.89 | (0.134, 0.098) | 42 |
| Example 88 | 32 | 4.50 | 6.71 | (0.134, 0.097) | 41 |
| Example 89 | 34 | 5.02 | 6.51 | (0.134, 0.103) | 31 |
| Example 90 | 39 | 5.76 | 4.21 | (0.134, 0.108) | 29 |
| Example 91 | 44 | 5.23 | 6.61 | (0.134, 0.103) | 33 |
| Example 92 | 53 | 6.00 | 6.11 | (0.134, 0.110) | 24 |
| Example 93 | 65 | 5.09 | 6.67 | (0.134, 0.105) | 35 |
| Example 94 | 70 | 5.41 | 6.11 | (0.134, 0.106) | 28 |
| Example 95 | 72 | 4.57 | 6.82 | (0.134, 0.100) | 45 |
| Example 96 | 77 | 5.91 | 6.21 | (0.134, 0.109) | 23 |
| Example 97 | 80 | 4.48 | 6.91 | (0.134, 0.098) | 44 |
| Example 98 | 82 | 6.21 | 6.11 | (0.134, 0.107) | 30 |
| Example 99 | 86 | 5.70 | 6.00 | (0.134, 0.109) | 31 |
| Example 100 | 95 | 5.81 | 6.12 | (0.134, 0.110) | 33 |
| Example 101 | 104 | 6.09 | 6.09 | (0.134, 0.111) | 31 |
| Example 102 | 105 | 5.61 | 6.11 | (0.134, 0.101) | 29 |
| Example 103 | 110 | 5.55 | 6.56 | (0.134, 0.100) | 35 |
| Example 104 | 113 | 5.99 | 6.07 | (0.134, 0.100) | 24 |
| Example 105 | 117 | 5.88 | 6.14 | (0.134, 0.105) | 26 |
| Example 106 | 120 | 6.09 | 6.03 | (0.134, 0.109) | 25 |
| Example 107 | 124 | 4.79 | 6.77 | (0.134, 0.102) | 34 |
| Example 108 | 125 | 5.88 | 6.01 | (0.134, 0.108) | 26 |
| Example 109 | 128 | 4.88 | 6.75 | (0.134, 0.102) | 32 |
| Example 110 | 130 | 4.90 | 6.78 | (0.134, 0.100) | 33 |
| Example 111 | 138 | 4.78 | 6.77 | (0.134, 0.101) | 32 |
| Example 112 | 146 | 4.41 | 6.93 | (0.134, 0.099) | 41 |
| Example 113 | 149 | 5.89 | 5.94 | (0.134, 0.110) | 29 |
| Example 114 | 155 | 5.81 | 6.16 | (0.134, 0.110) | 27 |
| Example 115 | 160 | 5.98 | 6.28 | (0.134, 0.109) | 27 |
| Example 116 | 171 | 5.66 | 6.34 | (0.134, 0.108) | 25 |
| Example 117 | 174 | 5.58 | 6.18 | (0.134, 0.109) | 29 |
| Example 118 | 176 | 6.01 | 6.11 | (0.134, 0.114) | 31 |
| Example 119 | 178 | 5.77 | 6.11 | (0.134, 0.105) | 26 |
| Example 120 | 179 | 4.50 | 6.90 | (0.134, 0.100) | 42 |
| Example 121 | 184 | 5.78 | 6.23 | (0.134, 0.102) | 27 |
| Example 122 | 187 | 5.89 | 4.91 | (0.134, 0.101) | 26 |
| Example 123 | 195 | 5.79 | 6.19 | (0.134, 0.109) | 28 |
| Example 124 | 196 | 5.80 | 6.20 | (0.134, 0.102) | 25 |
| Example 125 | 198 | 5.88 | 6.11 | (0.134, 0.101) | 29 |
| Example 126 | 208 | 5.01 | 6.60 | (0.134, 0.101) | 31 |
| Example 127 | 209 | 6.04 | 6.10 | (0.134, 0.110) | 25 |
| Example 128 | 211 | 5.29 | 6.50 | (0.134, 0.101) | 30 |
| Example 129 | 218 | 5.89 | 6.33 | (0.134, 0.109) | 27 |
| Example 130 | 224 | 4.57 | 6.81 | (0.134, 0.098) | 39 |
| Example 131 | 226 | 4.54 | 6.87 | (0.134, 0.098) | 39 |
| Example 132 | 236 | 5.91 | 5.21 | (0.134, 0.110) | 25 |
| Example 133 | 248 | 5.99 | 6.11 | (0.134, 0.105) | 24 |
| Example 134 | 261 | 6.09 | 5.41 | (0.134, 0.106) | 25 |
| Example 135 | 271 | 6.13 | 5.23 | (0.134, 0.101) | 26 |
| Example 136 | 280 | 5.80 | 6.19 | (0.134, 0.105) | 27 |
| Example 137 | 284 | 5.99 | 6.09 | (0.134, 0.105) | 23 |
| Example 138 | 291 | 5.98 | 6.01 | (0.134, 0.106) | 31 |
| Example 139 | 298 | 5.22 | 6.54 | (0.134, 0.100) | 28 |
| Example 140 | 303 | 5.02 | 6.65 | (0.134, 0.100) | 29 |
| Example 141 | 316 | 5.81 | 6.23 | (0.134, 0.105) | 22 |
| Example 142 | 320 | 5.93 | 6.23 | (0.134, 0.104) | 23 |
| Example 143 | 323 | 5.92 | 6.22 | (0.134, 0.104) | 24 |
| Example 144 | 328 | 5.87 | 4.28 | (0.134, 0.101) | 23 |
| Example 145 | 329 | 5.71 | 6.28 | (0.134, 0.105) | 24 |
| Example 146 | 332 | 5.21 | 6.52 | (0.134, 0.100) | 30 |
| Example 147 | 337 | 5.21 | 6.11 | (0.134, 0.110) | 23 |
| Example 148 | 341 | 5.50 | 6.23 | (0.134, 0.100) | 24 |
| Example 149 | 349 | 5.51 | 6.09 | (0.134, 0.110) | 22 |
| Example 150 | 357 | 5.60 | 6.11 | (0.134, 0.104) | 23 |
| Example 151 | 360 | 5.81 | 6.09 | (0.134, 0.110) | 24 |
| Example 152 | 361 | 5.33 | 6.33 | (0.134, 0.109) | 29 |
| Example 153 | 392 | 5.40 | 6.10 | (0.134, 0.110) | 25 |
| Example 154 | 395 | 5.71 | 6.33 | (0.134, 0.108) | 28 |
| Example 155 | 399 | 5.51 | 6.01 | (0.134, 0.111) | 22 |
| Example 156 | 400 | 5.33 | 6.12 | (0.134, 0.107) | 26 |

TABLE 9-continued

| | Compound | Driving Voltage (V) | Light Emission Efficiency (cd/A) | CIE (x, y) | Lifespan (T95) |
|---|---|---|---|---|---|
| Example 157 | 401 | 5.45 | 6.09 | (0.134, 0.110) | 24 |
| Example 158 | 402 | 5.70 | 6.23 | (0.134, 0.110) | 26 |
| Comparative Example 2 | Bphen | 5.82 | 6.23 | (0.134, 0.110) | 27 |

As shown from the results of Table 9, the organic electroluminescent devices using the charge generation layer material of the blue organic electroluminescent device of the present disclosure had a low driving voltage and improved light emission efficiency compared to Comparative Example 2. Particularly, it was identified that Compounds 13, 14, 15, 27, 32, 72, 80, 146, 179, 224, 226, 361 and 395 were significantly excellent in all of driving, efficiency and lifespan.

The presumed reason for such results is that the compound of the present disclosure used as an N-type charge generation layer formed with an invented skeleton having proper length, strength and flat property and a proper heterocompound capable of binding with metals is doped with an alkali metal or an alkali-earth metal to form a gap state within the N-type charge generation layer, and electrons produced from a P-type charge generation layer are readily injected to the electron transfer layer through the gap state produced within the N-type charge generation layer. Accordingly, the P-type charge generation layer favorably carried out electron injection and electron transfer to the N-type charge generation layer, and as a result, it is considered that a driving voltage of the organic light emitting device decreased, and efficiency and lifespan were improved.

Experimental Example 3

1) Manufacture of Organic Light Emitting Device

A transparent electrode ITO thin film obtained from glass for an OLED (manufactured by Samsung Corning Advanced Glass) was ultrasonic cleaned consecutively using trichloroethylene, acetone, ethanol and distilled water for 5 minutes each, placed in isopropanol and stored, and then used.

Next, the ITO substrate was installed in a substrate folder of vacuum deposition equipment, and the following 4,4',4"-tris(N,N-(2-naphthyl)-phenylamino)triphenyl amine (2-TNATA) was introduced to a cell in the vacuum deposition equipment.

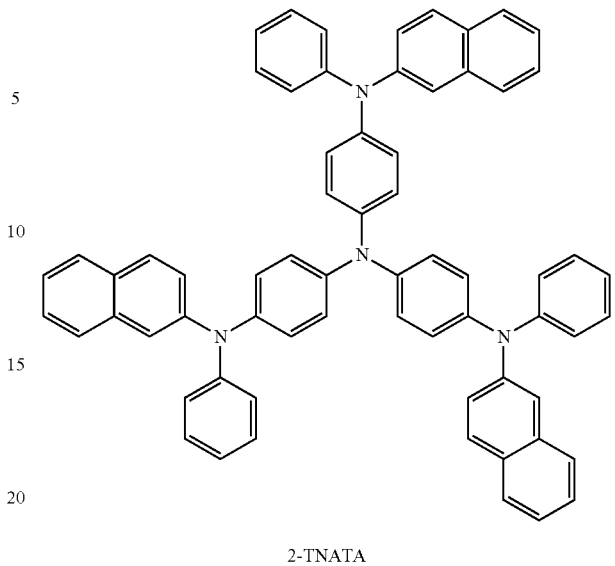

2-TNATA

Subsequently, the chamber was exhausted until the degree of vacuum inside the chamber reached $10^{-6}$ torr, and then a current was applied to the cell to evaporate the 2-TNATA to deposit a hole injection layer having a thickness of 600 Å on the ITO substrate.

The following N,N'-bis(α-naphthyl)-N,N'-diphenyl-4,4'-diamine (NPB) was introduced to a different cell in the vacuum deposition equipment, a current was applied to the cell to evaporate to deposit a hole transfer layer having a thickness of 300 Å on the hole injection layer.

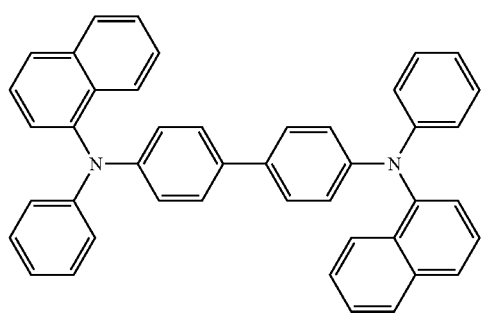

NPB

After forming the hole injection layer and the hole transfer layer as above, a blue light emitting material having a structure as follows was deposited thereon as a light emitting layer. Specifically, H1, a blue light emitting host material, was vacuum deposited to a thickness of 200 Å on one cell in the vacuum deposition equipment, and D1, a blue light emitting dopant material, was vacuum deposited thereon in 5% with respect to the host material.

H1

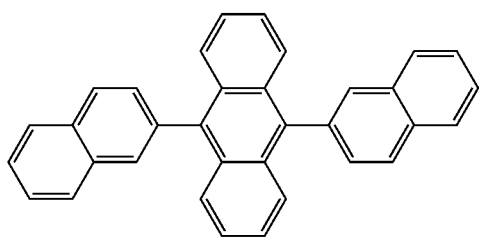

D1

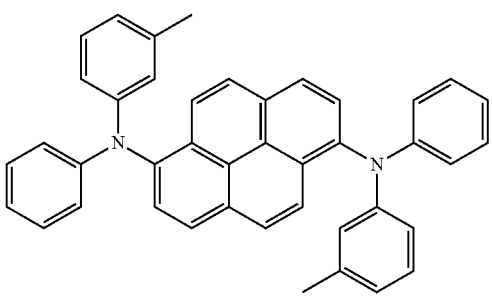

Subsequently, a compound of the following structural formula E1 was deposited to a thickness of 300 Å as an electron transfer layer.

E1

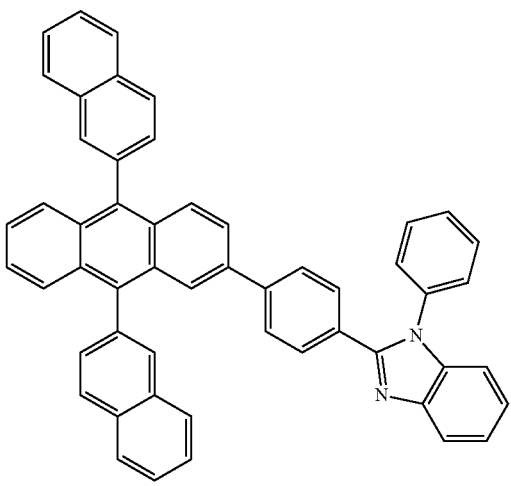

As an electron injection layer, lithium fluoride (LiF) was deposited to a thickness of 10 Å, and an Al cathode was formed to a thickness of 1000 Å to manufacture an OLED device.

Meanwhile, all the organic compounds required to manufacture the OLED device were vacuum sublimation purified under $10^{-6}$ torr to $10^{-8}$ torr by each material to be used in the OLED manufacture.

2) Driving Voltage and Light Emission Efficiency of Organic Electroluminescent Device For the organic electroluminescent devices manufactured as above, electroluminescent light emission (EL) characteristics were measured using M7000 manufactured by McScience Inc., and with the measurement results, $T_{95}$ when standard luminance was 700 cd/m² was measured using a lifetime test system (M6000) manufactured by McScience Inc. Results of measuring a driving voltage, light emission efficiency, external quantum efficiency and a color coordinate (CIE) of the white organic electroluminescent devices manufactured according to the present disclosure are as shown in Table 10.

TABLE 10

| Compound | | Driving Voltage (V) | Light Emission Efficiency (cd/A) | CIE (x, y) | Lifespan (T95) |
|---|---|---|---|---|---|
| Example 159 | 1 | 4.48 | 7.01 | (0.134, 0.098) | 40 |
| Example 160 | 6 | 5.01 | 6.59 | (0.134, 0.100) | 36 |
| Example 161 | 9 | 5.89 | 5.78 | (0.134, 0.100) | 31 |
| Example 162 | 10 | 4.50 | 7.11 | (0.134, 0.099) | 41 |
| Example 163 | 13 | 5.55 | 6.02 | (0.134, 0.105) | 29 |
| Example 164 | 14 | 5.49 | 6.00 | (0.134, 0.101) | 31 |
| Example 165 | 15 | 5.33 | 5.89 | (0.134, 0.102) | 29 |
| Example 166 | 27 | 5.49 | 5.98 | (0.134, 0.100) | 28 |
| Example 167 | 32 | 5.50 | 6.22 | (0.134, 0.100) | 30 |
| Example 168 | 34 | 5.00 | 6.75 | (0.134, 0.100) | 36 |
| Example 169 | 39 | 6.23 | 6.01 | (0.134, 0.102) | 31 |
| Example 170 | 44 | 5.01 | 6.62 | (0.134, 0.101) | 36 |
| Example 171 | 53 | 4.52 | 6.90 | (0.134, 0.100) | 42 |
| Example 172 | 65 | 5.11 | 6.62 | (0.134, 0.102) | 37 |
| Example 173 | 70 | 5.00 | 6.01 | (0.134, 0.100) | 31 |
| Example 174 | 72 | 5.63 | 5.88 | (0.134, 0.105) | 32 |
| Example 175 | 77 | 4.39 | 6.99 | (0.134, 0.100) | 40 |
| Example 176 | 80 | 5.48 | 6.01 | (0.134, 0.105) | 31 |
| Example 177 | 82 | 5.67 | 6.05 | (0.134, 0.101) | 31 |
| Example 178 | 86 | 5.51 | 5.97 | (0.134, 0.102) | 29 |
| Example 179 | 95 | 5.54 | 5.96 | (0.134, 0.100) | 34 |
| Example 180 | 104 | 5.31 | 5.67 | (0.134, 0.103) | 29 |
| Example 181 | 105 | 5.22 | 5.94 | (0.134, 0.101) | 30 |
| Example 182 | 110 | 4.90 | 6.67 | (0.134, 0.101) | 40 |
| Example 183 | 113 | 4.35 | 7.17 | (0.134, 0.099) | 41 |
| Example 184 | 117 | 4.51 | 7.09 | (0.134, 0.098) | 42 |
| Example 185 | 120 | 4.44 | 7.15 | (0.134, 0.099) | 42 |
| Example 186 | 124 | 4.98 | 6.38 | (0.134, 0.101) | 37 |
| Example 187 | 125 | 5.50 | 5.67 | (0.134, 0.101) | 29 |
| Example 188 | 128 | 5.02 | 6.76 | (0.134, 0.100) | 35 |
| Example 189 | 130 | 5.05 | 6.45 | (0.134, 0.099) | 36 |
| Example 190 | 138 | 5.16 | 6.66 | (0.134, 0.100) | 36 |
| Example 191 | 146 | 6.22 | 6.09 | (0.134, 0.105) | 28 |
| Example 192 | 149 | 5.88 | 5.99 | (0.134, 0.101) | 33 |

TABLE 10-continued

| Compound | | Driving Voltage (V) | Light Emission Efficiency (cd/A) | CIE (x, y) | Lifespan (T95) |
|---|---|---|---|---|---|
| Example 193 | 155 | 4.39 | 7.02 | (0.134, 0.100) | 40 |
| Example 194 | 160 | 4.40 | 7.21 | (0.134, 0.099) | 44 |
| Example 195 | 171 | 4.55 | 7.12 | (0.134, 0.100) | 41 |
| Example 196 | 174 | 4.53 | 6.97 | (0.134, 0.099) | 42 |
| Example 197 | 176 | 5.61 | 6.13 | (0.134, 0.100) | 31 |
| Example 198 | 178 | 4.42 | 7.32 | (0.134, 0.100) | 42 |
| Example 199 | 179 | 5.56 | 6.11 | (0.134, 0.102) | 29 |
| Example 200 | 184 | 4.44 | 7.21 | (0.134, 0.099) | 40 |
| Example 201 | 187 | 5.68 | 6.14 | (0.134, 0.100) | 32 |
| Example 202 | 195 | 4.49 | 7.09 | (0.134, 0.100) | 41 |
| Example 203 | 196 | 4.51 | 6.99 | (0.134, 0.099) | 40 |
| Example 204 | 198 | 5.59 | 6.11 | (0.134, 0.099) | 31 |
| Example 205 | 208 | 4.82 | 6.75 | (0.134, 0.100) | 35 |
| Example 206 | 209 | 5.83 | 5.90 | (0.134, 0.100) | 31 |
| Example 207 | 211 | 4.97 | 6.49 | (0.134, 0.101) | 35 |
| Example 208 | 218 | 4.55 | 6.96 | (0.134, 0.099) | 39 |
| Example 209 | 224 | 5.49 | 6.00 | (0.134, 0.100) | 32 |
| Example 210 | 226 | 5.60 | 5.98 | (0.134, 0.102) | 31 |
| Example 211 | 236 | 5.88 | 5.71 | (0.134, 0.102) | 36 |
| Example 212 | 248 | 5.59 | 5.99 | (0.134, 0.100) | 32 |
| Example 213 | 261 | 5.66 | 5.28 | (0.134, 0.101) | 31 |
| Example 214 | 271 | 5.78 | 5.67 | (0.134, 0.099) | 33 |
| Example 215 | 280 | 4.55 | 7.05 | (0.134, 0.100) | 40 |
| Example 216 | 284 | 4.41 | 7.16 | (0.134, 0.099) | 40 |
| Example 217 | 291 | 5.71 | 6.01 | (0.134, 0.100) | 27 |
| Example 218 | 298 | 5.11 | 6.75 | (0.134, 0.102) | 37 |
| Example 219 | 303 | 4.88 | 6.82 | (0.134, 0.100) | 38 |
| Example 220 | 316 | 4.49 | 7.00 | (0.134, 0.099) | 40 |
| Example 221 | 320 | 4.38 | 7.02 | (0.134, 0.098) | 44 |
| Example 222 | 323 | 4.50 | 7.03 | (0.134, 0.099) | 41 |
| Example 223 | 328 | 5.87 | 5.98 | (0.134, 0.100) | 33 |
| Example 224 | 329 | 4.59 | 7.17 | (0.134, 0.098) | 42 |
| Example 225 | 332 | 4.99 | 6.60 | (0.134, 0.100) | 35 |
| Example 226 | 337 | 5.99 | 5.01 | (0.134, 0.098) | 44 |
| Example 227 | 341 | 5.58 | 5.00 | (0.134, 0.099) | 41 |
| Example 228 | 349 | 5.50 | 5.99 | (0.134, 0.100) | 28 |
| Example 229 | 357 | 5.94 | 5.60 | (0.134, 0.100) | 35 |
| Example 230 | 360 | 5.57 | 5.77 | (0.134, 0.100) | 31 |
| Example 231 | 361 | 5.56 | 5.90 | (0.134, 0.100) | 32 |
| Example 232 | 392 | 5.46 | 5.22 | (0.134, 0.100) | 44 |
| Example 233 | 395 | 5.91 | 5.88 | (0.134, 0.098) | 37 |
| Example 234 | 399 | 5.48 | 5.88 | (0.134, 0.100) | 38 |
| Example 235 | 400 | 5.21 | 5.61 | (0.134, 0.100) | 30 |
| Example 236 | 401 | 5.99 | 5.00 | (0.134, 0.099) | 32 |
| Example 237 | 402 | 5.66 | 5.90 | (0.134, 0.098) | 33 |
| Comparative Example 3 | E1 | 5.56 | 5.91 | (0.134, 0.100) | 30 |

As shown from the results of Table 10, the organic electroluminescent devices using the electron transfer layer material of the blue organic electroluminescent device of the present disclosure had a low driving voltage and significantly improved light emission efficiency and lifespan compared to Comparative Example 3. Particularly, it was identified that Compounds 1, 10, 53, 77, 113, 117, 120, 155, 166, 171, 174, 178, 184, 195, 196, 218, 280, 284, 316, 320, 323 and 329 were significantly excellent in all of driving, efficiency and lifespan.

The presumed reason for such results is that, when the invented compound having proper length, strength and flat property is used as an electron transfer layer, a compound in an excited state is produced by receiving electrons under a specific condition, and particularly, when the excited state is formed in the heteroskeleton site of the compound, excited energy moves to a stable state before the excited heteroskeleton site goes through a different reaction, and the relatively stabilized compound is capable of efficiently transferring electrons without compound decomposition or destruction. As a reference, it is considered that those having a stable state when excited are aryl or acene series compounds or multicyclic hetero-compounds. Accordingly, it is considered that the compound of the present disclosure enhances electron-transport properties or improved stability resulting in excellency in all of driving, efficiency and lifespan.

The invention claimed is:

1. A hetero-cyclic compound represented by the following Chemical Formula 1:

[Chemical Formula 1]

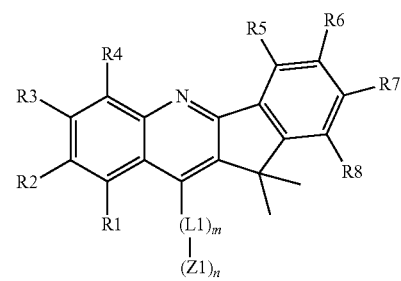

wherein, in Chemical Formula 1,
L1 is a substituted or unsubstituted $C_6$ to $C_{60}$ arylene group; or a substituted or unsubstituted $C_2$ to $C_{60}$ heteroarylene group;

Z1 is selected from the group consisting of hydrogen; deuterium; a halogen group; —CN; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group;

m is an integer of 1 to 4;

n is an integer of 1 to 4;

R5 is R8 are hydrogen; or deuterium,

R1 to R4 are the same as or different from each other, and each independently selected from the group consisting of hydrogen; and deuterium; or two or more groups adjacent to each other bond to each other to form a substituted or unsubstituted aliphatic or aromatic hydrocarbon ring; and R, R' and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

2. The hetero-cyclic compound of claim 1, wherein Chemical Formula 1 is represented by any one of the following Chemical Formulae 2 to 7:

[Chemical Formula 2]

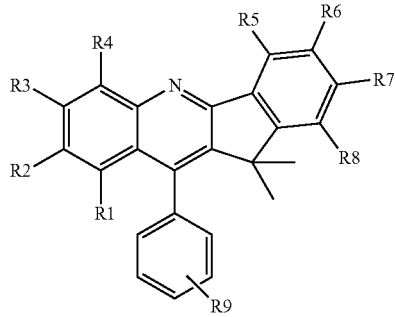

[Chemical Formula 3]

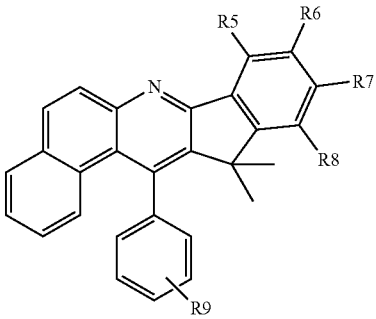

[Chemical Formula 4]

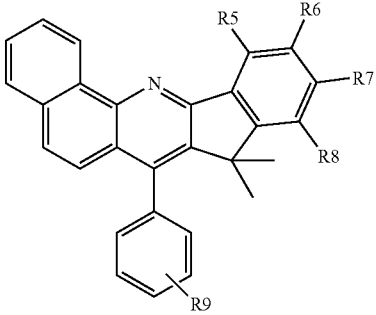

[Chemical Formula 5]

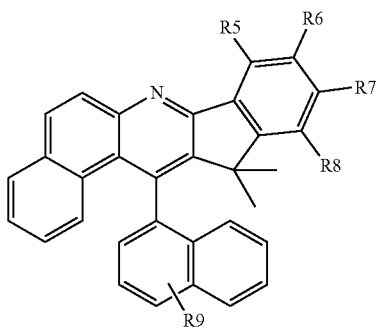

[Chemical Formula 6]

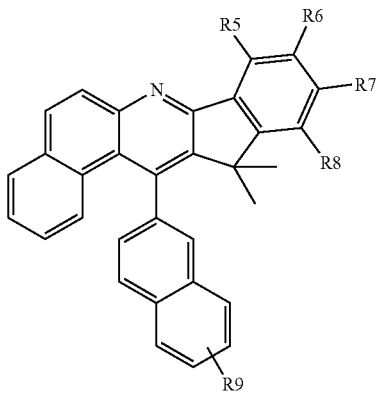

[Chemical Formula 7]

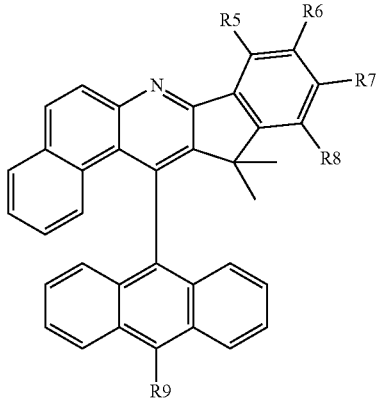

wherein, in Chemical Formulae 2 to 7,

R9 is represented by -(L2)p-(Z2)q;

L2 has the same definition as L1 of Chemical Formula 1 and Z2 has the same definition as Z1 of Chemical Formula 1;

p is an integer of 0 to 3;

q is an integer of 1 to 4; and

R1 to R8 have the same definitions as in Chemical Formula 1.

3. The hetero-cyclic compound of claim 1, wherein Z1 is selected from the group consisting of hydrogen; deuterium; a substituted or unsubstituted $C_6$ to $C_{60}$ aryl group; a substituted or unsubstituted $C_2$ to $C_{60}$ heteroaryl group; and —P(=O)RR', and R, R' and R" are the same as or different from each other and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

4. The hetero-cyclic compound of claim 1, wherein R1 and R2 bond to each other to form an aromatic hydrocarbon ring, or R3 and R4 bond to each other to form an aromatic hydrocarbon ring, and, among R1 to R4, groups that do not form the aromatic hydrocarbon ring are hydrogen or deuterium, and R5 to R8 are each independently hydrogen or deuterium.
5. The hetero-cyclic compound of claim 1, wherein Chemical Formula 1 is represented by any one of the following compounds:
1
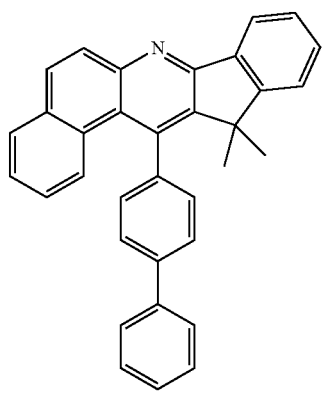
2
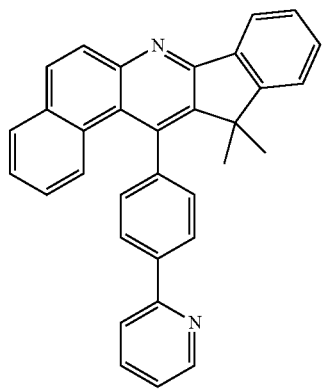
3
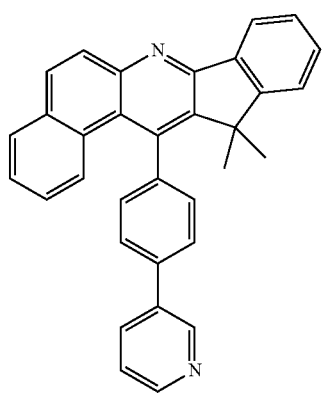
4
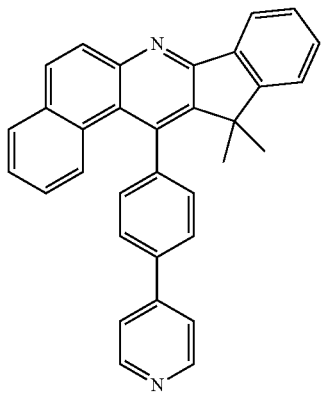
5
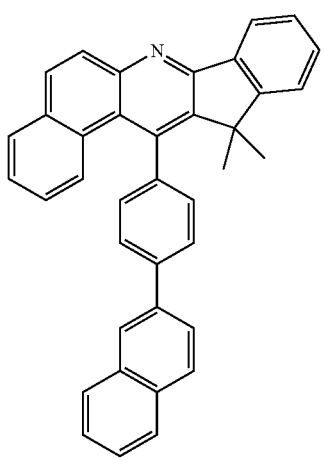
6
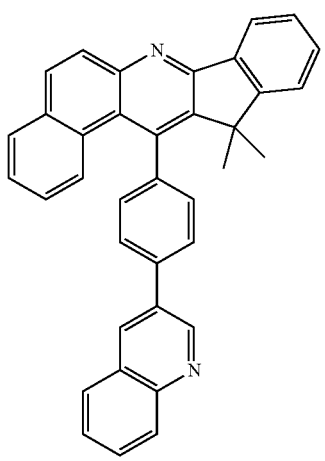

251
-continued
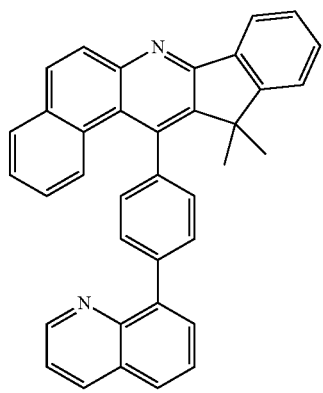
7
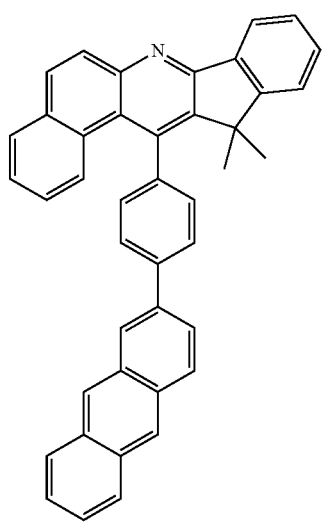
8
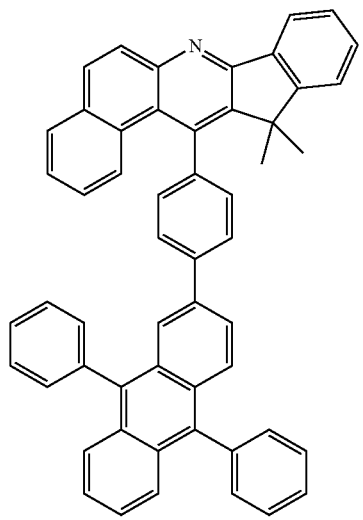
9
252
-continued
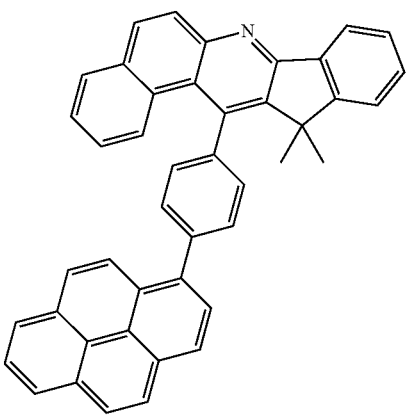
10
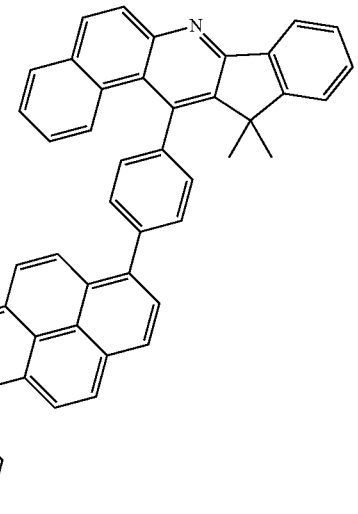
11
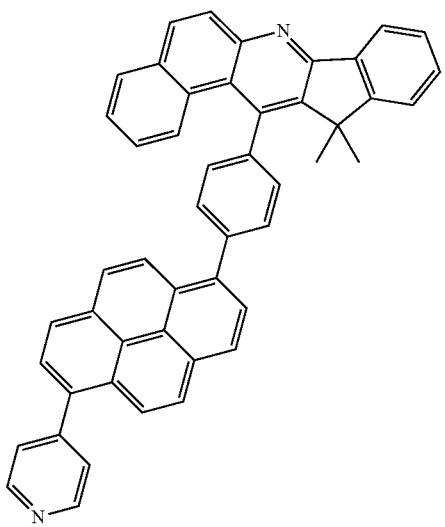
12

-continued
13
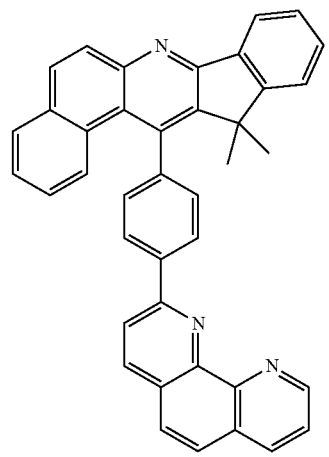
14
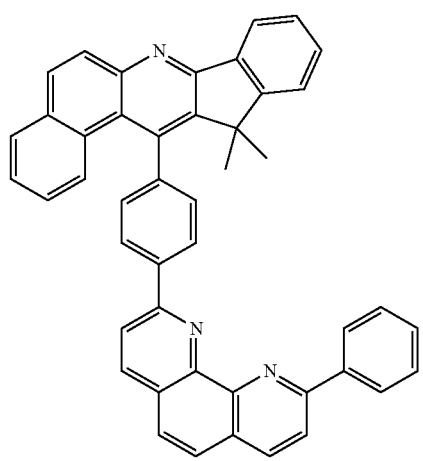
15
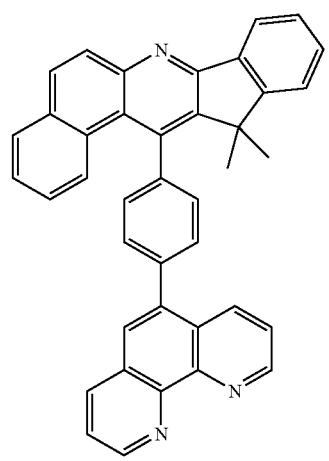
-continued
16
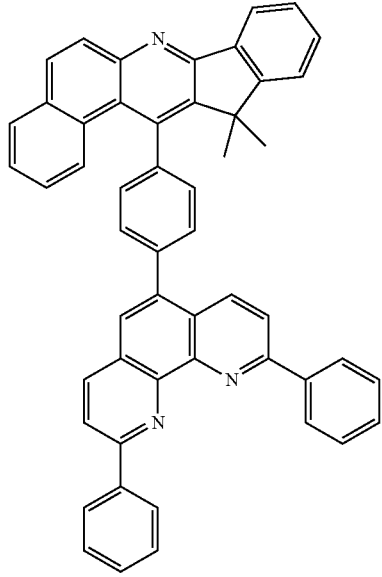
17
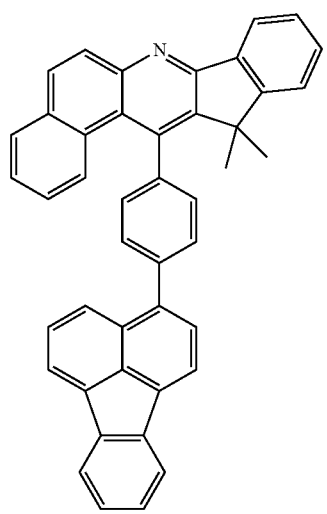
18
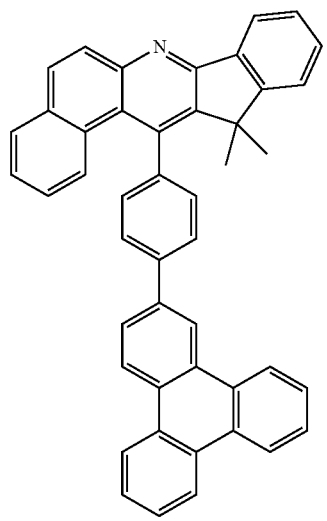

19
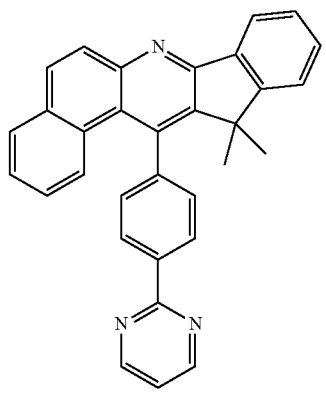
20
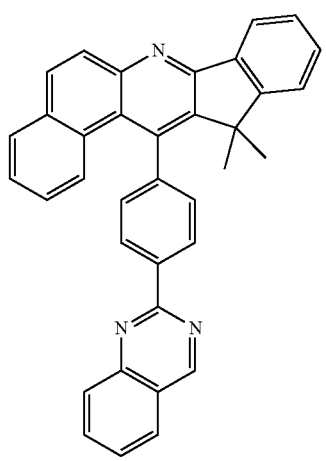
21
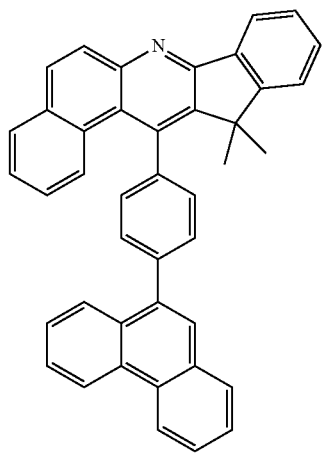
22
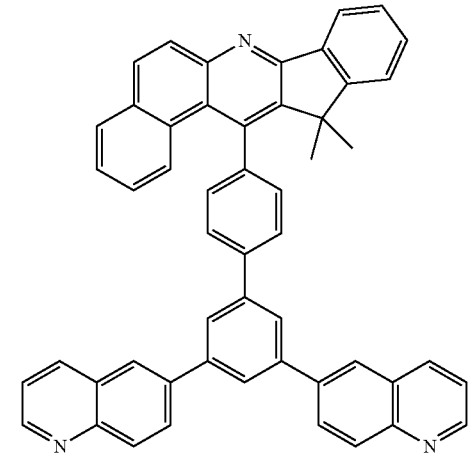
23
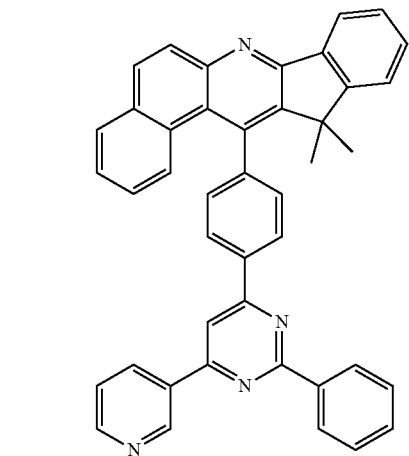
24
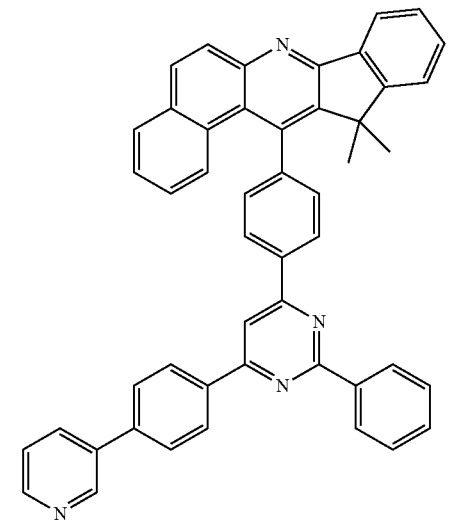

257
-continued
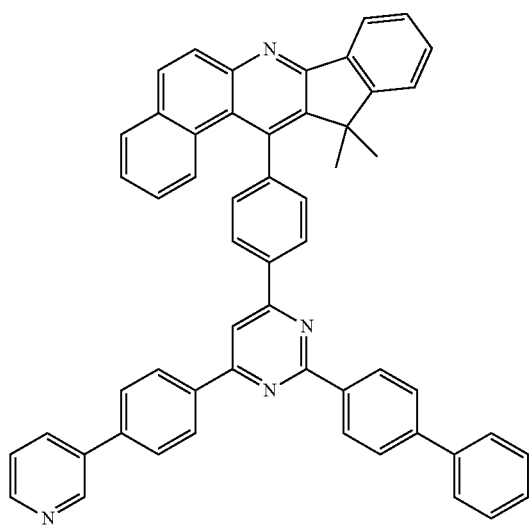
25
258
-continued
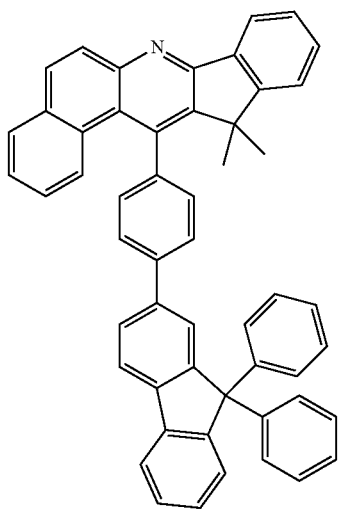
28
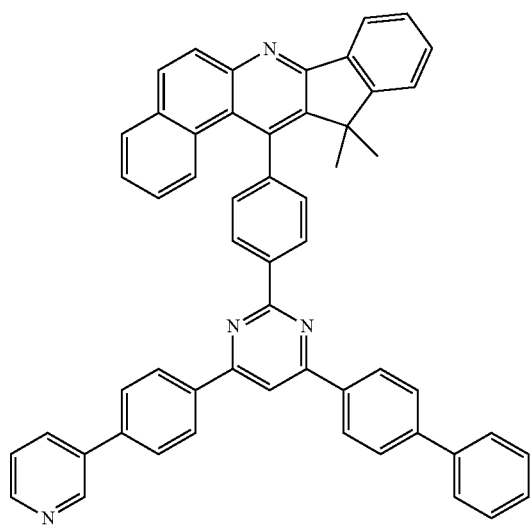
26
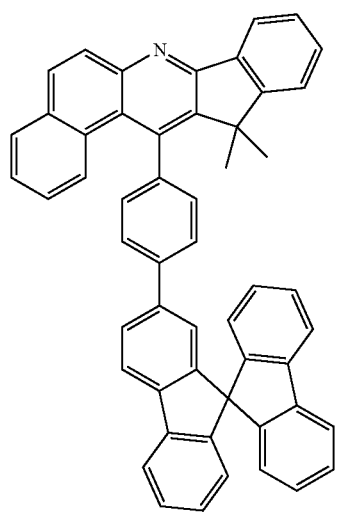
29
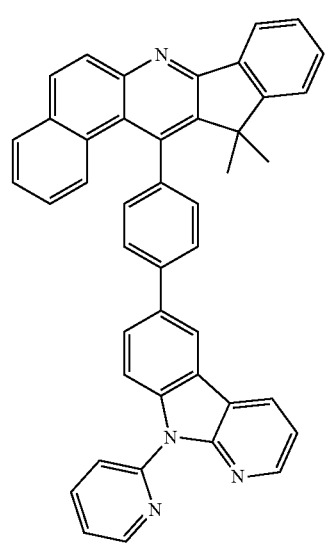
27
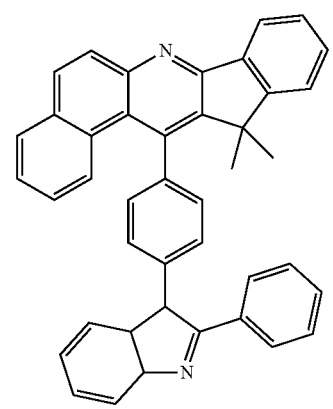
30

31
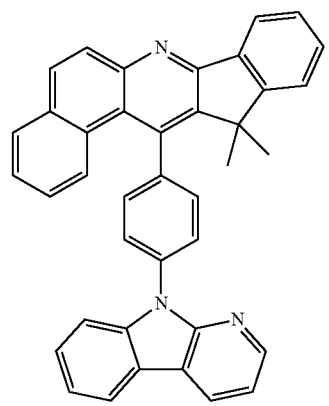
32
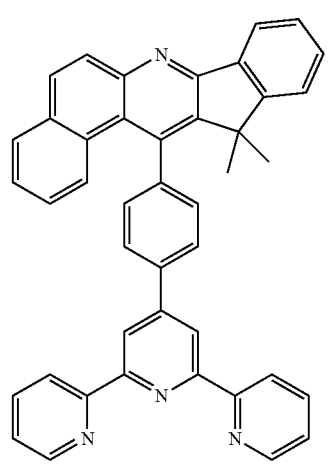
33
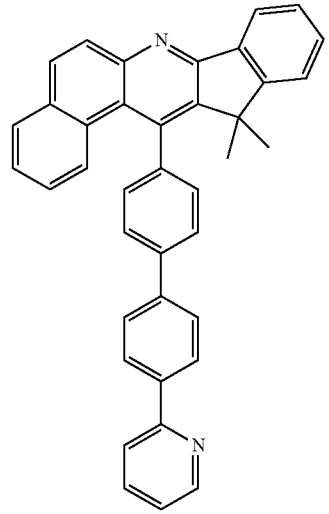
34
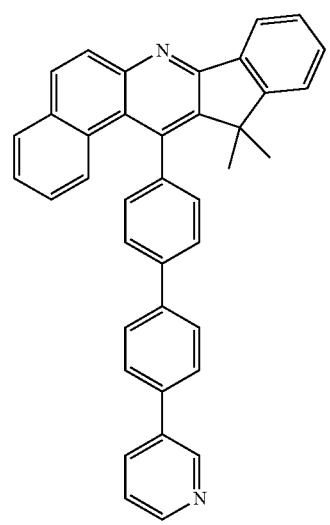
35
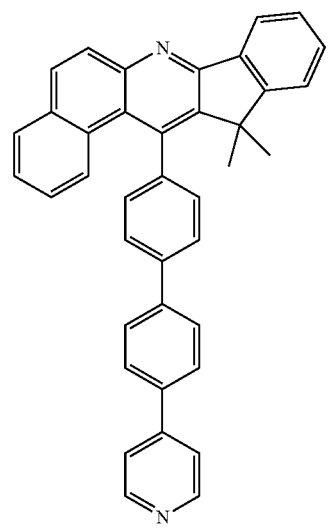
36
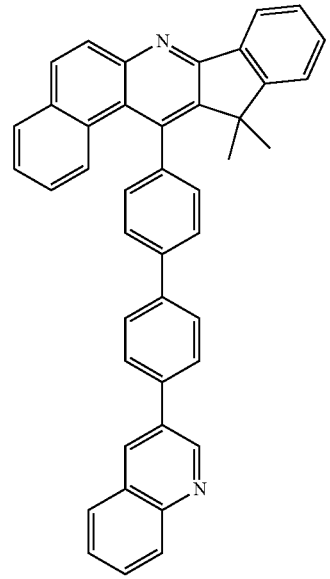

37
261
-continued
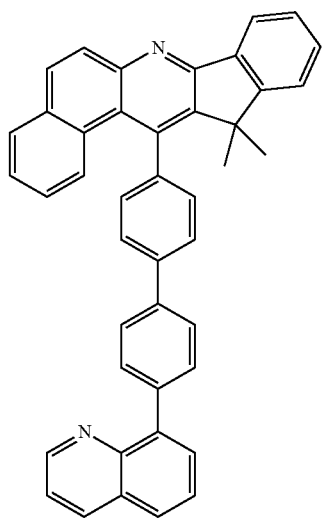
38
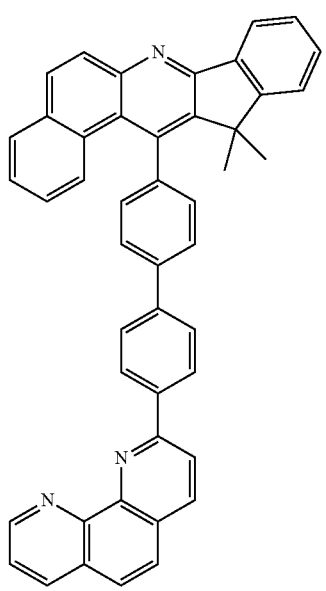
39
262
-continued
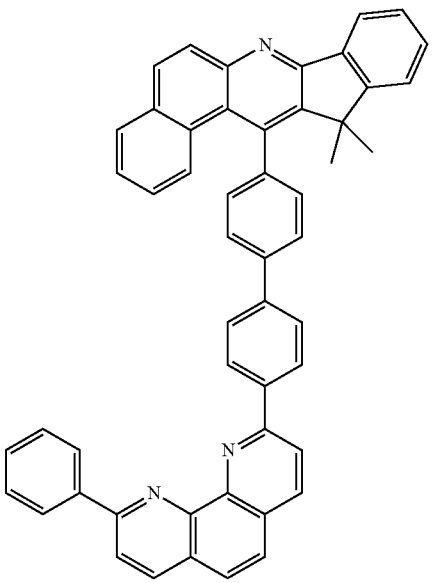
40
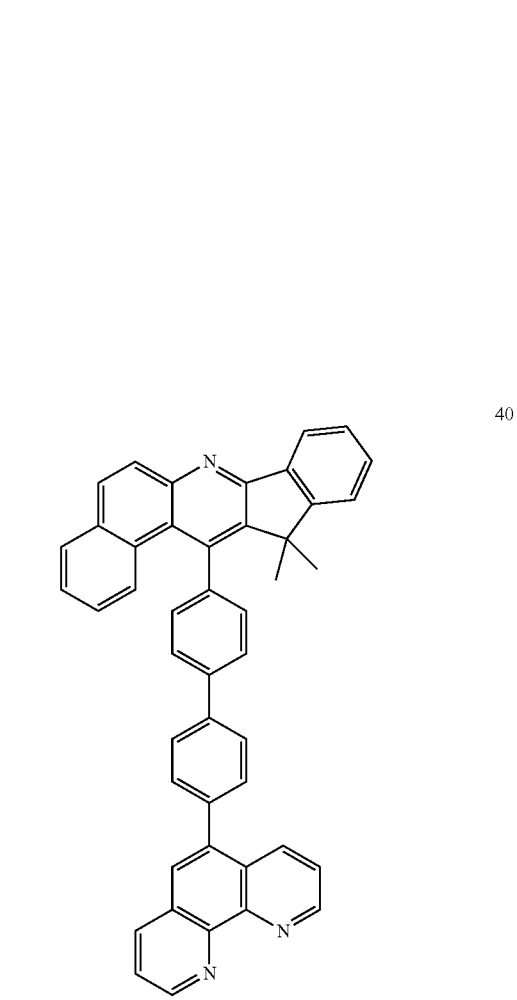

41
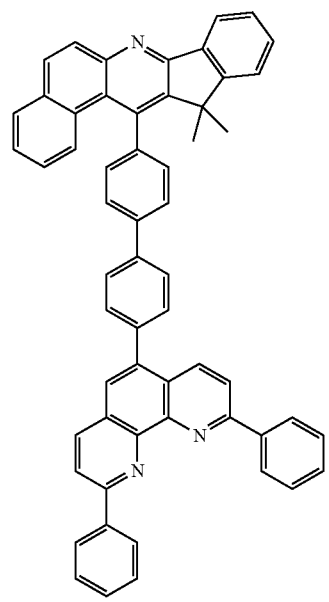
42
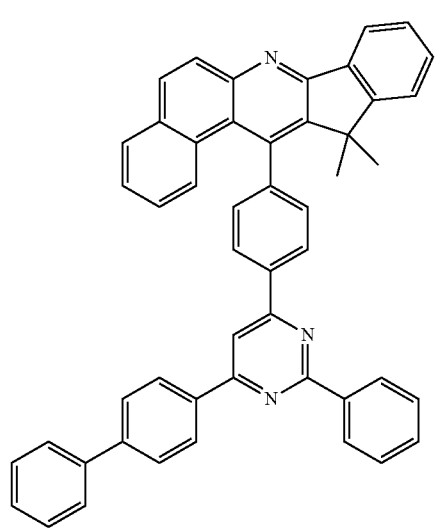
43
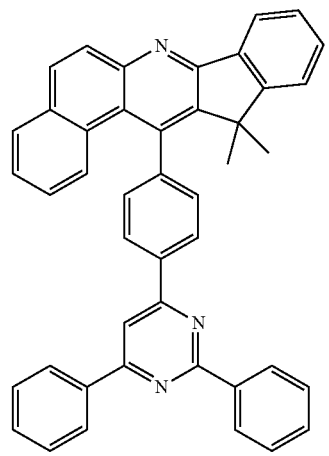
44
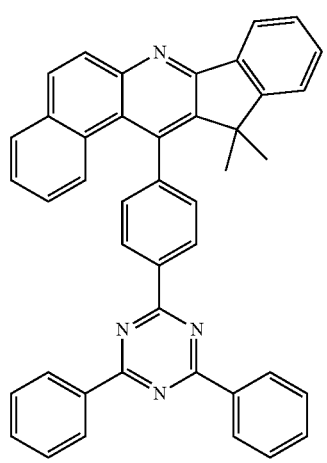
45
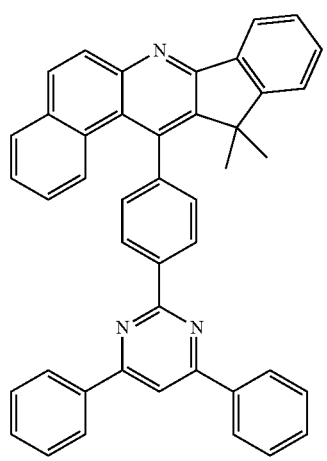
46
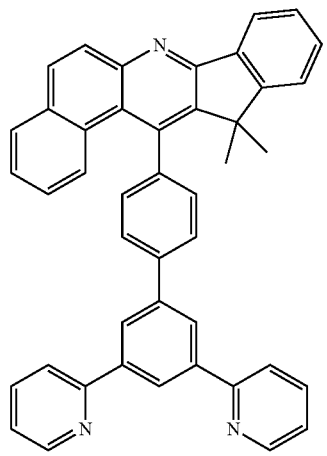

47
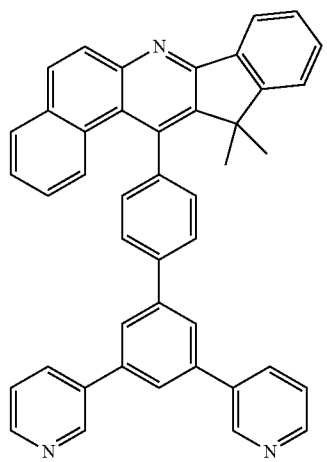
48
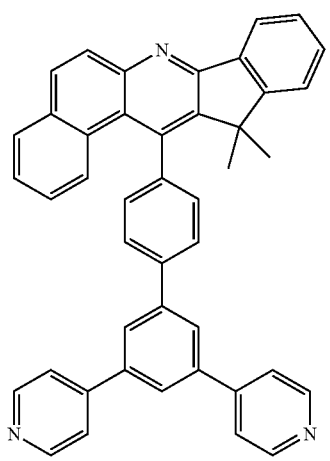
49
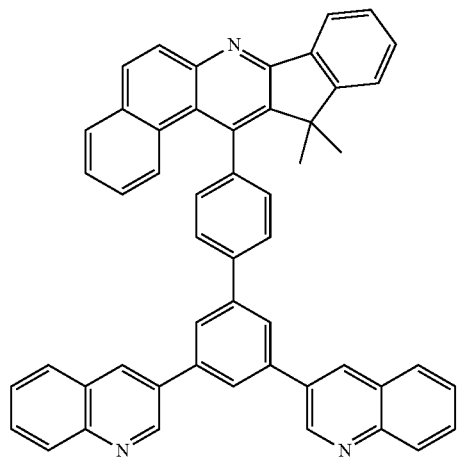
50
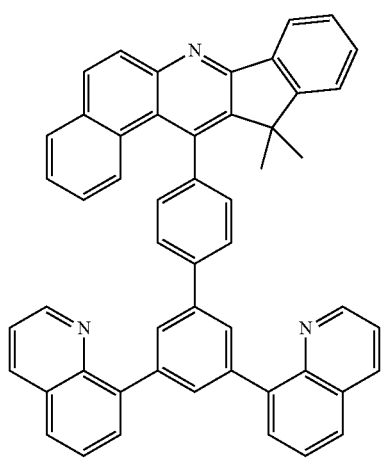
51
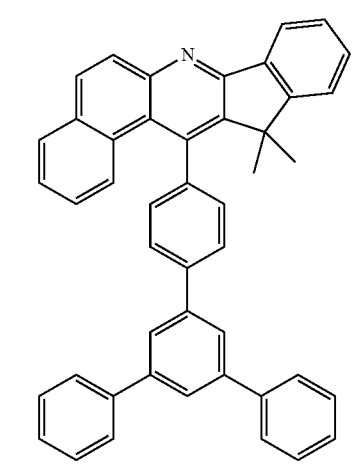
52
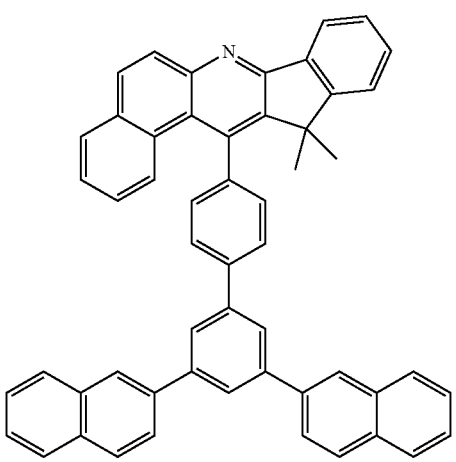

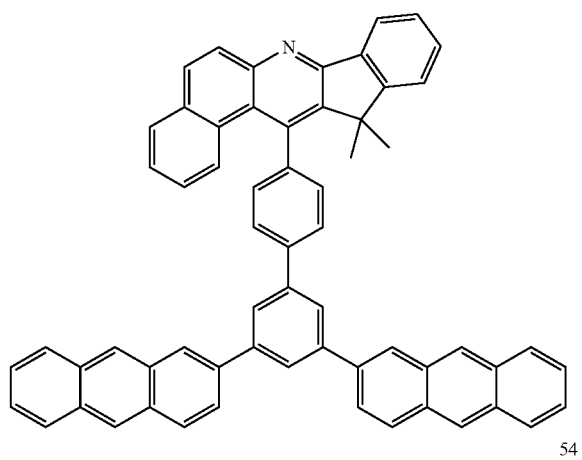
53
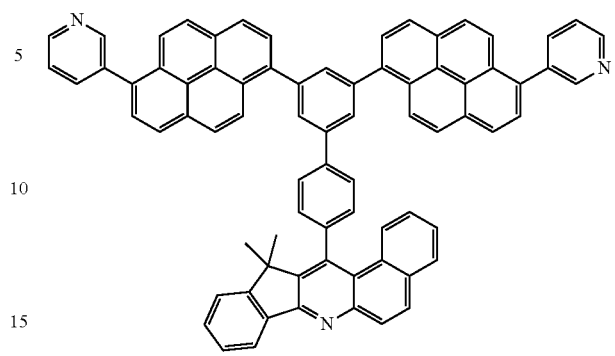
56
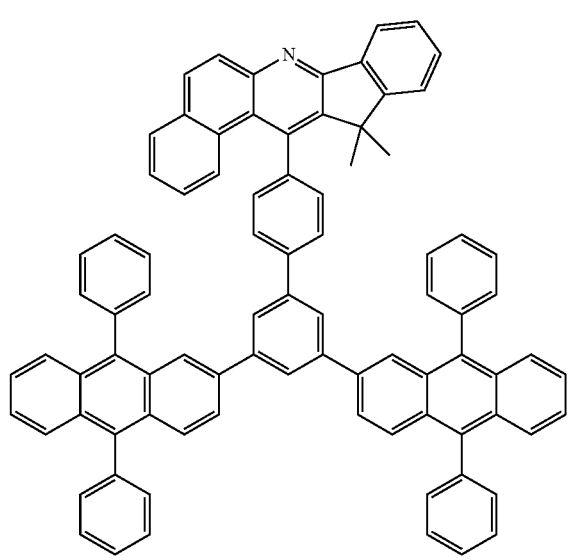
54
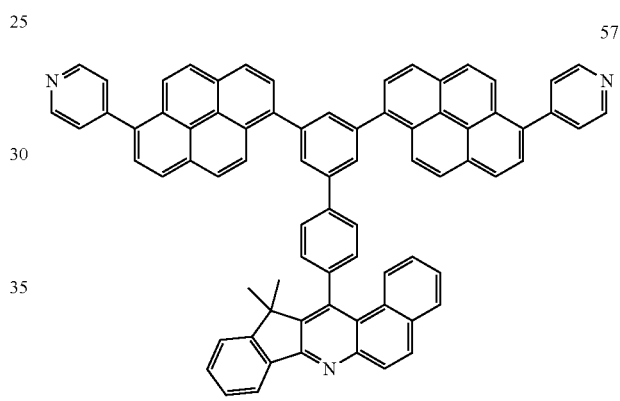
57
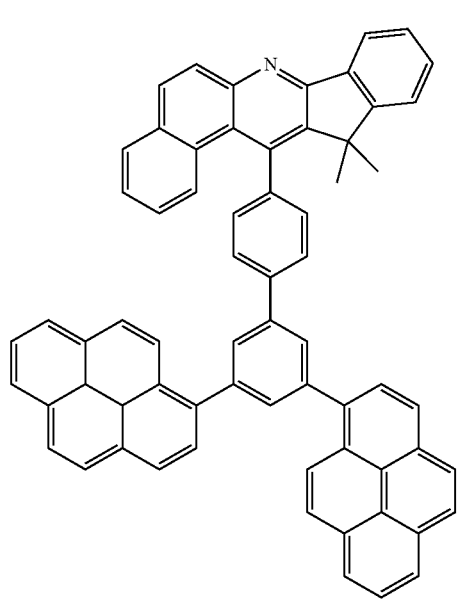
55
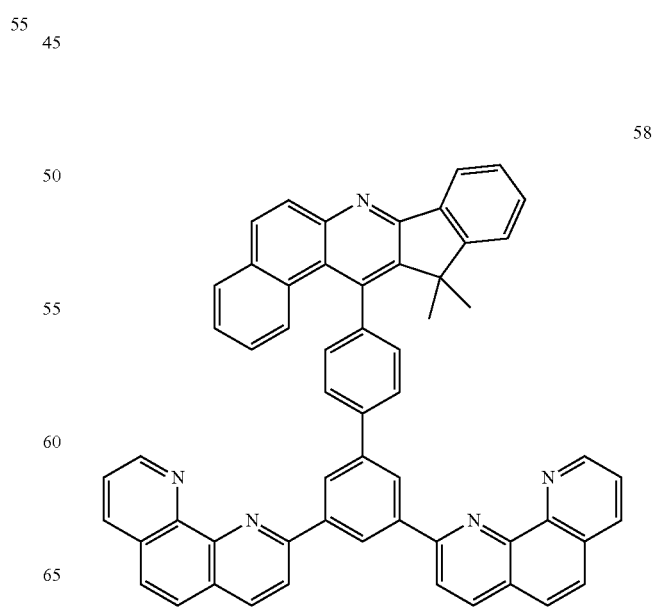
58

59
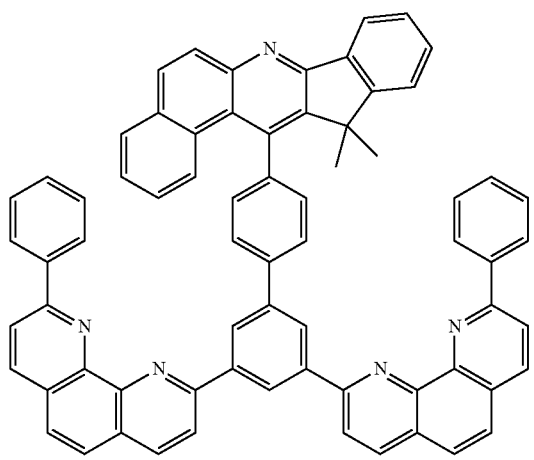
60
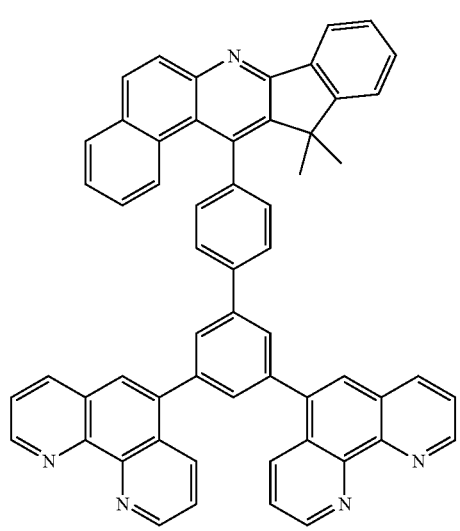
61
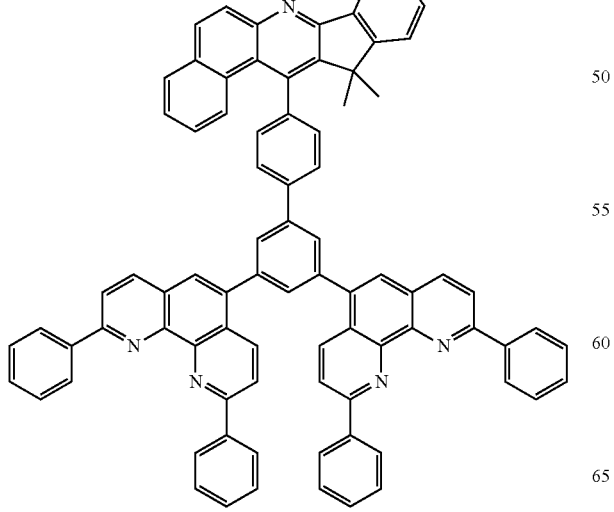
62
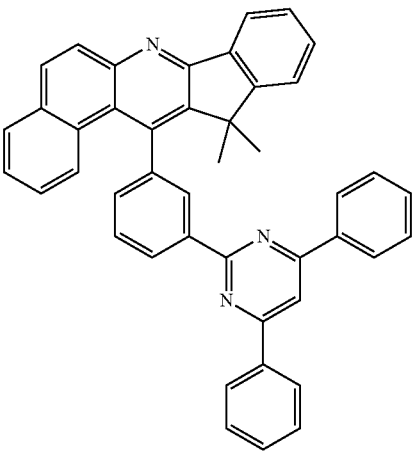
63
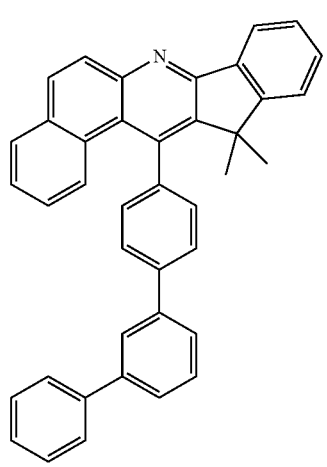
64
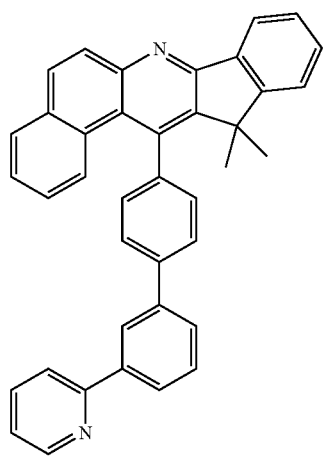

65
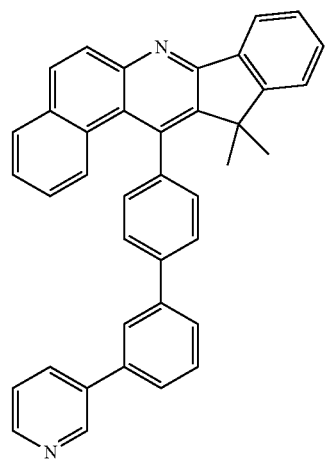
68
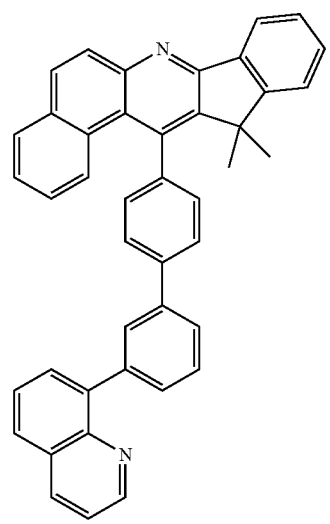
66
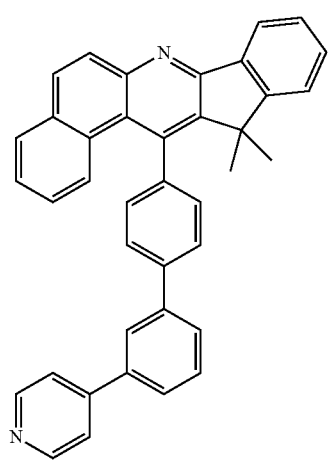
69
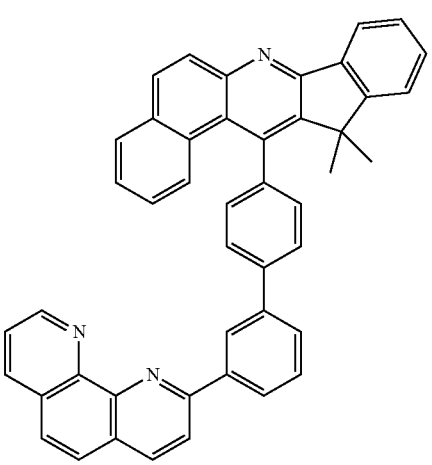
67
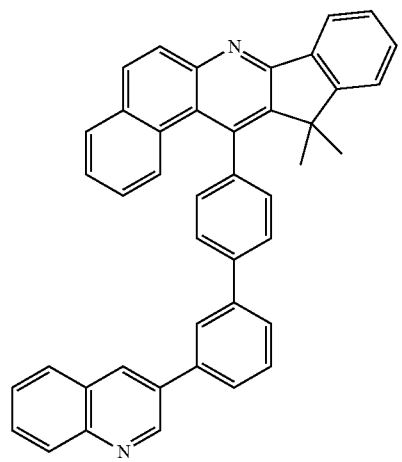
70
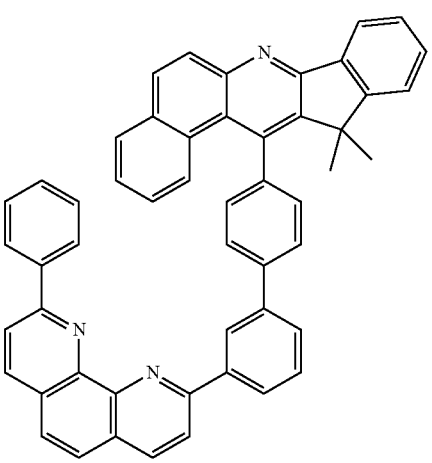

71
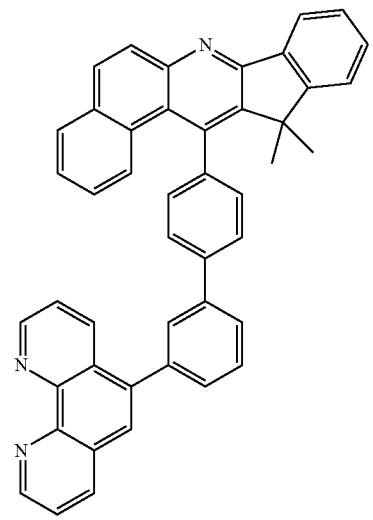
72
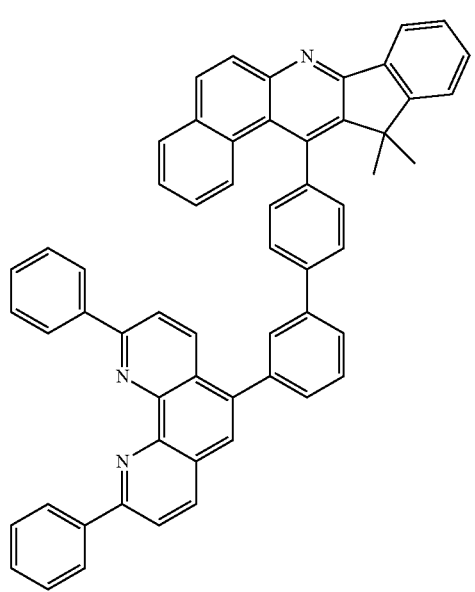
73
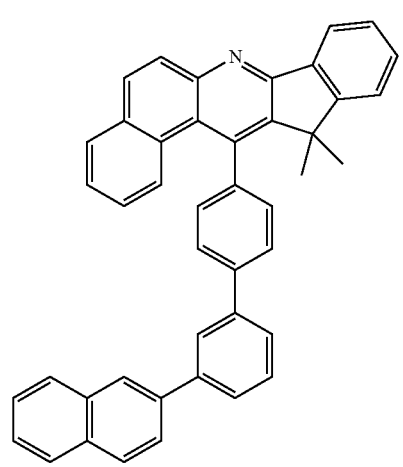
74
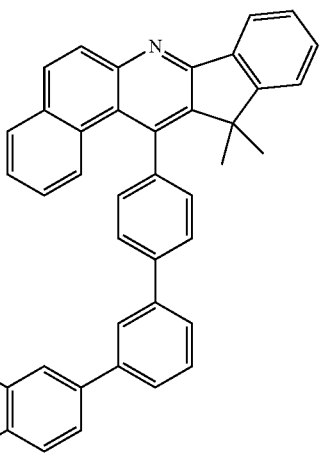
75
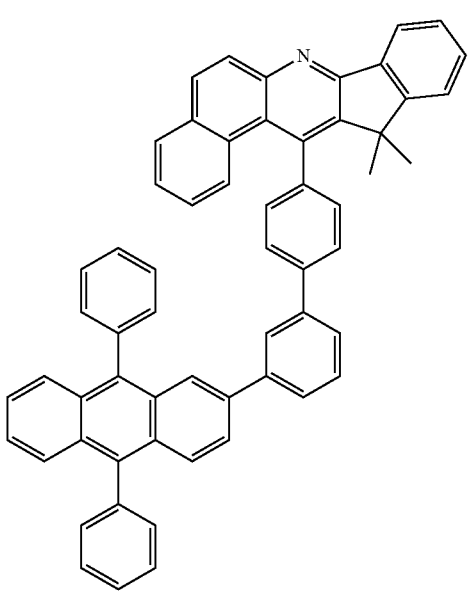
76
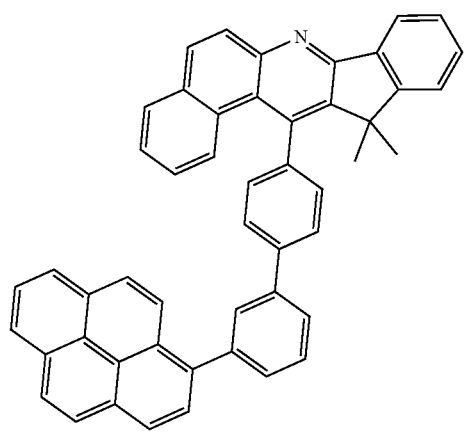

275
-continued
77
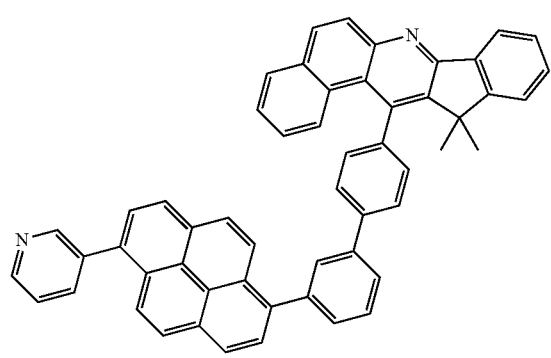
78
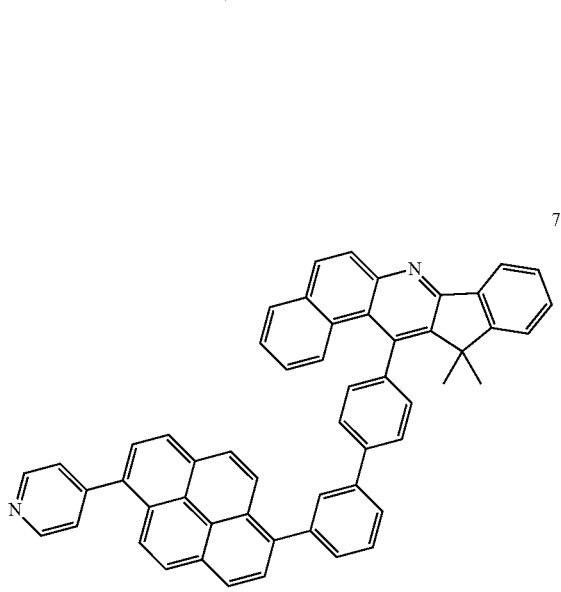
79
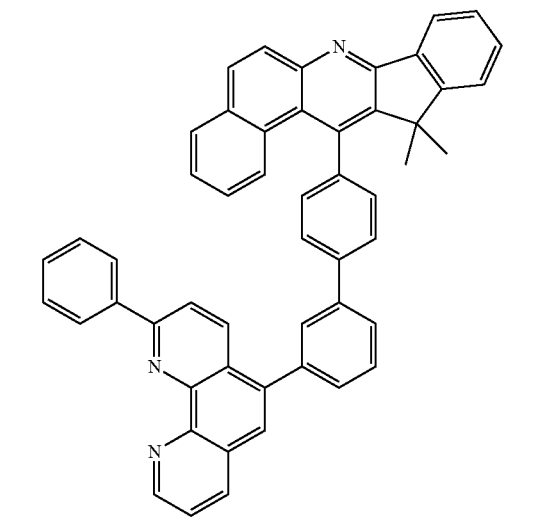
276
-continued
80
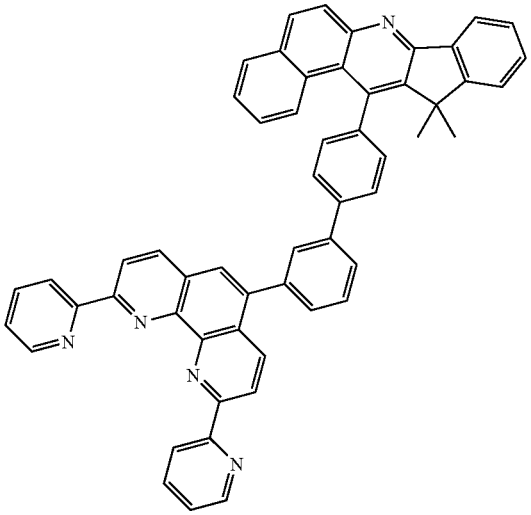
81
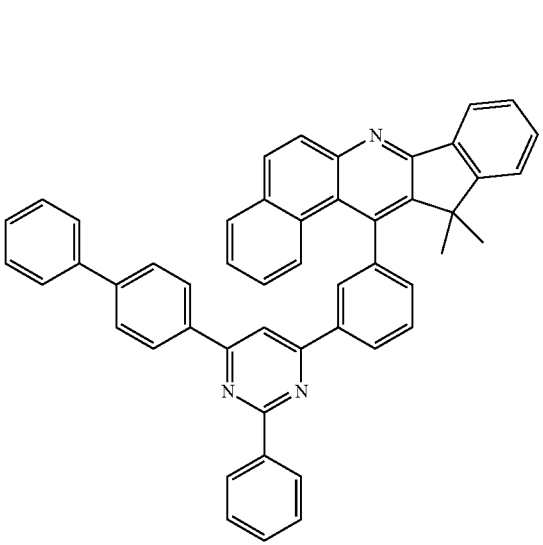
82
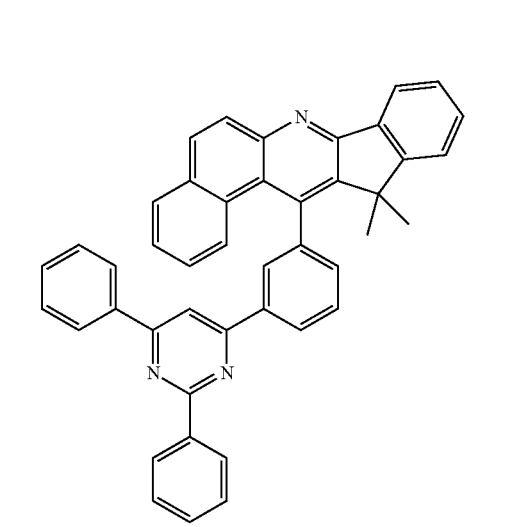

83
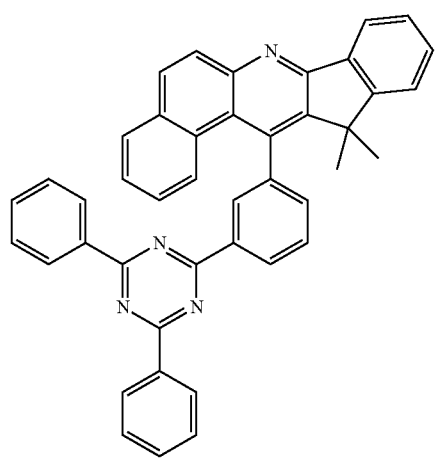
84
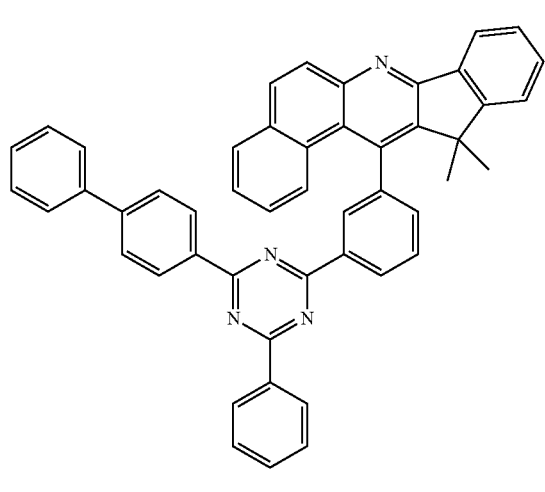
85
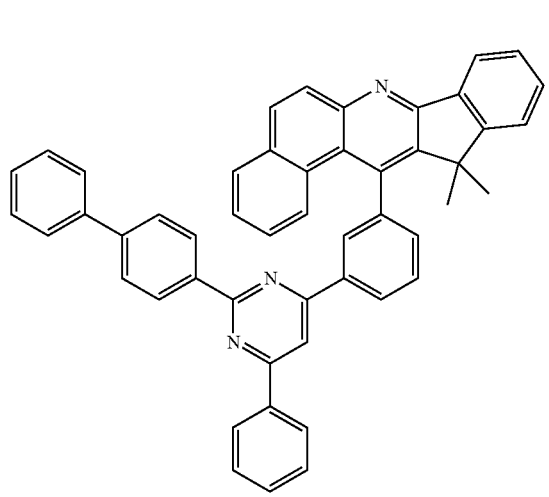
86
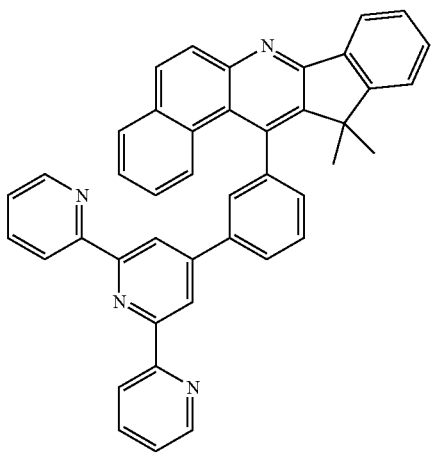
87
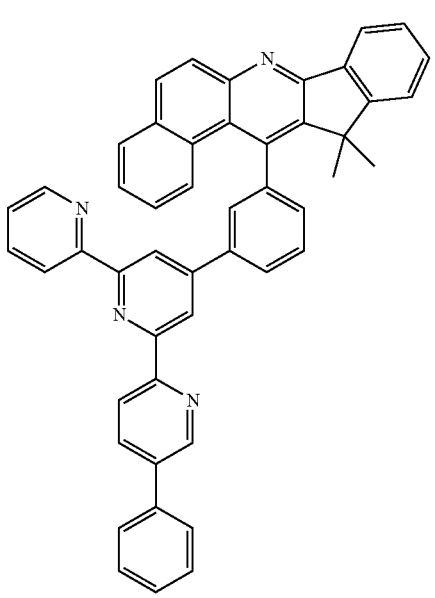
88
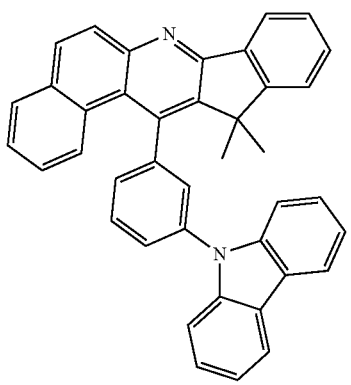

279
-continued
89
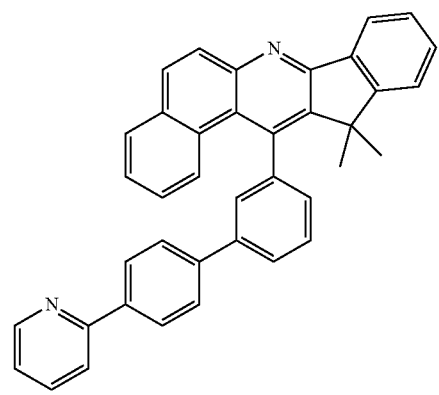
90
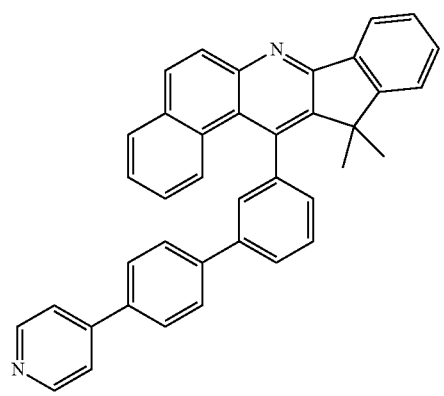
91
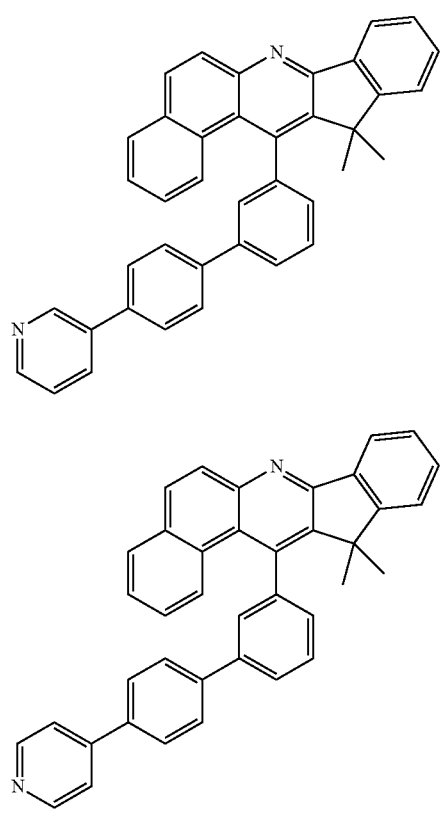
92
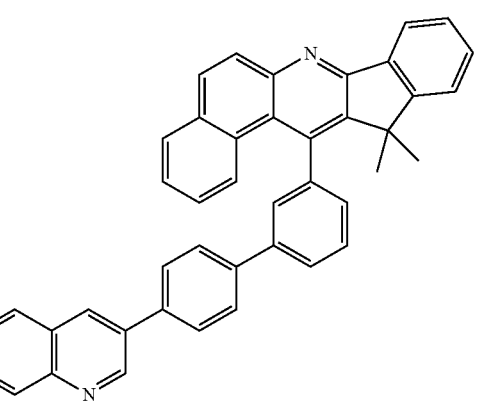
280
-continued
93
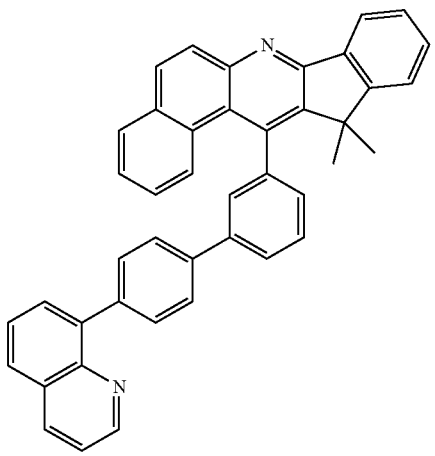
94
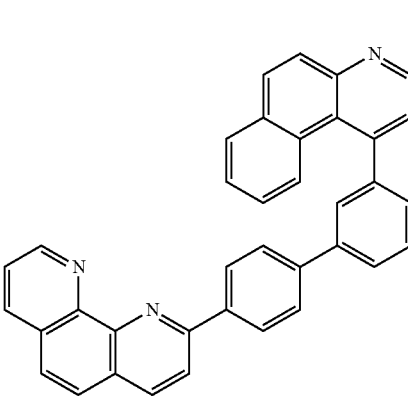
95
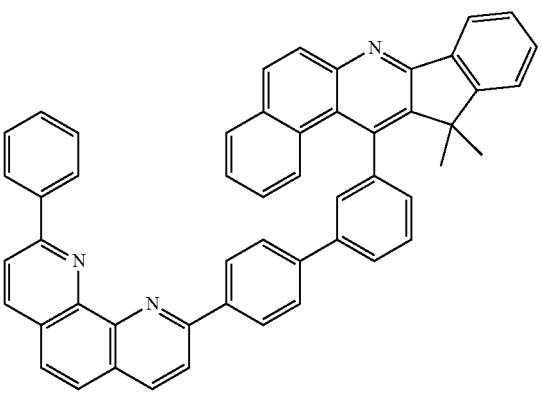

96
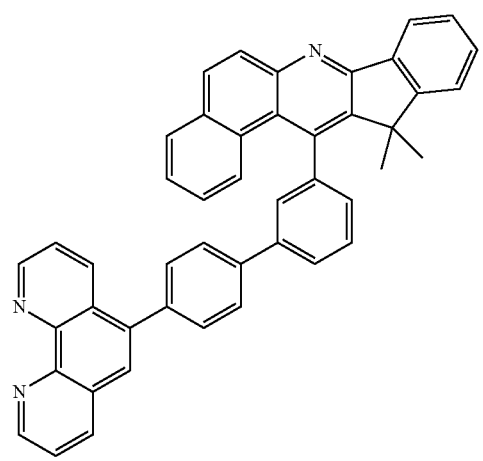
97
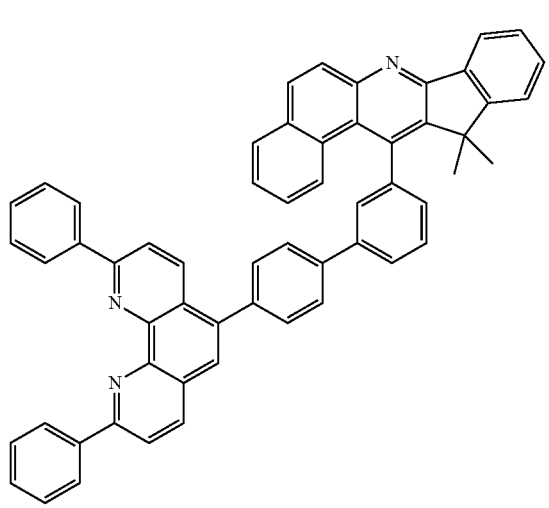
98
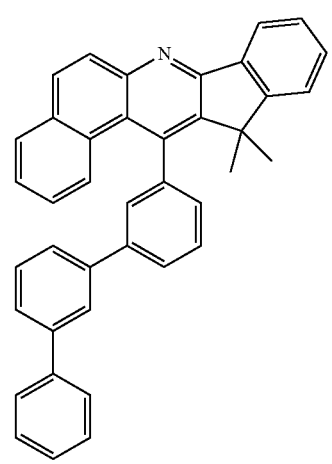
99
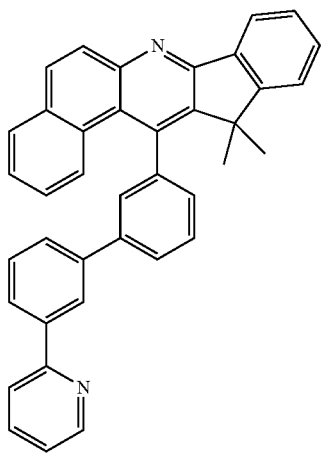
100
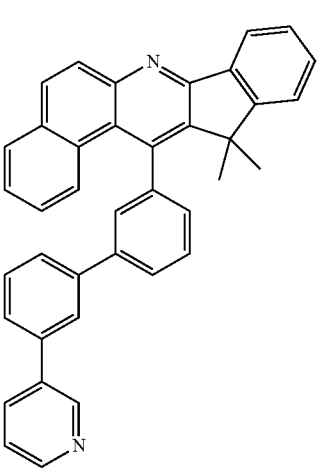
101
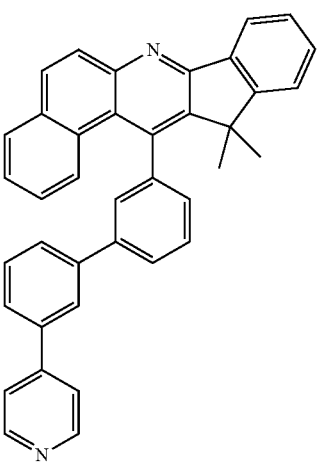

102
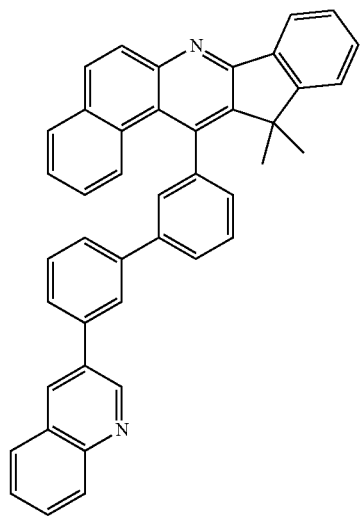
103
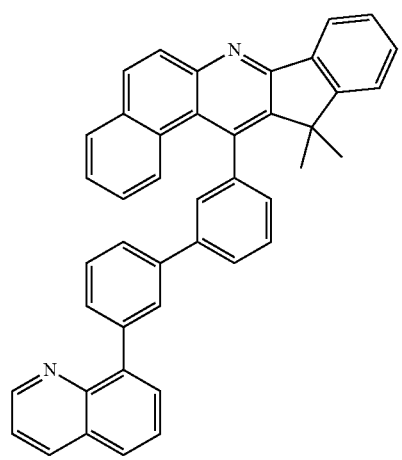
104
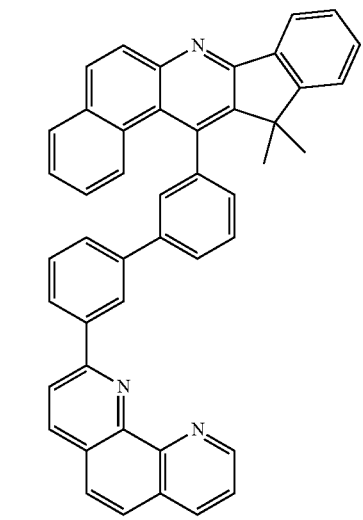
105
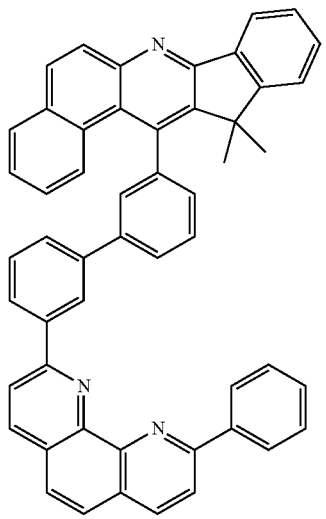
106
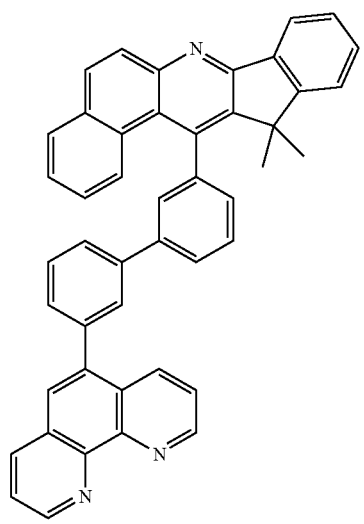
107
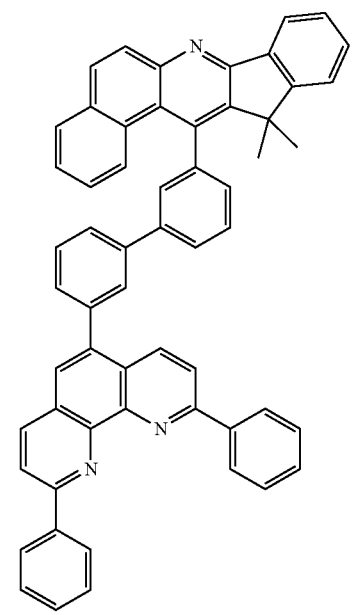

108
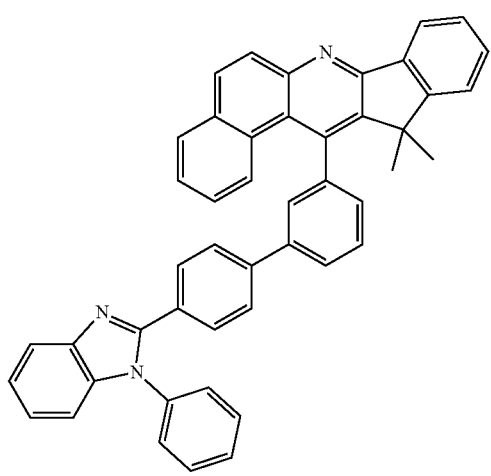
109
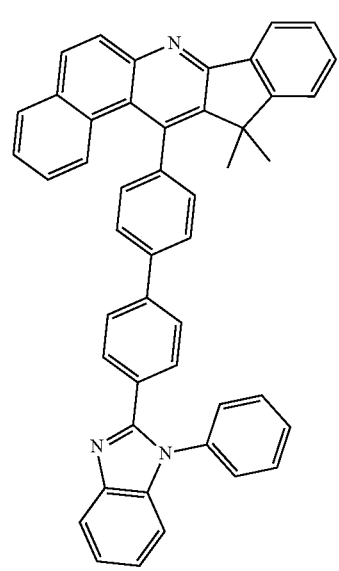
110
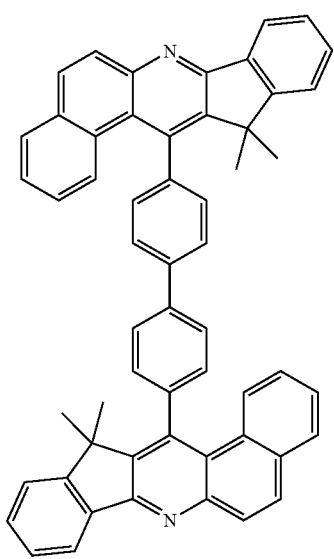
111
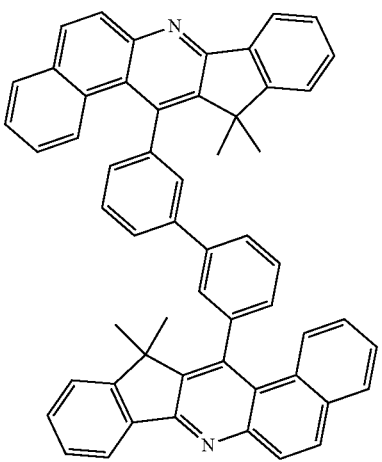
112
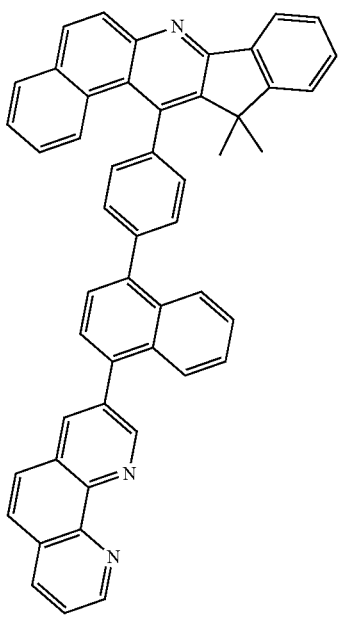

113
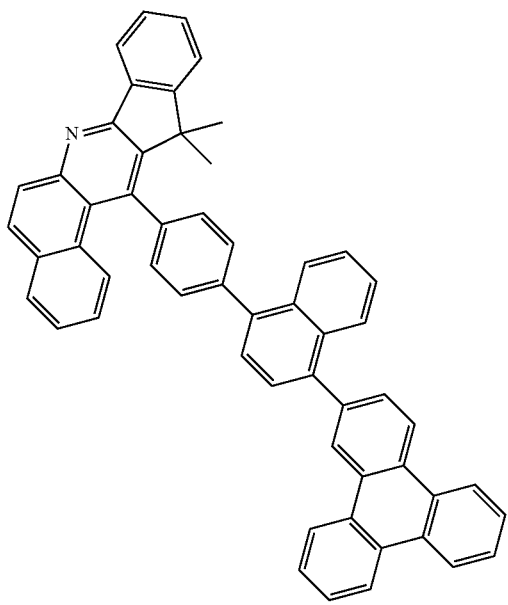
114
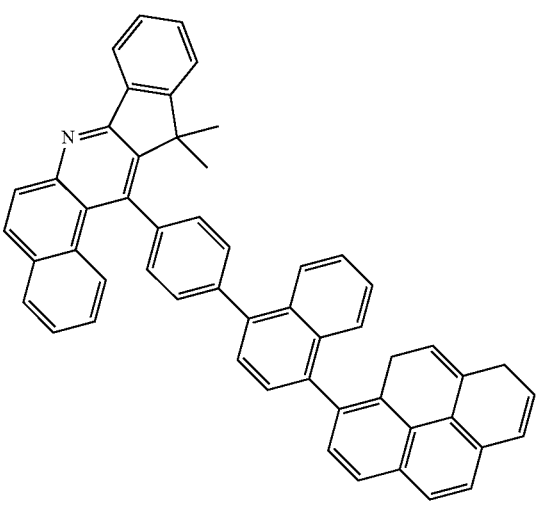
115
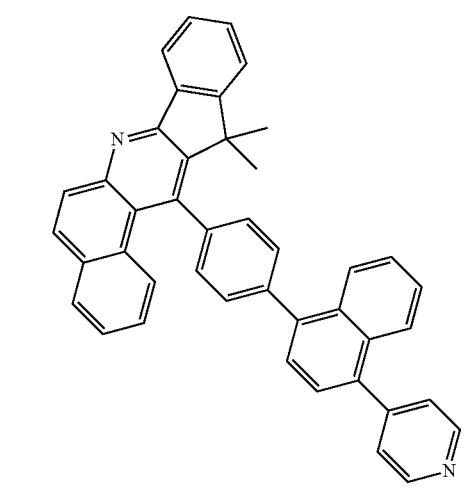
116
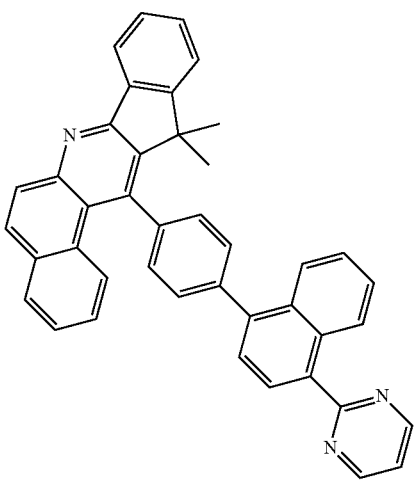
117
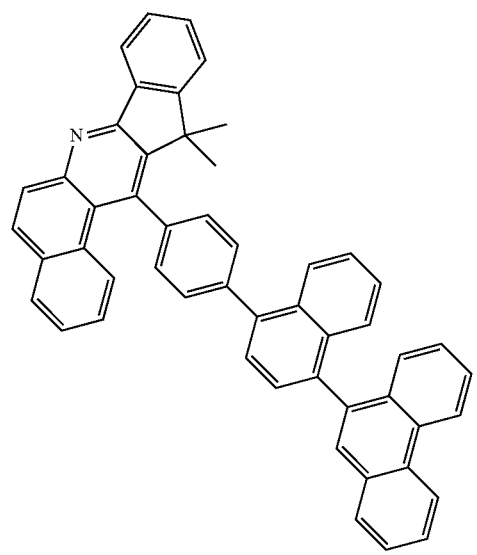
118
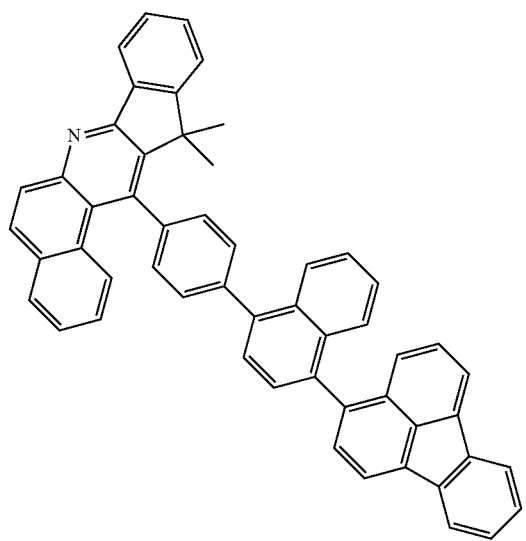

289
-continued
119
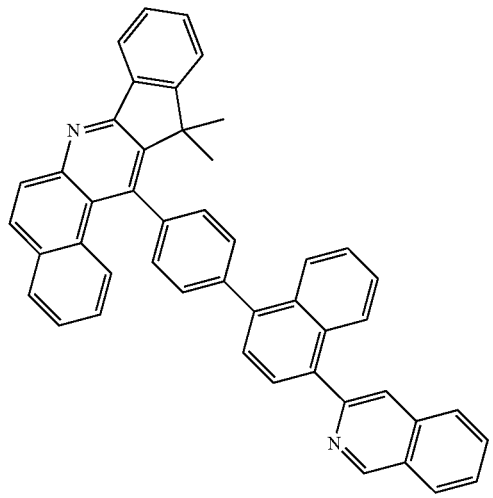
120
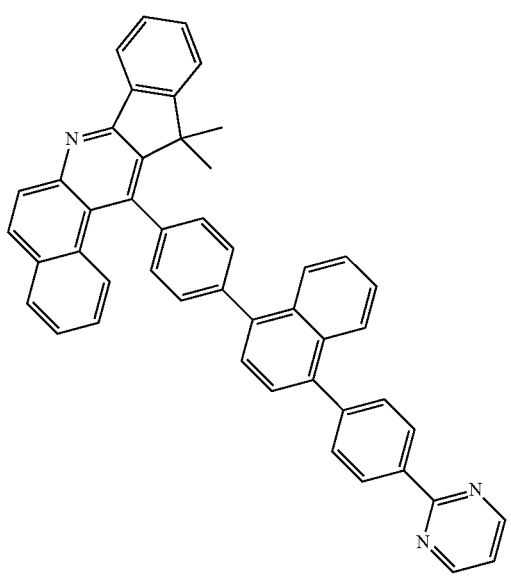
121
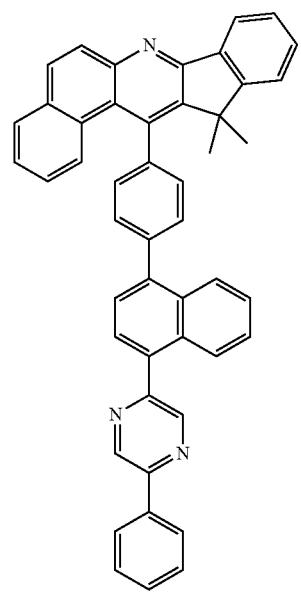
290
-continued
122
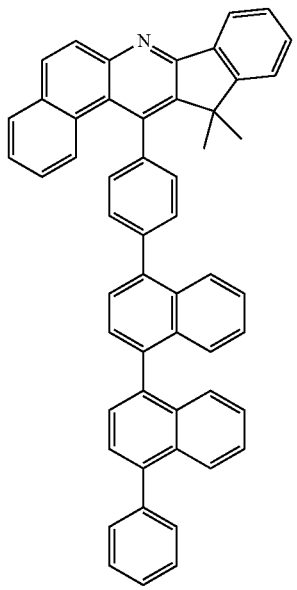
123

291
-continued
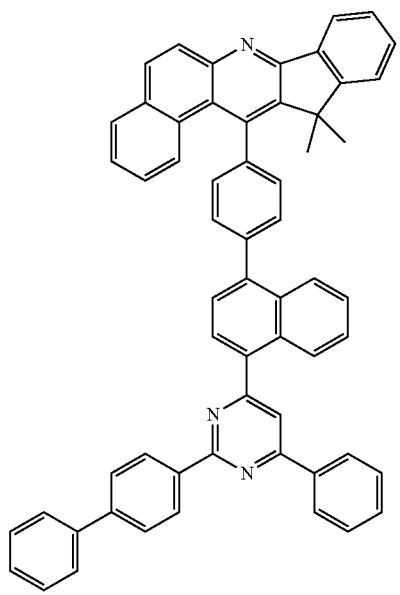
124
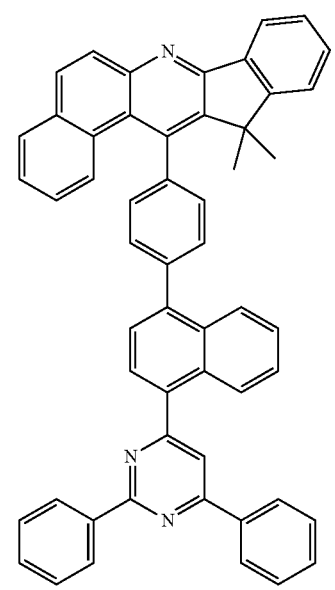
125
292
-continued
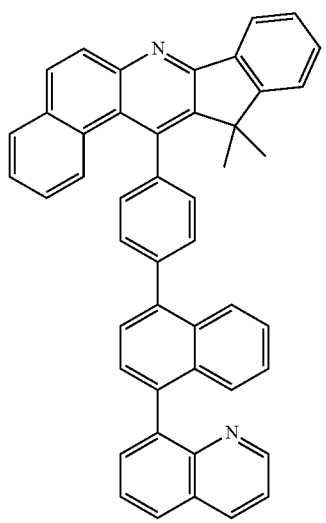
126
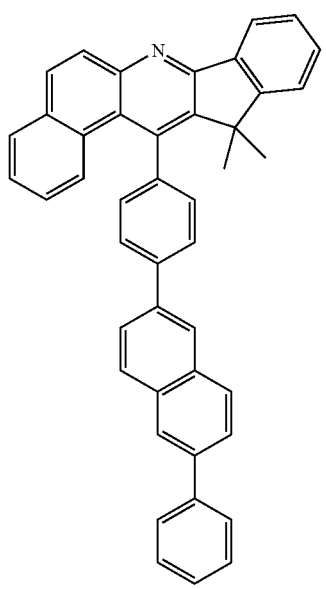
127

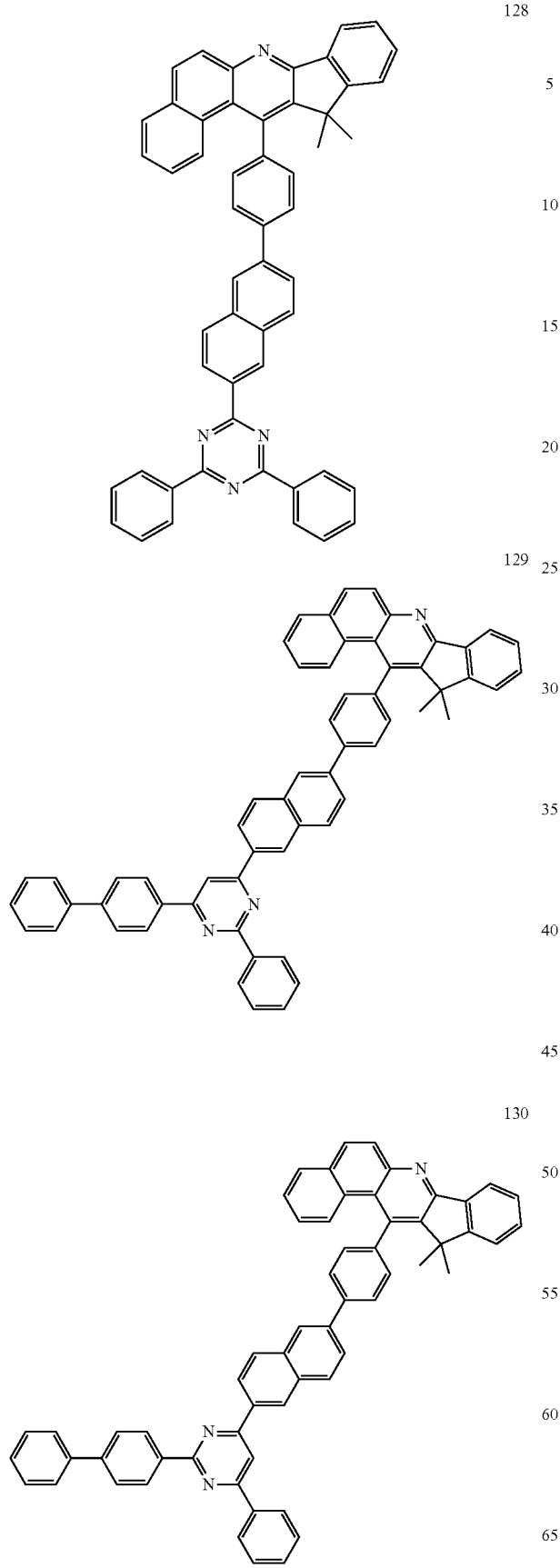
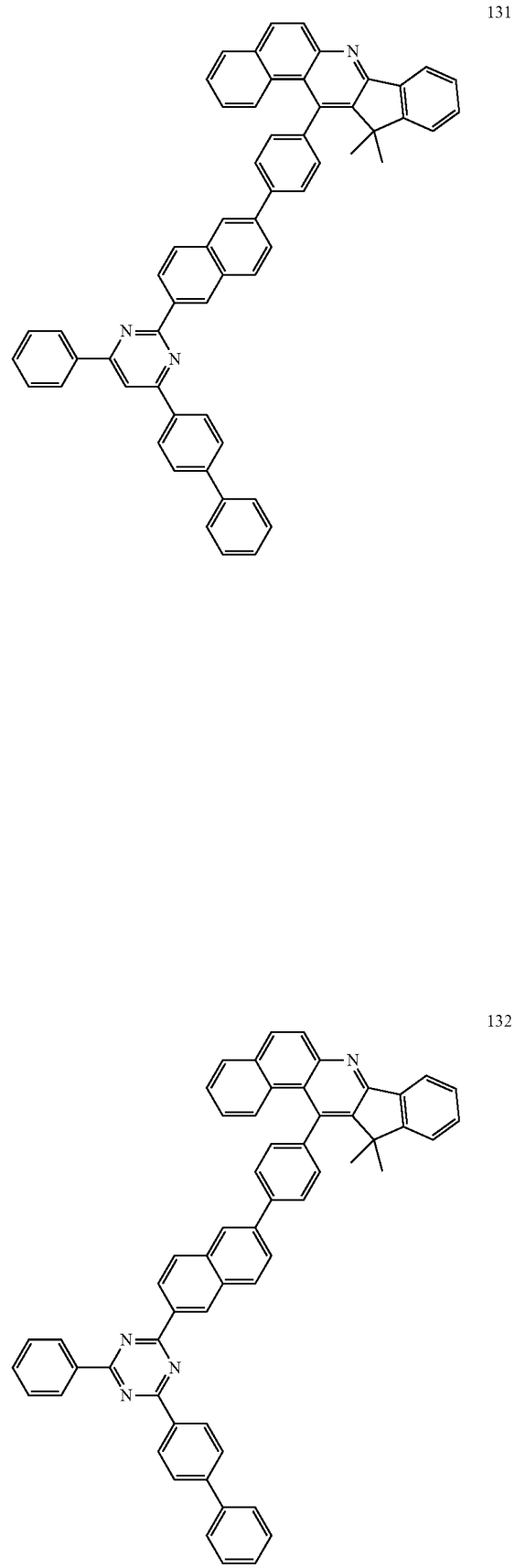

133
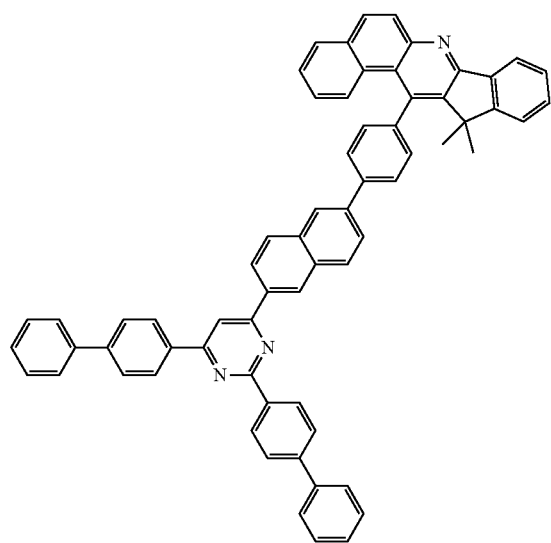
134
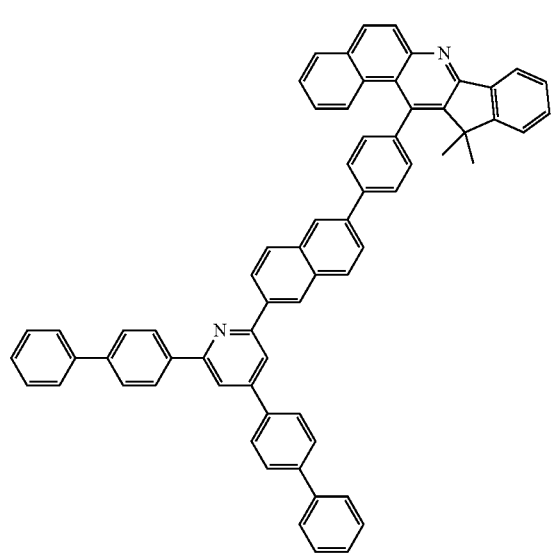
135
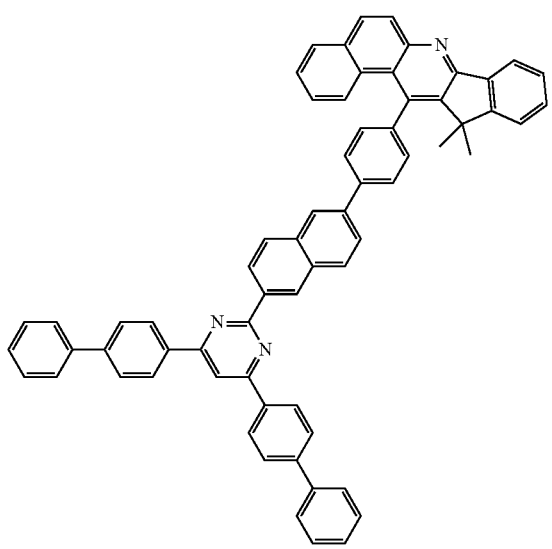
136
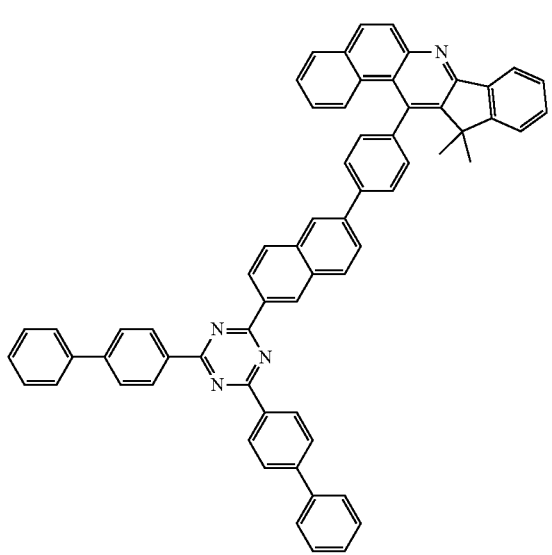

-continued
137
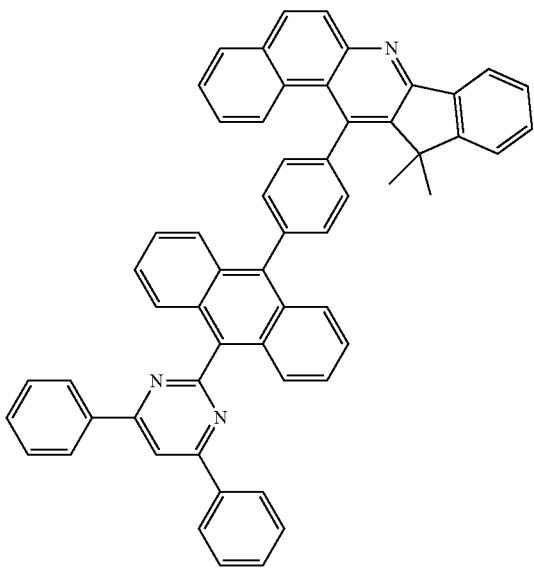
138
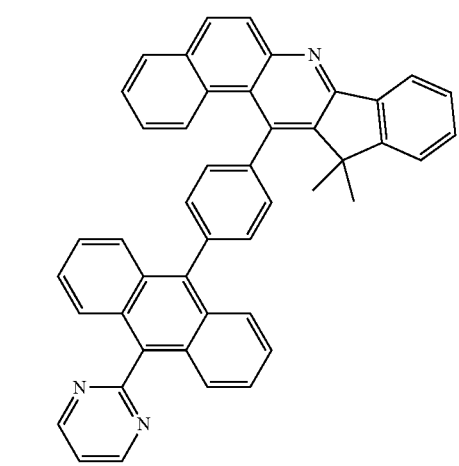
139
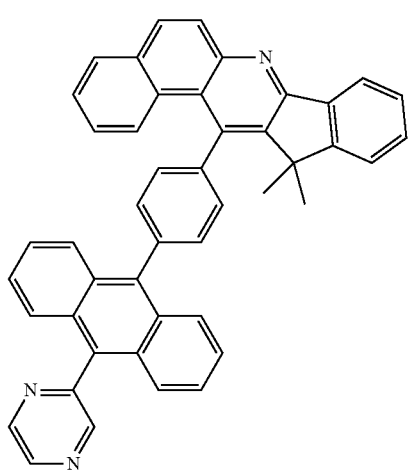
-continued
140
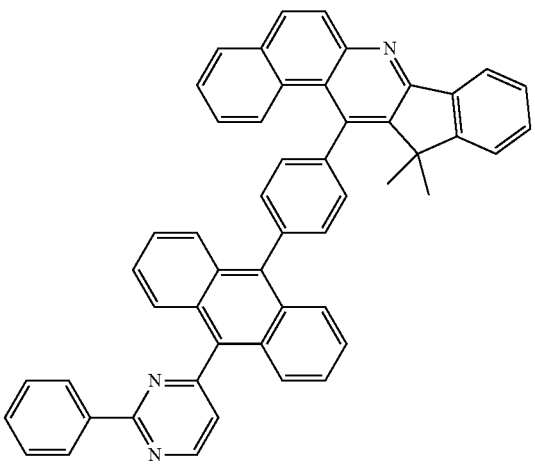
141
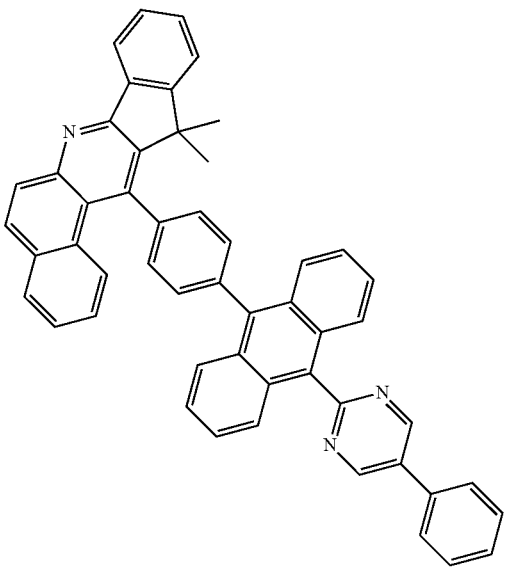
142
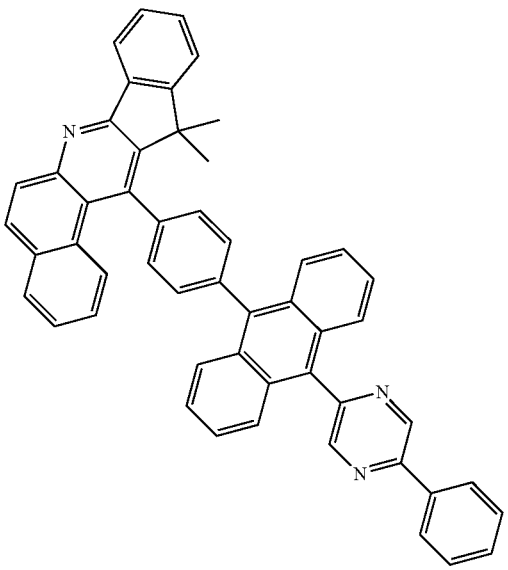

143 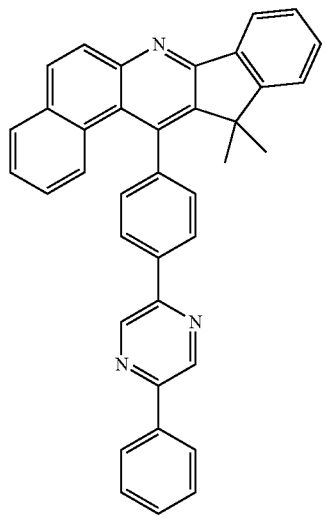
144 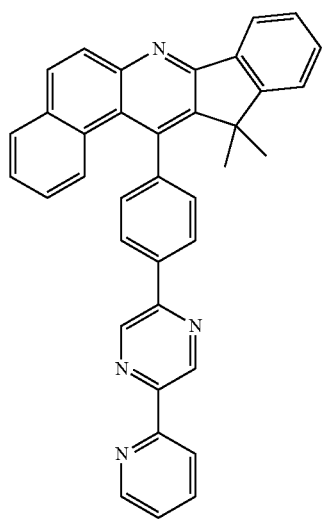
145 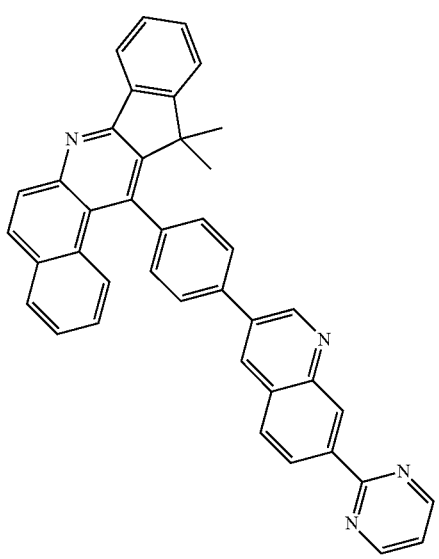
146 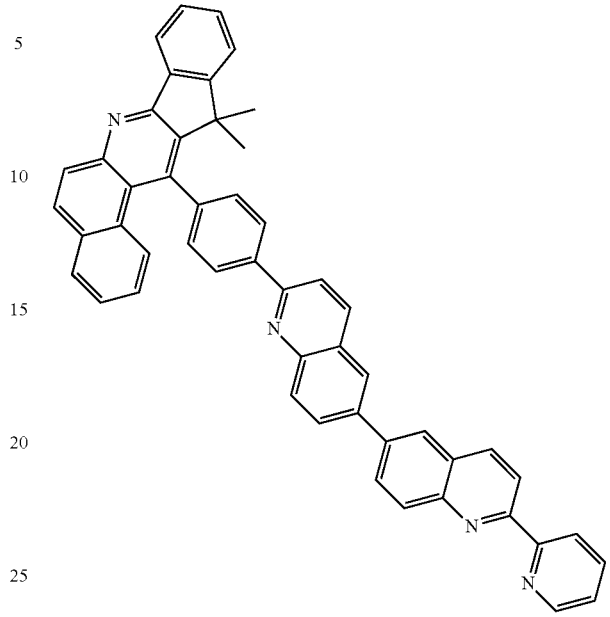
147 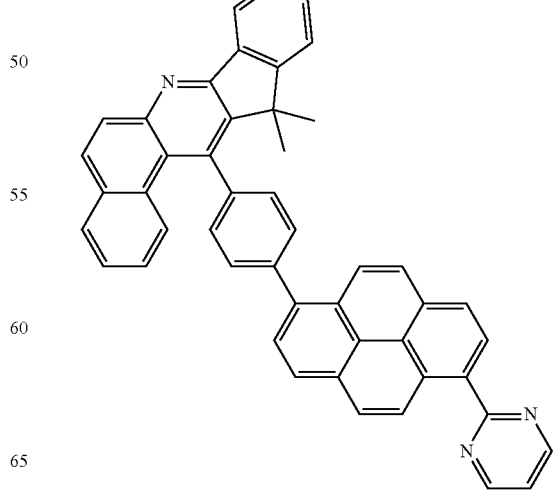

301
-continued
148
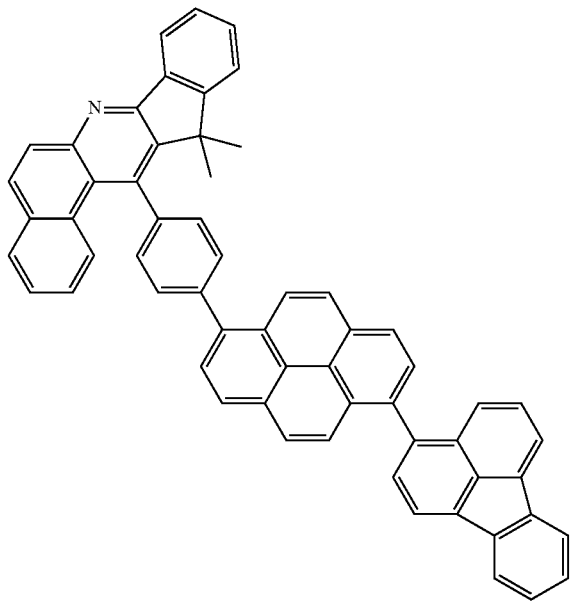
302
-continued
150
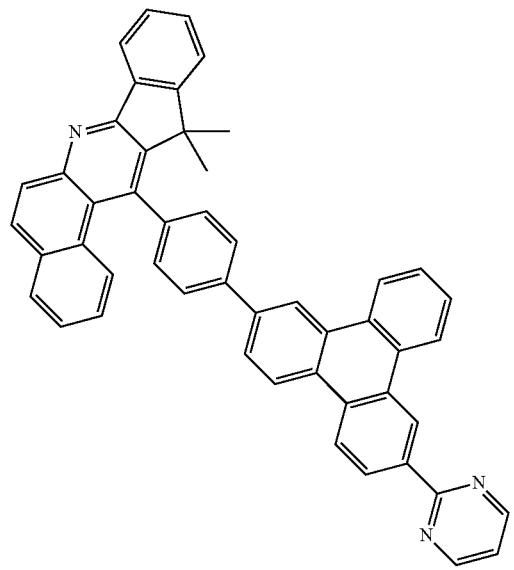
149
151
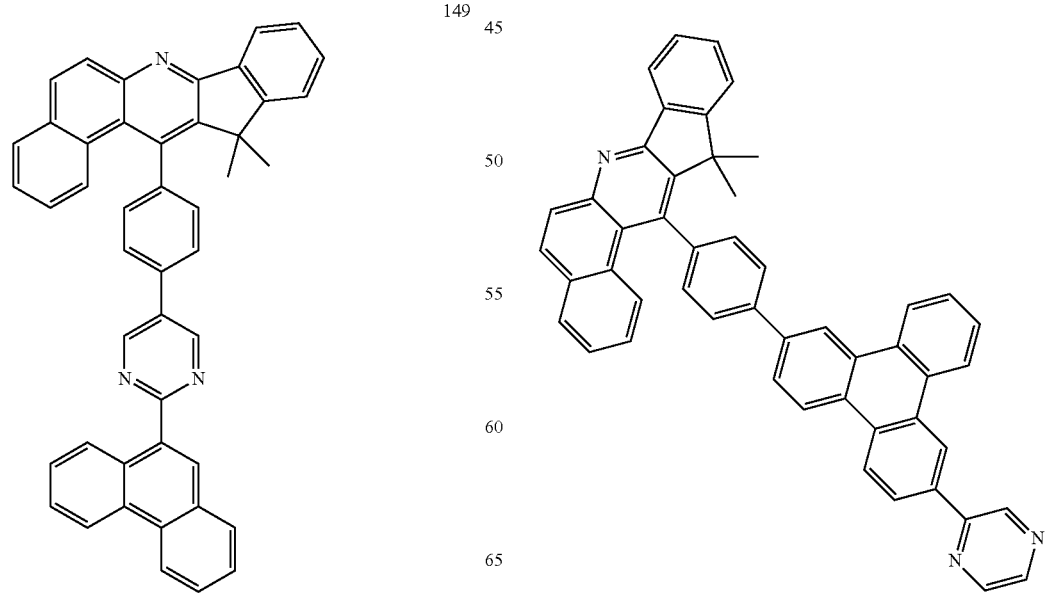

303
-continued
152
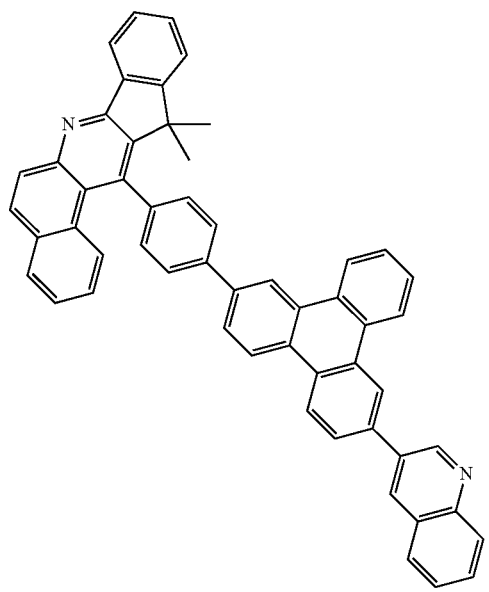
153
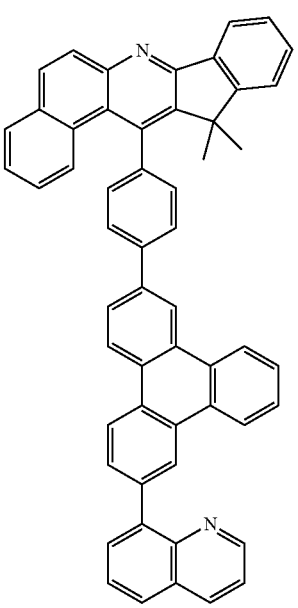
304
-continued
154
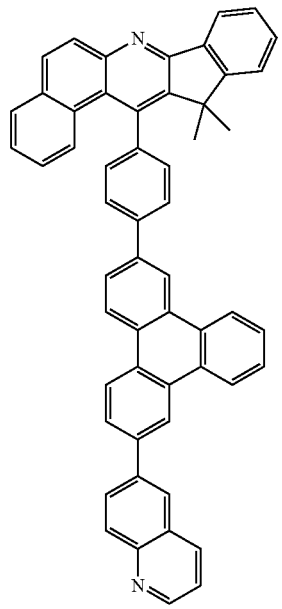
155
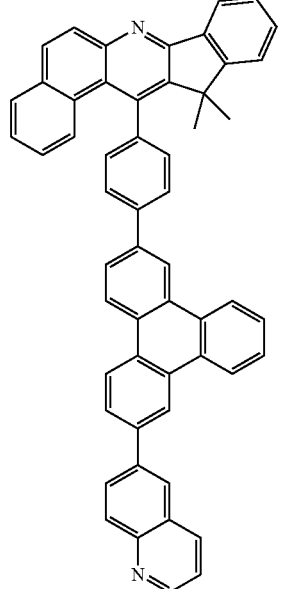

305
-continued
156
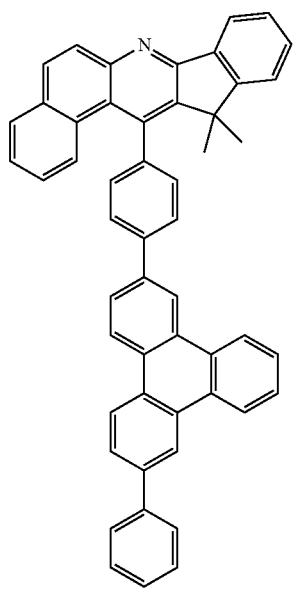
157
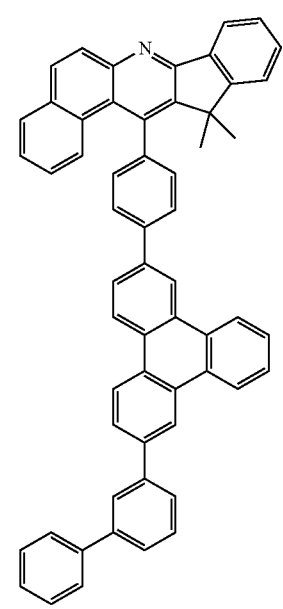
306
-continued
158
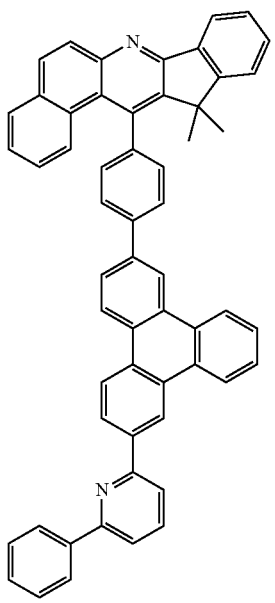
159

307
-continued
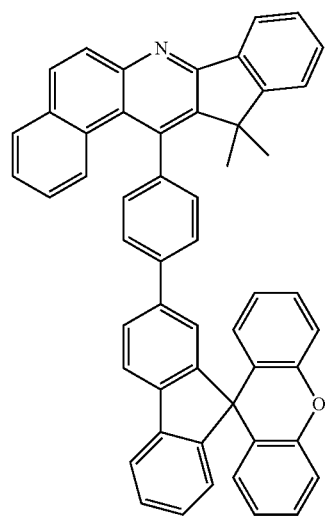
160
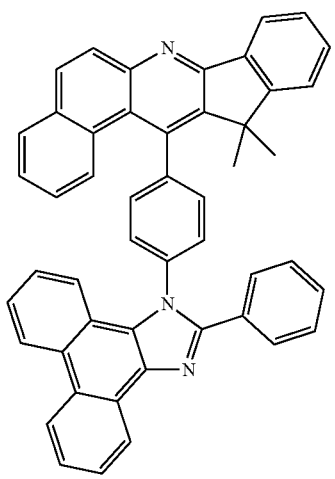
161
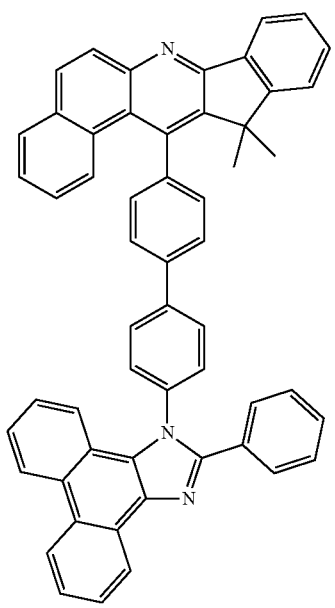 [SMILES: CC1(C)c2ccccc2-c2nc3ccc4ccccc4c3c(-c3ccc(-c4ccc(-n5c(-c6ccccc6)nc6c7ccccc7c7ccccc7c65)cc4)cc3)c21]
162
308
-continued
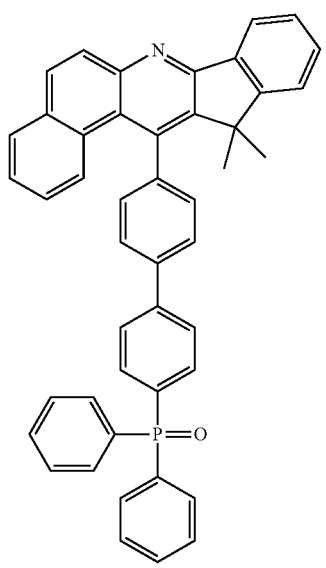
163
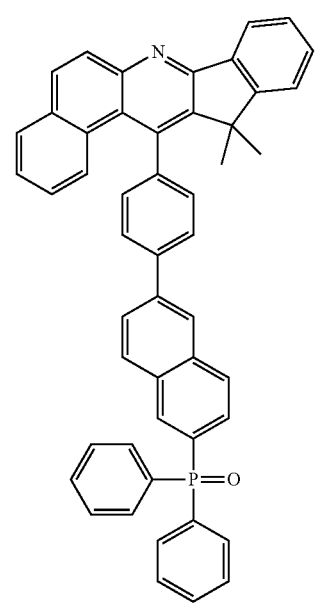 [SMILES: CC1(C)c2ccccc2-c2nc3ccc4ccccc4c3c(-c3ccc(-c4ccc5cc(P(=O)(c6ccccc6)c6ccccc6)ccc5c4)cc3)c21]
164

165
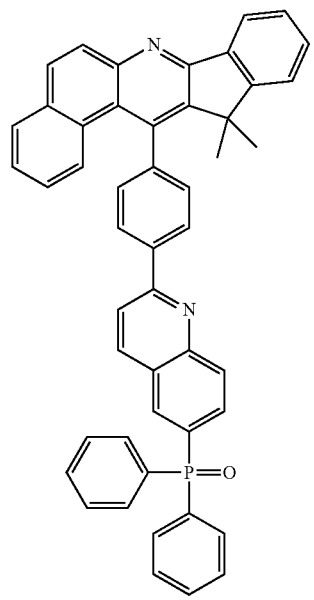
166
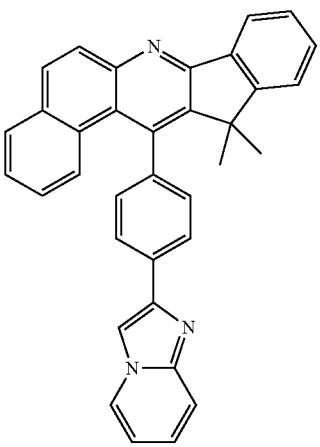
167
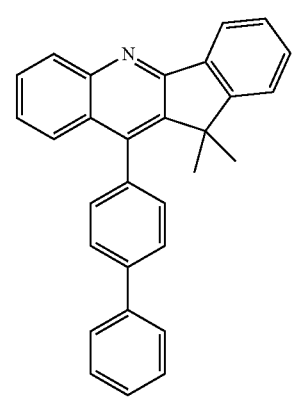
168
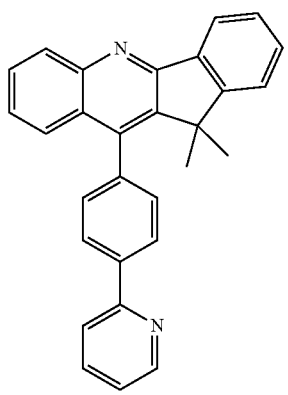
169
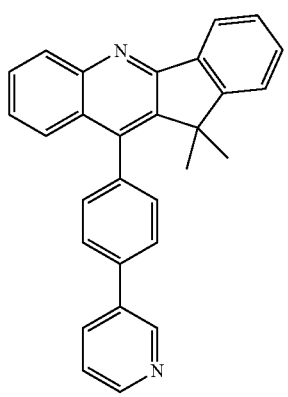
170
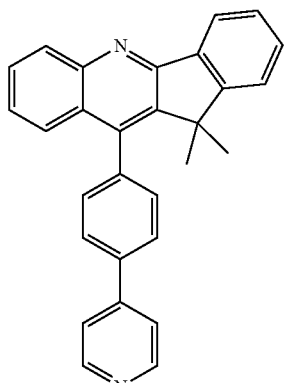
171
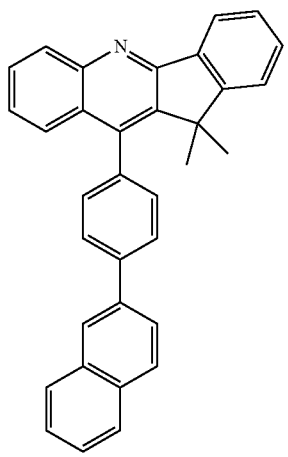

311
-continued
172
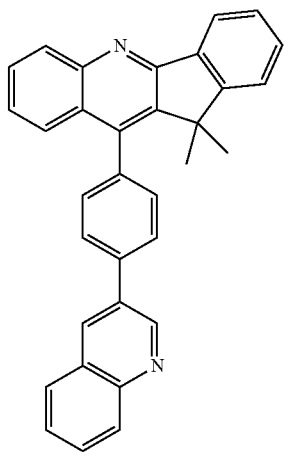 [SMILES: CC1(C)c2ccccc2-c2nc3ccccc3c(-c3ccc(-c4ccc5ccccc5c4)cc3)c21]
173
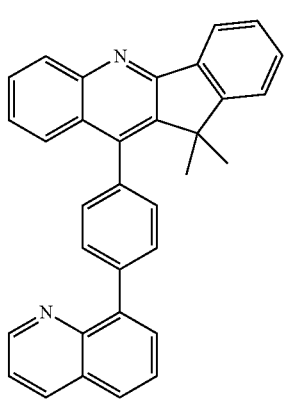
174
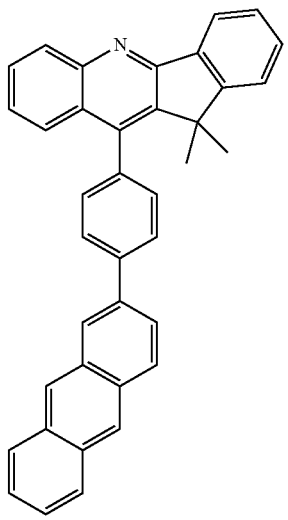 [SMILES: CC1(C)c2ccccc2-c2nc3ccccc3c(-c3ccc(-c4ccc5cc6ccccc6cc5c4)cc3)c21]
312
-continued
175
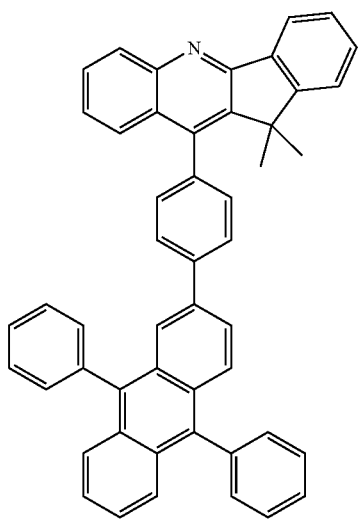
176
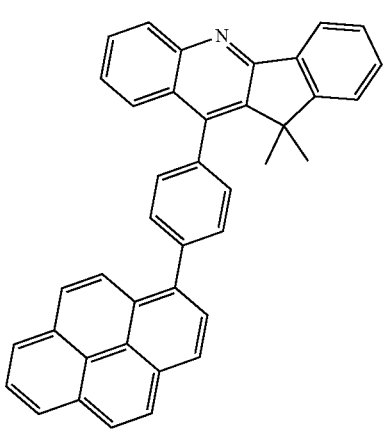
177
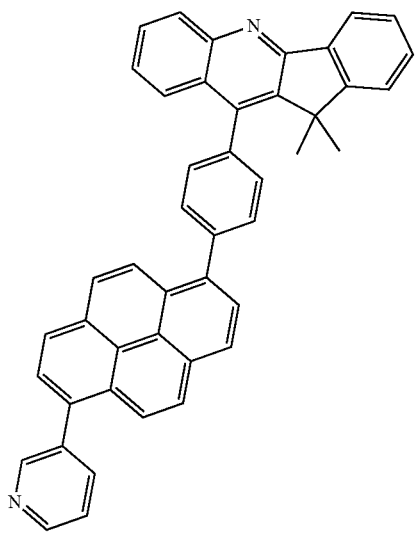

178
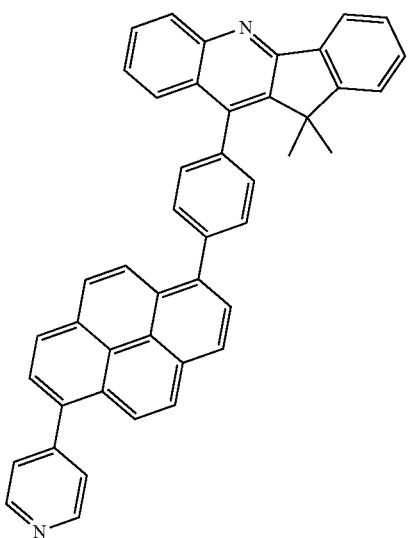
179
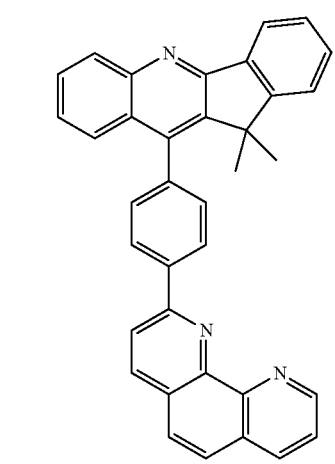
181
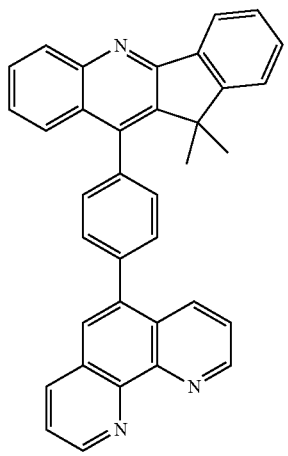
182
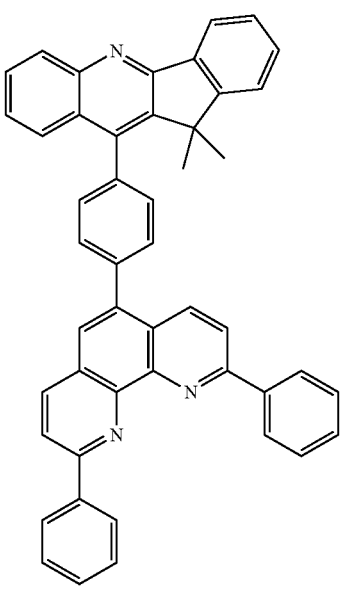
183
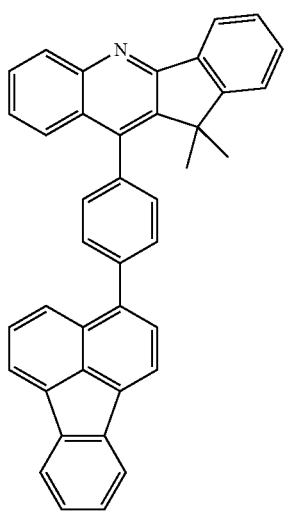

315
-continued
184
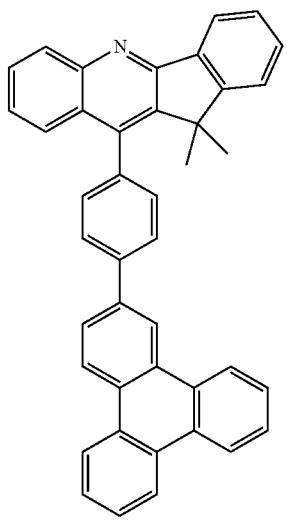 [SMILES: CC1(C)c2ccccc2-c2nc3ccccc3c(-c3ccc(-c4ccc5c6ccccc6c6ccccc6c5c4)cc3)c21]
185
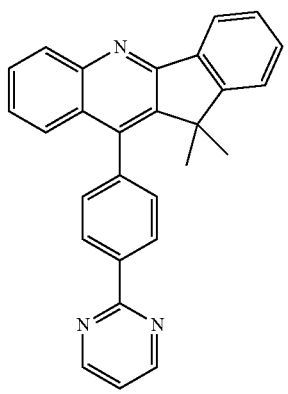
186
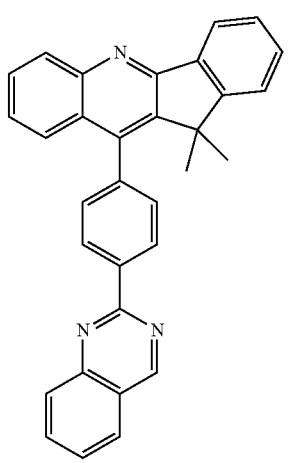
316
-continued
187
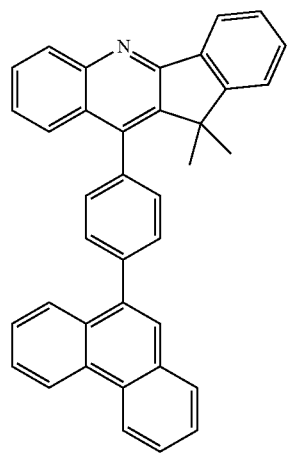
188
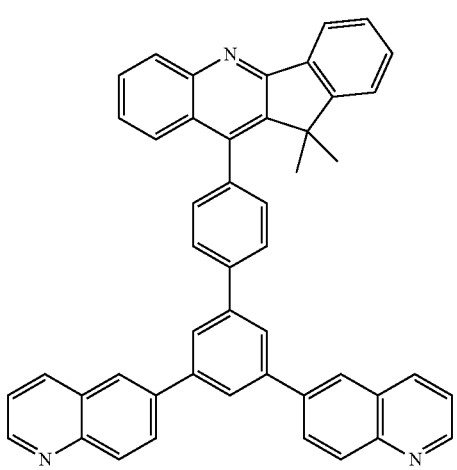
189
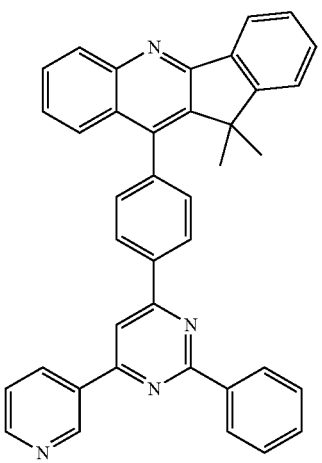

190
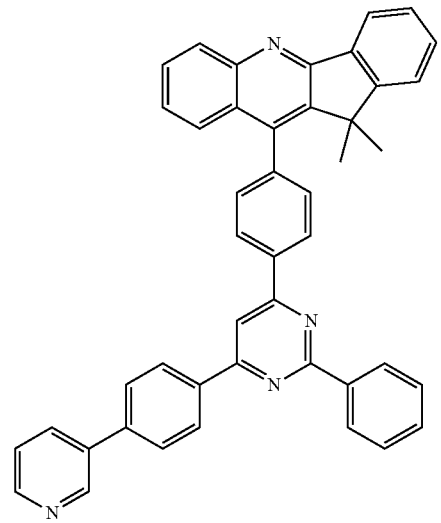
191
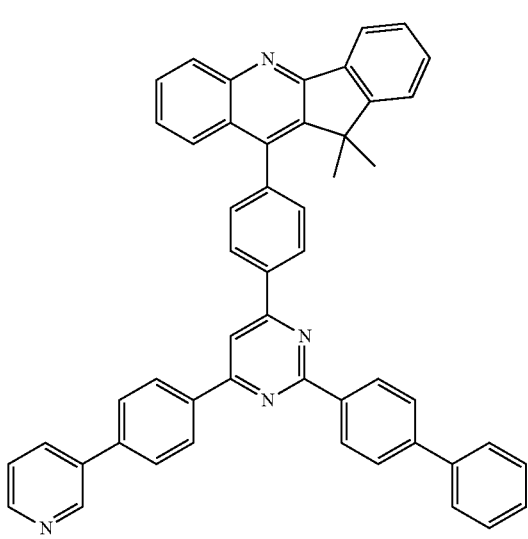
192
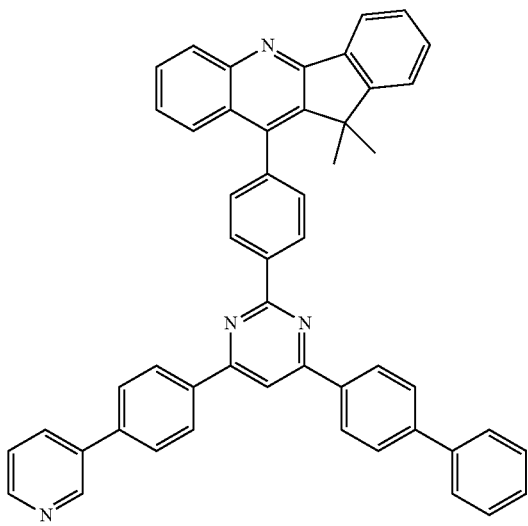
193
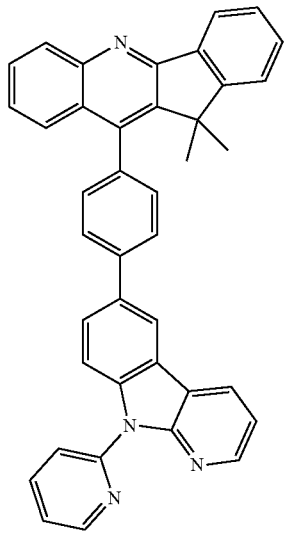
194
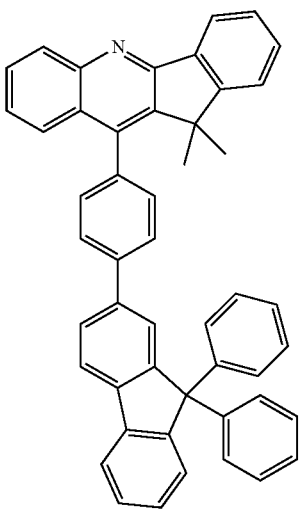
195
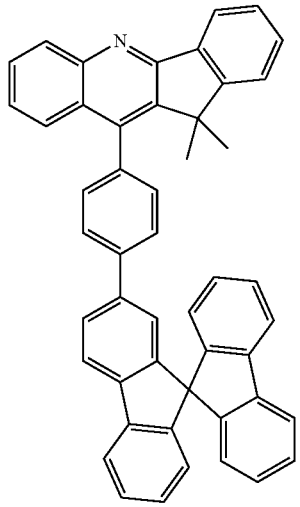 [SMILES: CC1(C)c2ccccc2-c2nc3ccccc3c(-c3ccc(-c4ccc5c(c4)C4(c6ccccc6-c6ccccc64)c4ccccc4-5)cc3)c21]

-continued
196
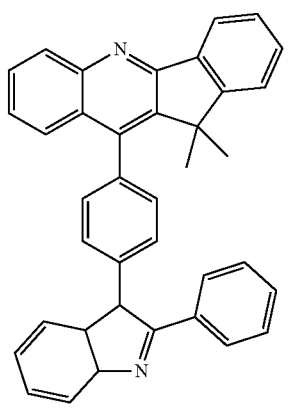 [SMILES: CC1(C)c2ccccc2-c2nc3ccccc3c(-c3ccc(C4C(c5ccccc5)=NC5C=CC=CC54)cc3)c21]
197
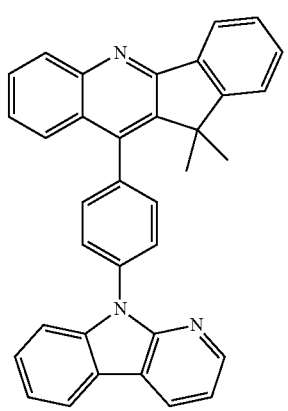
198
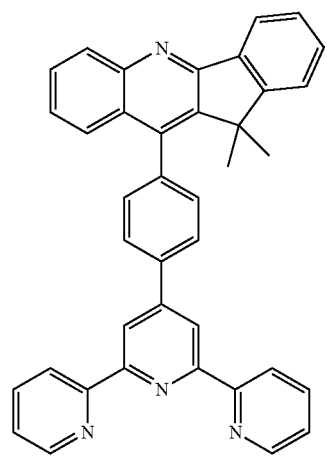
-continued
199
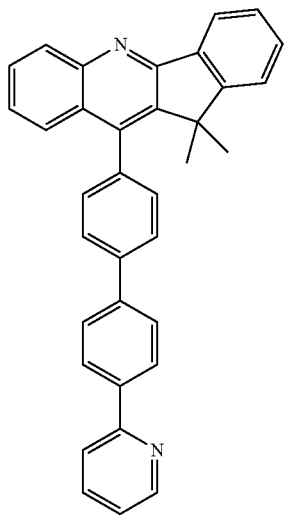
200
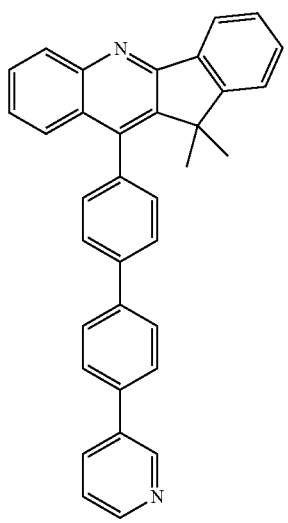
201
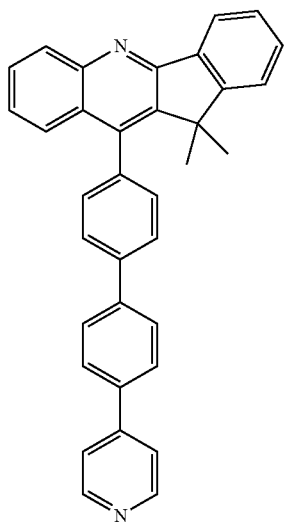

321
-continued
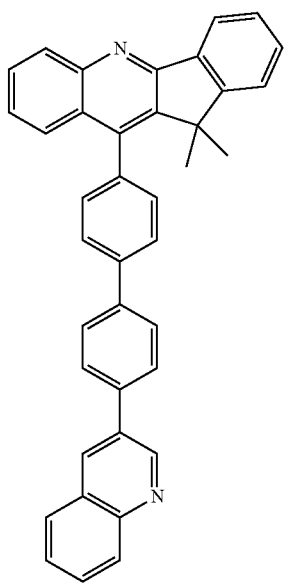
202
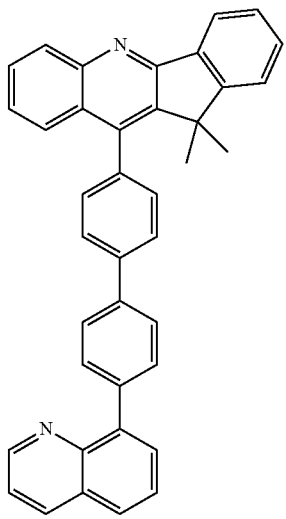
203
322
-continued
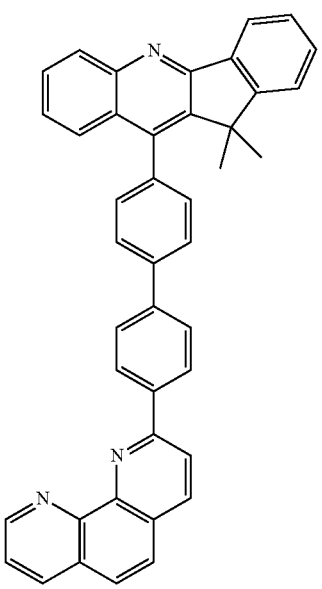
204
205

323
-continued
206
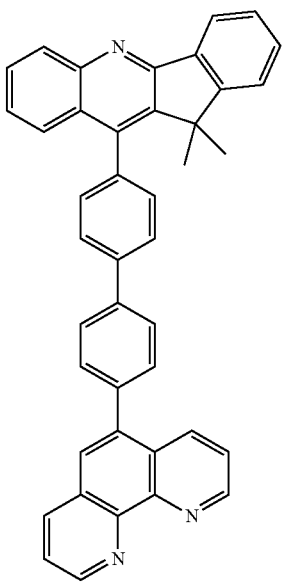
207
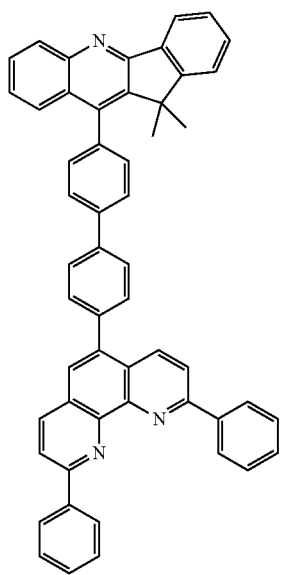
324
-continued
208
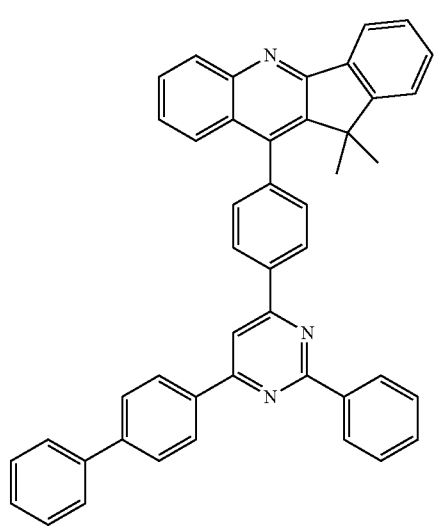 [SMILES: CC1(C)c2ccccc2-c2nc3ccccc3c(-c3ccc(-c4cc(-c5ccc(-c6ccccc6)cc5)nc(-c5ccccc5)n4)cc3)c21]
209
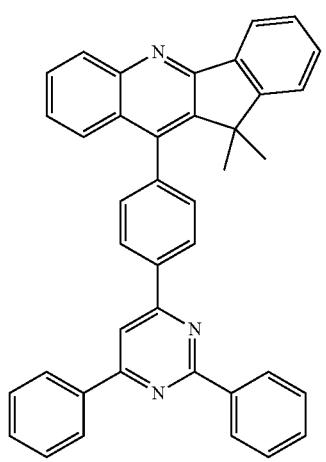
210
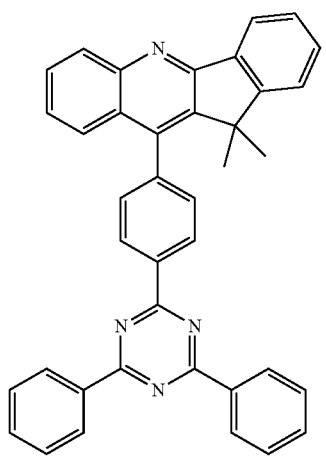

| 325 | 326 |
|---|---|
| 211 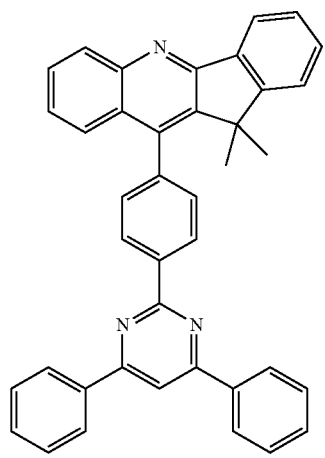 [SMILES: CC1(C)c2ccccc2-c2nc3ccccc3c(-c3ccc(-c4nc(-c5ccccc5)cc(-c5ccccc5)n4)cc3)c21] | 214 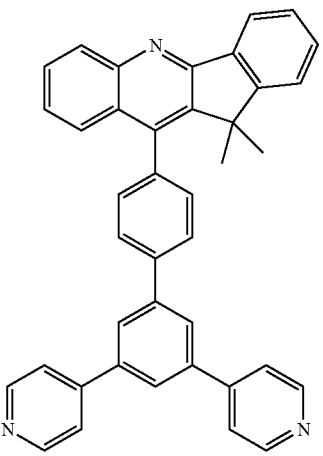 |
| 212 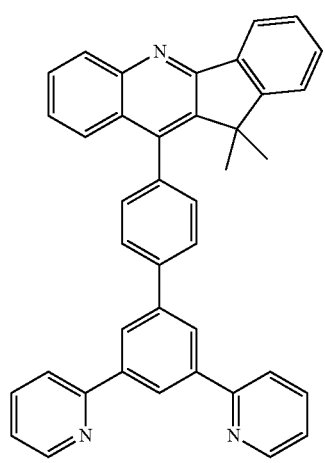 | 215 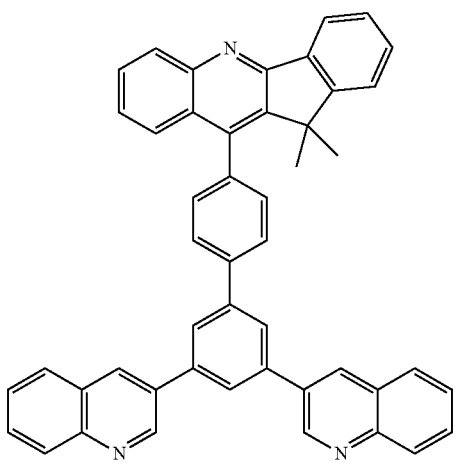 |
| 213 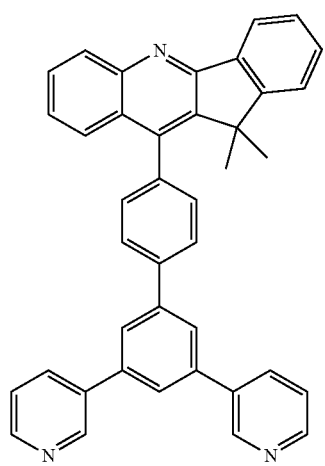 | 216 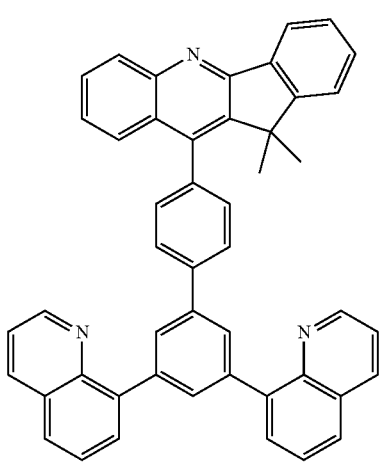 |

327
-continued
217
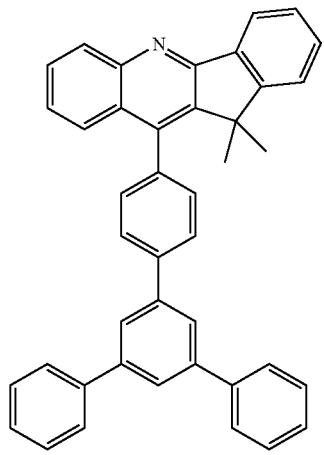
218
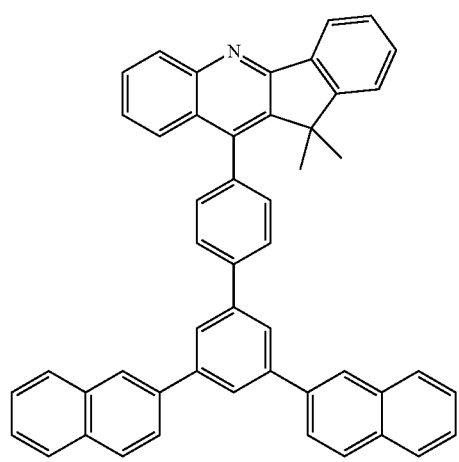 [SMILES: CC1(C)c2ccccc2-c2nc3ccccc3c(-c3ccc(-c4cc(-c5ccc6ccccc6c5)cc(-c5ccc6ccccc6c5)c4)cc3)c21]
219
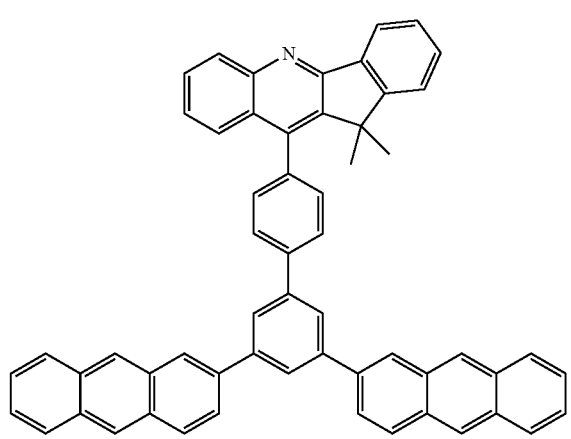
328
-continued
220
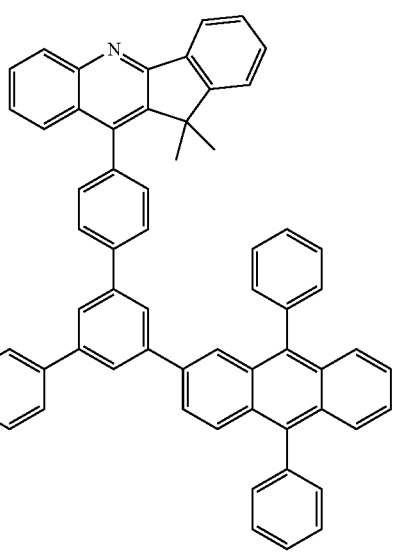
221
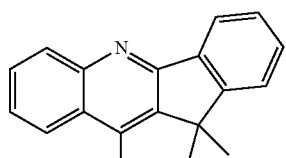
222
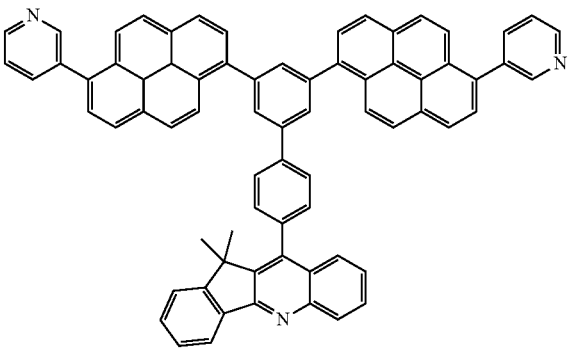

329
-continued
330
-continued
223
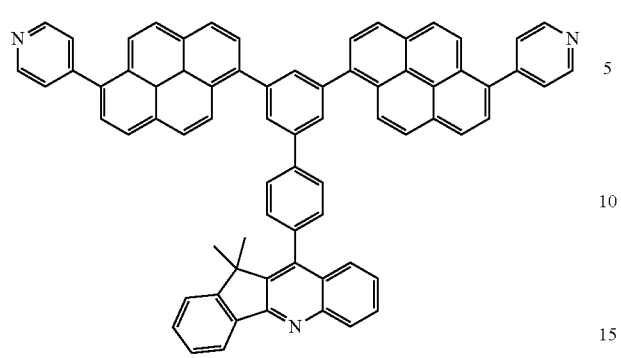
226
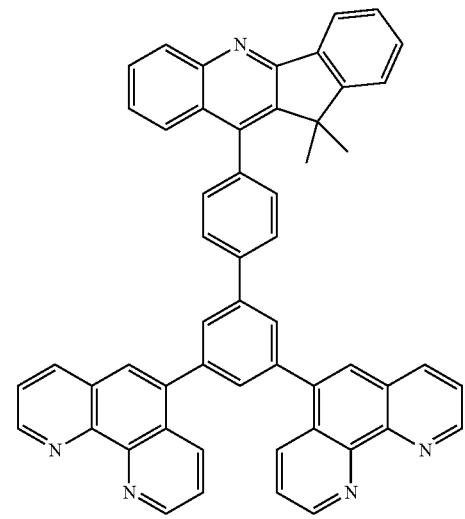
224
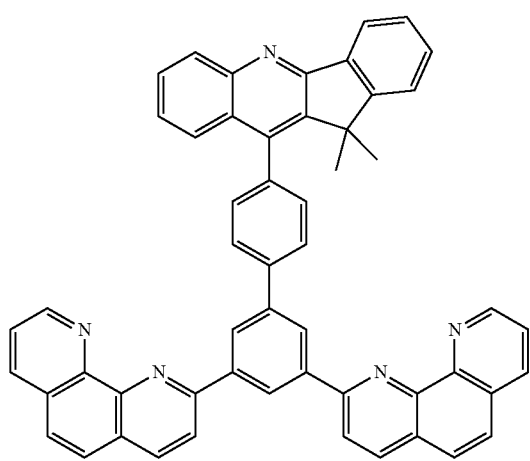 [SMILES: CC1(C)c2ccccc2-c2nc3ccccc3c(-c3ccc(-c4cc(-c5ccc6ccc7cccnc7c6n5)cc(-c5ccc6ccc7cccnc7c6n5)c4)cc3)c21]
227
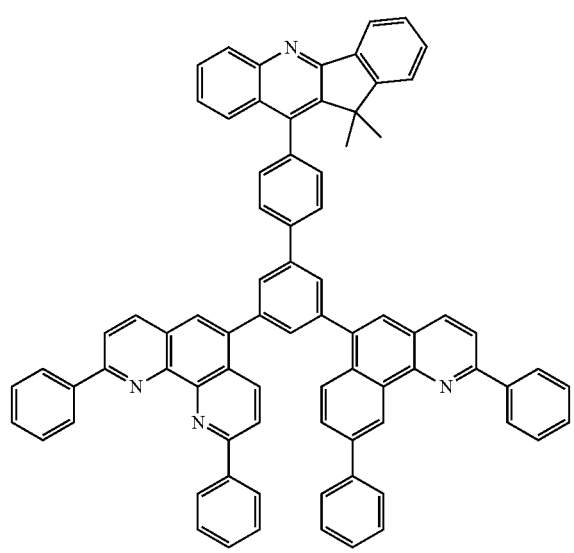
225
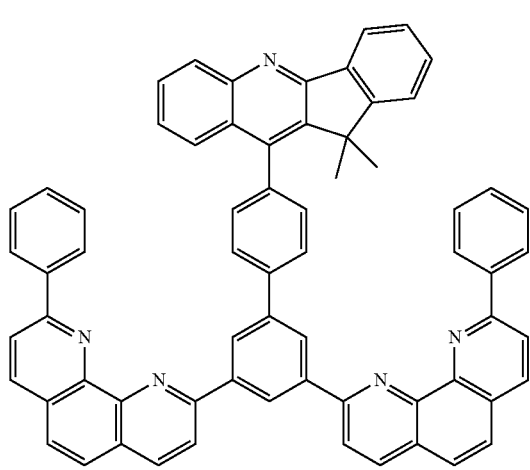
228
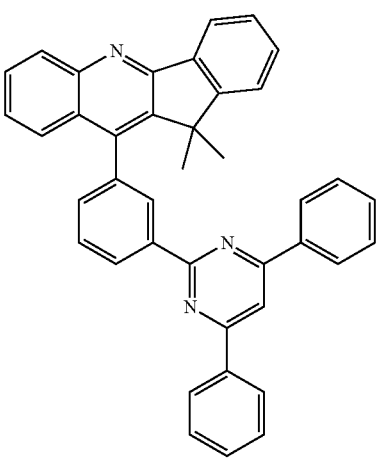

331
-continued
332
-continued
229
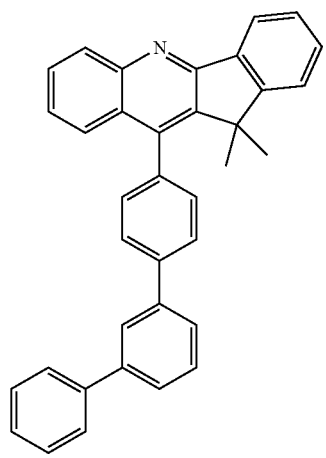
232
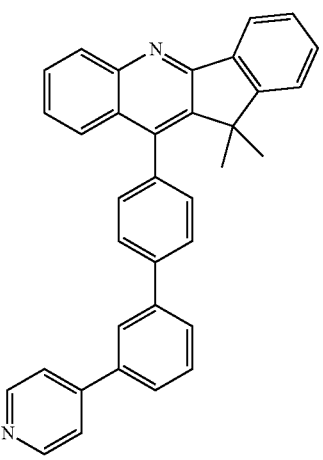
230
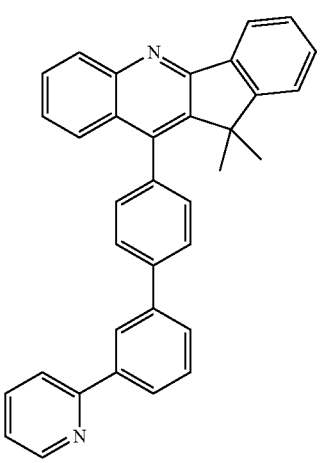
233
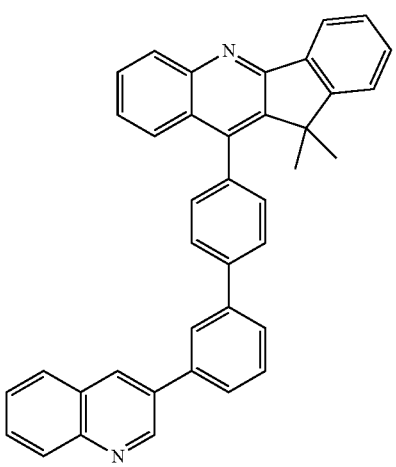
231
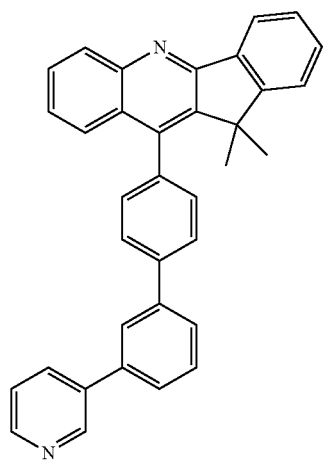
234
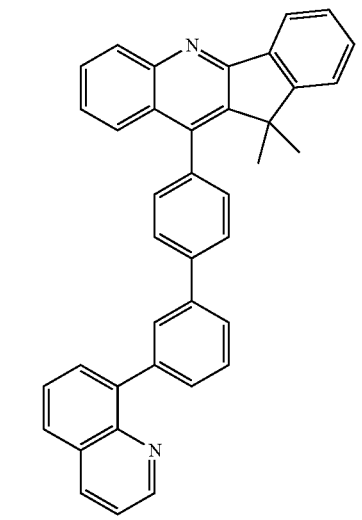

-continued
235
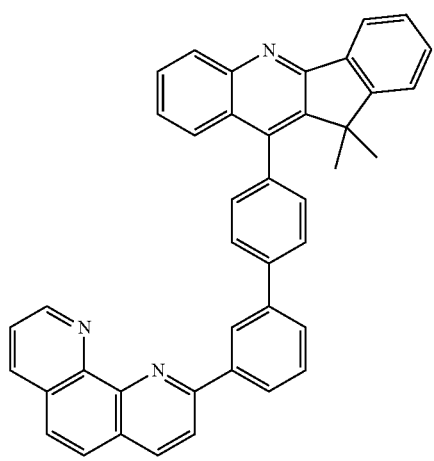
236
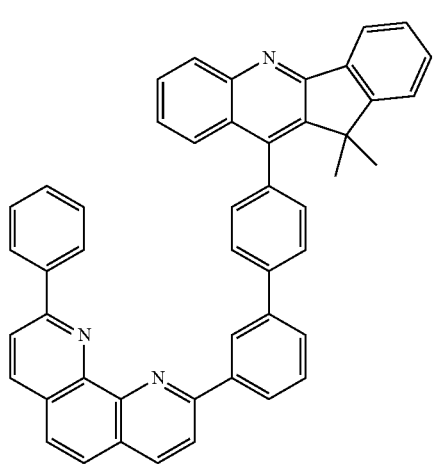
237
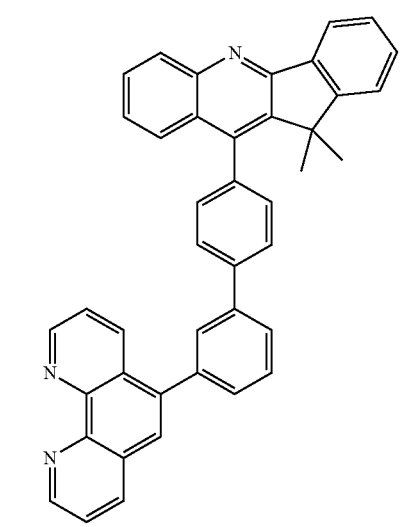
-continued
238
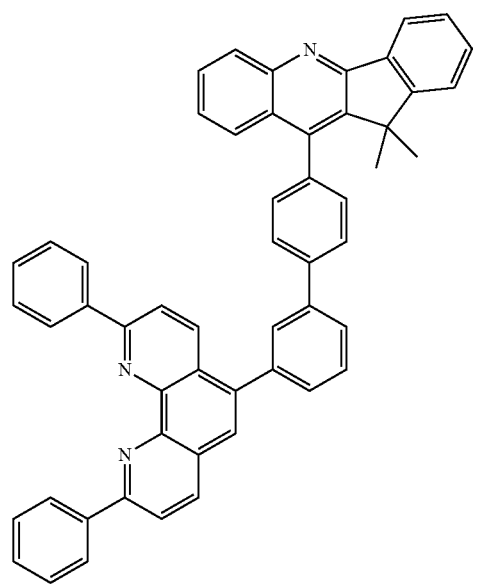
239
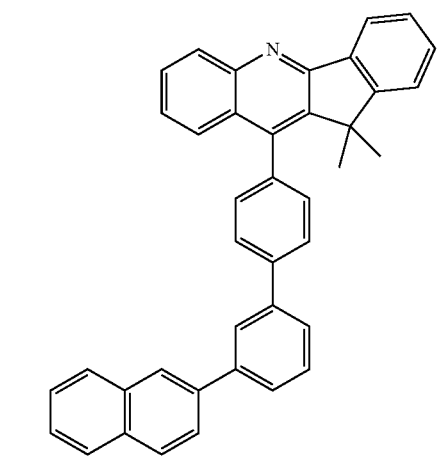
240
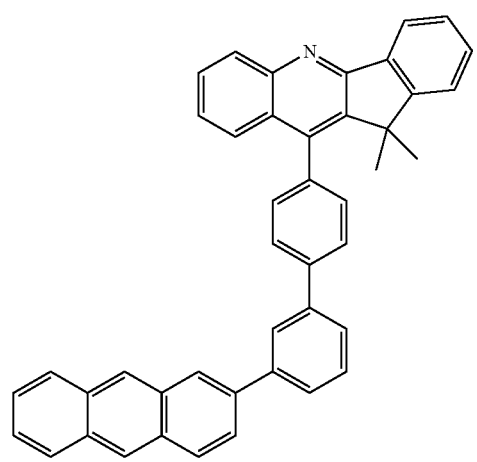

241
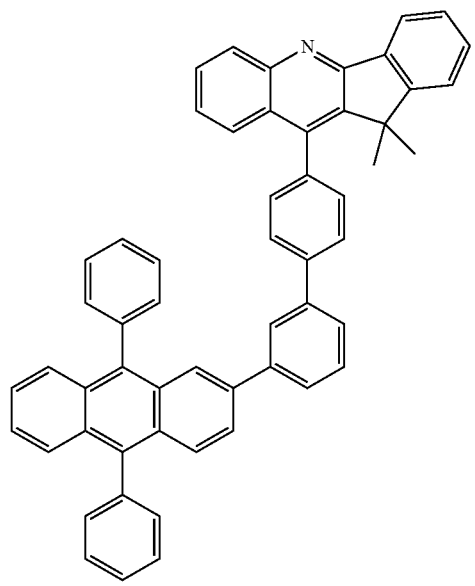
242
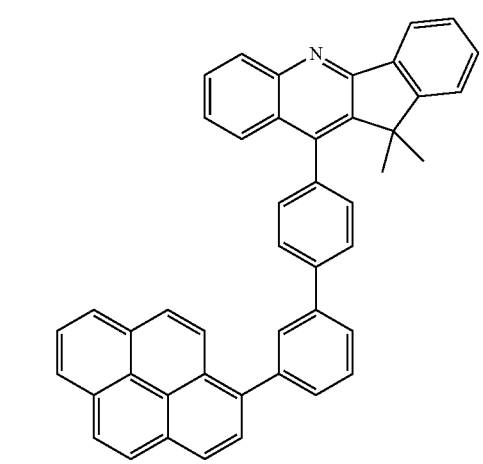
243
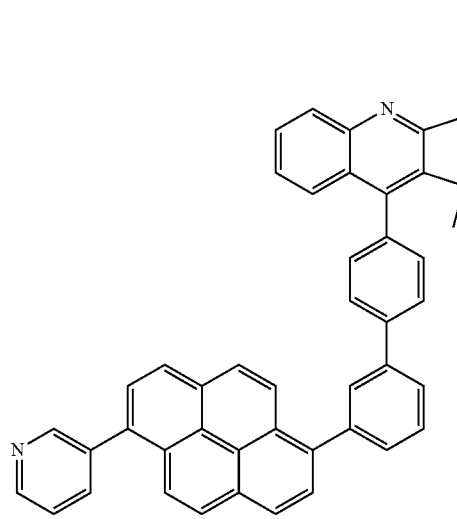
244
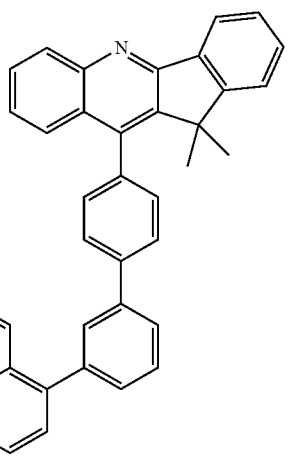
245
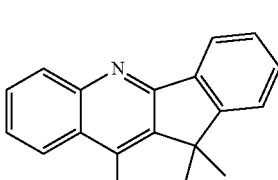
246
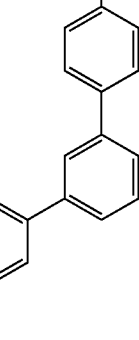

247
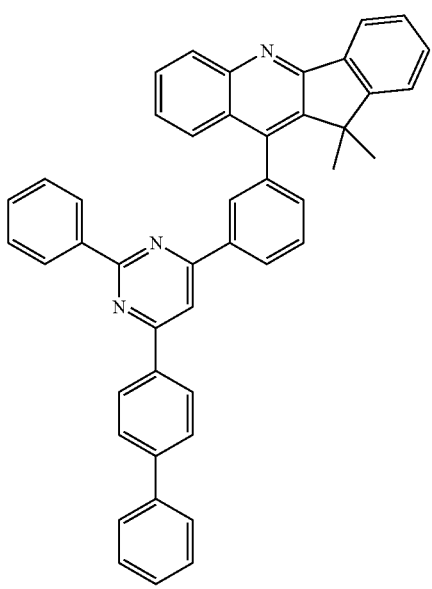
248
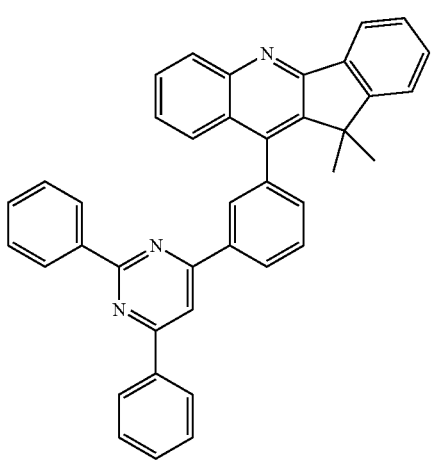
249
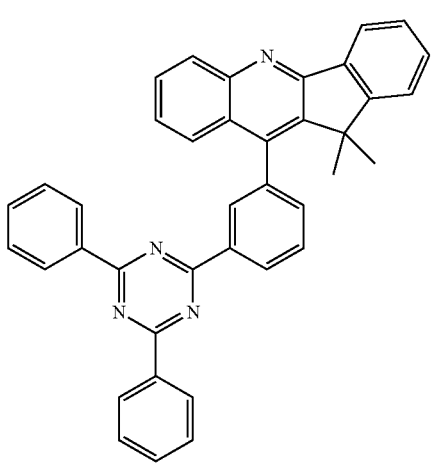
250
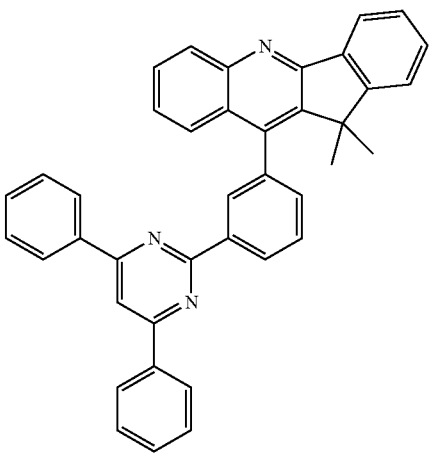
251
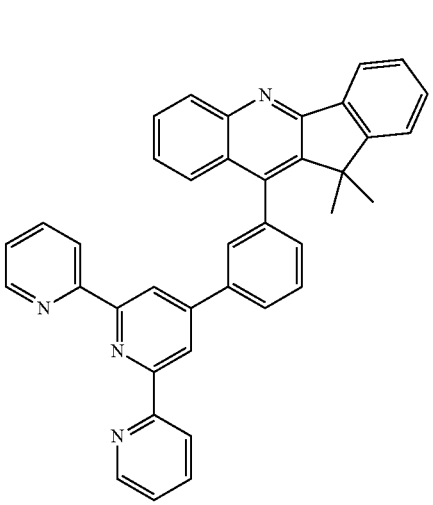
252
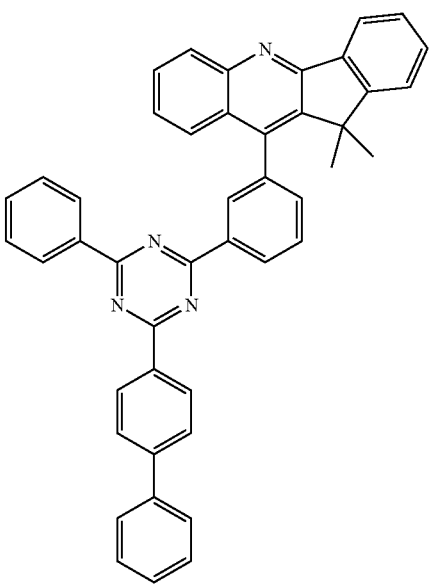

253
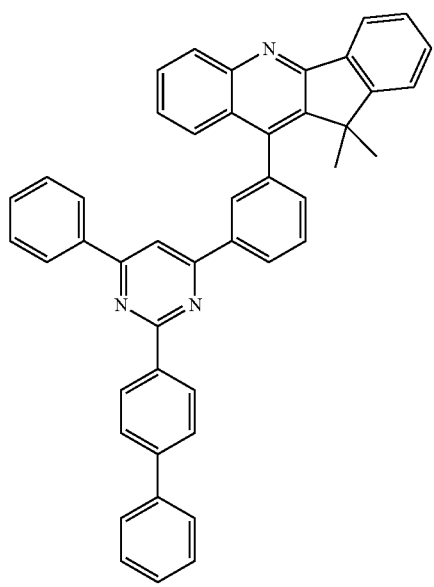
254
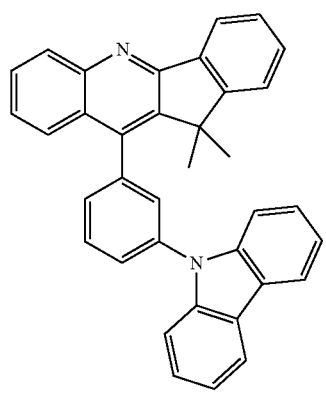
255
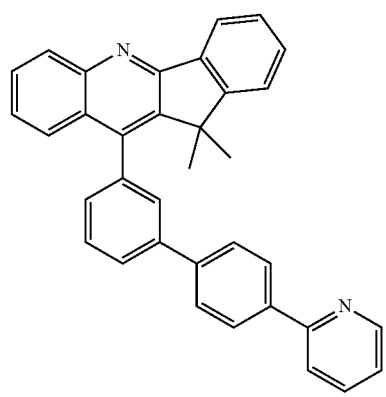
256
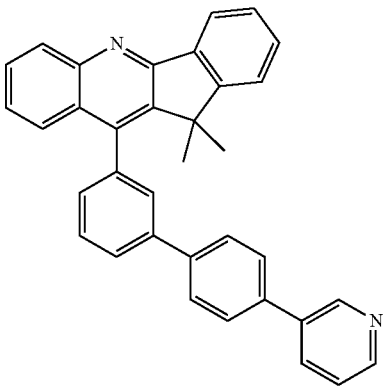
257
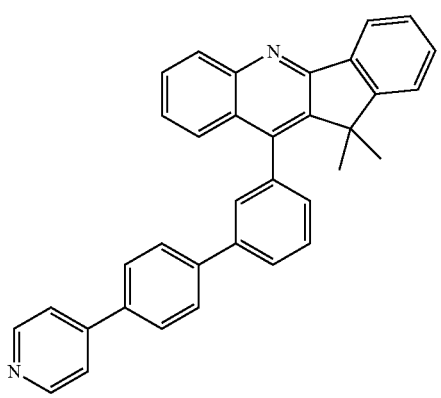
258
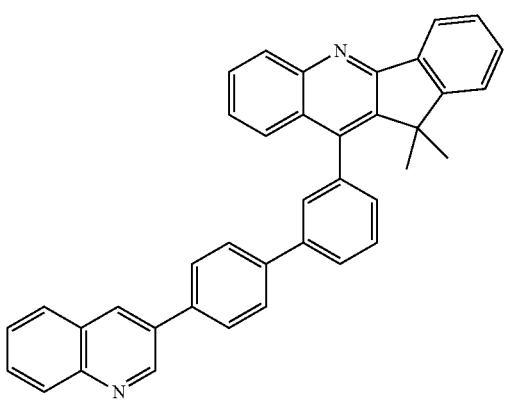

341
-continued
259
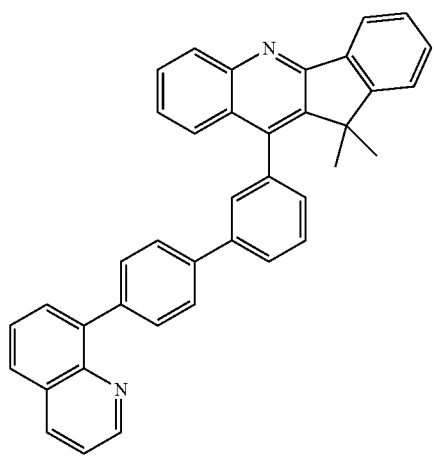
260
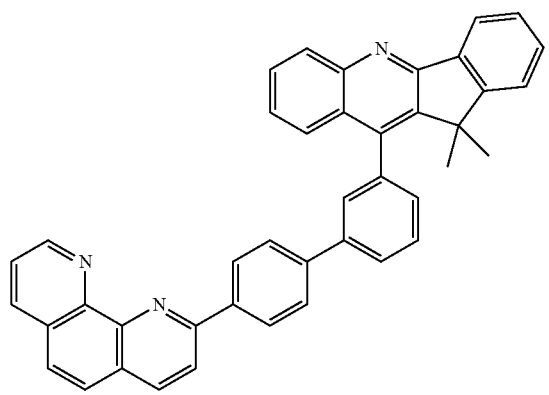
261
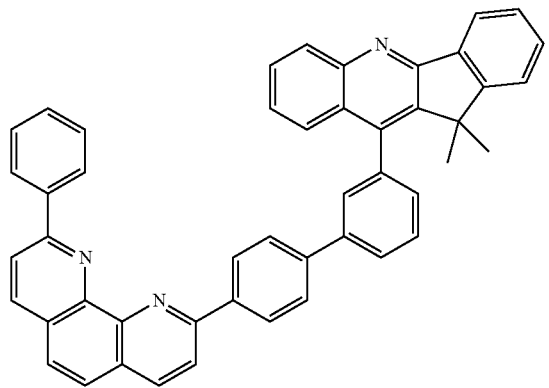
342
-continued
262
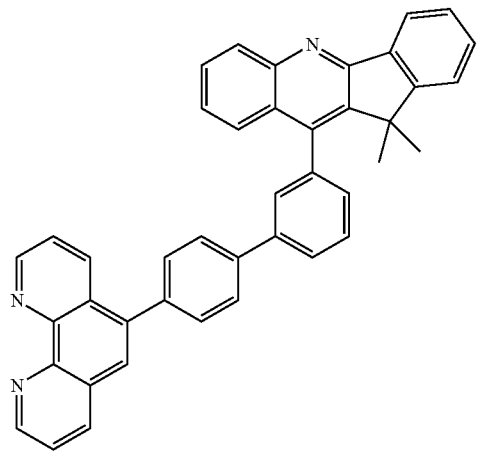
263
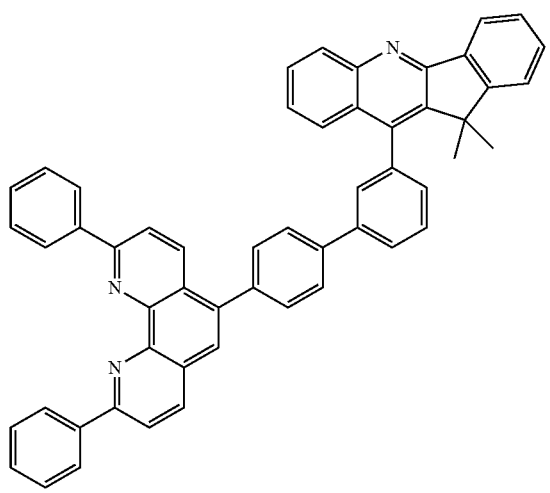
264
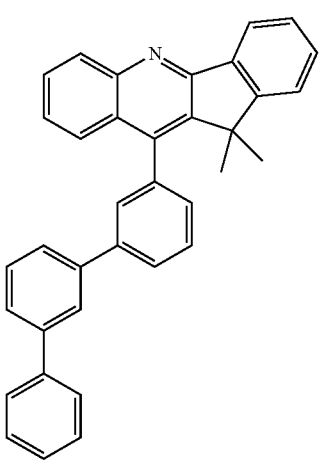

265
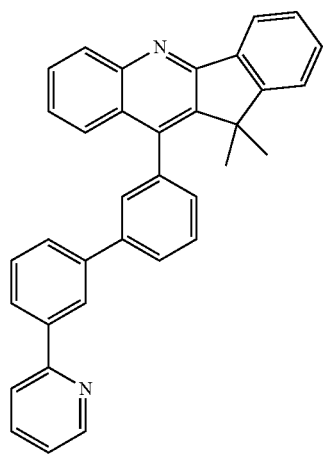
266
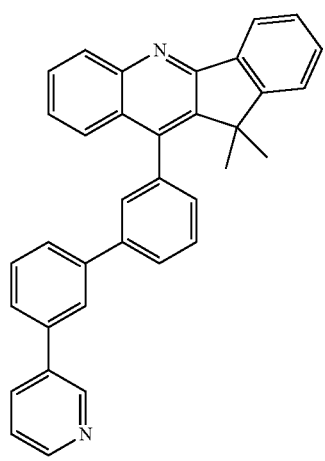
267
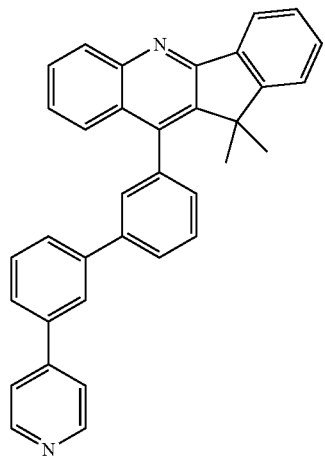
268
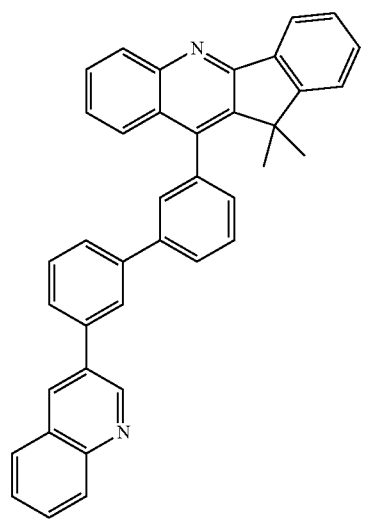
269
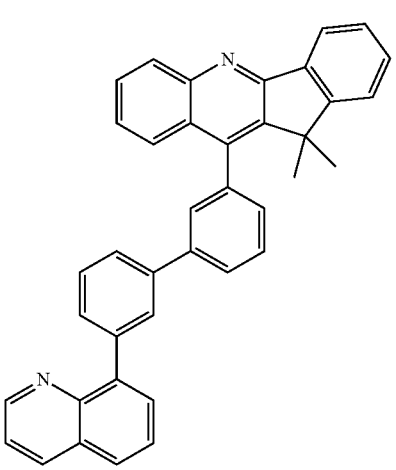
270
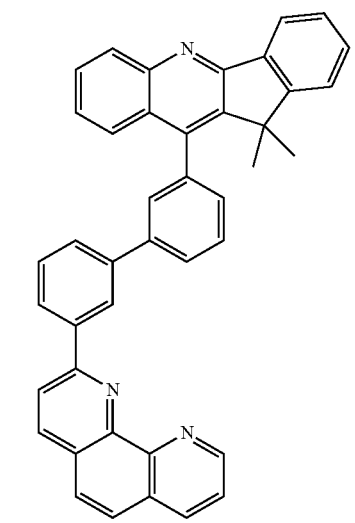

-continued
271
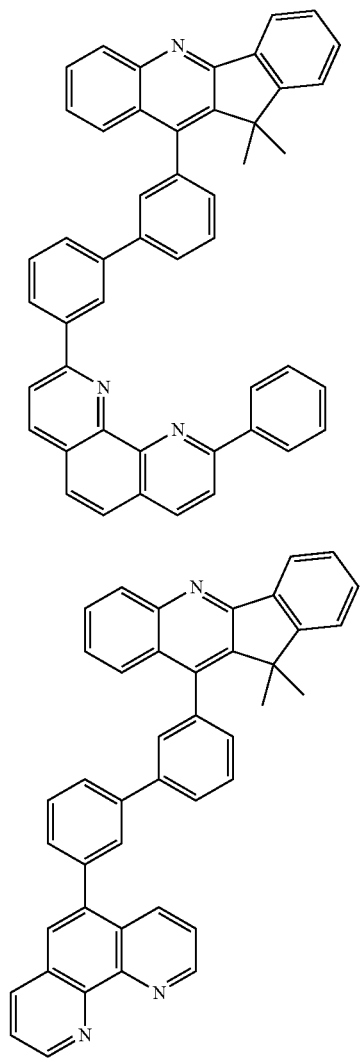
272
273
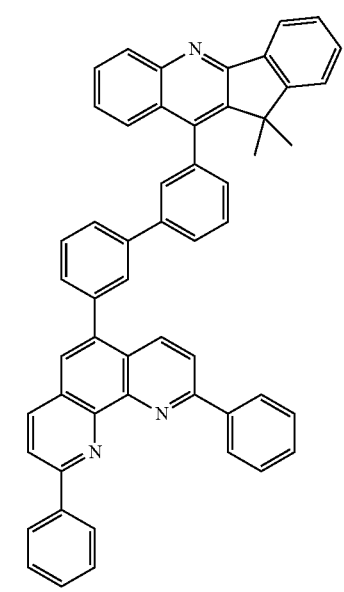
-continued
274
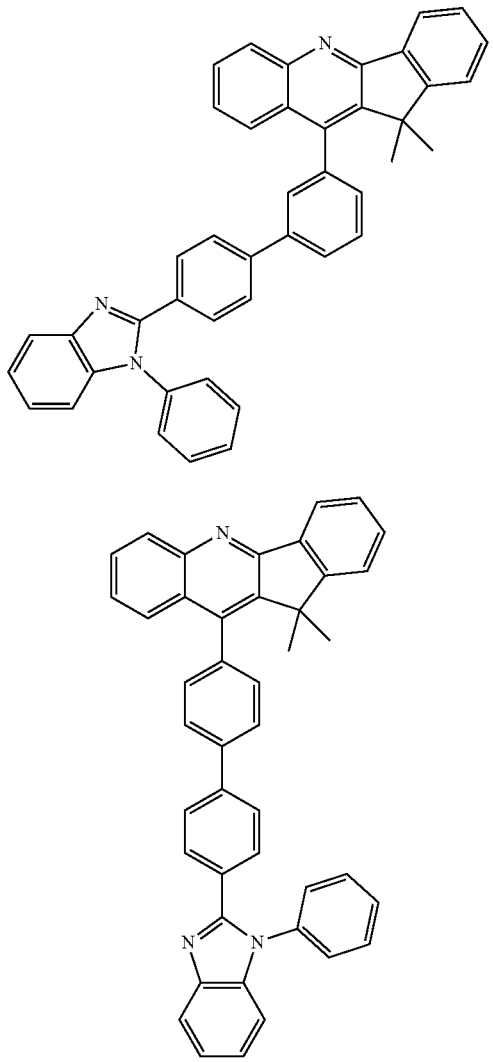
275
276
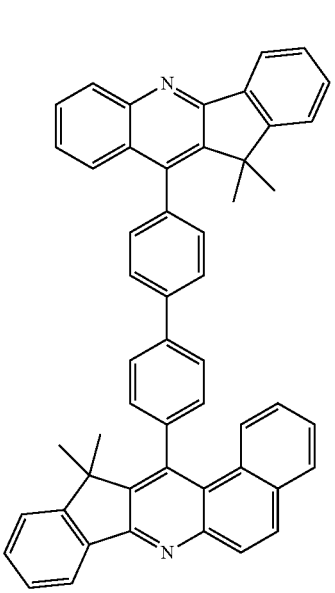

277
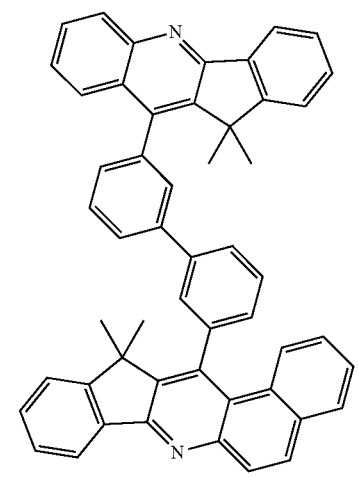
278
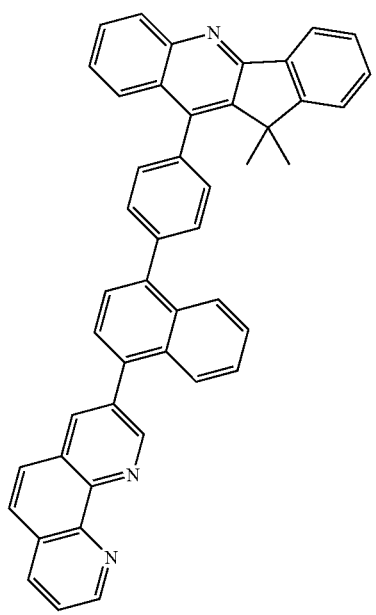
279
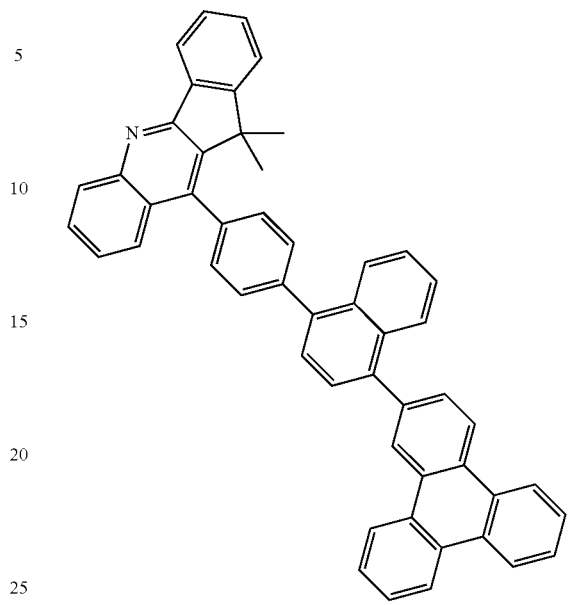
280
281
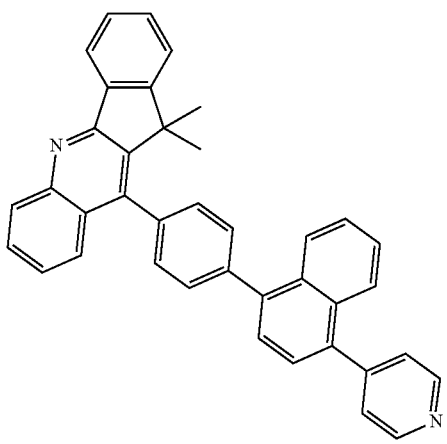

282
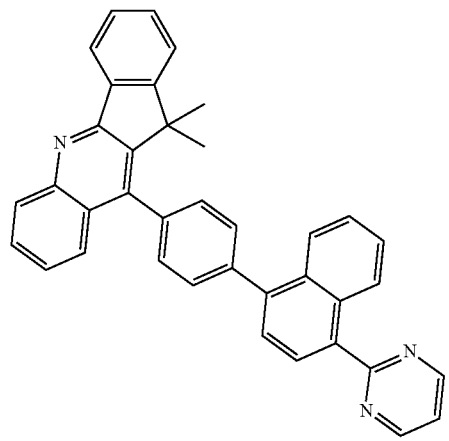
283
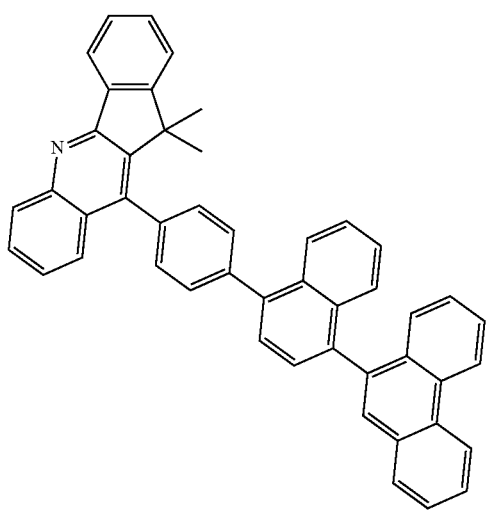
284
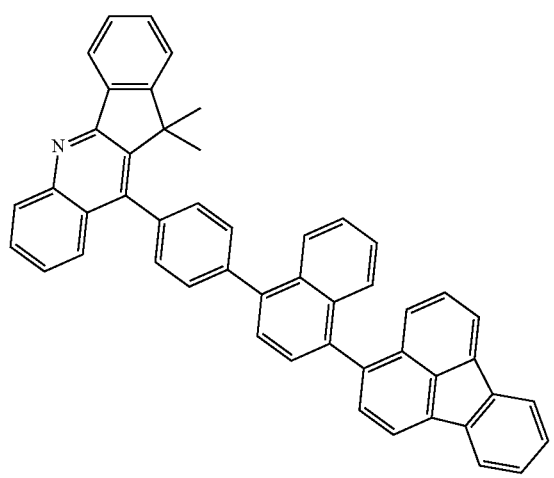
285
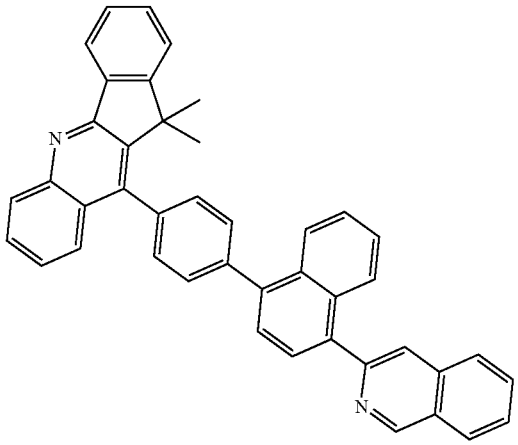
286
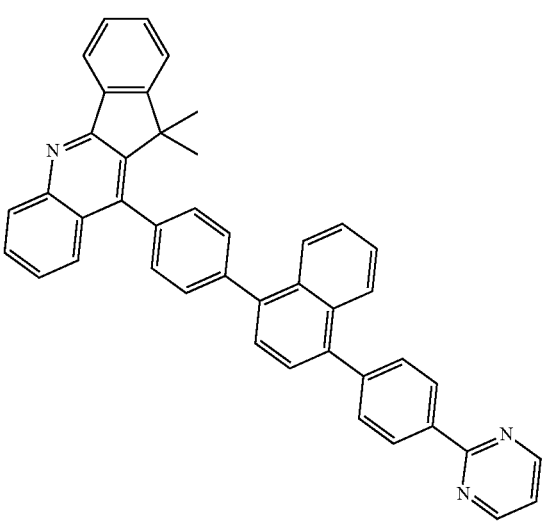
287
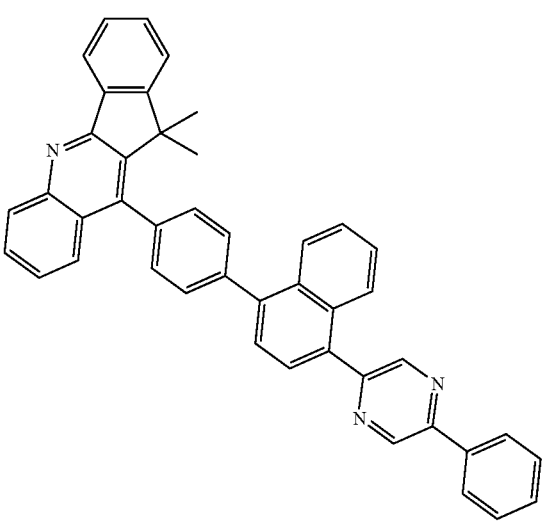

351
-continued
288
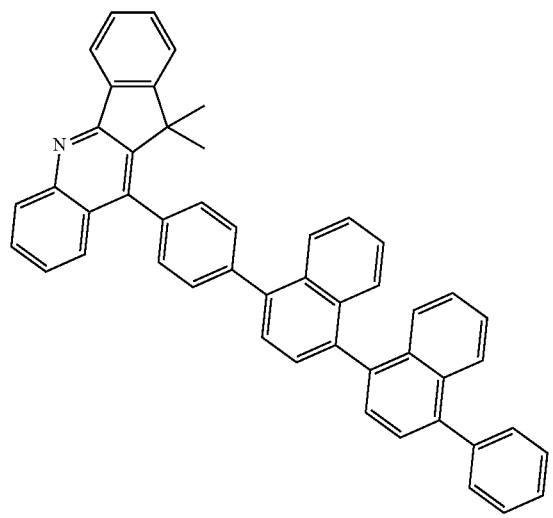
289
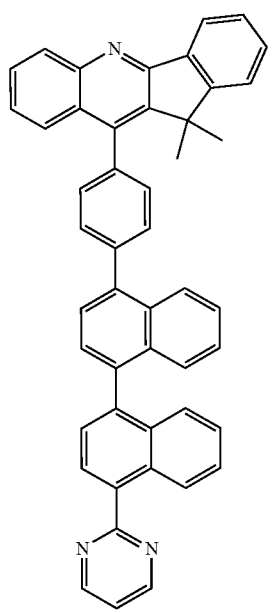
352
-continued
290
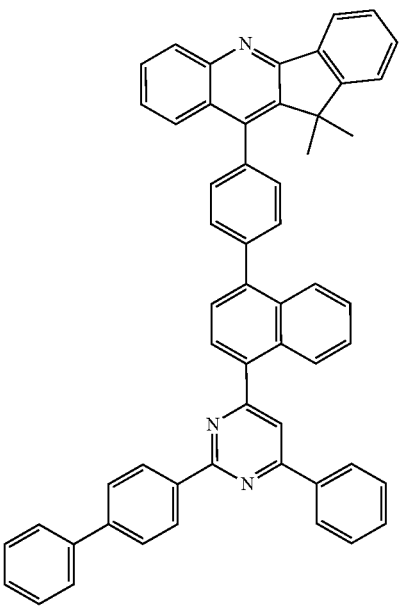 [SMILES: CC1(C)c2ccccc2-c2nc3ccccc3c(-c3ccc(-c4ccc(-c5cc(-c6ccccc6)nc(-c6ccc(-c7ccccc7)cc6)n5)c5ccccc45)cc3)c21]
291
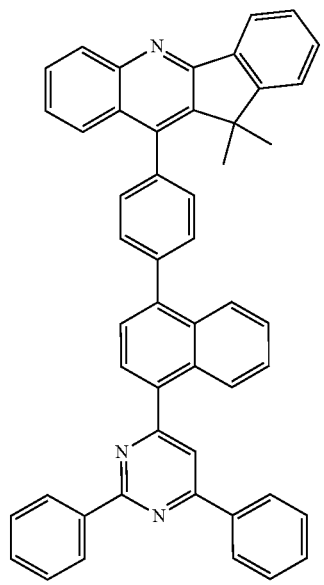

292
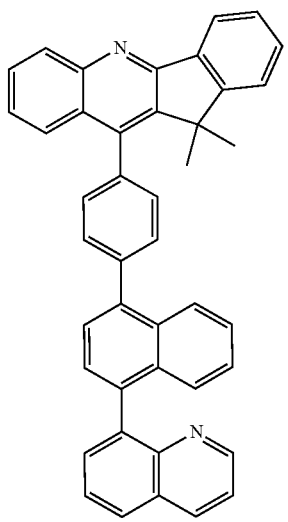
293
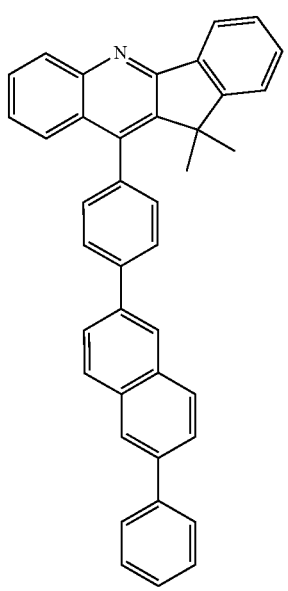
294
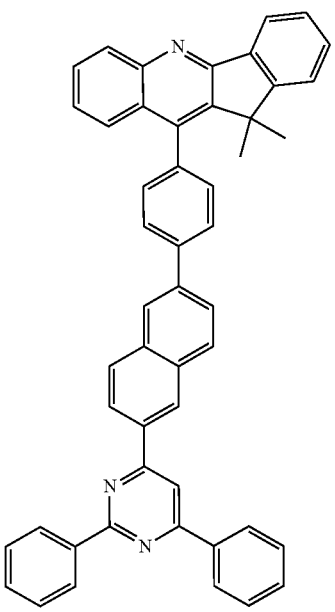
295
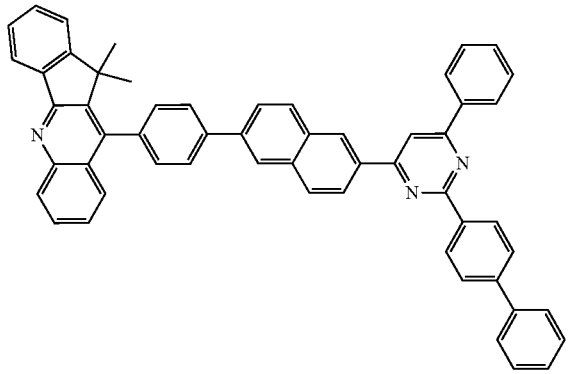
296

297
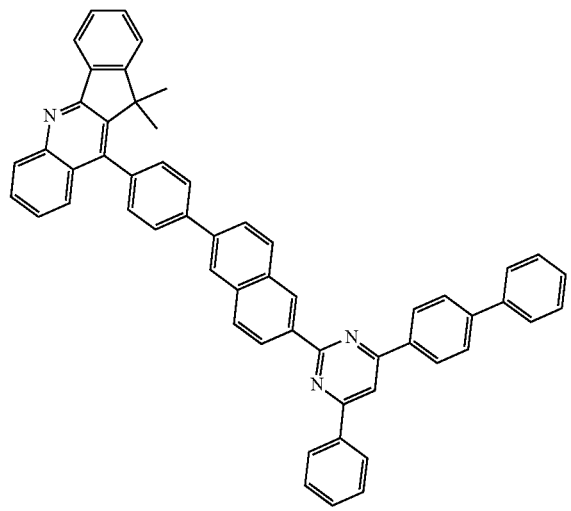
298
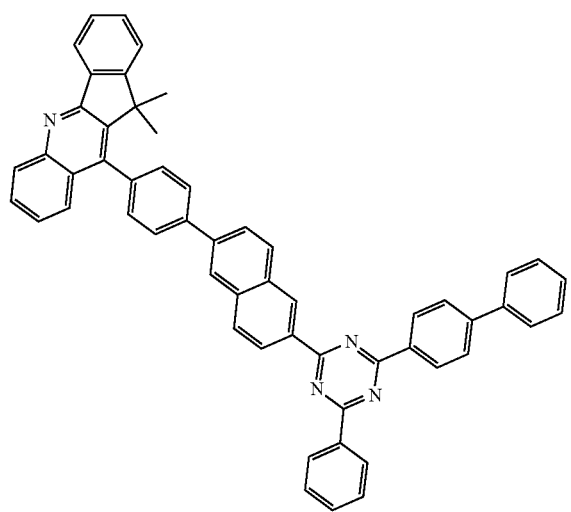
299
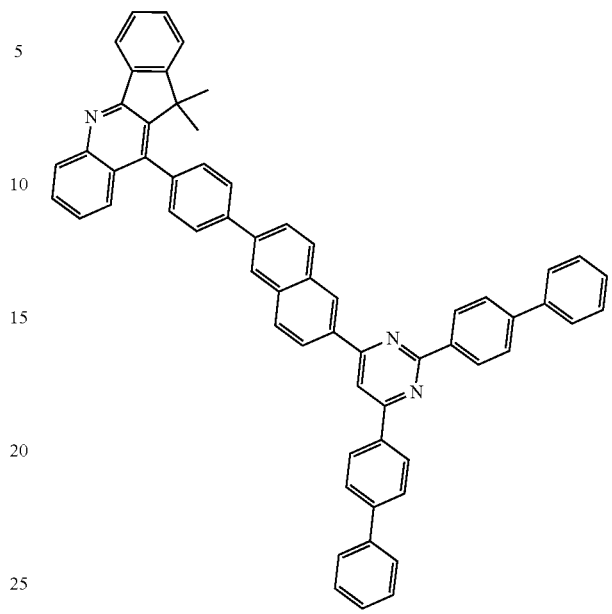
300
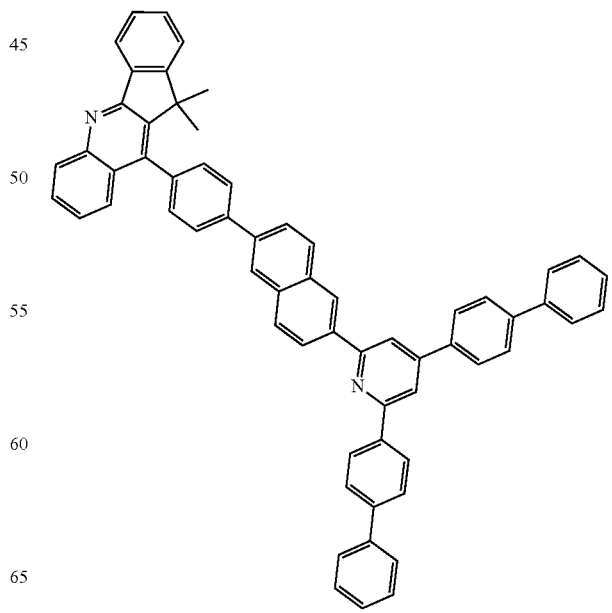

-continued
301
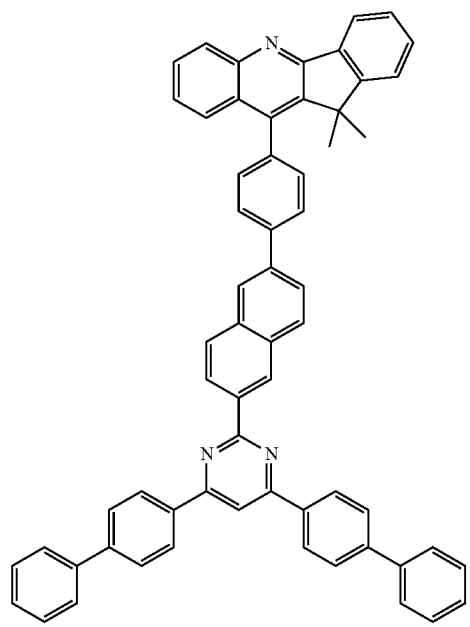
302
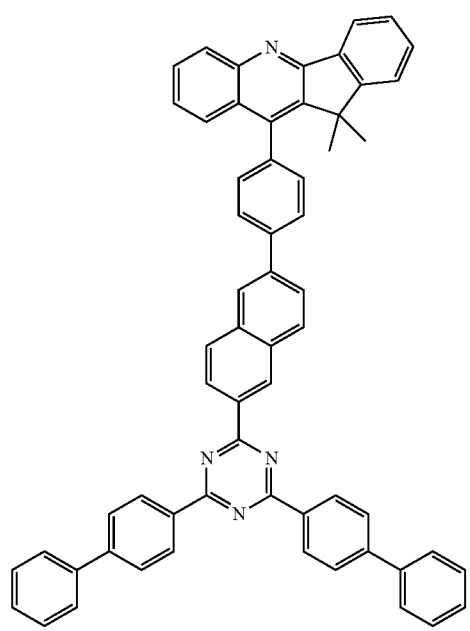
-continued
303
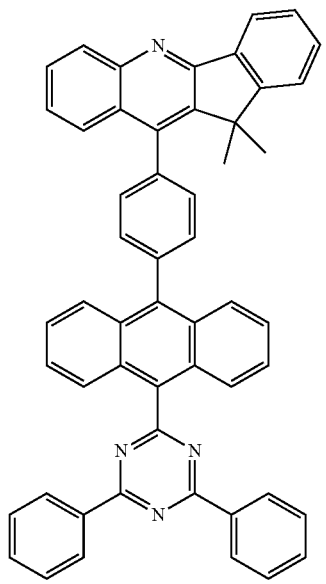 [SMILES: CC1(C)c2ccccc2-c2nc3ccccc3c(-c3ccc(-c4c5ccccc5c(-c5nc(-c6ccccc6)cc(-c6ccccc6)n5)c5ccccc45)cc3)c21]
304
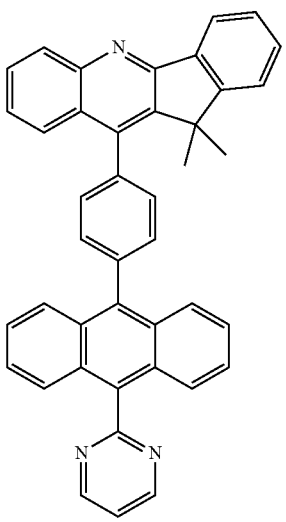
305

359
-continued
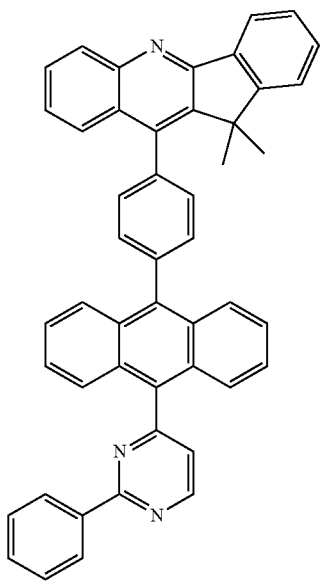
306
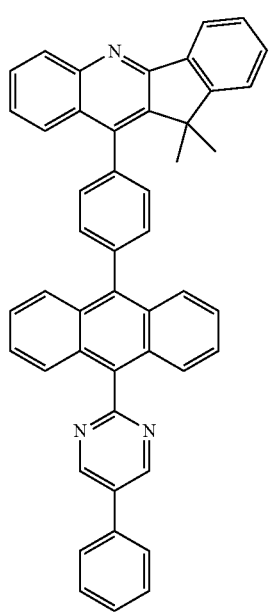
307
360
-continued
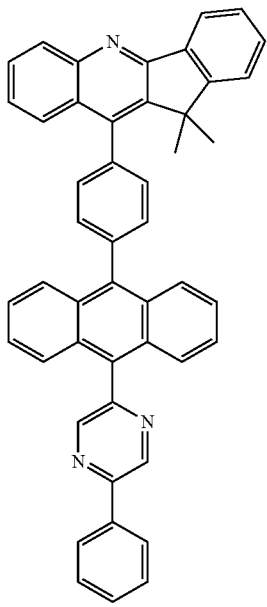
308
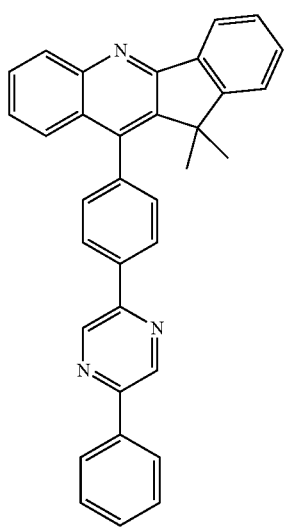
309
310

311
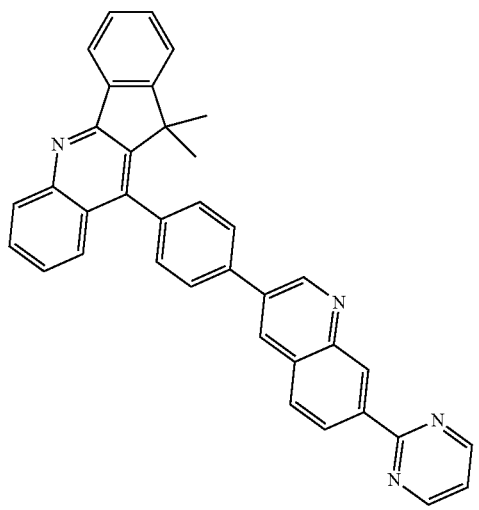
312
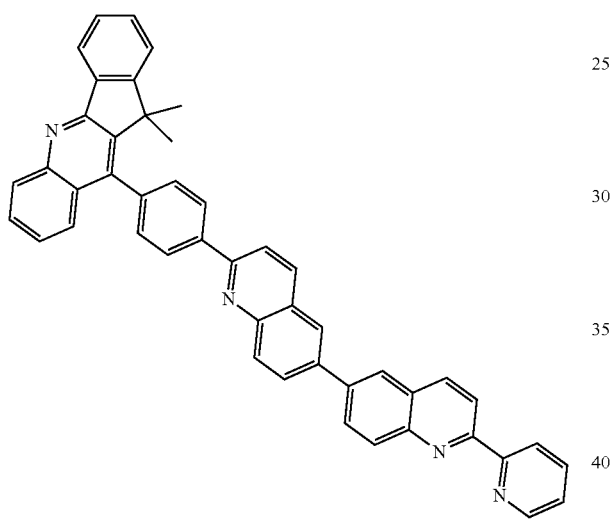
313
314
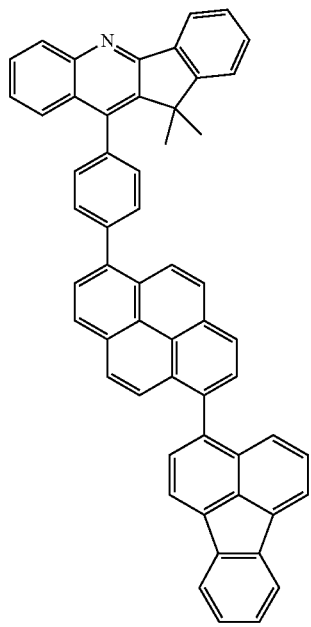
315
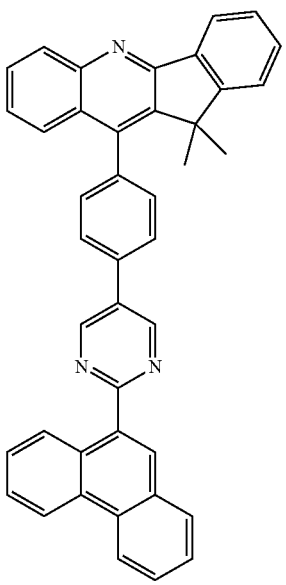

363
-continued
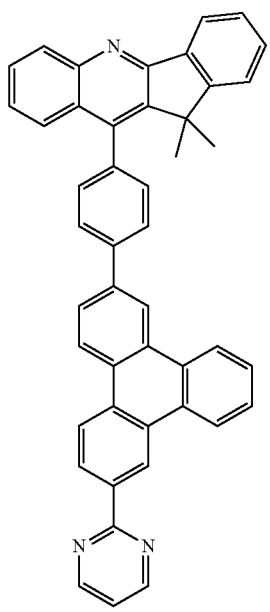
316
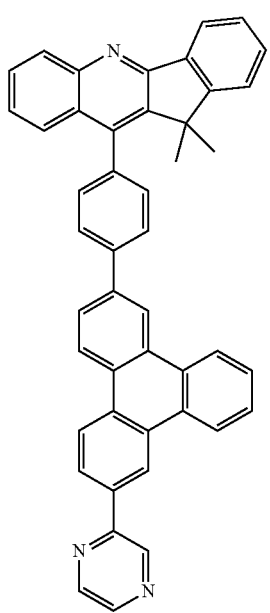
317
364
-continued
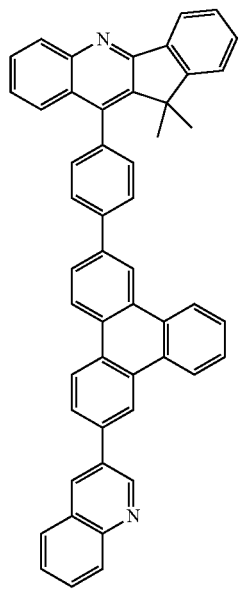
318
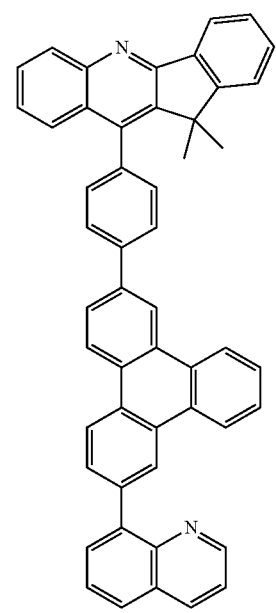
319

365
-continued
320
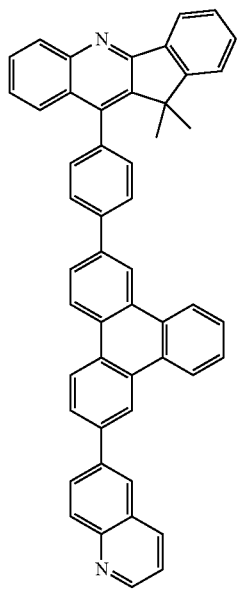
321
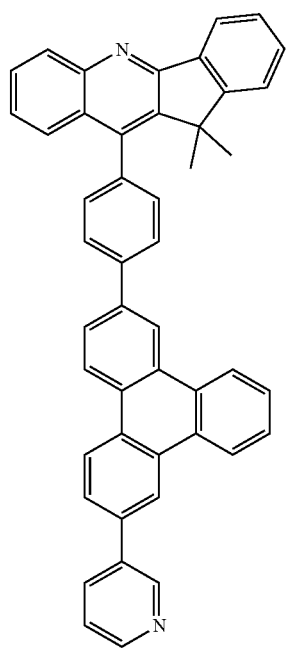
366
-continued
322
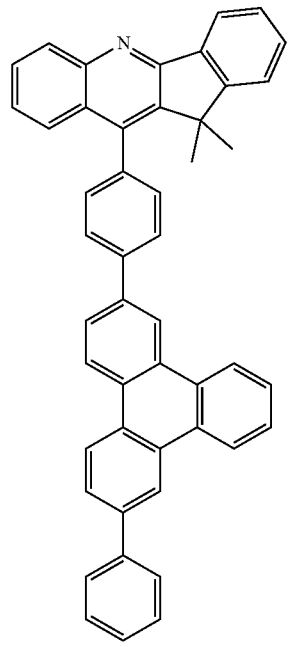 [SMILES: CC1(C)c2ccccc2-c2nc3ccccc3c(-c3ccc(-c4ccc5c6ccc(-c7ncccn7)cc6c6ccccc6c5c4)cc3)c21]
323
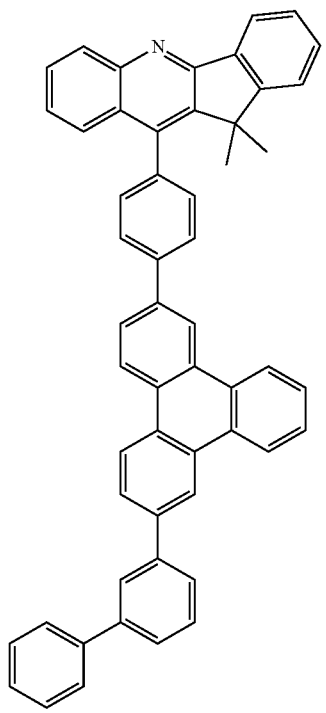

367
-continued
324
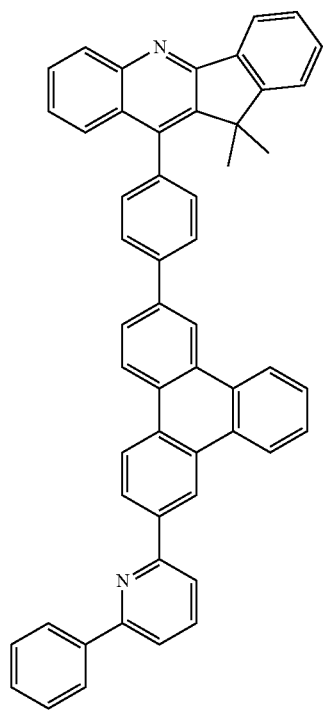 [SMILES: CC1(C)c2ccccc2-c2nc3ccccc3c(-c3ccc(-c4ccc5c6ccc(-c7cccc(-c8ccccc8)c7)cc6c6ccccc6c5c4)cc3)c21]
325
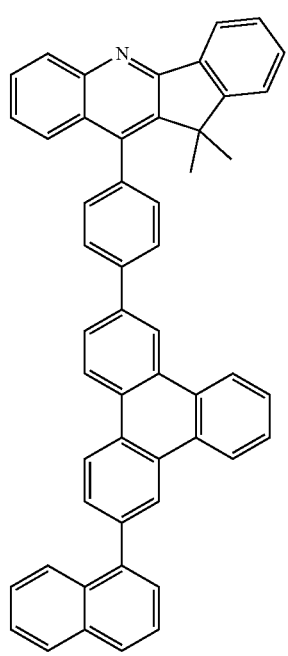
368
-continued
326
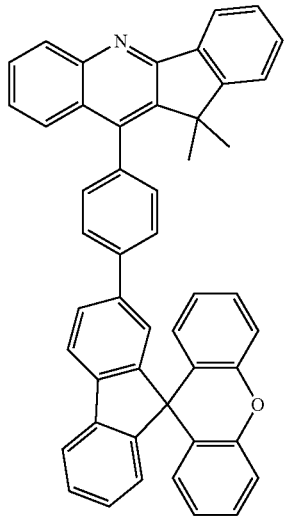
327
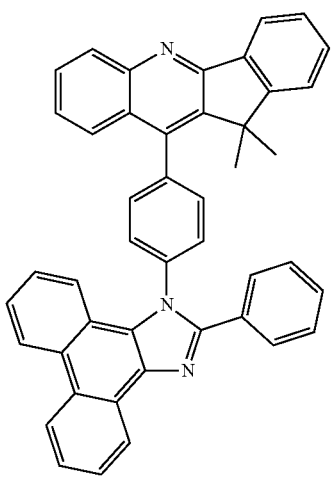
328
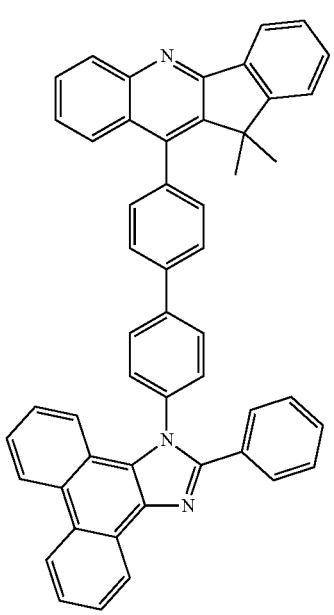

329
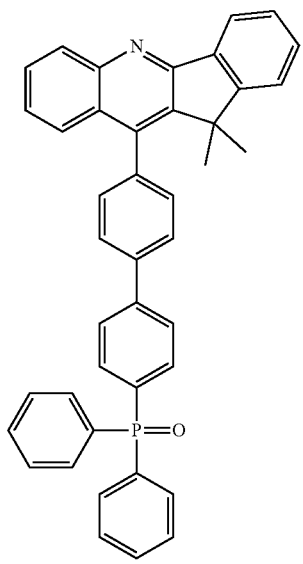 [SMILES: CC1(C)c2ccccc2-c2nc3ccccc3c(-c3ccc(-c4ccc(P(=O)(c5ccccc5)c5ccccc5)cc4)cc3)c21]
330
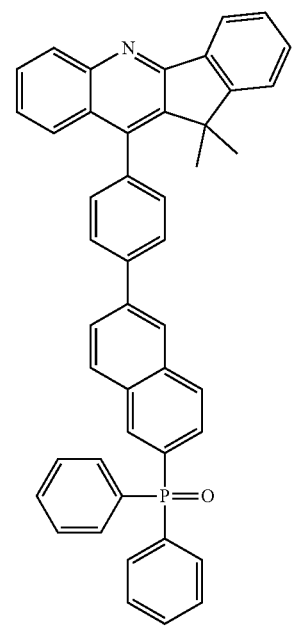
331
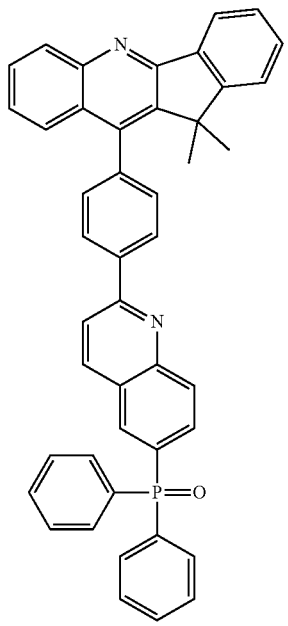
332
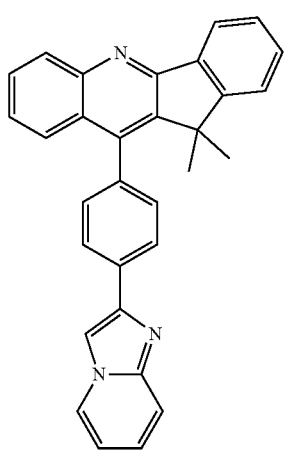 [SMILES: CC1(C)c2ccccc2-c2nc3ccccc3c(-c3ccc(-c4cn5ccccc5n4)cc3)c21]
333
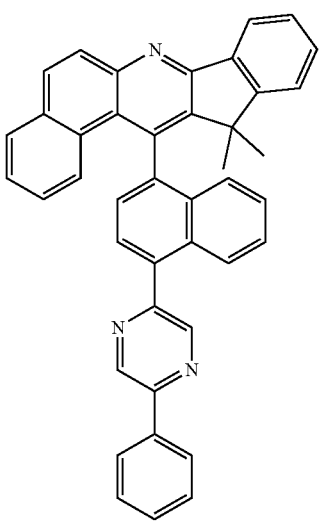

334
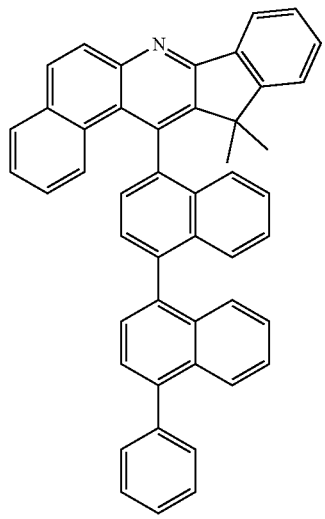
335
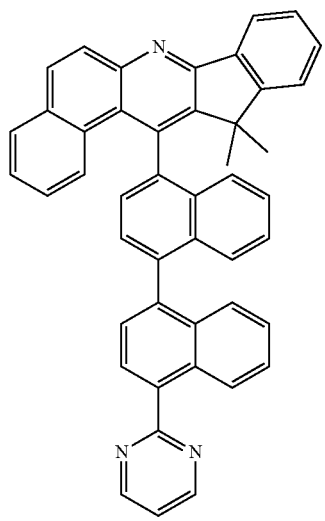
336
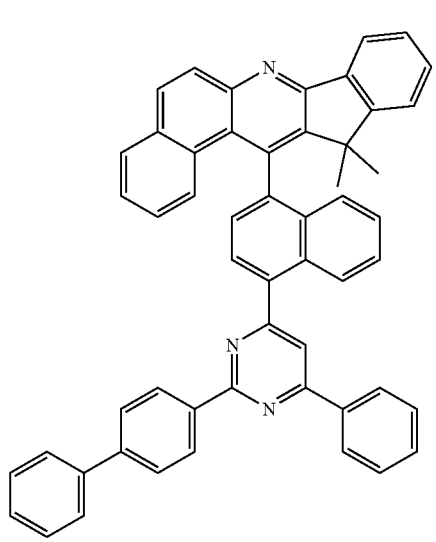
337
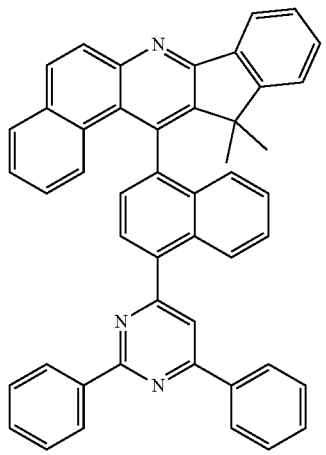
338
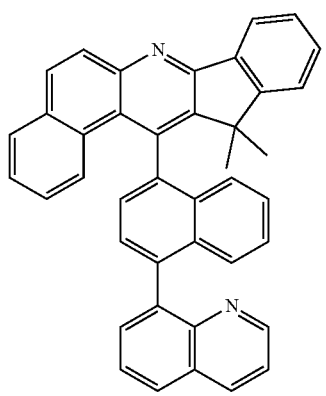
339
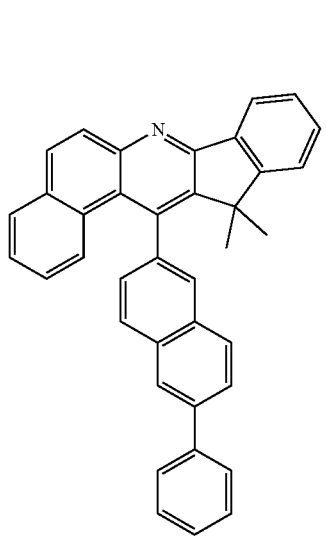

373
-continued
340
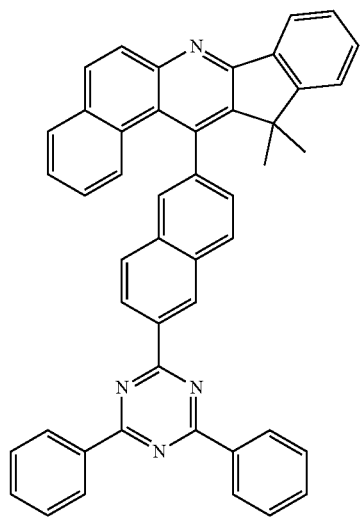
341
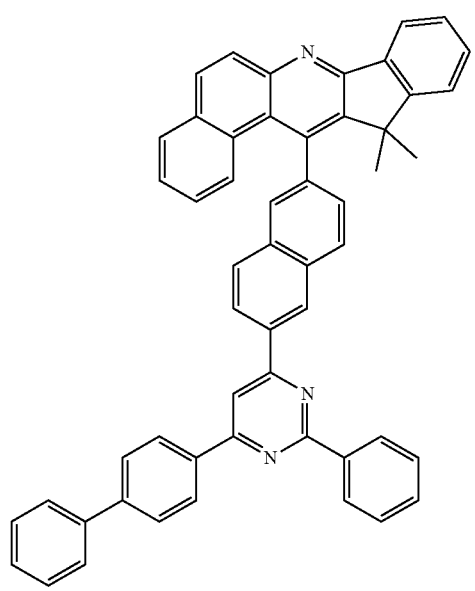 [SMILES: CC1(C)c2ccccc2-c2nc3ccc4ccccc4c3c(-c3ccc4cc(-c5cc(-c6ccc(-c7ccccc7)cc6)nc(-c6ccccc6)n5)ccc4c3)c21]
374
-continued
342
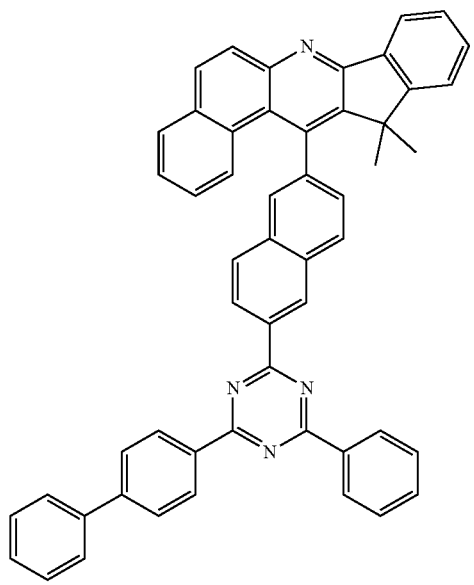
343
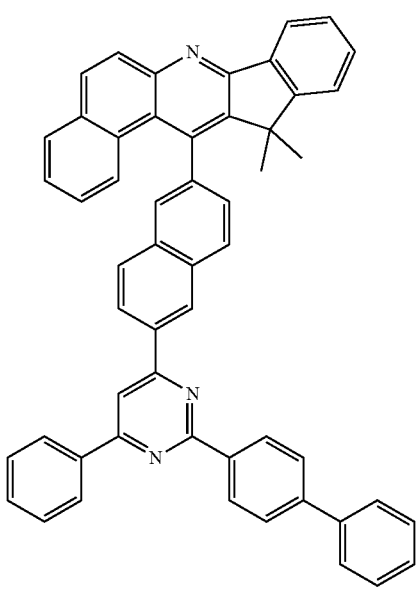

375
-continued
344
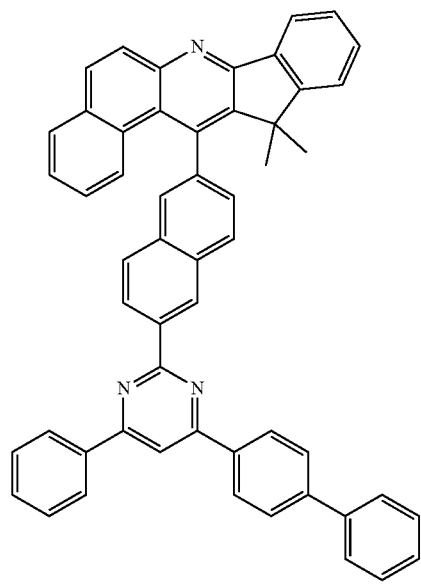
345
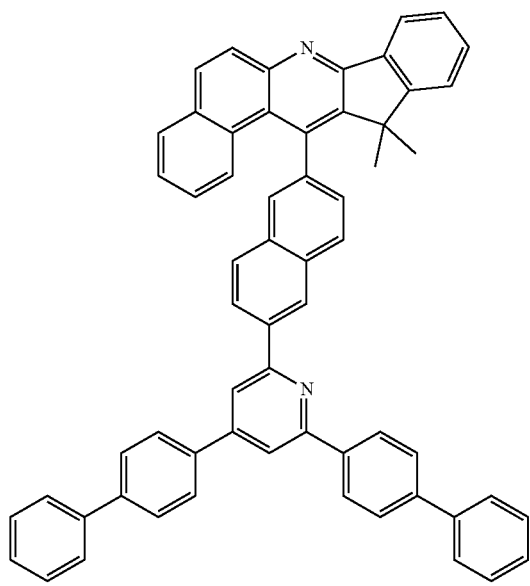
376
-continued
346
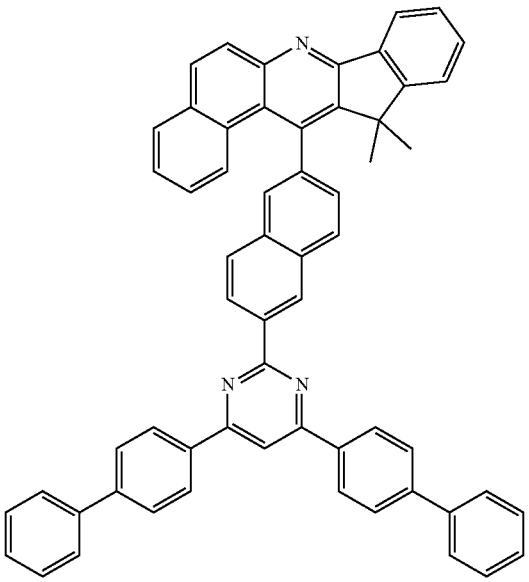
347
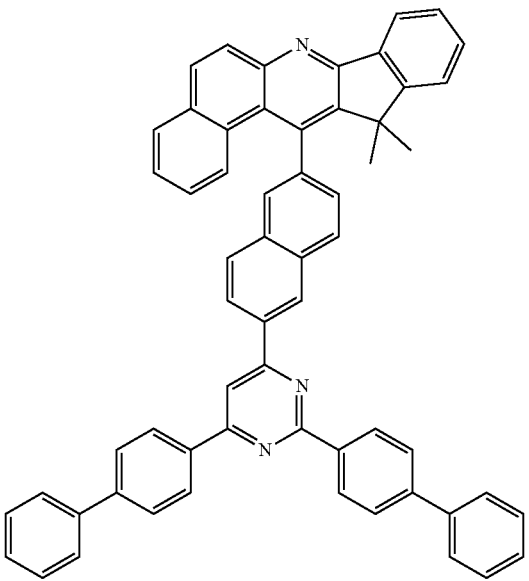

348
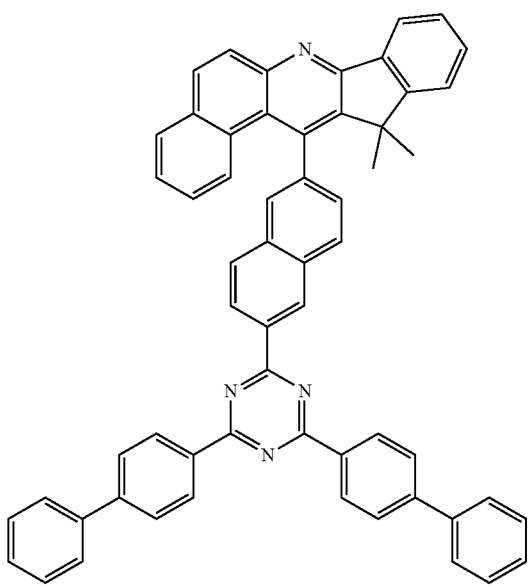
349
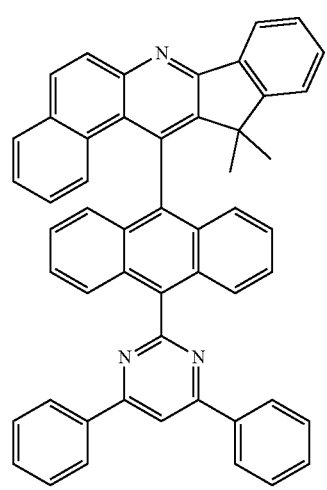 [SMILES: CC1(C)c2ccccc2-c2nc3ccc4ccccc4c3c(-c3c4ccccc4c(-c4nc(-c5ccccc5)cc(-c5ccccc5)n4)c4ccccc34)c21]
350
351
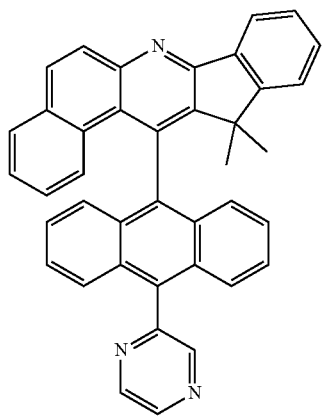
352
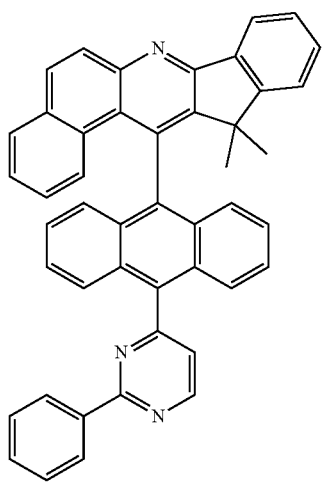
353
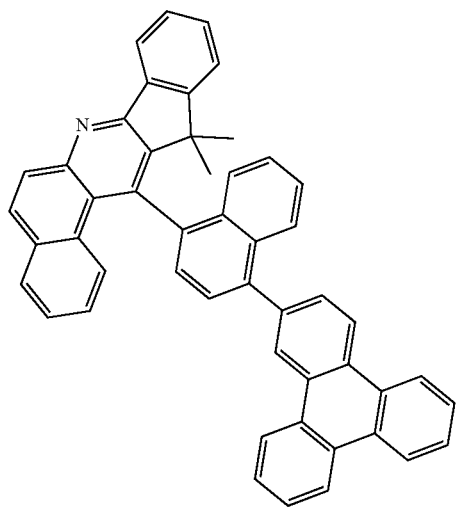

379
-continued
354
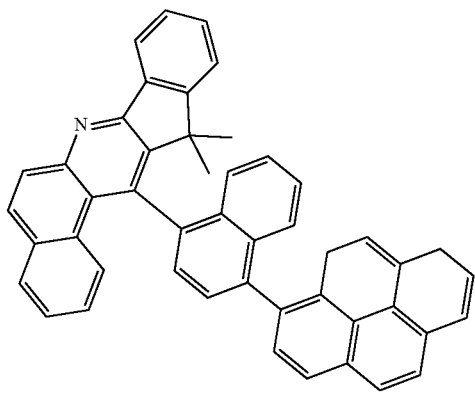
355
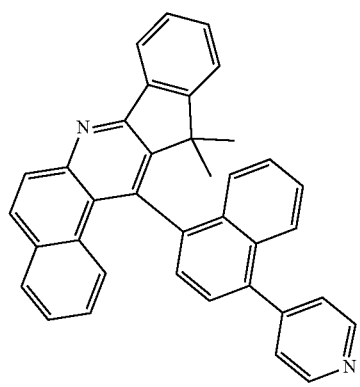
356
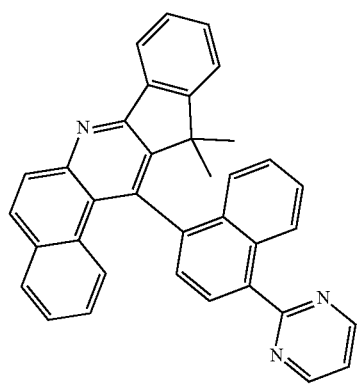
357
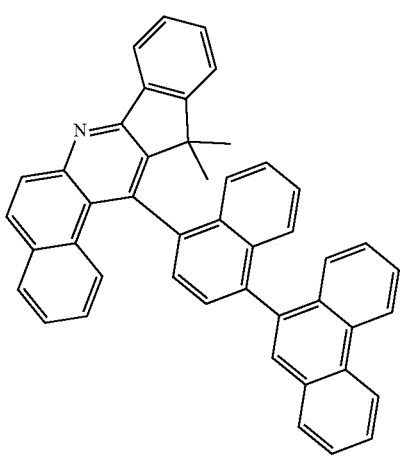
380
-continued
358
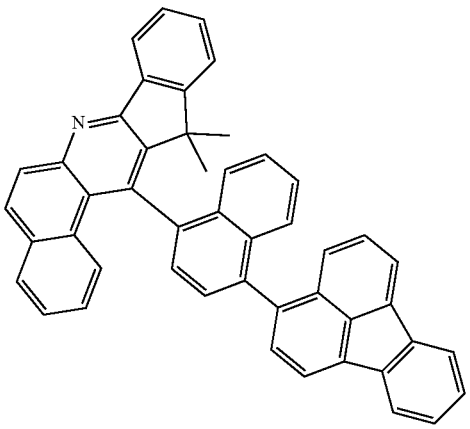
359
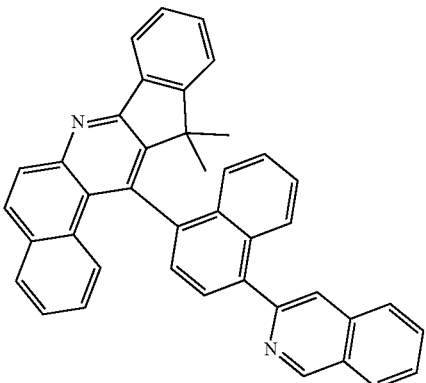
360
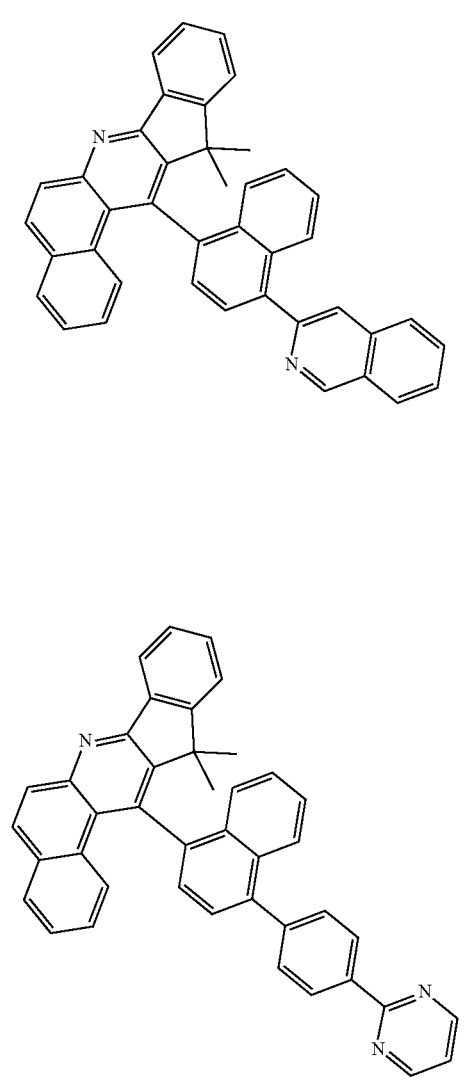

361
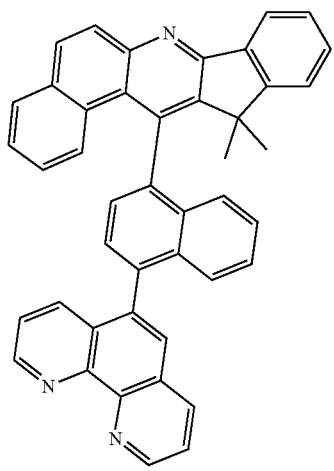
362
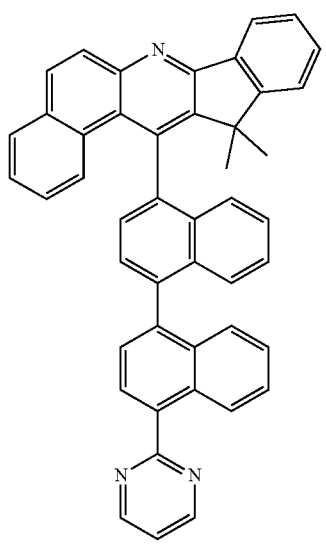
363
364
365
366
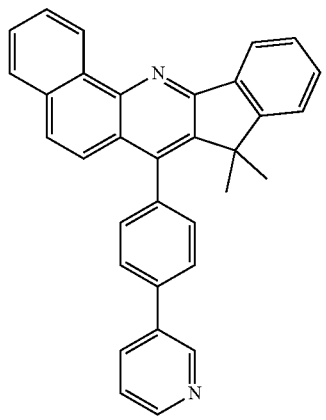
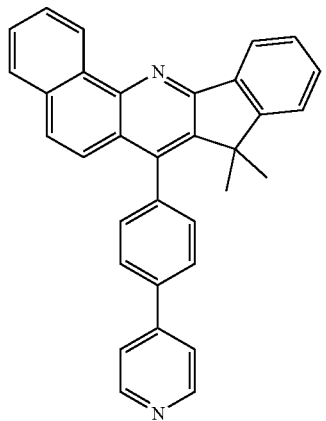

383
-continued
367
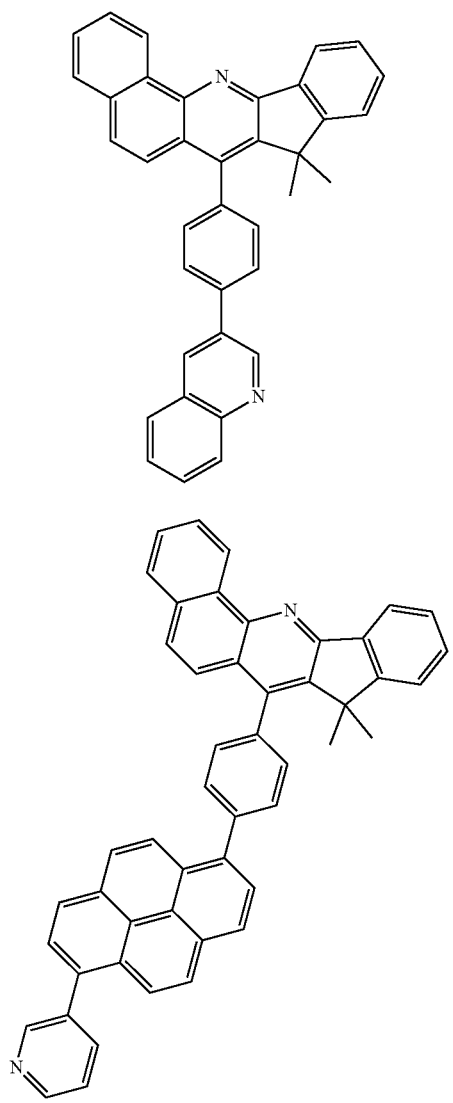
368
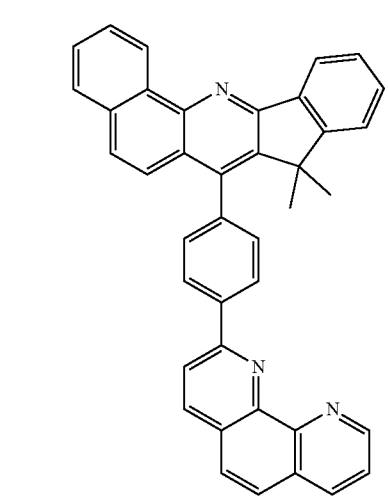
384
-continued
370
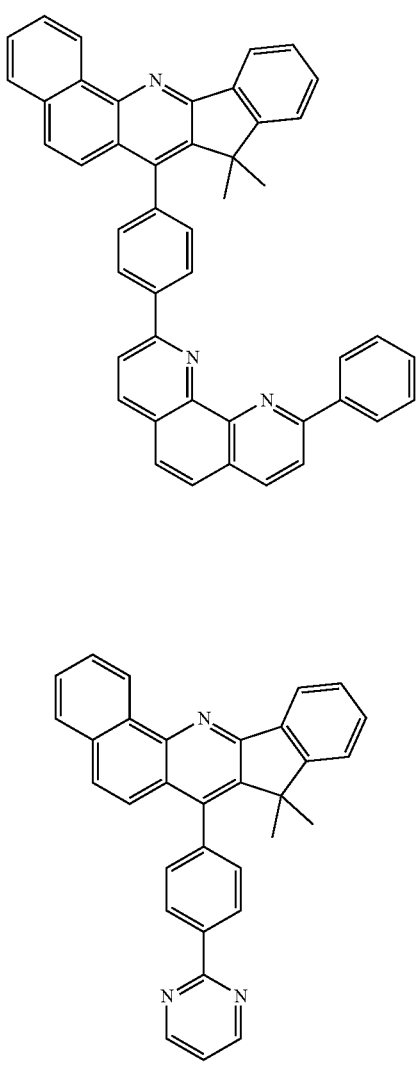
371
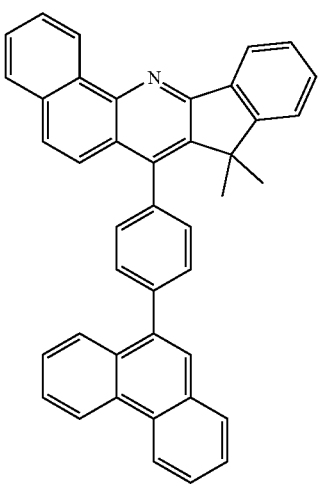
369
372

385
-continued
373
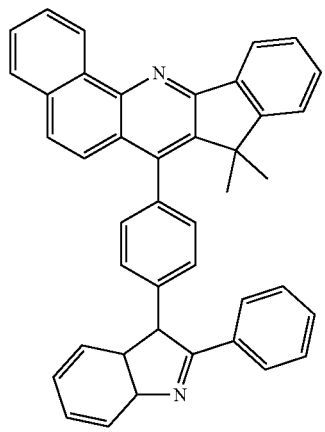
374
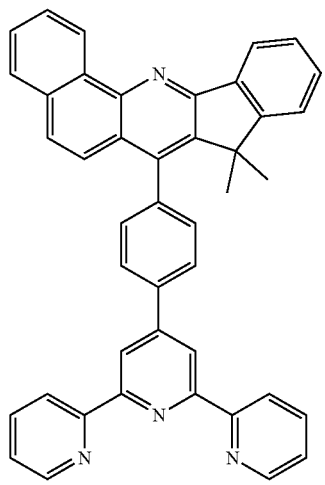
375
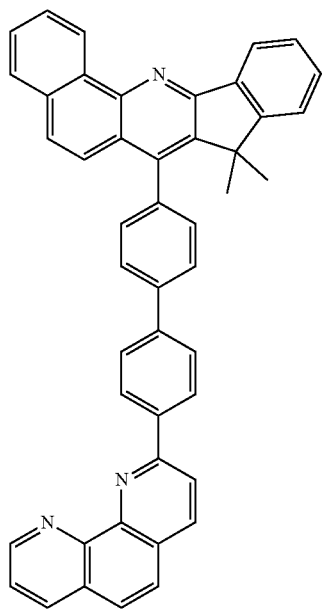
386
-continued
376
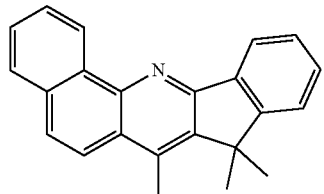
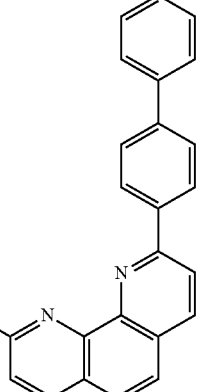
377
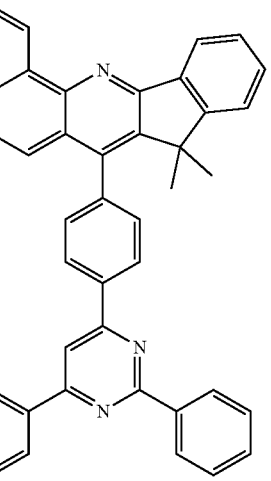
378
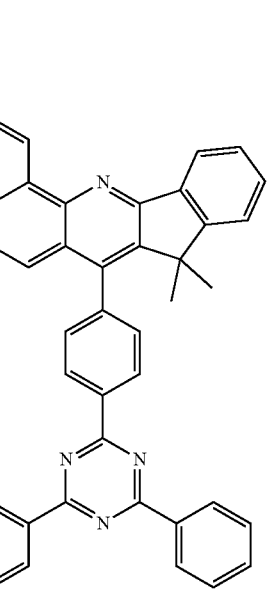
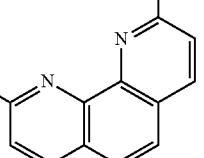

387
-continued
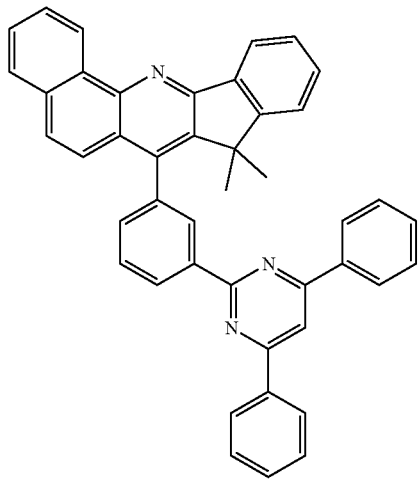
379
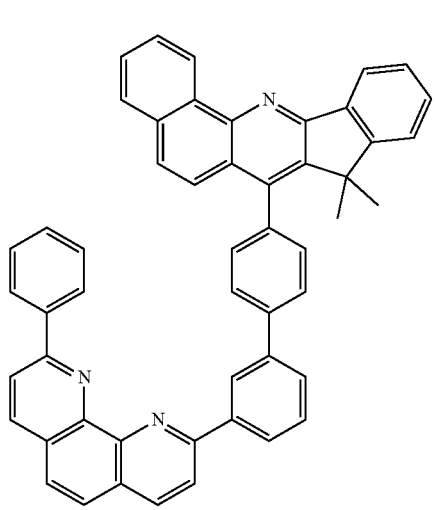
380
380
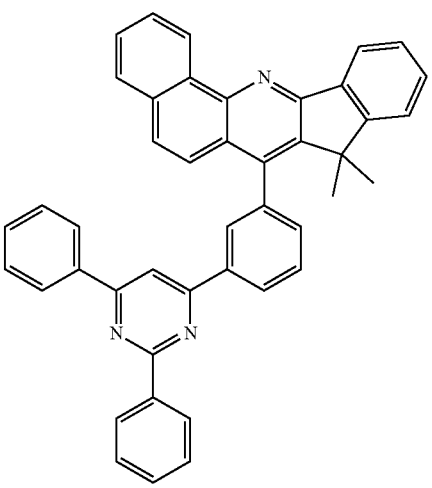
382
388
-continued
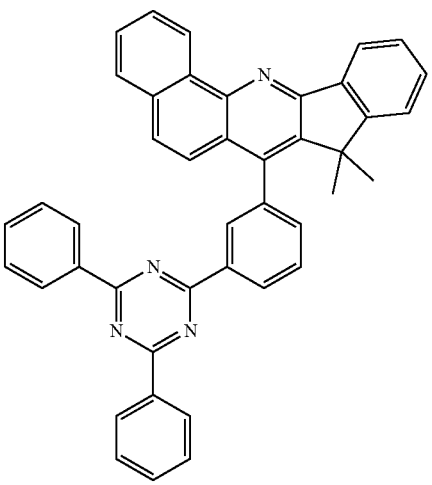
383
381
384

385
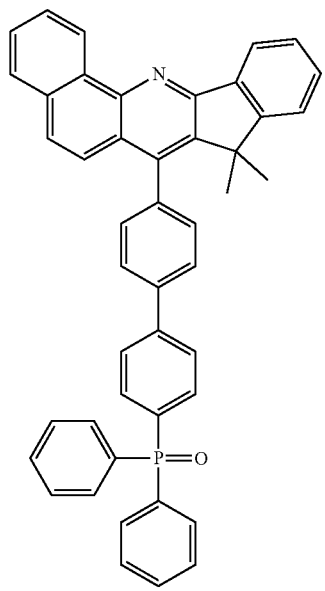
386
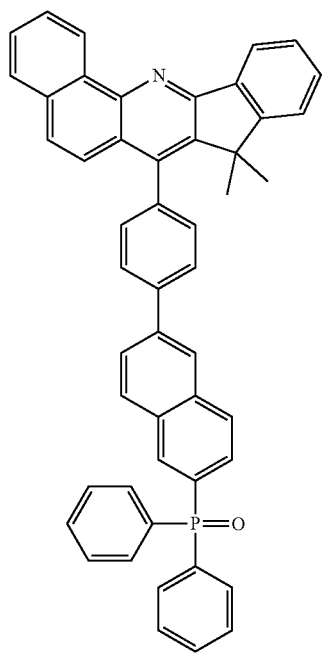
387
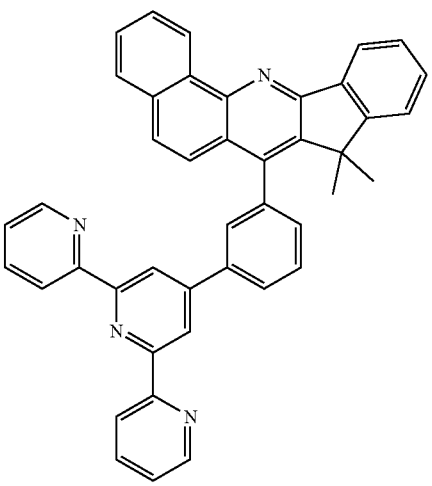
388
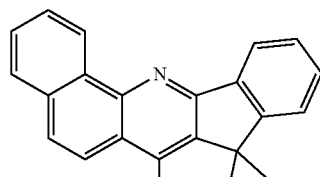
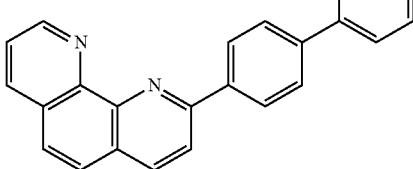
389
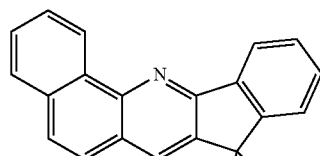
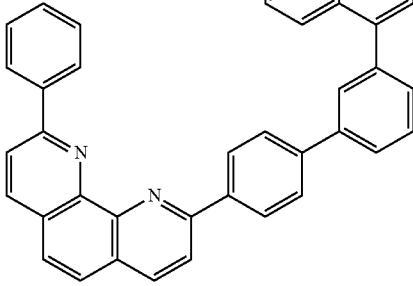

391
-continued
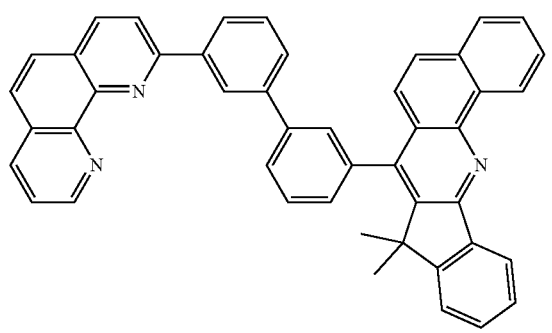
390
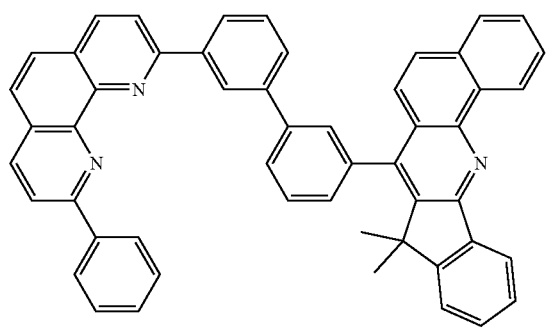
391
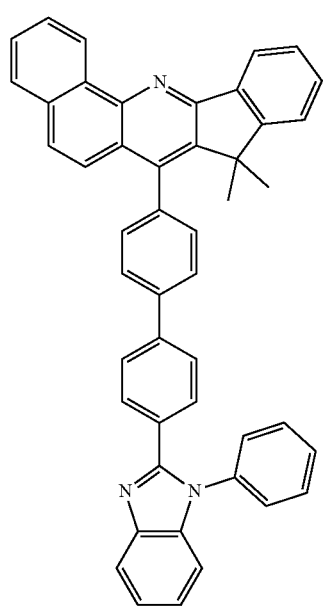 [SMILES: CC1(C)c2ccccc2-c2nc3c(ccc4ccccc43)c(-c3ccc(-c4ccc(-c5nc6ccccc6n5-c5ccccc5)cc4)cc3)c21]
392
392
-continued
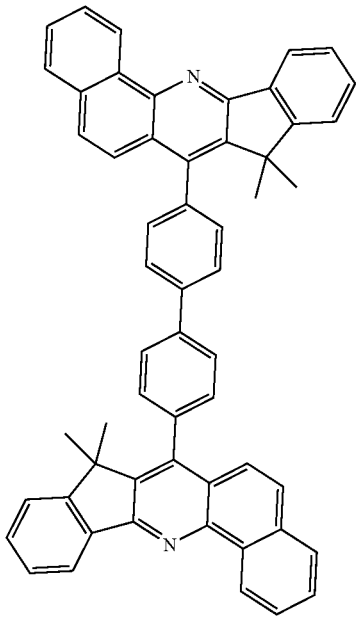
393
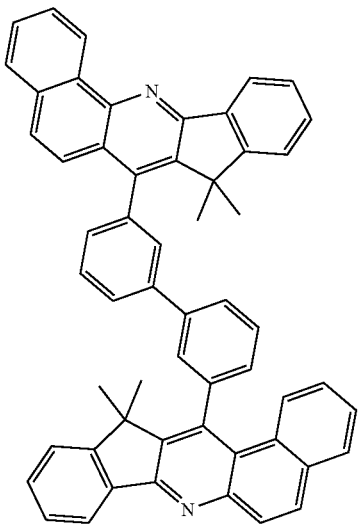
394

393
-continued
395
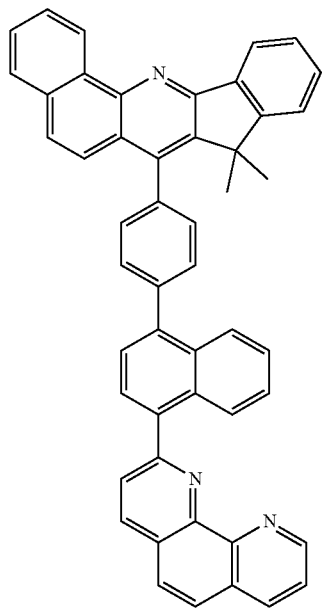 [SMILES: CC1(C)c2ccccc2-c2nc3c(ccc4ccccc43)c(-c3ccc(-c4ccc(-c5ccc6ccc7cccnc7c6n5)c5ccccc45)cc3)c21]
396
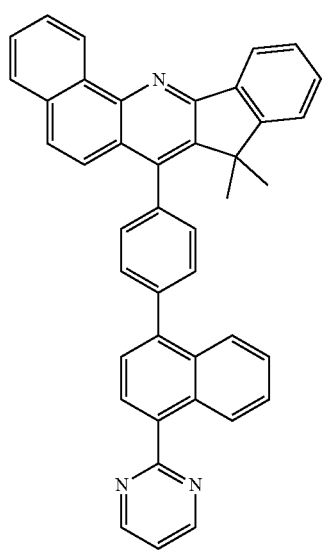
394
-continued
397
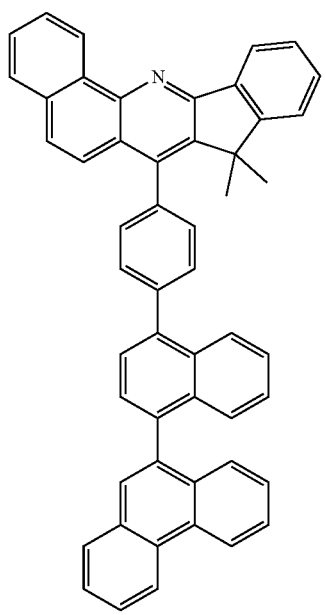
398
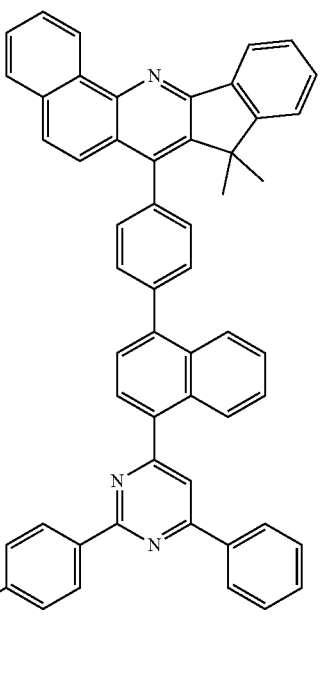

395
-continued

399

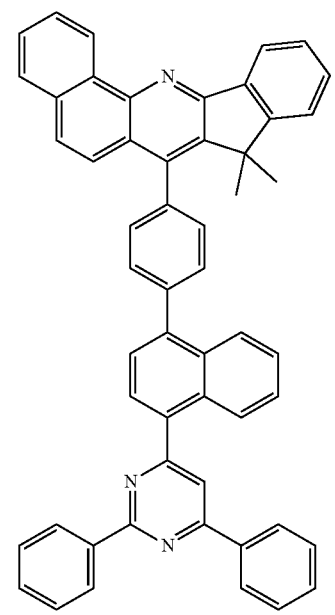 [SMILES: CC1(C)c2ccccc2-c2nc3c(ccc4ccccc43)c(-c3ccc(-c4ccc(-c5cc(-c6ccccc6)nc(-c6ccccc6)n5)c5ccccc45)cc3)c21]

400

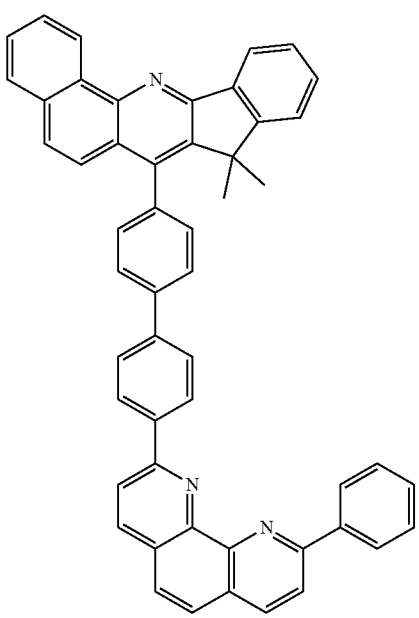

396
-continued

401

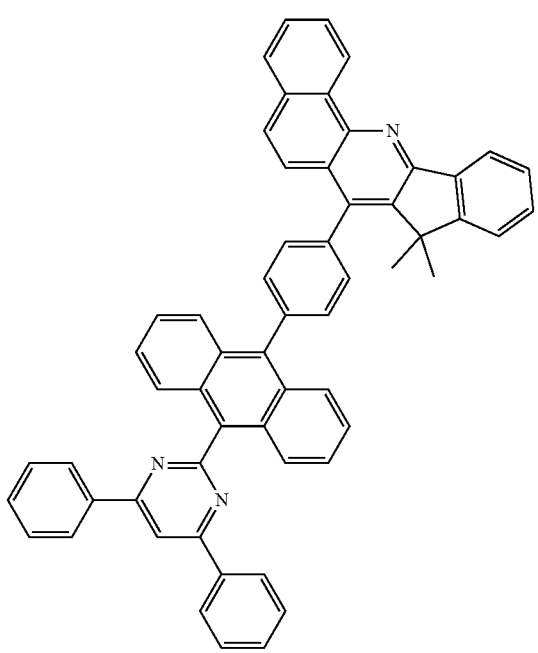 [SMILES: CC1(C)c2ccccc2-c2nc3c(ccc4ccccc43)c(-c3ccc(-c4c5ccccc5c(-c5nc(-c6ccccc6)cc(-c6ccccc6)n5)c5ccccc45)cc3)c21]

402

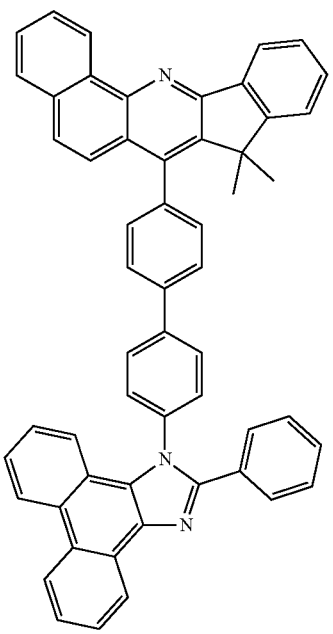 [SMILES: CC1(C)c2ccccc2-c2nc3c(ccc4ccccc43)c(-c3ccc(-c4ccc(-n5c(-c6ccccc6)nc6c7ccccc7c7ccccc7c65)cc4)cc3)c21]

6. An organic light emitting device comprising:
an anode;
a cathode; and
one or more organic material layers provided between the anode and the cathode,
wherein one or more layers of the organic material layers comprise the hetero-cyclic compound of claim 1.

7. The organic light emitting device of claim 6, wherein the organic material layer comprises at least one of a hole blocking layer, an electron injection layer and an electron transfer layer, and at least one of the hole blocking layer, the electron injection layer and the electron transfer layer comprises the hetero-cyclic compound.

8. The organic light emitting device of claim 6, wherein the organic material layer comprises a light emitting layer, and the light emitting layer comprises the hetero-cyclic compound.

9. The organic light emitting device of claim 6, wherein the organic material layer comprises one or more of a hole injection layer, a hole transfer layer, and a layer carrying out hole injection and hole transfer at the same time, and one of the above-mentioned layers comprises the hetero-cyclic compound.

10. The organic light emitting device of claim 6, wherein the organic material layer comprises a charge generation layer, and the charge generation layer comprises the hetero-cyclic compound.

11. The organic light emitting device of claim 6, comprising:
- an anode;
- a first stack provided on the anode and comprising a first light emitting layer;
- a charge generation layer provided on the first stack;
- a second stack provided on the charge generation layer and comprising a second light emitting layer; and
- a cathode provided on the second stack.

* * * * *